US010337072B2

(12) United States Patent
Hudson et al.

(10) Patent No.: US 10,337,072 B2
(45) Date of Patent: Jul. 2, 2019

(54) COPY NUMBER DETECTION AND METHODS

(71) Applicant: THE BOARD OF TRUSTEES OF THE UNIVERSITY OF ILLINOIS, Urbana, IL (US)

(72) Inventors: Matthew E. Hudson, West Lafayette, IN (US); Brian W. Diers, Urbana, IL (US); Tong Geon Lee, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 159 days.

(21) Appl. No.: 14/991,733

(22) Filed: Jan. 8, 2016

(65) Prior Publication Data
US 2016/0265070 A1    Sep. 15, 2016

Related U.S. Application Data

(60) Provisional application No. 62/101,253, filed on Jan. 8, 2015, provisional application No. 62/120,872, filed on Feb. 25, 2015.

(51) Int. Cl.
*C12Q 1/68*    (2018.01)
*C12Q 1/6895*    (2018.01)
*A01H 1/04*    (2006.01)
*A01H 5/10*    (2018.01)

(52) U.S. Cl.
CPC .............. *C12Q 1/6895* (2013.01); *A01H 1/04* (2013.01); *A01H 5/10* (2013.01); *C12Q 2600/13* (2013.01); *C12Q 2600/156* (2013.01)

(58) Field of Classification Search
CPC .................................................. C12Q 1/6895
USPC ........................................................... 506/2
See application file for complete search history.

(56) References Cited

U.S. PATENT DOCUMENTS

| 5,487,972 A | 1/1996 | Gelfand et al. |
| 2011/0091900 A1 | 4/2011 | Williams et al. |
| 2013/0305410 A1 | 11/2013 | Bent et al. |
| 2013/0340115 A1 | 12/2013 | Daines et al. |

FOREIGN PATENT DOCUMENTS

| WO | WO 92/02638 A1 | 2/1992 |
| WO | WO 2013/170258 A2 | 11/2013 |
| WO | WO 2013/170258 A3 | 11/2013 |

OTHER PUBLICATIONS

Ihira et al. 2013 Journal Virological Methods 193:308-313.*
TaqMan manual 2012, 16 pages, TaqMan Assay for genetic variation research.*
Cook et al. 2012, Science 338:1206-1209.*
Avula et al., "Alternative method of allelic discrimination," *Bio Techniques* 57:88-90, 2014.
Bourdon et al., "Evidence for karyoplasmic homeostasis during endoreduplication and a ploidy-dependent increase in gene transcription during tomato fruit growth," *Development* 139:3817-3826, 2012.
Chen et al., "Single nucleotide polymorphism genotyping: biochemistry, protocol, cost and throughput," *The Pharmacogenomics Journal* 3:77-96, 2003.
Cook et al., "Copy Number Variation of Multiple Genes at Rhg1 Mediates Nematode Resistance in Soybean," *Science* 338:1206-1209, 2012.
Cook et al., "Distinct Copy Number, Coding Sequence, and Locus Methylation Patterns Underlie Rhg1-Mediated Soybean Resistance to Soybean Cyst Nematode," *Plant Physiology*, 165:630-647, 2014.
Cronn et al., "PCR-mediated recombination in amplification products derived from polyploid cotton," *Theor Appl Genet* 104:482-489, 2002.
D'Haene et al., "Accurate and objective copy number profiling using real-time quantitative PCR," *Methods* 50:262-270, 2010.
Estivill et al., "Copy Number Variants and Common Disorders: Filling the Gaps and Exploring Complexity in Genome-Wide Association Studies," *PLoS Genetics* 3(10):1787-1799, 2007.
Fedick et al., "Development of TaqMan allelic discrimination based genotyping of large DNA deletions," *Genomics* 99:127-131, 2012.
Henrichsen et al., "Copy number variants, diseases and gene expression," *Human Molecular Genetics* 18(R1):R1-R8, 2009.
Holland et al., "Detection of specific polymerase chain reaction product by utilizing the 5' → 3' exonuclease activity of *Thermus aquaticus* DNA polymerase," *Proc. Natl. Acad. Sci. USA* 88:7276-7280, 1991.
Imabayashi et al., "A New HLA-DRB1 Genotyping Method Using Single Nucleotide Polymorphism (SNP) Analysis with Multiplex Primer Extension Reactions and Its Application to Mixed Samples," *Acta Med. Okayama* 59(5):179-194, 2005.

(Continued)

*Primary Examiner* — Li Zheng
(74) *Attorney, Agent, or Firm* — Klarquist Sparkman, LLP

(57) ABSTRACT

Described herein are methods of measuring, in a genomic sample from an individual, the relative frequency of a target sequence (that is, its copy number) with respect to a control sequence of known copy number at a different genomic locus in the same genome, wherein the target and control sequences differ by at least one single nucleotide variation (SNV). These methods involve both the target sequence and the control sequence in a single reaction/container, using a pair of primers that prime amplification of both the target sequence and the control sequence, or a single downstream primer and two upstream primers (that differs only at the position of the SNV between the target and control sequences), and measuring the abundance of each of the target sequence and the control sequence using SNV-specific labeled probes or primers, or a melting curve analysis that distinguishes between the amplified control and target sequences. The methods are exemplified with various different amplifications process. Also provided are methods of using these copy number detection methods, for instance, in breeding programs, identification, diagnosis, and so forth.

8 Claims, 22 Drawing Sheets
(5 of 22 Drawing Sheet(s) Filed in Color)
Specification includes a Sequence Listing.

(56) References Cited

OTHER PUBLICATIONS

Ingham et al., "Quantitative Real-Time PCR Assay for Determining Transgene Copy Number In Transformed Plants," *BioTechniques* 31:132-140, 2001.
Kadam et al., "Genomic-assisted phylogenetic analysis and marker development for next generation soybean cyst nematode resistance breeding," *Plant Science* 242:342-350, 2016.
Kalinina et al., "Nanoliter scale PCR with TaqMan detection," *Nucleic Acids Research* 25(10):1999-2004, 1997.
Larsson et al., "Viral Load, Integration and Methylation of E2BS3 and 4 in Human Papilloma Virus (HPV) 16-Positive Vaginal and Vulvar Carcinomas," *PLoS One* 9(11):e112839. doi:10.1371/journal. pone.0112839, 2014 (11 pages).
Lee et al., "Evolution and selection of Rhg1, a copy-number variant nematode-resistance locus," *Molecular Ecology* 24:1774-1791, 2015.
Lehmann et al., "Detection of Gene Amplification in Archival Breast Cancer Specimens by Laser-Assisted Microdissection and Quantitative Real-Time Polymerase Chain Reaction," *American Journal of Pathology* 156(6):1855-1864, 2000.
Livak et al., "Oligonucleotides with Fluorescent Dyes at Opposite Ends Provide a Quenched Probe System Useful for Detecting PCR product and Nucleic Acid Hybridization," *PCR Methods Appl.* 4(6):357-362, 1995.
Luthra et al., "Novel 5' Exonuclease-Based Real-Time PCR Assay for the Detection of t(14;18)(q32;q21) in Patients with Follicular Lymphoma," *American Journal of Pathology* 153(1):63-68, 1998.
Maron et al., "Aluminum tolerance in maize is associated with higher MATE1 gene copy number," *PNAS* 110(13):5241-5246, 2013.
Marras, "Selection of Fluorophore and Quencher Pairs for Fluorescent Nucleic Acid Hybridization Probes," *Methods Mol Biol.* 335:3-16, 2006.
McCarroll et al., "Copy-number variation and association studies of human disease," *Nature Genetics Supplement* 39:S37-S42, 2007.
Ota et al., "Determination of interactions between structured nucleic acids by fluorescence resonance energy transfer (FRET): selection of target sites for functional nucleic acids," *Nucleic Acids Research* 26(3):735-743, 1998.
Pozzi et al., "Comparison of three PCR-based methods to detect a Piedmontese cattle point mutation in the *Myostatin* gene," *Animal* 3(6):773-778, 2009.
Ryschkewitsch et al., "Comparison of PCR-southern hybridization and quantitative real-time PCR for the detection of JC and BK viral nucleotide sequences in urine and cerebrospinal fluid," *J Virol Methods.* 121(2):217-221, 2004.
Swan et al., "Human Papillomavirus (HPV) DNA Copy Number Is Dependent on Grade of Cervical Disease and HPV Type," *Journal of Clinical Microbiology* 37(4):1030-1034, 1999.
Traherne et al., "Human MHC architecture and evolution: implications for disease association studies," *International Journal of Immunogenetics* 35:179-192, 2008.
Usher et al., "Complex and multi-allelic copy number variation in human disease," *Briefings in Functional Genomics* 14(5):329-338, 2015.
Walling et al., "Chromosome-Level Homeology in Paleopolyploid Soybean (*Glycine max*) Revealed Through Integration of Genetic and Chromosome Maps," *Genetics* 172:1893-1900, 2006.
Xue et al., "Selection of Suitable Endogenous Reference Genes for Relative Copy Number Detection in Sugarcane," *Int. J. Mol. Sci.* 15:8846-8862, 2014.
Agilent Technologies, Inc., "Brilliant II QPCR Master Mix with ROX, Instruction Manual," Catalog #600805, #600806, #600816, #600817, Revision E.0 2015 (19 pages).
Applied Biosystems, "Allelic Discrimination Using the 5' Nuclease Assay," Publication 790910-004, 2001 (8 pages).
Applied Biosystems, "Creating Standard Curves with Genomic DNA or Plasmid DNA Templates for Use in Quantitative PC," tutorial, 2003 (9 pages).
Applied Biosystems, "Allelic Discrimination Getting Started Guide for 7300/7500/7500 Fast Systems," Part No. 4347822 Rev. E, Jun. 2010 (86 pages).
Applied Biosystems, "TaqMan® Copy Number Assays Protocol," by *Life Technologies Corporation*, Part No. 4397425 Rev. D, 2010 (45 pages).
Applied Biosystems, "TaqMan® Copy Number Assays," by *Life Technologies Corporation*, Product Bulletin, CO011161 0814, 2014 (4 pages).
Life Technologies Corporation, "TaqMan® Assays for genetic variation research," 2012 (16 pages).

\* cited by examiner

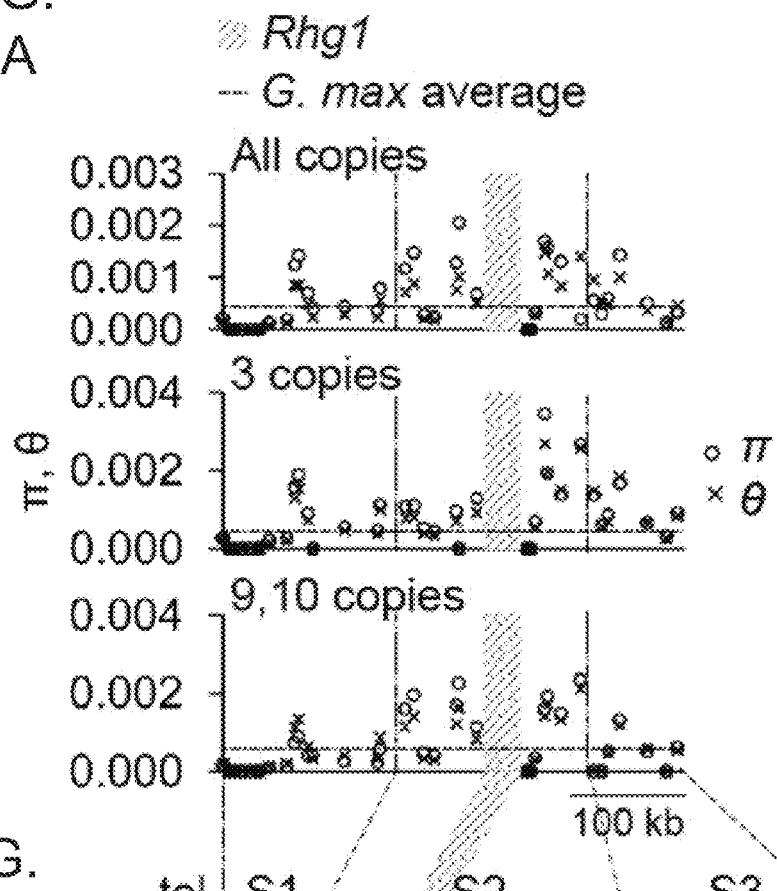
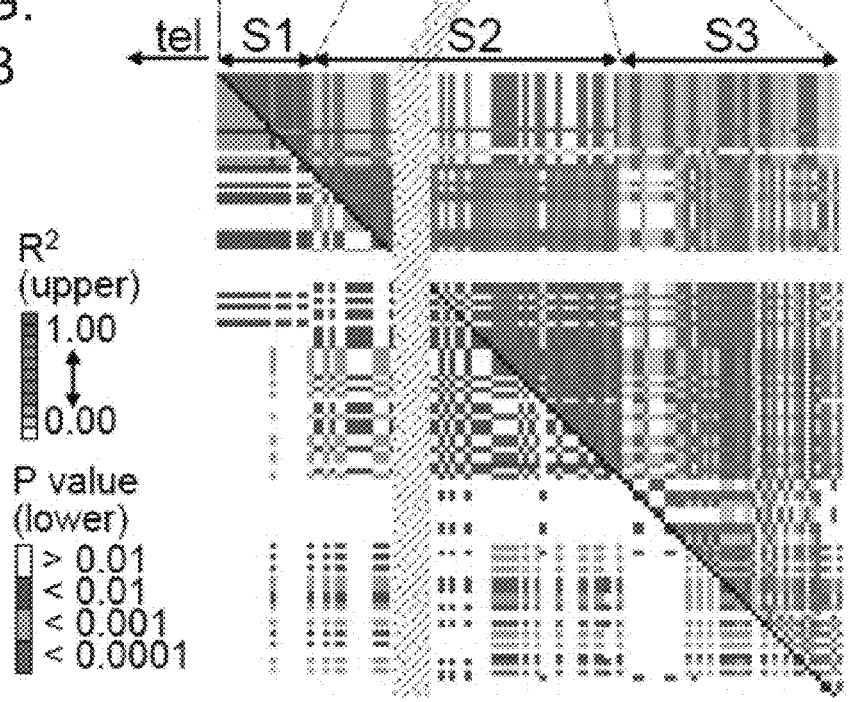

■ *Rhg1*
○ π
× θ
▲ Tajima's *D* (*q* ≤ 0.01)
▲ Tajima's *D* (0.01 < *q* ≤ 0.05)
△ Tajima's *D* (*q* > 0.05)
--- whole genome mean Tajima's *D*
--- 75th percentile of whole genome Tajima's *D*
--- 95th percentile of whole genome Tajima's *D*

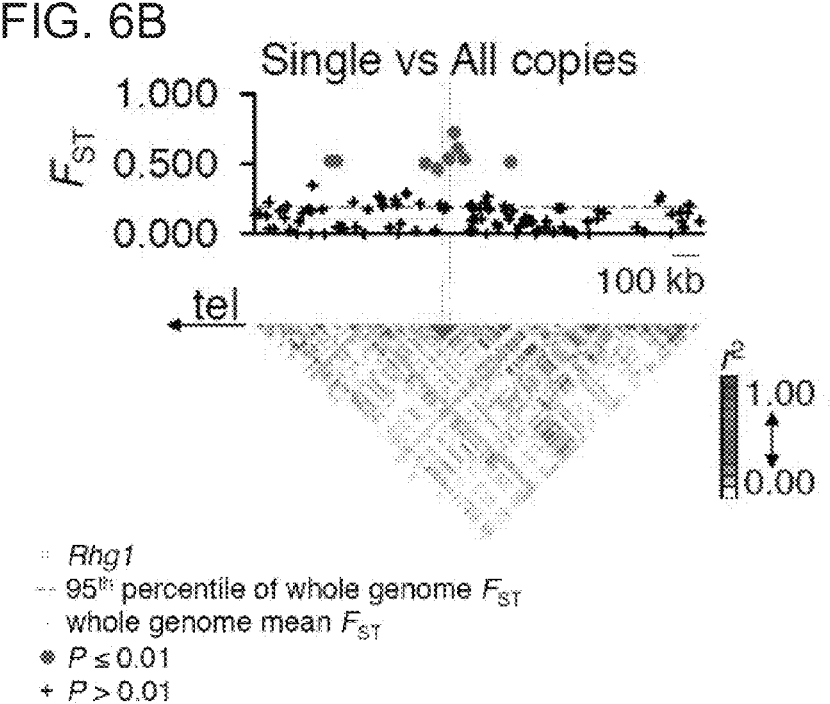
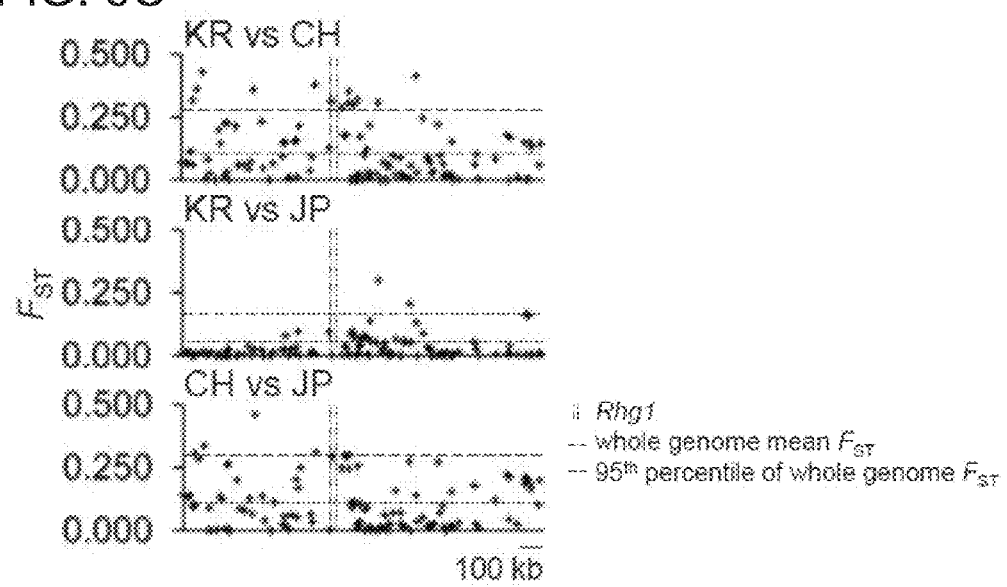

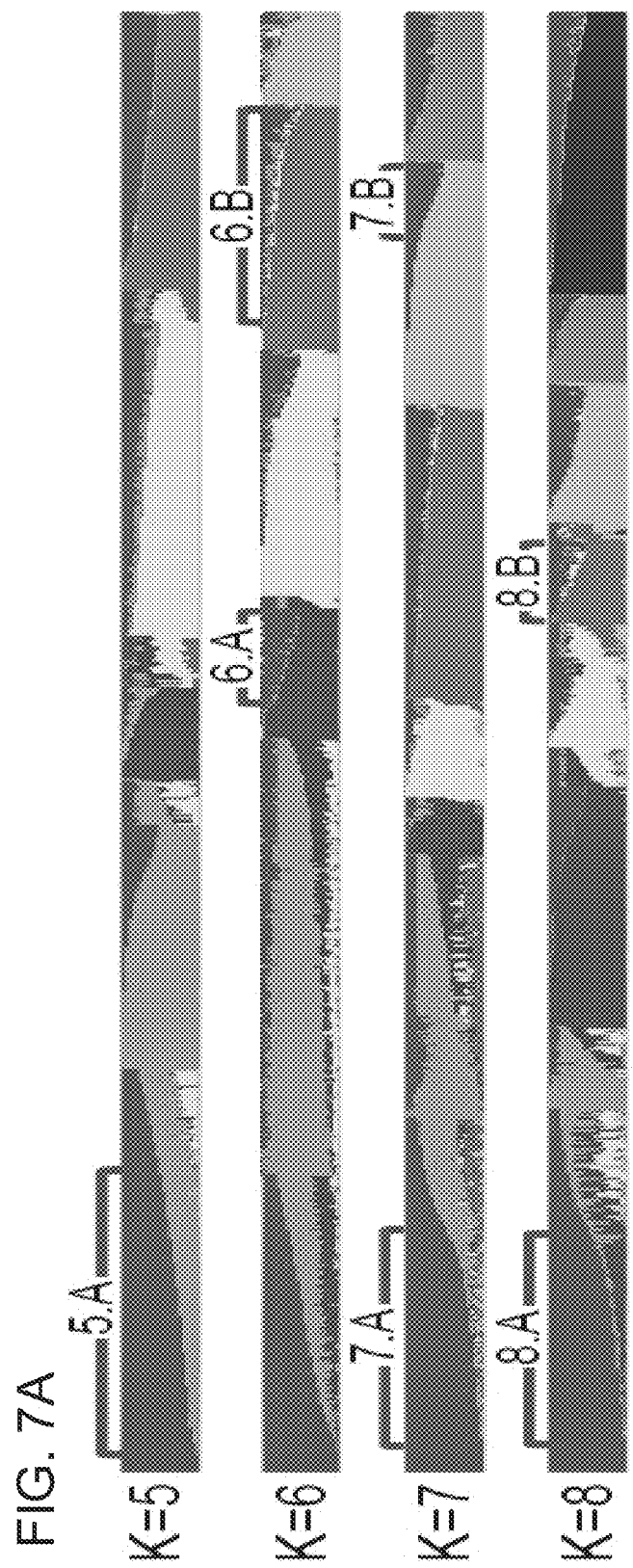

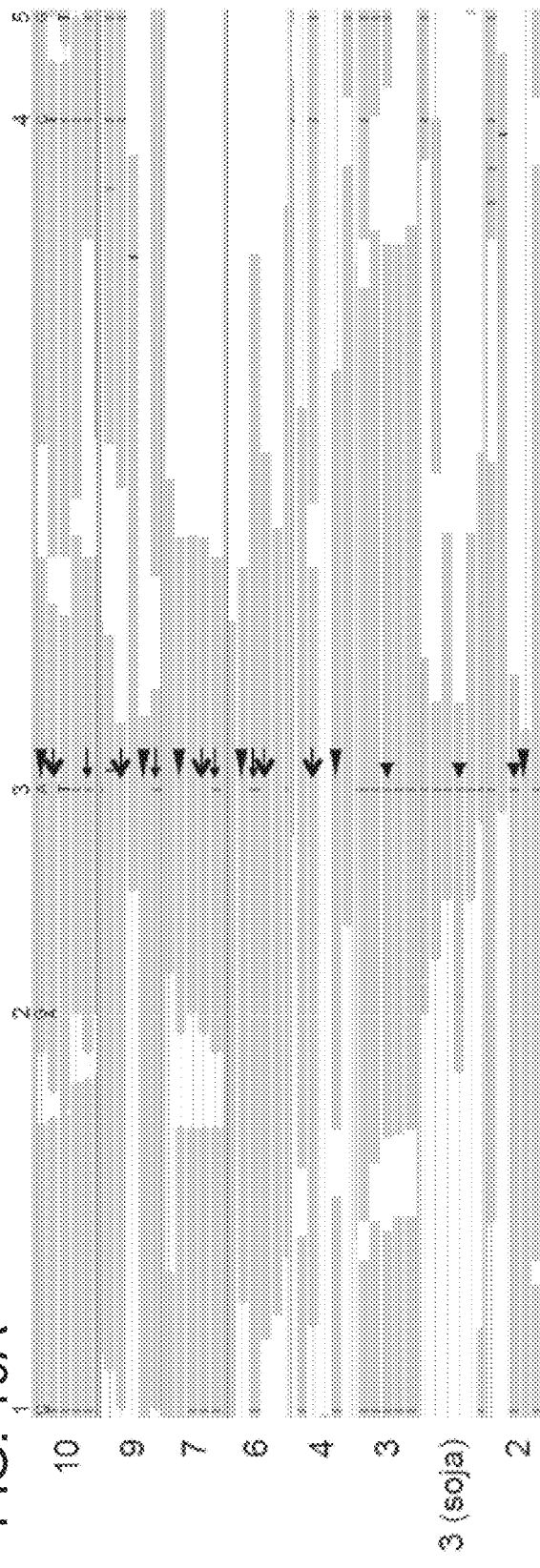
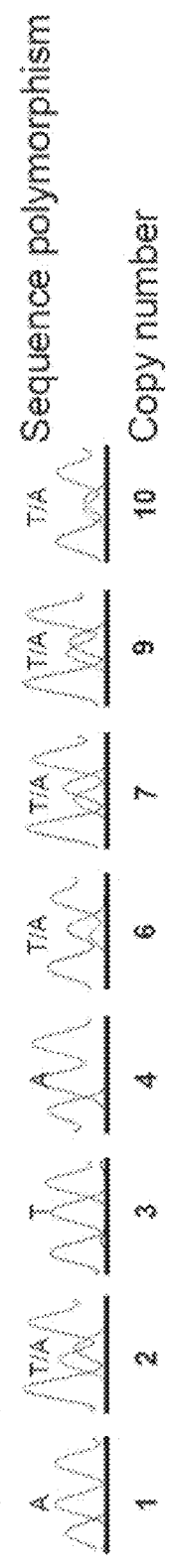
FIG. 10A
FIG. 10B

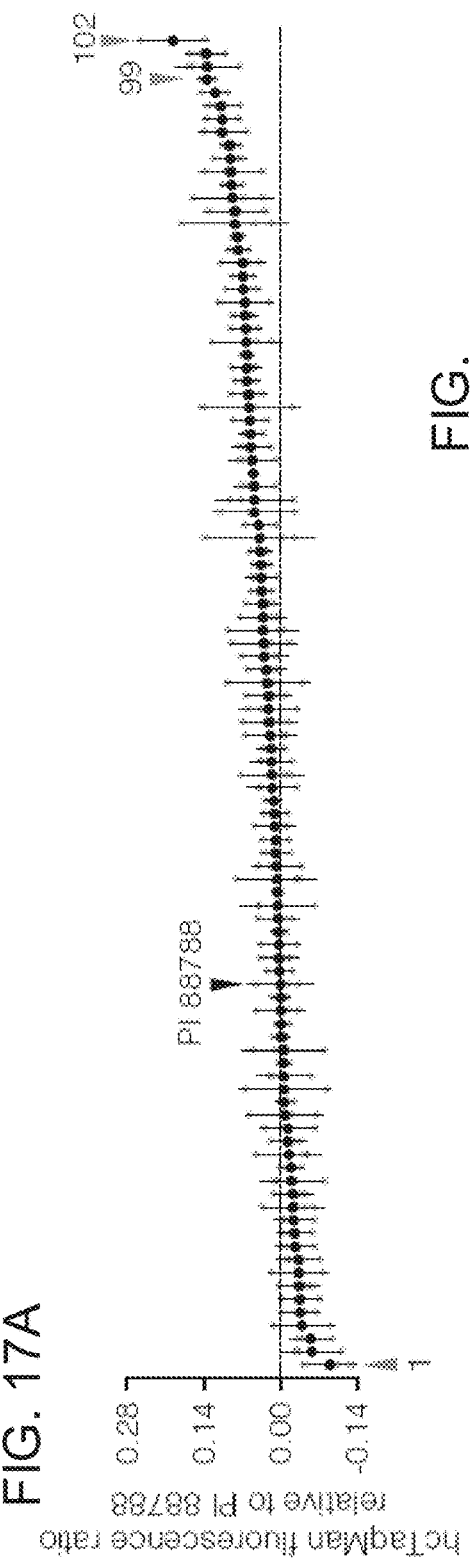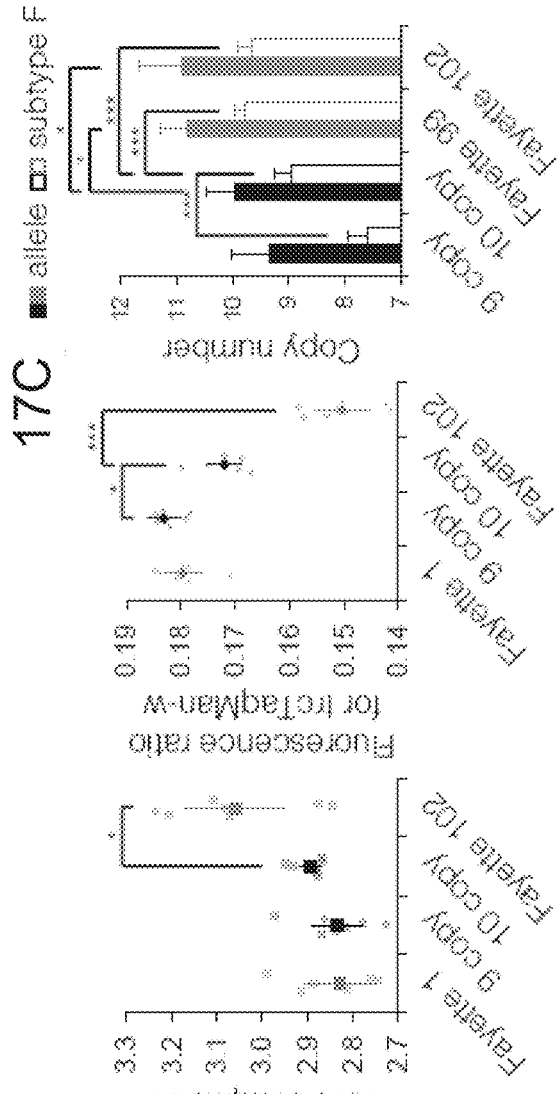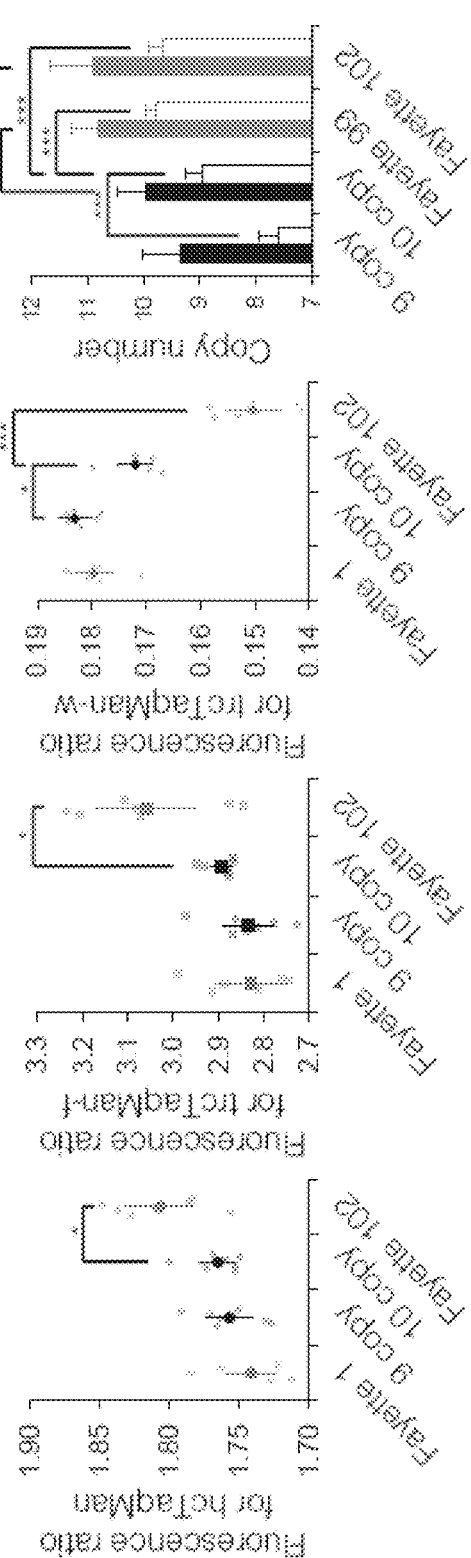
FIG. 17A
FIG. 17B
FIG. 17C

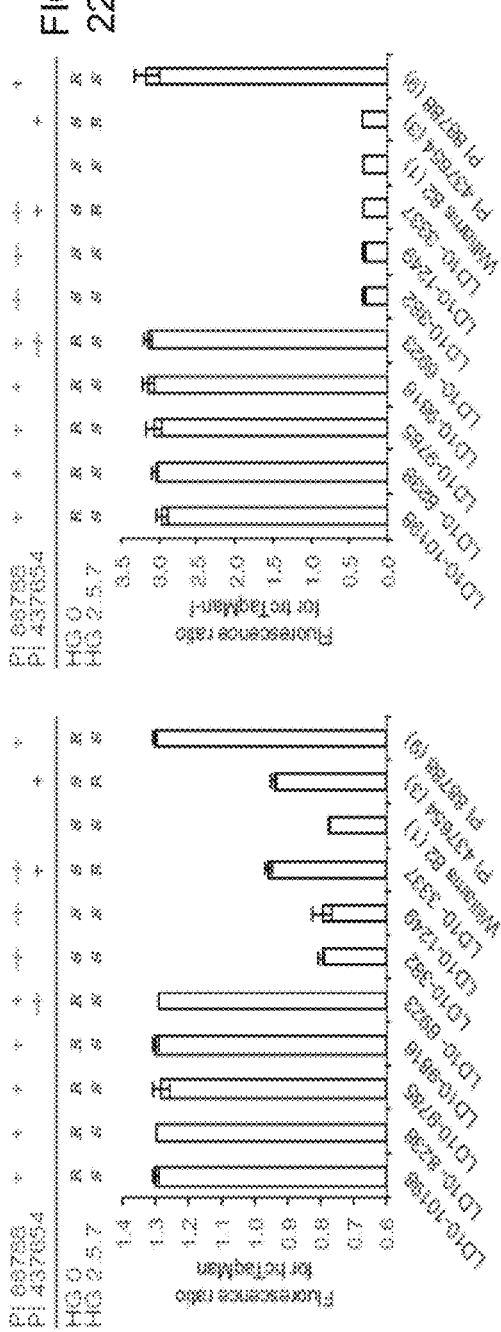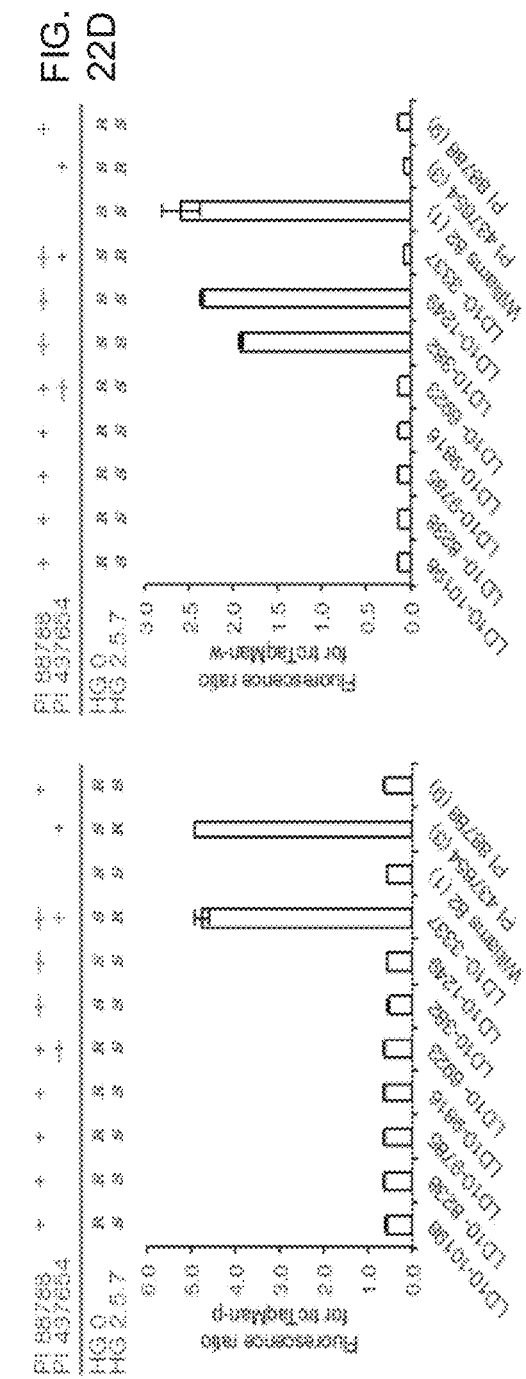

COPY NUMBER DETECTION AND METHODS

CROSS REFERENCE TO RELATED APPLICATIONS

Benefit is claimed to the earlier filing date of U.S. Provisional Application No. 62/101,253, filed on Jan. 8, 2015; and No. 62/120,872, filed on Feb. 25, 2015. The disclosure of each of these applications is incorporated herein by reference in its entirety.

FIELD

The present disclosure relates to, inter alia, genetic copy number detection and methods of plant breeding.

BACKGROUND

Currently, there are no practical ways to measure sequence (e.g., gene) copy number accurately, especially for high copy numbers, as part of a plant breeding program or other mass analysis. Some assays exist, such as whole-genome sequencing and fiber-FISH (Fluorescence In-Situ Hybridization); however these are impractically slow and expensive to apply to hundreds or thousands of samples for the purpose of measuring copy number. Quantitative PCR methods tend to be inaccurate and require very high quality DNA (such as high quality genomic DNA) as starting material, which is difficult and expensive to obtain. The existing TAQMAN® PCR Copy Number assay requires a separate control locus reaction to ensure accuracy which doubles costs and leads to inaccuracy caused by differential amplification of the different control and target sequences, making it expensive and impractical for large numbers of plants or high copy number loci.

SUMMARY

Described herein are methods of measuring the number of copies of a target sequence in the genome compared to the copy number of a corresponding closely related gene or sequence in the same genome, for instance measuring the copy number of soybean cyst nematode genetic resistance trait Rhg1 in the genome of a soybean plant.

Examples of the method comprise comparing the number of copies of the target gene (such as a resistance or other beneficial gene) to the number of copies of a homeologous gene (a nearly identical gene on another chromosome, which can be assumed to be present in one copy per haploid genome). In exemplified uses, the method employs an adaptation of TAQMAN® real-time quantitative PCR technology, though other detection methods can be used. Quantitative PCR in examples of the provided methods is used it to measure the number of copies of a target genomic region by measuring a ratio between that target region and another within the genome that is of very similar sequence that can be assumed to be of a single copy in a haploid genome. The provided methods therefore provide a way of measuring copy number of any gene with a similar copy that can be assumed to be present in a single dose, which is common for most genes in plants with a history of polyploidy.

Soybean cyst nematode (SCN) resistance via Rhg1 is known to be highly variable, but several competing ideas have existed for some time about why. Provided herein are both an explanation for the variability and a way to eliminate it in breeding populations, by selecting for individuals with altered copy number using methods described herein; it is believed individuals with certain copy number/sequence combinations have greater resistance to SCN.

Other plant, human and animal traits have been shown to be affected by copy number. The methods described herein provide high throughput systems to measure copy number, which can be applied in additional organisms and in the detection/measurement of copy number of nucleic acids—including any target nucleic acid for which the target genome includes a separate but closely (sequence) related sequence that can be assumed to occur consistently in a set copy number (for instance, one copy per 1N genome).

The methods provided herein for measuring nucleic acid copy number remove the requirement of some methods for high quality DNA, and of others for a second control assay. The provided methods are more accurate, as they measure a ratio of two loci within the same genome extracted from a single sample and assayed in the same reaction.

Thus, there is provided herein a method of measuring in a genomic sample from an individual (or individual cell) the relative frequency of a target sequence with respect to a control sequence of known copy number at a different genomic locus, wherein the target and control sequences differ by at least one single nucleotide variation (SNV), the method involving amplifying both the target sequence and the control sequence within the genome of the individual, in a single reaction/container. In various embodiments, the amplification uses (1) a single upstream and a single downstream primer, the pair of which prime amplification of both the target sequence and the control sequence, or (2) a single downstream primer and two upstream primers, wherein the sequence of the two upstream primers differs only at the position of a SNV between the target and control sequences, each upstream/downstream pair of which prime amplification of only either the target sequence or the control sequence. The methods further involve measuring the abundance of each of the target sequence and the control sequence using (1) two labeled probes or two labeled primers, one of each of which is specific for the target or control sequence, or (2) a melting curve, where the amplification products of the target and control sequences, or their hybridized product comprising a fluorescent probe, melt at different temperatures; and calculating a ratio of the two abundances, thereby determining the relative frequency of the target sequence with respect to the control sequence.

Also provided are methods of selecting an organism with a desired trait or characteristic that is influenced by the copy number of a gene or sequence in its genome, using a copy number assay described herein. By way of example, one such method provides selecting a plant or germplasm (exemplified with soybean plants and germplasm) that exhibits one or more of increased resistance to soybean cyst nematode (SCN), optimized yield, or emergence compared to a control soybean plant, the method comprising quantifying the number of Rhg1 copies in the genome of the soybean plant or the soybean germplasm using a copy number detection/quantification method taught herein; selecting the soybean plant or germplasm from a population of plants, some of which having an increased or decreased number of Rhg1 copies relative to an ancestor; crossing the selected soybean plant or a soybean plant derived from the selected germplasm; and selecting one or more progeny of the crossing having an altered number of Rhg1 copies.

Another embodiment is a method of determining copy number of a variable copy number version of a replicated target nucleic acid sequence in a sample, which method involves contacting a sample comprising single-stranded genomic nucleic acids with (1) a pair of oligonucleotide primers that anneal upstream (sense) and downstream (antisense), respectively, of a sequence within the both the defined copy number version and the variable copy number versions of replicated target nucleic acid sequence; (2) a first non-extendable oligonucleotide probe, with a first 5' fluorescent reporter label and an internal or 3' quencher dye, which first probe anneals specifically to the defined copy number version of the replicated target sequence downstream of the sense primer; and (3) a second non-extendable oligonucleotide probe, with a second 5' fluorescent reporter label and an internal or 3' quencher dye, which second probe anneals specifically to the variable copy number version of the replicated target sequence downstream of the sense primer to produce a mixture. This mixture is maintained (incubated) with a template-dependent nucleic acid polymerase having a 5' to 3' nuclease activity under conditions sufficient to permit the 5' to 3' nuclease activity of the polymerase to cleave the annealed probes and release labeled fragments (and also, in many embodiments, this amplifies both of the target sequences, yielding amplicons corresponding to the variable copy number or defined copy number versions of the replicated target nucleic acid sequence). The methods further involve measuring the release of nucleic acid fragments containing fluorescent report label; and determining the relative amount of released first and second fluorescent reporter fragments, thereby determining copy number of the variable copy number version of the replicated target nucleic acid sequence.

In examples of the various methods described herein, the defined copy number version of the replicated target nucleic acid sequence is one or more of: a homeolog of the variable copy number version; a related paralogous sequence other than a homeolog; a member of a tandem repeat, of which the variable copy number version is also a member; a sequence native to the genome, while the variable copy number version has been artificially introduced into the genome through transformation or infection; occurs in a single copy in the genome; or occurs in more than a single copy in the genome.

Without wishing to be bound by any particular theory, there can be discussion herein of beliefs or understandings of underlying principles or mechanisms relating to embodiments of the disclosure. It is recognized that regardless of the ultimate correctness of any explanation or hypothesis, an embodiment of the disclosure can nonetheless be operative and useful.

The foregoing and other objects and features of the disclosure will become more apparent from the following detailed description, which proceeds with reference to the accompanying figures.

Further embodiments, forms, features, aspects, benefits, objects, and advantages of the present application shall become apparent from the detailed description and figures provided herewith.

DESCRIPTION OF THE DRAWINGS

The patent or application file contains at least one drawing executed in color. Copies of this patent or patent application publication with color drawing(s) will be provided by the Office upon request and payment of the necessary fee.

(FIG. 4A) Five of the SNVs used for reconstruction of repeat units in an intergenic region between Glyma18g02610 and Glyma18g02620 are displayed. Each pattern belongs to one of four separate repeat units ($F_A$ & $F_B$; two subtypes of PI 88788, P; a subtype of Peking, & W; a subtype of Williams 82). SNV positions are given relative to the first nucleotide (1,632,225 bp on chromosome 18) of the 31.2 kb repeat in the reference genome assembly. (FIG. 4B) Classification of repeat units using maximum parsimony. Individual sequences of the Glyma18g02590 gene are labeled according to copy number and relative abundance in the accession (e.g. '4-low' means the less abundant sequence present in a four-copy genotype) or by position relative to the telomere if equally abundant (e.g. 2-first). Bootstrap support values are given above key nodes. (FIG. 4C) Interpretation of the Rhg1 repeat structure. Bold black labels are cloned sequences; grey labels are inferred from short-read shotgun sequence data classified by the parsimony analysis in FIG. 4D. Rhg1 copy number in the G. max accession genome is denoted on the left. Three different fusion sequences at the centromere-proximal end are marked by open squares, filled squares and filled circles. tel: telomere. (FIG. 4D) Amino acid variation (shown also in SEQ ID NOs: 24-26) in the predicted α-SNAP protein, Glyma18g02590. Amino acid positions are from the Williams 82 reference. Bold lines represent exons 6 and 9 respectively.

FIG. 5A-5C. Diversity, linkage disequilibrium (LD) and sequence analysis of the region surrounding the Rhg1 locus. (FIG. 5A) Nucleotide diversity within 38 protein-coding genes surrounding Rhg1 in eighteen germplasm accessions (with 1-10 copies at Rhg1) is displayed in the uppermost graph. Those accessions with three copies (center graph) and nine and ten copies (bottom graph) were also analyzed separately. The average nucleotide diversity ($\pi$; 0.00053) of all coding regions in *G. max* is marked by a horizontal line. (FIG. 5B) LD plot using the $R^2$ metric for the 400 kb region surrounding the Rhg1 locus. The same 18 accessions were used. Regions S1, S2 and S3 represent three linkage blocks used in further analysis. tel: telomere. (FIG. 5C) Phylogenetic tree derived from parsimony analysis of the three LD blocks. The result in the linkage block S2 that contains Rhg1 is consistent with the analysis of the repeat sequence (FIG. 4). The copy number of each accession is in parentheses. The consensus trees were created after collapsing branches with bootstrap values<60%, based on 10,000 replications. Bootstrap support values are shown above key nodes.

FIG. 6A-6C. Signatures of selection at the Rhg1 locus. (FIG. 6A) Nucleotide diversity ($\pi$ and $\theta$), Tajima's D, and linkage disequilibrium were measured in the 1.5 Mbp region across the locus in 19,548 accessions (18,383 *Glycine max* & 1,165 *Glycine soja*). The mean, $75^{th}$ and $95^{th}$ percentiles of whole genome Tajima's D are marked by horizontal lines in corresponding graphs. (FIG. 6B) $F_{ST}$ was calculated for lines with experimentally determined copy number (46 single copy vs. 48 multiple copy). A strong LD block surrounding Rhg1 was observed. tel: telomere. The mean and $95^{th}$ percentile of whole genome $F_{ST}$ is marked by a horizontal line. (FIG. 6C) $F_{ST}$ between geographic subpopulations. One hundred thirty-five SNPs were used to compare: Top graph, between 3311 germplasm accessions from Korea and 3858 from China; center, between 3311 from Korea and 2466 from Japan; bottom, between 3858 from China and 2466 from Japan. The mean and $95^{th}$ percentile of whole genome $F_{ST}$ is marked by a horizontal line in corresponding graphs.

FIG. 7A-7B. Signatures of selection at the Rhg1 locus are independent of population demography. (FIG. 7A) Soybean population clustered by genetic structure. Each individual is represented by a thin vertical line, which is partitioned into K colored segments that represent the individual's estimated membership fractions in K clusters. Selected clusters were labeled on top of each K. (FIG. 7B) Neutrality in subpopulations with shared genetic structure was tested by Tajima's D. The pie chart represents the geographic origin of the members of each subpopulation. Two separate D values are displayed for each subpopulation: that of all accessions in the subpopulation, and that for accessions without the largest single geographic origin. An additional test without either Chinese or USA accessions was performed on the 6. A subpopulation. The East Asia group represents countries other than Korea, Japan and China. America represents South and North America except the USA. The whole-genome mean Tajima's D of each subpopulation is marked by a horizontal line.

FIG. 10A-10B. Reconstruction of the sequences of individual repeat units. (FIG. 10A) Whole genome sequencing alignment view. Eight separate copy numbers are displayed in the Integrative Genomics Viewer (IGV) window. Copy number of *G. max* is denoted on the left. Copy number variation in *G. soja* is in parenthesis. Single nucleotide variants (SNVs) phased with sequences derived from the same DNA molecule are selectively noted with numbers (1 through 5). Positions of each SNV are as follows: 1; 1,656,898 bp on chromosome 18, 2; 1,656,979, 3; 1,657, 025, 4; 1,657,162, and 5; 1,657,183. Representative reads with phased variants are labeled with colored arrows: isosceles triangles; subtype W, equilateral triangles; subtype P, open arrows; subtype $F_B$, and arrows; subtype $F_A$ (FIG. 10B) Sanger confirmation of the presence of multiple sequences at each position. Multiple sequences at 1,657,025 bp on chromosome 18, which is equivalent to 24,801 bp within the repeat, were clearly detected from germplasm carrying two or more than two subtypes.

(FIG. 15A) A single nucleotide difference between a gene from the multiple copy Rhg1 locus on chromosome 18 and a single copy, homeologous sequence on chromosome 11 was selected for the development of a homeolog-controlled TAQMAN® PCR (hcTaqMan) marker assay. A T residue at position 16,067 bp in the repeat unit, and the homeologous C residue at 37,413,212 bp on chromosome 11, were used to design a pair of TAQMAN® PCR probes. (FIG. 15B) Known copy number variants were assayed using hcTaqMan. Black filled or open (showing a second genotype with the same copy number) dots show the mean value. The error bars show the 95% confidence interval. Statistical significance (* $P<0.05$, ***$P<0.001$ based on a two-tailed unpaired t-test) is indicated between each copy number and the next higher copy number.

(FIG. 16A) Three tandem repeat-controlled assays (trcTaqMan-f, p & w), each of which distinguishes one repeat subtype from the other two, were developed. For each assay, a single nucleotide variant (SNV) that differentiates one subtype from the two other subtypes) at the position was used to design TAQMAN® PCR probe sets. (FIG. 16B) Genotyping tandem repeat composition. The known copy number and subtype composition of each accession are displayed on x-axis. Heavy dots represent the mean, pale dots represent individual replicates. Unfilled dots show a second accession with the same copy number. Error bars show the 95% confidence interval. Statistical significance (* $P<0.05$, ***$P<0.001$ based on a two-tailed unpaired t-test) is indicated between the smaller copy number sample and the next higher copy number.

FIG. 17A-17C. Copy number variability at the Rhg1 allele within a population of the SCN-resistant cultivar Fayette. (FIG. 17A) Screening for copy number variability within a population of one hundred and two soybean plants from genotype Fayette using hcTaqMan. The mean fluorescence ratio of the PI 88788 genotype (9 copy) was set to 0 (a black triangle). The mean±95% confidence interval was plotted (black dots with vertical bars) and the individual replicate values are shown as gray dots. Three plants selected for additional analysis were labeled with green (individual 1) or red (99 & 102) triangles. (FIG. 17B) Replicated genotyping on selected Fayette plants. Nine and 10 copy controls in the figures represent PI 88788 and PI 209332, respectively. Significant differences (*$P<0.05$, ***$P<0.001$ based on one-way ANOVA followed by a two-tailed Tukey test) are indicated between the 10 copy control and the tested sample in FIGS. 17B and 17C. (FIG. 17C) Confirmation that eleven copies of the repeat unit exist in two selected plants (99 & 102) using whole-genome sequencing read depth (color-filled bars).

FIG. 22A-22D. Prediction of SCN resistance phenotypes using marker assays. Eight germplasm lines with SCN resistance phenotype data and their complete pedigree were selected for use in testing the combined capability of all four assays (FIG. 22A: hcTaqMan; FIG. 22B: trcTaqMan-f; FIG. 22C: trcTaqMan-p; FIG. 22D: trcTaqMan-w) to predict resistance phenotypes in breeding lines. + on the top of each bar notes the presence of the resistance source (PI 88788, PI 437654, or both) based on its pedigree. A strikethrough for + is an indication of an absence of the corresponding resistance allele evidenced by genotyping assays developed in this study. R and S for HG types, represent resistance or susceptible phenotype to the corresponding SCN race classification system respectively. Known copy number variants (1, 3 and 9 copies) are included as genotyping controls and labeled on x-axis (e.g. "Williams 82 (1)" means Williams 82 carrying a single copy of the repeat.). Three technical replicates were prepared to generate fluorescence signal values for each individual. The mean±95% confidence interval was plotted.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 96166-03_SeqList2.txt, created on May 24, 2016, 8 KB, which is incorporated by reference herein.

SEQ ID NOs: 1 and 2 are representative forward (1F) and reverse (9R-1) primers used to detect the junction between two tandem repeat copies of Rhg1; they amplify a short segment at the junction of a 31.2 kb repeat unit, if a repeat is present.

SEQ ID NOs: 3 and 4 are representative forward (2590-forward) and reverse (2590-reverse) primers used to amplify part of Glyma18g02590, a Rhg1 gene within the repeat unit.

SEQ ID NOs: 5-8 are the forward and reverse primers, and VIC and FAM probes, for the hcTaqMan assay described herein.

SEQ ID NOs: 9-12 are the forward and reverse primers, and VIC and FAM probes, for the trcTaqMan-f assay described herein.

SEQ ID NOs: 13-16 are the forward and reverse primers, and VIC and FAM probes, for the trcTaqMan-p assay described herein.

SEQ ID NOs: 17-20 are the forward and reverse primers, and VIC and FAM probes, for the trcTaqMan-w assay described herein.

SEQ ID NO: 21 and 22 are the nucleotide sequences at the junction between adjacent single-copy sequence and the first repeat, and the junction between the last repeat and adjacent single-copy sequence, respectively.

SEQ ID NO: 23 is the nucleotide sequence of a DNA insertion between positions +63 and +64 on Chromosome 18, where relative position −1 is the end of the tandem repeat, 1663442 bp on Chromosome 18. This insertion is found in soybean strains PI 209332, PI 518674, LD09-15087a, PI 88788, PI 548316, PI 87631-1, PI 89008, PI 548402, PI 90763, PI 437654, PI 89772 compared to soybean strain PI 518671 (Williams 82) (see Table 5).

Figure 4A:
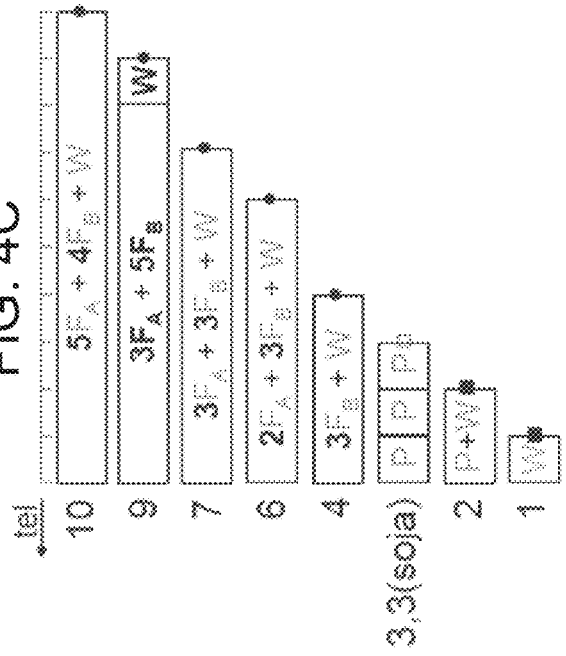
FIG. 4A-4D. Sequence of the Rhg1 repeat units.
Figure 4B:
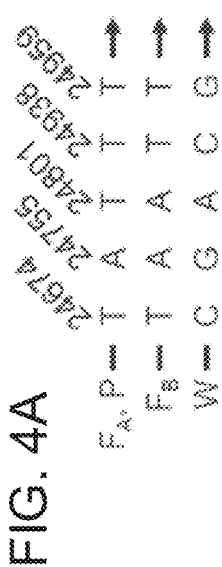
Figure 4C:
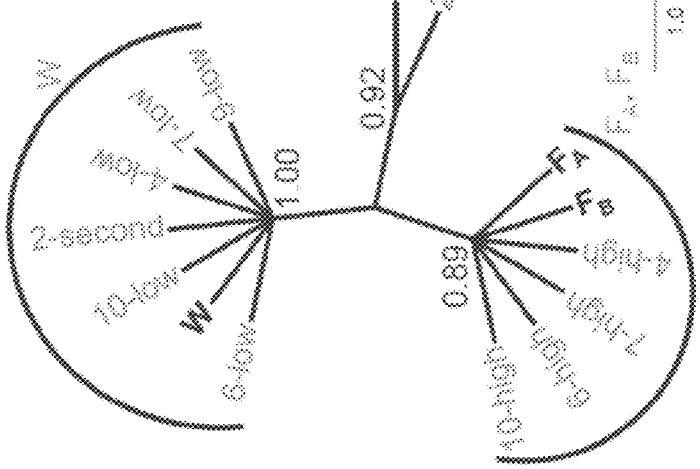
Figure 4D:
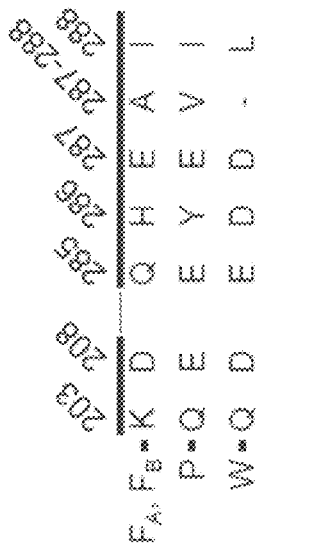

SEQ ID NOs: 24-26 are the amino acid sequences of positions 285-288 or 285-289 of the α-SNAP protein, Glyma18g02590, in soybean subtypes $F_A$ and $F_B$ (SEQ ID NO: 24), P (SEQ ID NO: 25), and W (SEQ ID NO: 26) (see FIG. 4D).

DETAILED DESCRIPTION

I. Abbreviations

CGH comparative genomic hybridization
CNV copy number variation
Fiber-FISH fiber-fluorescence in situ hybridization
hcTaqMan homeolog-controlled TAQMAN® PCR assay
PI plant introduction
qPCR quantitative polymerase chain reaction
SCN soybean cyst nematode (*Heterodera glycines* Ichinohe)
SNV single nucleotide variant (variation)
trcTaqMan tandem repeat-controlled TAQMAN® PCR assay
WGS whole genome sequence(ing)

II. Terms

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise. "Comprising" means "including"; hence, "comprising A or B" means "including A" or "including B" or "including A and B." All references cited herein are incorporated by reference.

"3' end" is the end of a nucleic acid molecule that does not have a nucleotide bound to it 3' of the terminal residue.

"5' end" is the end of a nucleic acid sequence where the 5' position of the terminal residue is not bound by a nucleotide.

"Allele" means any of one or more alternative forms of a genetic sequence. In a diploid cell or organism, the two alleles of a given sequence typically occupy corresponding loci on a pair of homologous chromosomes.

An "amplicon" is an amplified nucleic acid, e.g., a nucleic acid that is produced by amplifying a template nucleic acid by any available amplification method.

"Backcrossing" is a process in which a breeder crosses a progeny variety back to one of the parental genotypes one or more times.

The term "chromosome segment" designates a contiguous linear span of genomic DNA that resides in planta on a single chromosome. "Chromosome interval" refers to a chromosome segment defined by specific flanking marker loci.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic linkage relationships among loci on one or more chromosomes (or linkage groups) within a given species, generally depicted in a diagrammatic or tabular form.

"Genotype" refers to the genetic constitution of a cell or organism.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

"Haplotype" refers to a combination of particular alleles present within a particular plant's genome at two or more linked marker loci, for instance at two or more loci on a particular linkage group. For instance, in one example, two specific marker loci on LG-O are used to define a haplotype for a particular plant. In still further examples, 3, 4, 5, 6, 7, 8, 9, 10, 11, 12, 13, 14, 15, 16, 17, 18, 19, 20, or more linked marker loci are used to define a haplotype for a particular plant.

A "homeolog" is a special case of paralogy (duplicate genes or genetic regions in the same genome) resulting from polyploidy (usually, whole genome duplication in an organism). The term homeolog must not be confused with homolog—which means that a genomic sequence (or feature of an organism) shares a common (genetic) ancestor. Homeologous chromosomes are created through chromosome duplication events. Homeologous genes are often found in plants due to widespread polyploidy and/or paleopolyploidy (whole genome duplication) events that have been detected in all angiosperm genomes sequenced to date. For instance, many cultivated plants are triploid (e.g., cultivated bananas, seedless watermelons), tetraploid (e.g., domesticated potato), hexaploid (e.g., bread wheat, *Triticum aestivum*), octaploid (e.g., strawberries, *F.×ananassa*) and so forth. Though portions of duplicated genomes may be lost through fractionation over generations, homeologous gene sequences may remain in genomes. Synonyms for homeolog in fields other than crop plant genetics include ohnolog, syntelog and syntenic paralog. In mammalian genetics some paralogs originated as homeologs but the distinction is not commonly made as a result of relatively rare recent whole genome or chromosome duplications. Nonetheless mammalian paralogs with sufficiently similar sequences are also valid targets for the method described herein. See, for instance, Walling et al. (*Genetics* 172(3): 1893-1900, 2000), which discuss analysis of homeology in soybean.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

The terms "hybridization" and "annealing" refer to the formation of base pairs between complementary regions of DNA, RNA, or between DNA and RNA of nucleic acids. Examples of annealing and hybridization include formation of base pairs between two separate nucleic acid molecules, as well as formation of base pairs between nucleic acids on a single nucleic acid molecule.

In some examples, hybridization is between two complementary nucleic acid sequences, for example nucleic acid sequences that are at least 90% complementary to each other, such as at least 91%, 92%, 93%, 94%, 95%, 96%, 97%, 98%, 99%, or 100% complementary to each other.

In additional embodiments, hybridization conditions resulting in particular degrees of stringency and specificity will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11). Conditions for hybridization used with 5'-exonuclease amplification and quantification (qPCR) reactions (such as TAQMAN® PCR and TAQMAN®-like reactions) are well known; see, for instance, Current Protocols in Microbiology, Supplement 15, "Example of Use of TaqMan Real-Time RT-PCR to Analyze Gene Transcript Levels: *Haemophilus influenzae*" by Johnston (published online Nov. 1, 2009; DOI: 10.1002/9780471729259.mc01d01s15), which is herein incorporated by reference in its entirety.

In some embodiments, the probes and primers disclosed herein can hybridize to nucleic acid molecules under low stringency, high stringency, and very high stringency conditions.

"Introgression" means the entry or introduction of a gene, QTL, marker, haplotype, marker profile, trait, or trait locus from the genome of one plant into the genome of another plant.

"In vitro amplification" is a general term encompassing various techniques that increases the number of copies of a nucleic acid molecule in a sample or specimen. An example of amplification is the polymerase chain reaction (PCR), in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification may be characterized by electrophoresis, restriction endonuclease cleavage patterns, oligonucleotide hybridization or ligation, and/or nucleic acid sequencing, using standard techniques.

Other examples of amplification include quantitative real-time polymerase chain reaction (qPCR), strand displacement amplification, as disclosed in U.S. Pat. No. 5,744,311; transcription-free isothermal amplification, as disclosed in U.S. Pat. No. 6,033,881; repair chain reaction amplification, as disclosed in PCT publication WO 90/01069; ligase chain reaction amplification, as disclosed in European patent publication EP-A-320,308; gap filling ligase chain reaction amplification, as disclosed in U.S. Pat. No. 5,427,930; and NASBA RNA transcription-free amplification, as disclosed in U.S. Pat. No. 6,025,134. Several embodiments include multiplex qPCR assays, which are useful for amplifying and detecting multiple nucleic acid sequences in a single reaction.

One real-time PCR assay is based on the hybridization of a dual-labelled probe to the PCR product, and the development of a signal by loss of fluorescence quenching as PCR degrades the probe. This system is sold commercially under the trade name TAQMAN® (Roche Molecular Systems, Inc.). TAQMAN® probes are linear, dual labeled "hydrolysis probes" used with the 5' exonuclease activity of the enzyme Taq Polymerase for analyzing target nucleic acid sequences in a samples. Typically, a TAQMAN® probe consist of a ~18-22 bp oligonucleotide labeled with a reporter fluorophore at the 5' end and a quencher fluorophore at or near the 3' end. Several different fluorophores (e.g. 6-carboxyfluorescein, acronym: FAM; tetrachlorofluorescein, acronym: TET; 6-carboxy-4',5'-dichloro-2',7'-dimethoxyfluoresceine, acronym: JOE; hexachloro-fluoresceine, actonym: HEX; and VIC®, a proprietary fluorescent dye developed by Applied Biosysems) and quenchers (e.g. tetramethylrhodamine, acronym: TAMRA; and non-fluorescent quenchers, acronym: NFQ) are available (Kutyavin et al., *Nucleic Acids Res* 28 (2): 655-661, 2000). The quencher molecule quenches the fluorescence emitted by the fluorophore when excited by the cycler's light source via FRET (Fluorescence Resonance Energy Transfer) (Bustin, *J. Mol. Endocrinol.* 25 (2): 169-93, 2000). See also Marras, *Meth Mol Biol* 335:3-16 VV Didenko ed., Humana Press Inc., 2006.

As long as the fluorophore and the quencher are in proximity (that is, contained within the same oligonucleotide molecule), quenching inhibits significant fluorescence signal from the label. This proximity however, does not completely quench the fluorescence of the reporter dye and a background fluorescence may be observed.

While carrying out a TAQMAN®-based analysis amplification reaction, a fluorogenic probe that is complementary to the target sequence is added to the PCR reaction mixture. Upon melting of the double-stranded target molecule, the probe anneals to the target specifically between the sites to which forward and reverse primer anneal—that is, to an internal region of the PCR product. The Taq polymerase (or another DNA polymerase with 5' exonuclease activity) then extends the primer, replicating the template to which the probe is bound and displacing the first few nucleotides of the probe from the template. The 5' exonuclease activity of the polymerase then cleaves the probe, releasing the fluorescent label such that it moves away from the quencher molecule. This 5' exonuclease mechanism is the source of the term "hydrolysis probe" for this type of probe. Degradation of the probe relieves the quenching effect and allows fluorescence of the reporter dye. So long as there is an excess of probe in the reaction mix, this process repeats in each amplification cycle and does not significantly interfere with the production of PCR product. Fluorescence can be detected during each PCR cycle, and fluorescence accumulates during the course of the amplification. Fluorescence is directly proportional to the fluorophore released and the amount of DNA template present in the PCR.

Other quantitative PCR methods that measure the ratio between two sequence variants are also contemplated for use in the methods provided herein, including for example melt curve assays and KASP assays (LGC Genomics, Beverly, Mass.; information available online at, for instance, lgc-group[dot]com/products/kasp-genotyping-chemistry/#.Voq25PgwlVo).

The terms "label" and "detectable label" refer to a molecule capable of detection. Usually, a label is a molecule that is conjugated directly or indirectly to a second molecule (resulting in a non-naturally occurring "labelled" molecule), such as a nucleic acid molecule, to facilitate its detection. The person of ordinary skill in the art is familiar with detectable markers for labeling nucleic acid molecules and their use. Specific, non-limiting examples of detectable markers include fluorophores, fluorescent proteins, chemiluminescent agents, enzymatic linkages, radioactive isotopes and heavy metals or compounds. In several embodiments, the detectable markers are designed for use with PCR, for instance qPCR such as multiplex qPCR. Various methods of labeling nucleic acid molecules are known in the art and may be used.

A detectable label can also include a combination of a reporter and a quencher, such as are employed in FRET probes or TAQMAN® probes.

The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state non-radiatively transfers to the quencher where it either dissipates non-radiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, tolerance, etc.).

"Linkage" refers to a phenomenon wherein alleles on the same chromosome tend to segregate together more often than expected by chance if their transmission was independent. Genetic recombination occurs with an assumed random frequency over the entire genome. Genetic maps are constructed by measuring the frequency of recombination between pairs of traits or markers. The closer the traits or markers are to each other on the chromosome, the lower the frequency of recombination, and the greater the degree of linkage. Traits or markers are considered herein to be linked if they generally co-segregate. A 1/100 probability of recombination per generation is defined as a map distance of 1.0 centiMorgan (1.0 cM). The genetic elements or genes located on a single chromosome segment are physically linked. Two loci can be located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 9, 8, 7, 6, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 9%, 8%, 7%, 6%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). Put another way, closely linked loci co-segregate at least about 90% of the time. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 4 Kb, about 3 Kb, about 2 Kb, about 1 Kb, about 500 nucleotides, about 250 nucleotides, or less.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (that is, the two loci are "out of phase" with each other).

"Linkage disequilibrium" refers to a phenomenon wherein alleles tend to remain together in linkage groups when segregating from parents to offspring, with a greater frequency than expected from their individual frequencies.

"Linkage group" refers to traits or markers that generally co-segregate. A linkage group generally corresponds to a chromosomal region containing genetic material that encodes the traits or markers.

"Locus" is a defined segment of DNA.

A "map location" or "map position" or "relative map position" is an assigned location on a genetic map relative to linked genetic markers where a specified marker can be found within a given species. Map positions are generally provided in centimorgans. A "physical position" or "physical location" or "physical map location" is the position, typically in nucleotide bases, of a particular nucleotide, such as a single nucleotide variant (SNV) nucleotide, on a chromosome.

"Mapping" is the process of defining the linkage relationships of loci through the use of genetic markers, populations segregating for the markers, and standard genetic principles of recombination frequency.

"Marker" or "molecular marker" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of soybean markers have been mapped and linkage groups created, as described in Cregan et al. (*Crop Science* 39:1464-90, 1999), and more recently in Choi et al. (*Genetics* 176:685-96, 2007). Many soybean markers are publicly available at the USDA affiliated soybase website (on the World Wide Web at soybase[dot]org). All markers are used to define a specific locus on the soybean genome. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in soybeans. "Marker assisted selection" refers to the process of selecting a desired trait or traits in a plant or plants by detecting one or more nucleic acids from the plant, where the nucleic acid is linked to the desired trait, and then selecting the plant or germplasm possessing those one or more nucleic acids.

A "paralog" is a gene that is present in more than one copy per haploid genome of a specific organism. Paralogs may have redundant functions, partially overlapping functions or be "subfunctionalized" with the genes having distinct function, but they share sequence similarity and a common origin by duplication of an ancestor gene.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells, and the like. Grain is intended to mean the mature seed produced by commercial growers for purposes other than growing or reproducing the species.

"Polymorphisms" are changes or differences between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid sequence," "nucleic acid fragment," and "oligonucleotide" are used interchangeably herein. These terms encompass nucleotide sequences and the like. A polynucleotide is a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide (synthetic or occurring naturally), which is capable of acting as a point of initiation of nucleic acid synthesis or replication along a complementary nucleic acid strand when placed under conditions in which synthesis of a complementary strand is catalyzed by a polymerase. Primers may be provided in double-stranded form, though the single-stranded form is more typically used. A primer can further contain a detectable label, for example a 5' end label.

Primers are nucleic acid molecules, usually DNA oligonucleotides of about 10-50 nucleotides in length (longer lengths are also possible). Typically, primers are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 nucleotides in length. For example, a primer can be about 10-50 nucleotides in length, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40, 25-45, or 25-50 nucleotides in length. Primers can also be of a maximum length, for example no more than 15, 25, 25, 40, 50, 75 or 100 nucleotides in length.

Primers may be annealed to a complementary target DNA strand by nucleic acid hybridization to form a hybrid between the primer and the target DNA strand, and then extended along the target DNA strand by a DNA polymerase enzyme. One of skill in the art will appreciate that the hybridization specificity of a particular probe or primer typically increases with its length. Thus, for example, a probe or primer including 20 consecutive nucleotides typically will anneal to a target with a higher specificity than a corresponding probe or primer of only 15 nucleotides.

A "primer pair" is two primers (one "forward" and one "reverse") that can be used for amplification of a target nucleic acid sequence, for example by polymerase chain reaction (PCR) or other in vitro amplification methods. The forward and reverse primers of a primer pair do not hybridize to overlapping complementary sequences on the target nucleic acid sequence.

A "probe" includes an isolated nucleic acid (in this case of ~100 or fewer nucleotide residues, that is an oligonucleotide probe) attached to a detectable label or reporter molecule, which is used to detect a complementary target nucleic acid molecule by hybridization and detection of the label or reporter (though detection may occur after some or all of the probe or parts thereof are dissociated from the target nucleic acid, for instance in probe hydrolysis-based analyses). Isolated oligonucleotide probes are of use for detection and/or distinguishing of target sequence(s). Typically, probes are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 nucleotides in length. For example, a probe can be about 10-100 nucleotides in length, such as, 12-15, 12-20, 12-25, 12-30, 12-35, 12-40, 12-45, 12-50, 12-80, 14-15, 14-16, 14-18, 14-20, 14-25, 14-30, 15-16, 15-18, 15-20, 15-25, 15-30, 15-35, 15-40, 15-45, 15-50, 15-80, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 20-80, 21-22, 21-25, 21-30, 22-25, 22-30, 22-40, 22-50, 23-24, 23-25, 23-30, 24-25, 24-30, 25-35, 25-30, 25-35, 25-40, 25-45, 25-50 or 25-80 nucleotides in length. Probes can also be referred to as having a maximum length, for example no more than 15, 25, 25, 40, 50, 75 or 100 nucleotides in length.

In several embodiments, the oligonucleotide probe can be labeled, for example with a base-linked or terminally-linked fluorophore and non-fluorescent quencher for use, for instance, in qPCR assays. Fluorophores for use in qPCR assays are known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). Fluorophores can be conjugated to the oligonucleotides, for example by post-synthesis modification of oligonucleotides that are synthesized with reactive groups linked to bases. Useful fluorophores include: fluorescein, fluorescein isothiocyanate (FITC), carboxy tetrachloro fluorescein (TET), NHS-fluorescein, 5 and/or 6-carboxy fluorescein (FAM), 5-(or 6-) iodoacetamidofluorescein, 5-{[2(and 3)-5-(Acetyl-mercapto)-succinyl]amino} fluorescein (SAMSA-fluorescein), 5'-hexachloro-fluorescein (HEX), 6-carboxy-4',5'-dichloro-2',7'dimethoxyfluorescein, succinimidyl ester (JOE) and other fluorescein derivatives, rhodamine, Lissamine rhodamine B sulfonyl chloride, Texas red sulfonyl chloride, 5 and/or 6 carboxy rhodamine (ROX) and other rhodamine derivatives, coumarin, 7-amino-methyl-coumarin, 7-Amino-4-methylcoumarin-3-acetic acid (AMCA), and other coumarin derivatives, BODIPY fluorophores, Cascade Blue fluorophores such as 8-methoxypyrene-1,3,6-trisulfonic acid trisodium salt, Lucifer yellow fluorophores such as 3,6-Disulfonate-4-amino-naphthalimide, phycobiliproteins derivatives, Alexa fluor dyes (available from Molecular Probes, Eugene, Oreg.) and other fluorophores known to those of skill in the art. For a general listing of useful fluorophores, see also Hermanson, G. T., BIOCONJUGATE TECHNIQUES (Academic Press, San Diego, 1996).

Quenchers for use in qPCR assays are also known in the art and include, for example, 6-carboxytetramethylrhodamine,succinidyl ester (6-TAMRA; TAMRA) and "non-fluorescent quencher (NFP)" for use with TAQMAN™ probes available from Life Technologies (Gaithersburg, Md.).

"Quantitative real-time PCR" (qPCR) is a general term designating methods for detecting and measuring products generated during each cycle of a PCR, which are proportionate to the amount of template nucleic acid prior to the start of PCR. The information obtained, such as an amplification curve, can be used to determine the presence of a target nucleic acid and/or quantitate the initial amounts of a target nucleic acid sequence. Exemplary procedures for real-time PCR can be found in "Quantitation of DNA/RNA Using Real-Time PCR Detection" published by Perkin Elmer Applied Biosystems (1999); *PCR Protocols* (Academic Press, New York, 1989); *A-Z of Quantitative PCR*, Bustin (ed.), International University Line, La Jolla, Calif., 2004; and *Quantitative Real-Time PCR in Applied Microbiology*, Filion (Ed), Caister Academic Press, 2012. Multiplex qPCR is a procedure that involves amplification and detection of multiple nucleic acid species in a single qPCR reaction. By multiplexing, multiple target nucleic acids can be amplified in single tube.

In some examples, the amount of amplified target nucleic acid is detected using a labeled probe, such as a probe labeled with a fluorophore, for example a TAQMAN® probe. In this example, the increase in fluorescence emission is measured in real-time, during the course of the real-time PCR. This increase in fluorescence emission is directly related to the increase in target nucleic acid amplification. In some examples, the change in fluorescence (Delta Rn; dRn; ΔRn) is calculated using the equation dRn=$Rn^+$−$Rn^-$, with $Rn^+$ being the fluorescence emission of the product at each time point and $Rn^-$ being the fluorescence emission of the baseline. The dRn values are plotted against cycle number, resulting in amplification plots for each sample. The threshold value ($C_t$) is the PCR cycle number at which the fluorescence emission (dRn) exceeds a chosen threshold, which is typically 10 times the standard deviation of the baseline (this threshold level can, however, be changed if desired). A threshold value can alternatively be determined using an inflection point in the curve derived from the second differential of the curve.

The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(-1/slope)}$, for example. The efficiency of the PCR should be 90-100% meaning doubling of the amplicon at each cycle. This corresponds to a slope of −3.1 to −3.6 in the $C_t$ vs. log-template amount standard curve. The efficiency of the PCR amplification can vary between different primer pairs.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Self-crossing" or "self-pollination" or "selfing" is a process through which a breeder crosses a plant with itself; for example, a second generation hybrid F2 with itself to yield progeny designated F2:3.

"SNP" or "single nucleotide polymorphism" is a sequence variation that occurs when a single nucleotide in the genome sequence is altered or variable, and where each sequence option is present to some appreciable degree (that is, polymorphic) within a population (e.g. >1%). SNPs are often used for mapping.

"SNV" or "single nucleotide variation" means a sequence variation that occurs when a single nucleotide (A, T, C, or G) in the genome sequence is altered or variable. The term SNV includes single nucleotide variants between repeat units in the same genome but at different loci within that genome.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the invention or biologically active portion thereof is recombinantly produced, optimally culture medium represents less than about 30%, 20%, 10%, 5%, or 1% (by dry weight) of chemical precursors or non-protein-of-interest chemicals.

The term "target nucleic acid molecule" refers to a nucleic acid molecule whose detection, quantitation, qualitative detection, or a combination thereof, is intended. The nucleic acid molecule need not be in a purified form. Various other nucleic acid molecules can also be present in a sample to be analyzed, along with the target nucleic acid molecule. For example, the target nucleic acid molecule can be a specific nucleic acid molecule, the amplification of which is intended. In some examples, a target nucleic acid includes a region of a target genome that is known to occur consistently in a specific copy number for instance one copy in a 1N genome, or a region within the same genome that share significant sequence identity but that is known or suspected of displaying copy number variation in different samples or individuals or strains. By way of example, these two targets within a genome may be homeologs of each other, where one of the two is known to occur reliably in a single copy while another is subject to duplication or loss. Purification or isolation of the target nucleic acid molecule, if needed or desired, can be conducted by methods known to those in the art, such as by using a commercially available purification kit or the like.

"Tolerance", "resistance", and "improved tolerance" are used interchangeably herein and refer to any type of increase in resistance or tolerance to, or any type of decrease in susceptibility. A "tolerant plant" or "tolerant plant variety" need not possess absolute or complete tolerance. Instead, a "tolerant plant," "tolerant plant variety," or a plant or plant variety with "improved tolerance" will have a level of resistance or tolerance which is higher than that of a comparable susceptible plant or variety.

"Under conditions sufficient for" is a phrase used to describe any environment that permits a desired activity. In one example the desired activity is amplification of a nucleic acid molecule.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. Yield is the final culmination of all agronomic traits.

Standard recombinant DNA and molecular cloning techniques used herein are well known in the art and are described more fully in Sambrook et al., *Molecular Cloning: A Laboratory Manual*; CSHL Press Cold Spring Harbor, 1989.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein. Although the description herein contains many specificities, these should not be construed as limiting the scope of the disclosure but as merely providing illustrations of some of the presently preferred embodiments of the disclosure. For example, thus the scope of the disclosure should be determined by the appended aspects and their equivalents, rather than by the examples given.

All patents and publications mentioned in the specification are indicative of the levels of skill of those skilled in the art to which the disclosure pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are disclosed, it should be understood that compounds known and available in the art prior to this disclosure, including compounds for which an enabling disclosure is provided in the references cited herein, are not intended to be included in the composition of matter aspects herein. A reference that is partially inconsistent is incorporated by reference except for the partially inconsistent portion of the reference.

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments and any further applications of the principles of the disclosure as described herein are contemplated as would normally occur to one skilled in the art to which the disclosure relates.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be clear to one of skill in the art, methods, compositions and devices useful for the present methods can include a large number of optional composition and processing elements and steps.

III. Introduction

Genetic variation encompasses a wide range of distinct types of DNA sequence polymorphism, from single nucleotide variants (SNVs) to insertions, deletions, and Copy Number Variation of DNA segments (CNV) ranging in size from a few base pairs to entire chromosomes (Sebat et al., *Science,* 305, 525-528, 2004; Conrad et al., *Nature Genetics,* 38, 75-81, 2006; Redon et al., *Nature,* 444, 444-454, 2006). CNVs influence gene expression, cause disorders such as human disease, and are involved in adaptation during evolutionary process and drive phenotypic diversity in a wide range of organisms (McCarroll et al., *Nature Genetics,* 38, 86-92, 2006; Nguyen et al., *PLoS Genetics,* 2, e20, 2006; Repping et al., *Nature Genetics,* 38, 463-467, 2006; Stranger et al., *Science,* 315, 848-853, 2007). There is increasing evidence of high levels of CNV in plant genomes (Swanson-Wagner et al., *Genome Research,* 20, 1689-1699, 2010; Cao et al., *Nature Genetics,* 43, 956-963, 2011; Zheng et al., *Genome Biology,* 12, R114, 2011; McHale et al., *Plant Physiology,* 159, 1295-1308, 2012; Hanikenne et al., *PLoS Genetics* 9, e1003707, 2013; Iovene et al., *Plant Journal,* 75, 80-89, 2013) and evidence is emerging that CNVs mediate a number of valuable crop traits (Sutton et al., *Science,* 318, 1446-1449, 2007; Cook et al., *Science,* 338, 1206-1209, 2012; Díaz et al., *PLoS One,* 7, e33234, 2012). Many questions including the origin of these structural variations as well as their contributions to both evolutionary adaptation and phenotypic traits remain unresolved.

Soybean (*Glycine max* (L.) Merr.) is the world's most cultivated legume. It has provided on average 57% of oilseed production as well as 68% of protein meal consumption worldwide since 2000 (on the World Wide Web at soystats.com). In addition, soybean has been used to provide industrial resources such as biodiesel and plastics. The total value of the U.S. soybean crop was more than $43 billion in 2012 and doubled in the 5 years up to 2012. It has been estimated that the loss of soybean production caused by soybean cyst nematode (SCN, *Heterodera glycines* Ichinohe), the most damaging pest of soybean in the U.S. in yield loss terms, was equivalent to 4 to 6% of the total production from 2006 to 2010 (online at aes[dot]Missouri [dot]edu/delta/research/soyloss.stm). SCN has spread to most soybean producing areas worldwide and genetic resistance is a key component for its control (Niblack et al., *Annual Review of Phytopathology,* 44, 283-303, 2006).

SCN resistance is a quantitative trait, and the Rhg1 locus on soybean chromosome 18 was found to confer the strongest and most useful SCN resistance of any known quantitative trait locus (QTL) (Concibido et al., *Crop Science,* 44, 1121-1131, 2004; Kim M et al., *Plant Genome* 3, 81-89, 2010). Rhg1 has been successfully introgressed into high-yielding germplasm in the U.S. Approximately 95% of the commercially-cultivated, SCN-resistant soybean cultivars in the north-central U.S. utilize the Rhg1-b allele, originally derived from the soybean germplasm collection accession PI88788, as the main gene for resistance (Cregan et al., *Theoretical and Applied Genetics,* 99, 811-818, 1999). The Rhg1 alleles in the genomes of Fayette (a cultivar derived from PI 88788) and Peking (also known as PI 548402) are CNV loci carrying 10 and 3 tandemly replicated copies of a 31.2 kb segment of the genome, in nose-to-tail orientation. The sequence of the 31.2 kb repeated segment encodes four intact genes (Cook et al., *Science,* 338, 1206-1209, 2012). None of the genes in the repeat resemble a typical plant resistance gene, which contains a nucleotide-binding-site leucine-rich repeat (NBS-LRR) domain (McHale et al., *Genome Biology* 7:212, 2006). However, SCN resistance can be conferred on a susceptible plant by increasing the expression levels of three of the genes at the locus. Thus, enhanced expression of multiple genes (analogous to that caused by CNV of the genes) is capable of conferring resistance (Cook et al., *Science,* 338, 1206-1209, 2012).

Investigation of more germplasm accessions revealed that there is extensive variation in both the number of copies of the repeat and the sequence of the individual repeat units. Different sequences in the repeat units are present even in the same homozygous genotype (Cook et al., *Plant Physiology,* 165, 630-647, 2014). Thus, this locus consists of several genes per unit, and several units per locus, where the individual units and genes have different DNA sequences and occur in different permutations within the same organism. Since the tools of molecular biology provide limited opportunities to investigate such a complex system, here the tools of genomics, phylogenetics and population genetics are employed to probe the structure and evolution of this locus.

IV. Overview of Several Embodiments

Provided herein in a first embodiment is a method of measuring in a genomic sample from an individual the relative frequency of a target sequence with respect to a control sequence of known copy number at a different genomic locus, wherein the target and control sequences differ by at least one single nucleotide variation (SNV), the method comprising amplifying both the target sequence and the control sequence within the genome of the individual, in a single reaction/container, using (1) a single upstream and a single downstream primer, the pair of which prime amplification of both the target sequence and the control sequence, or (2) a single downstream primer and two upstream primers, wherein the sequence of the two upstream primers differs only at the position of a SNV between the target and control sequences, each upstream/downstream pair of which prime amplification of only either the target sequence or the control sequence; measuring the abundance of each of the target sequence and the control sequence using (1) two labeled probes or two labeled primers, one of each of which is specific for the target or control sequence, or (2) a melting curve, where the amplification products of the target and control sequences, or their hybridized product comprising a fluorescent probe, melt at different temperatures; and calculating a ratio of the two abundances, thereby determining the relative frequency of the target sequence with respect to the control sequence.

In examples of this method, measuring the abundance of each sequence comprises quantification of a SNV-specific amplification product.

By way of example, this method involves in some embodiments amplifying both the target sequence and the control sequence with one of the following amplification processes/chemistries: qPCR, dPCR, TAQMAN® qPCR, KASP, SYBR green qPCR using two forward primers, or RT-PCR. For instance, in one example embodiment of the method, amplifying both the target sequence and the control sequence involves KASP amplification, using the single downstream primer and the two upstream primers, wherein the sequence of the two upstream primers differs only at the position of a SNV between the target and control sequences, each upstream/downstream pair of which prime amplification of only either the target sequence or the control sequence.

Provided in another embodiment is a method of measuring in a genomic sample from an individual the relative frequency of a target sequence with respect to a control sequence of known copy number at a different genomic locus, wherein the target and control sequences differ by at least one single nucleotide variation (SNV), wherein the method further involves producing a mixture by contacting the genomic sample from the individual, in a single reaction/container, with: (1) a pair of oligonucleotide primers that bind upstream (sense) and downstream (antisense), respectively, of a sequence within the both the target sequence and the control sequence; (2) a first non-extendable oligonucleotide probe, with a first 5' fluorescent reporter dye and an internal or 3' quencher dye, which first probe hybridizes specifically within the target sequence downstream of the sense primer; and (3) a second non-extendable oligonucleotide probe, with a second 5' fluorescent reporter dye and an internal or 3' quencher dye, which second probe hybridizes specifically within the control sequence downstream of the sense primer; maintaining the mixture with a template-dependent nucleic acid polymerase having a 5' to 3' nuclease activity under conditions sufficient to permit the 5' to 3' nuclease activity of the polymerase to cleave the annealed probes and release labeled fragments; measuring the release of nucleic acid fragments containing fluorescent report dye; and determining the relative amount of released first and second fluorescent reporter fragments, thereby determining relative frequency of the target nucleic acid sequence with respect to the control sequence.

In the methods described herein, it is recognized that the control sequence in various examples will be one or more of: a homolog of the variable copy number target sequence; a related paralogous sequence other than a homolog; a member of a tandem repeat, of which the variable copy number version is also a member; a sequence native to the genome, while the variable copy number version has been artificially introduced into the genome through transformation or infection; occurs in a single copy in the genome; or occurs in more than a single copy in the genome.

In various examples of the provided methods, the genomic sample is from a plant, a fungus, a protist, a bacterium, an archaean, an animal, a virus, or viral sequences within the genome of a host organism.

Provided in yet another embodiment is a method of selecting a soybean plant or soybean germplasm with one or more of increased resistance to soybean cyst nematode (SCN), optimized yield, or emergence compared to a control soybean plant, the method involving quantifying the number of Rhg1 copies in the genome of the soybean plant or the soybean germplasm using a copy number detection/quantification described herein; selecting the soybean plant or germplasm from a population of plants, some of which having an increased or decreased number of Rhg1 copies relative to an ancestor; crossing the selected soybean plant or a soybean plant derived from the selected germplasm; and selecting one or more progeny of the crossing having an altered number of Rhg1 copies.

Another method of determining copy number of a variable copy number version of a replicated target nucleic acid sequence in a sample is provided. The sample, in various embodiments, is from a plant, a fungus, a protist, a bacterium, an archaean, an animal, a virus, or viral sequences within the genome of a host organism.

Such methods for determine copy number involve contacting a sample comprising single-stranded genomic nucleic acids with (1) a pair of oligonucleotide primers that anneal upstream (sense) and downstream (antisense), respectively, of a sequence within the both the defined copy number version and the variable copy number versions of replicated target nucleic acid sequence; (2) a first non-extendable oligonucleotide probe, with a first 5' fluorescent reporter label and an internal or 3' quencher dye, which first probe anneals specifically to the defined copy number version of the replicated target sequence downstream of the sense primer; and (3) a second non-extendable oligonucleotide probe, with a second 5' fluorescent reporter label and an internal or 3' quencher dye, which second probe anneals specifically to the variable copy number version of the replicated target sequence downstream of the sense primer to produce a mixture; maintaining the mixture with a template-dependent nucleic acid polymerase having a 5' to 3' nuclease activity under conditions sufficient to permit the 5' to 3' nuclease activity of the polymerase to cleave the annealed probes and release labeled fragments; measuring the release of nucleic acid fragments containing fluorescent report label; and determining the relative amount of released first and second fluorescent reporter fragments, thereby determining copy number of the variable copy number version of the replicated target nucleic acid sequence.

In examples of such methods of determining copy number, the first and second non-extendable probes bind to a sequence that differs by only one single nucleotide variation (SNV) between the variable copy number version and the defined copy number version of the replicated target sequence.

In examples of such methods of determining copy number, the defined copy number version of the replicated target nucleic acid sequence is one or more of a homeolog of the variable copy number version; related paralogous sequence other than a homeolog; a member of a tandem repeat, of which the variable copy number version is also a member; a sequence native to the genome, while the variable copy number version has been artificially introduced into the genome through transformation or infection; occurs in a single copy in the genome; or occurs in more than a single copy in the genome.

In specific examples of the methods for determining copy number of a variable copy number version of a replicated target nucleic acid sequence, the target sequence is soybean rhg1; soybean Rag1; soybean Rag2; maize MATE1; barley Bot1; wheat Photoperiod-B1 (Pbd-B1); wheat Vernalization-A1 (Vrn-A1); rice Grain Length on Chromosome 7 (GL7); a plant gene that impacts a crop trait through copy number; a human MHC sequence; or a DNA sequence of variable copy number known or suspected to impact the phenotype of an organism.

Optionally, any of the provided methods may be carried out multiple times on a single genome, thereby permitting the determination of the copy number of more than one (different) variable copy number version of a replicated sequence. For instance, such methods may further involve carrying out the method on at least one additional variable copy number version of the replicated target nucleic acid using a different non-extendable probe that binds to a different SNV at a different locus, thereby determining the copy number of at least a second variable copy number version of the replicated target nucleic acid.

Another embodiment is a method of selecting a soybean plant or soybean germplasm with one or more of increased resistance to soybean cyst nematode (SCN), optimized yield, or emergence compared to a control soybean plant, the method involving quantifying the number of Rhg1 copies in the genome of the soybean plant or the soybean germplasm using a copy number detection/determination method described herein; selecting the soybean plant or germplasm from a population of plants, some of which having an increased or decreased number of Rhg1 copies relative to an ancestor; crossing the selected soybean plant or a soybean plant derived from the selected germplasm; and selecting one or more progeny of the crossing having an altered number of Rhg1 copies. In such a selection method, optionally the copy number of the Rhg1 locus is maintained at a predetermined number of copies, which may be either higher or lower than in a starting plant material.

The provided selections methods optionally may further involve quantifying the number and type of different Rhg1 copies in the genome of the soybean plant or the soybean germplasm using the copy number detection method; and selecting soybean plant or germplasm having an altered diversity of Rhg1 sequence repeats. By way of specific example, in some cases soybean plant(s) or germplasm is selected so that it includes at least one Rhg1 P-type repeat and at least one Rhg1 F-type repeat.

Also encompassed herein are soybean plans and soybean germplasm selected using the provided selection methods, which involve tracking or determining the copy number of Rhg1. By way of example, there are contemplated soybean plants and soybean germplasm, wherein the copy number of the Rhg1 locus is precisely 3 copies; no fewer than 4 copies; no fewer than 6 copies; no fewer than 9 copies; precisely 9 copies; precisely 10 copies; or more than 9 copies.

V. Methods of Detecting Nucleic Acid Copy Number (Internally Controlled Amplification)

Copy number variations of DNA segments (CNV) mediate a number of valuable crop traits. Reliable methods to measure high genomic copy numbers of copy number variant sites are needed for many applications, one of which is to genotype the soybean cyst nematode (SCN) resistance Rhg1 allele of soybean. SCN resistance is a quantitative trait, and the soybean Rhg1 confers the most useful and widely utilized SCN resistance gene. The Rhg1 is a copy number polymorphism of a 31.2 kb unit, widely used for resistance SCN, especially in the major soybean producing areas in the U.S. where 95% of the soybeans grown rely on this one gene to protect a $41 bn crop (with a loss that is still $2.5 bn/year). Here we developed a genetic marker technology for Rhg1 copy number. The method measures copy number of the soybean Rhg1 genes as a method to rapidly and accurately measure the variability we have shown to be present in this gene within breeding populations. We show proof of concept that this could be used both to improve nematode resistance in soybeans and to explore other CNV-mediated traits in plants.

Copy number variations of DNA segments (CNV) mediate a number of valuable crop traits, including the soybean cyst nematode (SCN) resistance Rhg1 allele of soybean. The Rhg1 is a copy number polymorphism of a 31.2 kb unit, widely used for resistance to SCN, especially in the major soybean producing areas in the US. Here we describe a genetic marker technology developed in our group, homeolog controlled TAQMAN® PCR (hcTaqMan). The hcTaqMan method measures copy number of the soybean Rhg1 genes by comparing the number of copies at the resistance gene locus to the number of copies of a homeologous gene (a nearly identical gene on another chromosome, which can be assumed to be present in one copy per haploid genome). This is done by probe hybridization that discriminates a single nucleotide variation (SNV) between the target and homeologous sequence (or between the target and a tandem or other repeat thereof), and generates fluorescence signal in a quantitative PCR assay similar to the established TAQMAN® PCR method. The assay targets one of the Rhg1 genes in the duplicated region in the locus. The ultimate result of these hybridizations is that as the copy number increases, the fluorescence ratio from the PCR assay rises accordingly, with high accuracy up to 9 copies and some resolution beyond this (see Example 2).

The findings described herein indicate that not only does this technology predict how effective a given SCN resistance gene will be against different nematode types, it also shows that variation exists within existing soybean varieties (different plants within the same variety have different copy number. For some time, variation in SCN resistance in "resistant" varieties has been observed and has been a mystery to geneticists and breeders—the data provided herein explains why. Thus, the described internally-controlled amplification-based copy number determination assay provides a means for soybean breeders and seed companies to increase the effectiveness and uniformity of genetic resistance to SCN in commercial soybean seed. These methods are also equally applicable across a much broader field, including in other plants or for the detection or influencing of other plant traits influenced by gene/sequence copy number, as well as the detection of copy number of genes/sequences that influence animal (e.g., human or other mammal) disease or health.

The methods described herein can be employed in assays to develop high (or defined, including optionally lower) copy number individuals, or lines, through analysis of CNV during a selection program, for instance in soybean and other plants. For instance, it can be used across large numbers of lines to build on the herein described result that high copy lines can be selected and isolated. In soybean breading programs, these methods can be used to develop high Rhg1 copy lines that can be evaluated for resistance against different soybean cyst nematode (Hg) types. These techniques can also be applied to the selection of individuals or lines having specific combinations of different copies of a copy number variable sequence where the different copies may have different sequences (e.g., as with the tandem repeat controlled (trc) TAQMAN® PCR assays described herein). For instance, plants can be selected for that have diverse copies of Rhg1, however those copies are introduced into the population (e.g., breeding, transformation, etc.).

Figure 1A:
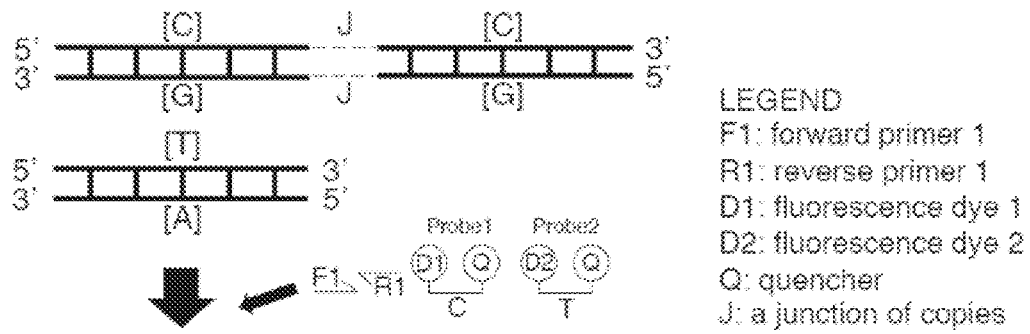
FIG. 1A-1C. Copy number assay process. Assay components and DNA template (FIG. 1A). A pair of primer sequences is similar enough to be aligned to both target sequence and control sequence of known copy number in the genome of the same individual. A single nucleotide variation (C residue in probe 1 and T in probe 2) was used to design a pair of probes. Denatured template and annealing assay components (FIG. 1B). Probe 1 linked to a fluorescence dye anneals specifically to the target sequence. Probe 2, however, is linked to another type of fluorescence dye, anneals to the control sequence. Polymerization and signal generation (FIG. 1C). While DNA polymerase extends the primers bound to the template DNA, the reporter dye separated from the probe generates fluorescence. The relative frequency of the target sequence with respect to the control sequence can be determined from the ratio of fluorescence of the two dyes.
Figure 1B:
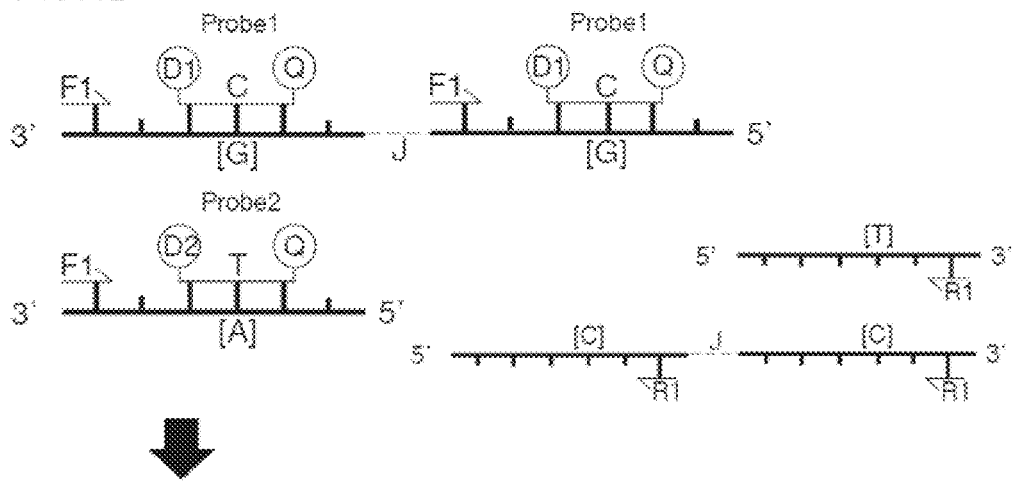
Figure 1C:
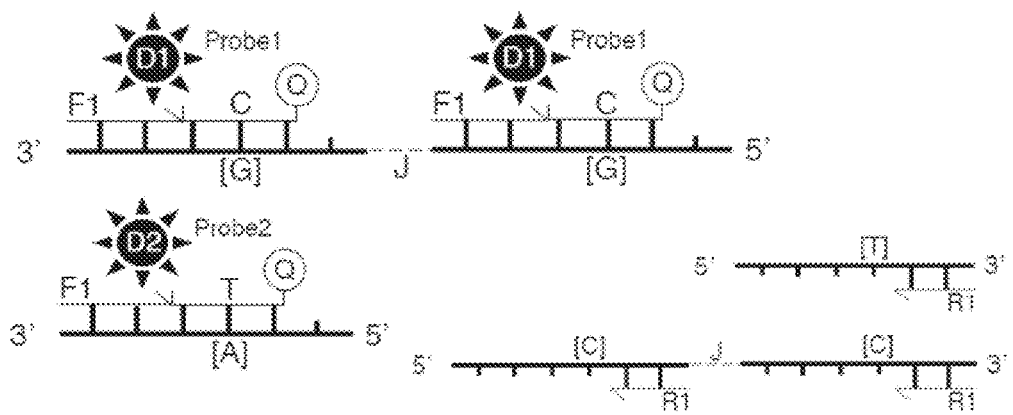
Figure 2:
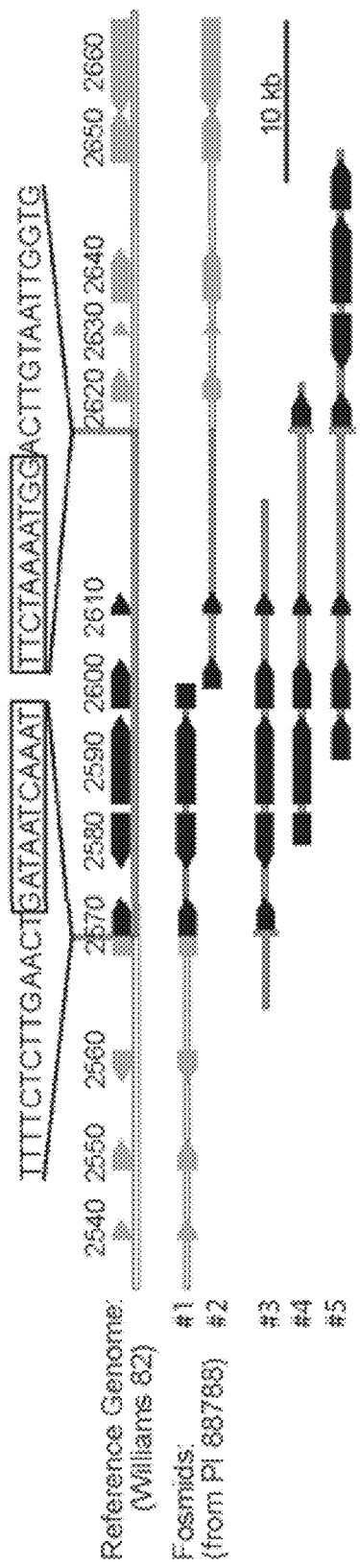
FIG. 2. Diagram of Rhg1 locus of Williams 82 (top) and five fosmid inserts from rhg1-b haplotype. Numbers and block icons refer to soybean genes (e.g., Glyma18g02540). Fosmids 3, 4, and 5 carry rhg1-b genome segments that span repeat junctions. From Cook et al., Science, 338, 1206-1209, 2012. SEQ ID NO: 21 and 22 are shown in the figure; they show the sequences at the junction between adjacent single-copy sequence and the first repeat, and the junction between the last repeat and adjacent single-copy sequence, respectively; the 3' portion of SEQ ID NO: 21 and the 5' portion of SEQ ID NO: 22 reflect the sequence at the junction of two 31.2 kb repeat units.

The method is based on probe hybridization that discriminates a SNV between the target and homeologous sequence, and generates the fluorescence signal, as in the classic TAQMAN® SNP assay. The herein described assay targets one of the Rhg1 genes, Glyma18g02600, in the duplicated region in the locus. Two probes were designed to anneal specifically to a sequence region where a single nucleotide mismatch (variant) exists between this gene (present in multiple copies in Rhg1 resistant lines) and a near-identical homeologous gene (present in one copy on Chromosome 11). Probe 1, which generates VIC-dye fluorescence, anneals specifically to the target repeat unit (possessing T on chromosome 18). Probe 2, however, which generates FAM-dye fluorescence, anneals to the single copy homeologous sequence on chromosome 11 (sequence C on chromosome 11). Therefore, probe 1, unlike probe 2 that consistently produce fluorescence signal from single copy homeologous region regardless of copy number variants, can generate increased amounts of reporter dye proportionally to the number of repeat units in multiple copy loci. See FIG. 1 and the corresponding Legend.

Though the internally controlled, amplification-based, copy number detection assays described herein are exemplified using TAQMAN® PCR-based amplification chemistry, and a SCN-resistance gene in soybean, the methods are by no means limited to these exemplifications. The methods provided herein can be carried out using a variety of amplification chemistries (with minor adaptations in certain embodiments based on the specific chemistry being used) and used to analyze the copy number of myriad different (duplicated) genes from any type of organism.

Generally, there is provided herein a method of measuring (in a genomic sample from an individual) the relative frequency of a target sequence with respect to a control sequence of known copy number at a different genomic locus, wherein the target and control sequences differ by at least one single nucleotide variation (SNV). The method involves amplifying, in a single reaction/container, both the target sequence and the control sequence, using in some embodiments (1) a single upstream and a single downstream primer, the pair of which prime amplification of both the target sequence and the control sequence, or in other embodiments (2) a single downstream primer and two upstream primers, wherein the sequence of the two upstream primers differs only at the position of a SNV between the target and control sequences, each upstream/downstream pair of which (that is, the downstream primer plus one of the two upstream primers) prime amplification of only either the target sequence or the control sequence. The abundance of each of the target sequence and the control sequence is the measured, using in some embodiments, (1) two labeled probes or two labeled primers one each of which is specific for the target or control sequence, or in other embodiments (2) a melting curve. A ratio of the two abundances is then calculated, thereby determining the relative frequency of the target sequence with respect to the control sequence.

VI. Selection of Targets for Copy Number Analysis

With the provision herein of methods for determining the (relative) copy number of a variable copy number version of a (replicated) target nucleic sequence in a sample, the method is enabled for analysis of copy number of myriad different variable copy number sequences. There are certain characteristics of target sequences that make them amenable to being analyzed using these methods. First, at least two versions of the sequence occur at different locations (loci) within a single genome (or complete complement of genetic material in a cell); in this sense, the sequence can be viewed as "duplicated" or more generally "replicated" within the genome. It is noted that this is different from two alleles that occur on different copies of the same chromosome, but at the same location (locus) from a genetic sense.

One of the at least two versions of the target sequence is reliably present in the genome, or can be artificially introduced into the genome, in a consistent copy number (e.g., one copy or two copies or so forth). This sequence serves as the control in calculating the relative copy number of another version of the target sequence (that is, the variable copy number version), and so the fidelity of the method is influenced by the reliability of the copy number of the control sequence. The other version(s) of the target sequence are presumed to vary in copy number (copy number variable, CNV), for instance between cells, tissues, individuals, populations, breeding lines, and so forth. The control sequence and the target sequence are sufficiently similar in sequence that the same set of primers, or forward primers identical but for a single nucleotide and the same reverse primer, amplify both the control and target sequences, causing the PCR efficiency of the two loci to be identical or close to identical. Such replicated and CNV sequences include, for instance, homeologs (as described herein), paralogs, and other sequences resulting from genomic or chromosomal duplication; gene/sequence copies that are tandemly repeated (as described herein); transgenes; multiple-copy transformation insertions; viral insertions into a host genome; or viral load in a sample from another organism.

The target sequence, and particularly that portion of the genome that will be amplified during the method, need not be particularly long. For instance, the sequence may be about 30-500 nt in length in some embodiments; in other embodiments, the amplified sequence is about 30-80 nt, 40-70 nt, 50-70 nt, 40-80 nt, 70-300 nt, 70-200 nt, 70-100 nt, 80-400 nt, 80-300 nt, 80-250 nt, 80-100 nt, 90-500 nt, 90-400 nt, 90-300 nt, 90-250 nt, 90-200 nt, 90-100 nt, 100-300 nt, 100-150 nt, and so forth. In certain embodiments, the amplicons are no more than about 300 nt in length, no more than about 150 nt in length, or no more than about 100 nt in length.

In many embodiments, the control and variable copy number versions of the replicated target sequences differ by as few as a single nucleotide variant (SNV) within the amplicon region, which SNV is used in the amplification method to distinguish between the two sequences (and their amplification products) (the "distinguishing SNV"). Thus, the same pair of primers can be used to amplify the control and variable copy number versions of the target sequence because the sequence where the primers anneal will be the same between the control and target loci, while the probe sequences are tailored to be specific for either the control or target including the SNV. When the amplification chemistry used is KASP™ based chemistry, the upstream "primer" sequence and the probe sequence are effectively fused; that is, the upstream primers include the SNV sequence and thus are not identical, though they still function in the provided methods as described.

Additional sequence differences (beyond the distinguishing SNV) between the control and variable copy number sequence are permitted. However, the accuracy of the method in calculating the relative copy number will be impacted to the extent that any such additional sequence differences change the amplification characteristics (specifically, the amplification efficiency) of the two versions of the target sequence. Thus, differences that substantially affect the length or the G+C content of the amplicon sequence between the target and control loci, while they may still serve to be sufficiently accurate, may reduce the accuracy of the relative determination of copy number.

Though exemplified herein in the context of screening in soybean and a selection program to increase resistance to SCN, the methods are equally applicable to additional plant genes that have variable copy numbers, as well as microbial, fungal, or animal genes that have variable copy numbers.

By way of example, the copy number determination methods are applied to detect and quantify copy number of soybean rhg1; soybean Rag1; soybean Rag2; maize MATE1; barley Bot1; wheat Photoperiod-B1 (Pbd-B1); wheat Vernalization-A1 (Vrn-A1); rice Grain Length on Chromosome 7 (GL7); or any other plant gene that impacts a trait (such as a crop or agronomic trait) through copy number.

In other embodiments, the copy number determination methods are applied to detect and quantify copy number of a human gene, such as for instance a human MHC sequence (given that copy number of MHC is recognized as having an impact on human biology and health; Traheme, *Int J Imunogenet.* 35, 179-192, 2008). There are also many human genes now recognized as influencing disease (or health) through copy number. See for instance: McCarroll & Altshuler, *Nat Genet* 39:537-542, 2007; Eichler, *Nature Education* 1(3):1, 2008; Henrichsen et al., *Human Mol Genet* 18(1):R1-R8, 2009; Girirajan et al., *Ann Rev Genet* 45:203-226, 2011; and Usher & McCarroll, *Briefings Func Genomics* 14(5): 329-338, 2015. Any of these genes may offer sequences the copy number of which can be analyzed (and quantified) using the herein described methods, either by comparison of copy number to a second similar locus in the genome, or comparison of a variant in a repeat to a second repeat sequence with one or more nucleotide differences.

In addition, the provided methods for quantifying copy number of a target gene or sequence (such as a copy number tag) in a genome is also amenable for examining viral copy number in infected host cells. The copy number of viral DNA in an infected cell can be clinically important, including viruses that influence or cause tumors (see, e.g., Swan et al., *J Clin Microb;* 37(4):1030-1034, 1999; Martin & Khoury, *Curr Top Microbiol & Immuno,* 73:35-65, 1976; Shukla et al., *Indian J Med Res* 139(4):531-543, 2014; Larsson et al., *PLos One* 9(11):e112839, 2014).

VII. Tandem Repeat-Controlled Copy Number Detection

When analyzing the copy number of replicated sequence copies from within a tandem repeat set, a defined copy number version of the tandemly repeated target sequence is selected as the control. By way of example, the W-type repeat version of Rhg1 can occur within a tandem repeat of the Rhg1 sequence, and in data obtained up to the present always occurs in only one copy per haploid genome; thus, this services as a control version. As discussed with regard to homeolog-controlled copy number determination, tandem repeat-controlled copy number determination relies on two very similar sequences, having at least one variant nucleotide (the distinguishing SNV), where the two sequences are at different loci in the genome. In the case of tandem repeats, the loci are generally but not always relatively close together on a single chromosome.

The detection and quantification of variable copy number of different versions of tandemly repeated target sequences is useful in tracking individual versions through a breeding or selection program. Since tandem repeats can be subject to high rates of illegitimate recombination in populations, variant copy numbers or combinations of previously separate loci can arise in populations spontaneously, or the rates of such variants may be increased by the use of chemicals or genes that affect the frequency of DNA crossover. This can be of particular interest where different versions have different impacts on the biology of the cell/tissue/subject in which the genome occurs. For instance, a breeding program to select soybean plants with altered resistance to SCN may include tracking and selecting for a diversity of different versions of the Rhg1 sequence. In one embodiment, such diversity includes at least one copy of a P-type repeat and at least one copy of a F-type repeat.

VIII. Transgene Copy Number Detection/Quantification

In addition to measurement of copy number of two loci in a genome, an alternative application of the internally controlled PCR assay is for transgene copy number quantitation to characterize individual transgenic events. A short sequence (a "copy number tag") may be introduced into the T-DNA or other cassette used to transform a target cell/tissue, which sequence that varies from a sequence in the endogenous (non-transformed) target genome by a single nucleotide difference or other easily recognized variation. The ratio of the endogenous sequence to the copy number tag sequence can be assayed using the same methods described for internally controlled copy number analysis. This would provide a low cost and accurate method for determining transgene (e.g., T-DNA) copy number. This method is applicable in plant transformation as well as transformation/transfection/introduction of genes or sequences to any type of cell.

Similarly, it is recognized that detection/quantification of transgene material can be used to influence decisions in a breeding or backcrossing program, since it enables selection of individuals with a desired number of copies of the target sequence.

IX. Characteristics of Amplification Probes and Primers

General characteristics of probes and primers (and methods of making them) are known to those of skill in the art, and exemplary characteristics are described or referenced herein. For methods described herein, the primers should be of appropriate length and G+C content to allow the ready and efficient amplification of the target loci, and be free of complementarity to themselves or each other (or the probes) that may create the production of "primer dimers" or other amplification artifacts not specific to the target genomic sequence. The probes are appropriately designed to allow a single nucleotide difference to strongly affect their ability to hybridize.

If the sequence(s) being analyzed occur in more than two versions in the genome (for instance, as is seen with Rhg1 and its several different homeologs), it is also important to design the primers (and probes) so that they are specific for the two control and target sequences for any particular reaction. This is illustrated herein, for instance in Example 2, where primers for hcTaqMan amplification were designed so they would specifically anneal to both the control homeolog sequence (on chromosome 11) as well as to sequences within Rhg1 (on chromosome 18), while not being compatible with other homeologs in the soybean genome.

X. Computer-Enabled Systems for Selecting Targets, Probes and Primers

Also contemplated are computer-based or remote computer services that can be used to screen a desired genome for appropriate targets, as well as appropriate probes and primers, to carry out the methods provided herein. Such services are enabled through this disclosure, specifically the provision herein of guidelines for how to select an appropriate replicated target nucleic acid sequence, including both the control and the variable copy number versions, as well as guidelines for how to select primers/probes for each such target as well as for each such amplification chemistry employed. Such programs could be deployed on pre-existing genome sequence data, or could be combined with high-throughput sequencing approaches to determine appropriate sequences for probes or primers.

XI. Representative Amplification Methods

As indicated above, the internally controlled copy number assays provided herein can be carried out using a variety of amplification chemistries (with minor adaptations in certain embodiments based on the specific chemistry being used). Exemplary amplification technologies are described below.

A. PCR, qPCR, and TAQMAN®

Several embodiments include the use of PCR and/or qPCR, and more specifically TAQMAN®-type chemistry for amplification of target sequences. PCR reaction conditions typically include either two or three step cycles. Two step cycles have a denaturation step followed by a hybridization/elongation step. Three step cycles include a denaturation step followed by a hybridization step during which the primer hybridizes to the strands of DNA, followed by a separate elongation step. The polymerase reactions are incubated under conditions in which the primers hybridize to the target sequences and are extended by a polymerase. The amplification reaction cycle conditions are selected so that the primers hybridize specifically to the target sequence and are extended.

Primers are typically designed so that all of the primers participating in a particular reaction have melting temperatures that are within at least five degrees Celsius, and more typically within two degrees Celsius of each other. Primers are further designed to avoid priming on themselves or each other. Primer concentration should be sufficient to bind to the amount of target sequences that are amplified so as to provide an accurate assessment of the quantity of amplified sequence. Those of skill in the art will recognize that the amount of concentration of primer will vary according to the binding affinity of the primers as well as the quantity of sequence to be bound. Typical primer concentrations will range from 0.01 µM to 0.5 µM.

In a typical PCR cycle, a sample including a DNA polynucleotide and a PCR reaction cocktail is denatured by treatment in thermal cycler at about 90-98° C. for 10-90 seconds. The denatured polynucleotide is then hybridized to oligonucleotide primers by treatment in a thermal cycler at a temperature of about 30-65° C. for 1-2 minutes. Chain extension then occurs by the action of a DNA polymerase on the polynucleotide annealed to the oligonucleotide primer. This reaction occurs at a temperature of about 70-75° C. for 30 seconds to 5 minutes. Any desired number of PCR cycles may be carried out depending on variables including but not limited to the amount of the initial DNA polynucleotide, the length of the desired product and primer stringency. The above temperature ranges and the other numbers are exemplary and not intended to be limiting. These ranges are dependent on other factors such as the type of enzyme, the type of container or plate, the type of biological sample, the size of samples, etc. One of ordinary skill in the art will recognize that the temperatures, time durations and cycle number can readily be modified as necessary.

Several embodiments include quantitative real-time polymerase chain reaction (qPCR), which is used to simultaneously quantify and amplify a specific part of a given nucleic acid molecule. It is used, for example, to determine whether or not a specific sequence is present in the sample; and if it is present, the number of copies in the sample.

qPCR monitors the fluorescence emitted during the reaction as an indicator of amplicon production during each PCR cycle, as opposed to endpoint detection. The real-time progress of the reaction can be viewed in some systems. Typically, real-time PCR uses the detection of a fluorescent reporter. Typically, the fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed. Thus, the procedure follows the general pattern of polymerase chain reaction, but the nucleic acid molecule is quantified after each round of amplification. In several embodiments the amplified nucleic acid molecule is quantified by the use of fluorescent dye that intercalates with double-strand DNA. In other embodiments (e.g., when multiplex qPCR assays are utilized) amplified nucleic acid molecule is quantified by use of oligonucleotide probes labeled with a reporter fluorophore that can be detected in the qPCR assay.

In certain embodiments, the amplified products are directly visualized with detectable label such as a fluorescent DNA-binding dye. In one embodiment the amplified products are quantified using an intercalating dye, including but not limited to SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin. For example, a DNA binding dye such as SYBR green binds double stranded DNA and an increase in fluorescence intensity can be measured. For example, the fluorescent dsDNA dye can be added to the buffer used for a PCR reaction. The PCR assay can be performed in a thermal cycler, and after each cycle, the levels of fluorescence are measured with a detector, such as a camera. The dye fluoresces much more strongly when bound to dsDNA (e.g., amplified PCR product). Because the amount of the dye intercalated into the double-stranded DNA molecules is typically proportional to the amount of the amplified DNA products, the amount of amplified nucleic acid can be quantified by detecting the fluorescence of the intercalated dye using detection instruments known in the art. When referenced to a standard dilution, the dsDNA concentration in the PCR can be determined.

In addition to the amplification of DNA from the genome, the PCR can also be performed on cDNA produced from RNA using reverse transcription (RT-PCR) reactions.

In addition to various kinds of fluorescent DNA-binding dye, other luminescent labels such as sequence specific oligonucleotide probes can be employed in the amplification reaction to facilitate the detection and quantification of the amplified product. Probe based quantitative amplification relies on the sequence-specific detection of a desired amplified product. Unlike the dye-based quantitative methods, it utilizes target-specific probe labeled with a detectable marker such as a base-linked or terminally-linked fluorophore and quencher. Such markers are known to the person of ordinary skill in the art and described herein. Further, methods for performing probe-based quantitative amplification are well established in the art (see, e.g., U.S. Pat. No. 5,210,015).

For detection using oligonucleotide probes, the reaction is prepared as usual for PCR conditions, with the addition of the sequence specific labeled oligonucleotide probe. After denaturation of the DNA, the labeled probe is able to bind to its complementary sequence in the region of interest of the template DNA. When the PCR reaction is heated to the proper extension temperature, the polymerase is activated and DNA extension proceeds. As the polymerization continues it reaches the labeled probe bound to the complementary sequence of DNA. The polymerase breaks the probe into separate nucleotides, and separates the fluorescent reporter from the quencher. This results in an increase in fluorescence as detected by the optical assembly. As PCR cycle number increases more and more of the fluorescent reporter is liberated from its quencher, resulting in a well-defined geometric increase in fluorescence. This allows accurate determination of the final, and initial, quantities of DNA.

In one embodiment, the fluorescently-labeled probes (such as probes disclosed herein) rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a donor fluorophore and an acceptor or quencher fluorophore on the same probe (for example, using a molecular beacon or a TAQMAN™ probe) can identify a probe that specifically hybridizes to the DNA sequence of interest. In some embodiments, the fluorescently-labeled DNA probes used to identify amplification products have spectrally distinct emission wavelengths, thus allowing them to be distinguished within the same reaction tube, for example in multiplex PCR, such as a multiplex real-time PCR.

Any type of thermal cycler apparatus can be used for the amplification of acids as described herein and/or the determination of hybridization. Examples of suitable apparatuses include the VERITI® thermal cycler (Applied Biosystems; Foster City, Calif.). For real-time PCR, any type of real-time thermocycler apparatus can be used. For example, ICYCLER IQ™ or CFX96™ real-time detection systems (Bio-Rad, Hercules, Calif.), LIGHTCYCLER® systems (Roche, Mannheim, Germany), a 7700 Sequence Detector (Perkin Elmer/Applied Biosystems; Foster City, Calif.), ABI™ systems such as the 7000, 7300, 7500, 7700, or 7900 systems (Applied Biosystems; Foster City, Calif.; Life Technologies Corp., Grand Island, N.Y.), QuantStudio® Real-Time PCR systems (Applied Biosystems, Life Technologies Corp., Grand Island, N.Y.), or an MX4000™, MX3000™ or MX3005™ qPCR system (Agilent/Stratagene; Santa Clara, Calif.), DNA ENGINE OPTICON® Continuous Fluorescence Detection System (Bio-Rad, Hercules, Calif.), ROTOR-GENE® Q real-time cycler (Qiagen, Valencia, Calif.), or SMARTCYCLER® system (Cepheid, Sunnyvale, Calif.) can be used to amplify and detect nucleic acid sequences in real-time.

In some embodiments, real-time PCR is performed using a TAQMAN® array format, for example, a microfluidic card in which each well is pre-loaded with primers and probes for a particular target. The reaction is initiated by adding a sample including nucleic acids and assay reagents (such as a PCR master mix) and running the reactions in a real-time thermocycler apparatus.

In one example, the multiplex real-time PCR can be performed in a total reaction volume of 50 µl containing 10 µl of DNA extract, 40 µl of 2×PCR master mix, the forward and reverse primers, and the first and second oligonucleotide probes corresponding to the first and second nucleic acid molecules amplified by the first and second oligonucleotide primer pairs, respectively. The concentration of the set of primers can be 300 nM and the probes can be 200 nM. In some examples, the following protocol can be used for the multiplex qPCR: 50° C. for 2 minutes; 95° C. for 10 minutes; followed by 40 cycles of 95° C. for 15 seconds and 60° C. for 1 minute. Each multiplex qPCR assay can include a standard dilution series for DNA quantification and/or determination of PCR efficiency. Further, samples can be analyzed in duplicate as part of a CLIA protocol, and replicated more extensively for statistical analysis. Negative reagent and extraction controls can be included with each assay along with positive controls.

In some embodiments, amplification and detection of the first and second nucleic acid sequences in the multiplex qPCR assays can be performed using any of the primer pairs and probes provided herein for amplification and detection of the first and second nucleic acid molecules.

Since the amplification reactions in the described methods involve amplifying, simultaneously and in the same container/reaction, both the control sequence and the copy number variant sequence, the oligonucleotide probes (or labeled primers) used for detecting the first (e.g., control) and second (e.g., variable copy number target) nucleic acid molecules are labeled with detectable markers that can be differentially detected in the same reaction using detection equipment available to the person of ordinary skill in the art. For example, the oligonucleotide probe for detecting the first nucleic acid can be labeled with a first fluorophore and quencher and the oligonucleotide probe for detecting the second nucleic acid can be labeled with a second fluorophore and quencher, wherein the first and second base-linked or terminally-linked fluorophore and quencher can be differentially detected.

In one example, the first and second oligonucleotide probes are labeled with TAQMAN™ fluorophores and quenchers that can be differentially detected, such as fluorophores and quenchers available from Applied Biosystems by Life Technologies, Carlsbad, Calif.). In one example, the oligonucleotide probe for detecting the first nucleic acid sequence is labeled with the VIC fluorophore and the NFQ™ quencher available from Applied Biosystems by Life Technologies, Carlsbad, Calif., and the oligonucleotide probe for detecting the second nucleic acid is labeled with the 6-carboxyfluorescein (FAM) fluorophore and the NFQ™ quencher available from Applied Biosystems by Life Technologies, Carlsbad, Calif.

For the conventional applications of PCR in genotyping, the ratio between two fluors is measured for each assay, the assays are grouped, and a qualitative assignment is made into AA, AB and BB genotypes, usually using a machine learning algorithm in a software package. For copy number analysis, instead of grouping the ratio by qualitative sets, the ratio itself is used as a quantitative measure of relative copy number. This is similar to that used for existing assays such as the CNV TAQMAN® PCR or any relative RNA qRT-PCR quantitation.

B. KASP™ Amplification

It is also contemplated that the copy number assays described herein can employ KASP™ amplification chemistry (see, for instance, Semagn et al., *Mol Breed* 33:1-14, 2014). In canonical C/Kompetitive Allele Specific PCR (KASP™) genotyping, rather than using two separate probes labeled with different fluorophores in addition to two primers, no probe is used. Rather, the forward primer of the two PCR primers is synthesized in two forms, two different sequences with an allele-specific sequence variant at the 3' end, each labeled with a different fluor. The reverse primer is unlabeled giving a total of three primers.

The KASP™ system can be used to measure copy number in an internally-controlled assay as follows: the 3' nucleotide of the first allele-specific forward primer would be designed to a sequence of known copy number, and the second allele-specific primer to the copy number variant locus. The ratio between the fluorescence signals generated by the primers would then be interpreted in terms of copy number the same manner as that described for TAQMAN® PCR chemistry.

C. Digital PCR (dPCR)

In another embodiment, the copy number assays described herein can employ dPCR (or droplet digital PCR, ddPCR), which uses multiple separate PCR reactions to create effective technical replication of a PCR assay, and this greatly improves the reproducibility of assays for copy number. The method described could be used in a digital PCR assay, and this would provide statistical replication that would increase its accuracy.

As described herein, a single assay is not currently reliably capable of differentiating between single copy differences when the copy number exceeds nine copies. If dPCR were used to provide replication of the assay, the ability to accurately differentiate single copy differences is expected to be extended to higher copy numbers of variable number target sequences.

D. Melt Curve Analysis

Another method capable of measuring a ratio between two variant sequences in a genome (and therefore applicable for use in the CNV detection assays provided herein) is melt curve technology (Ririe et al., *Anal Biochem* 245(2):154-160, 1997). In this method, a probe or primer is used with a single fluorescent label to produce a sequence that melts (denatures) at a different temperature according to which variant sequence is present. The fluorescence is measured at different temperatures, and genotyping is performed according to the shape of the curve of temperature versus fluorescence. This is most commonly represented as a plot of the first differential of fluorescence with respect to temperature, dF/dT, against temperature, giving two peaks for the two alleles, the area under each of which should be proportional to the quantity of DNA present from that allele.

By creating two probes or primers, one of which recognizes a sequence of known copy number, and the second the copy number variant locus, that melt at two distinct temperatures, the ratio between the double-stranded PCR products with the two variants can be measured by measuring the ratio between the fluorescence change at the melting temperature of the first primer or probe to the fluorescence change at the melting temperature of the second primer or probe.

A higher resolution of the ratio, and information about the methylation status of the repeats, could additionally be obtained using thermophoresis. See, for instance, Wienken et al., *Nucleic Acids Research* 39(8):e52-e52, 2011. Methylation information could additionally be derived by the addition of a digestion step using a methylation-sensitive restriction enzyme to any of the above procedures, including TAQMAN® PCR.

XII. Methods of Selection Based on Copy Number

Several possible applications of the described technology apply to plant breeding, for example to the analysis of copy number at Rhg1. We have now shown that copy number of Rhg1 can be highly variable within the population of a single released soybean variety (FIG. 17A). It is noted that copy number of Rhg1 repeats in a genome influences resistance to soybean cyst nematode (SCN), yield, and seedling emergence; thus methods enabled herein can be used to influence any of these traits in a plant breed program.

One application is to ensure that seed sold or supplied commercially is consistent in Rhg1 copy number, by analyzing the copy number as seed is bulked for sale as a quality control measure.

A second application is to select for plants carrying more optimal (higher or lower) copy numbers. Since it is known that Rhg1 tandem repeats are variable in number, and this is likely a result of high rates of illegitimate recombination in populations, by screening large numbers of plants for higher copy variants, propagating these high copy variants, and selecting from their progeny for still higher variant copy numbers, copy number may be dramatically increased in successive rounds of reciprocal or recurrent selection.

A third application is that the rates of such variants may be increased further before selection by the use of chemicals or genes that affect the frequency of DNA crossover. A fourth application would be that copies thought to have different function (for example, the P and F type repeats at the Rhg1 locus) may recombine at some frequency, and thus the marker can be used to select for the loci that contain both of these repeat types, each of which is thought to have different resistance activity against different SCN types.

In addition, the copy number assay can be used in place of or alongside traditional marker-assisted selection approaches to ensure that a specified copy number is introduced and maintained into a variety during development.

These methods can equally be applied to non-plant subjects, including for instance livestock or other animals. This enables the identification and selection of breed stock individuals with a specified copy number for genes (or other sequences) that influence animal health, productivity, market value, and so forth.

EXAMPLES

The disclosure may be further understood by the following non-limiting examples. All references cited herein are hereby incorporated by reference to the extent not inconsistent with the disclosure herewith.

Example 1: Evolution and Selection of Rhg1, a Copy-Number Variant Nematode-Resistance Locus This example describes the characterization of copy number and sequence variation of Rhg1 across 106 *Glycine max* and *Glycine soja* germplasm accessions using a genomic qPCR assay, validated with whole-genome sequencing (WGS) assays. At least some of the data presented in this Example are also published in Lee et al., *Mol. Ecol* 24(8): 1774-1791, 2015, which is herein incorporated by reference in its entirety.

The soybean cyst nematode (SCN) resistance locus Rhg1 is a tandem repeat of a 31 kb genome unit where each repeat carries four genes. One allele, Rhg1-b, is responsible for protecting most U. S. soybean production from SCN. Whole-genome sequencing was performed and PCR assays developed to investigate allelic variation of the Rhg1 locus across the population of soybean germplasm accessions. Four distinct sequences of the 31 kb repeat unit were identified, and some Rhg1 alleles carry up to three different types of repeat unit. The total number of copies of the repeat varies from 1 to 10 per haploid genome. Both copy number and sequence of the repeat correlate with the resistance phenotype, and the Rhg1 locus shows strong signatures of selection. Significant linkage disequilibrium in the genome around the boundaries of the repeat allows the Rhg1 genotype to be inferred using high-density SNP genotyping of 15,996 accessions. Over 860 germplasm accessions were found likely to possess Rhg1 alleles. The regions surrounding the repeat show indications of non-neutral evolution and high genetic variability in populations from different geographic locations, but without evidence of fixation of the resistant genotype.

In the present example, diversity at the Rhg1 locus across 106 *G. max* and *G. soja* germplasm accessions using a genomic qPCR assay, validated with whole genome sequencing (WGS) assays was examined. Duplication events at the Rhg1 locus, and find a wide distribution of copy number were examined and identified. The order of the individual units of the multi-copy versions of the locus, and use these sequences to perform evolutionary analysis on the individual repeats was interpreted. Using these data for 106 resistant accessions together with large-scale SNP data obtained by INFINIUM® genotyping of the entire soybean germplasm collection, signatures of selection at the Rhg1 locus were investigated. The implications of evolution at this locus for both soybean population genetics and future breeding approaches are provided.

Soybean Germplasm

The term "accession" is used here to mean a genetic line registered and stored by the USDA soybean germplasm collection (Urbana, Ill.). We use the term Plant Introduction (PI) as it is used by this collection, to designate a soybean or *Glycine soja* line originating outside the US that is registered in the US and stored by USDA. Some cultivars, especially those bred in the US, are not PIs but are still USDA germplasm accessions. All soybean germplasm used in this study, including PIs and soybean cultivars with resistance to SCN, was obtained from the USDA soybean germplasm collection. Based on two independent studies (Diers et al., *Crop Science,* 37, 1966-1972, 1997; Chen et al., *Genome,* 49, 938-949, 2006), SCN resistant germplasm with resistance to at least one of SCN types 1, 2, 3, 5, and 14 was chosen as "SCN resistant accessions". A total of 106 SCN resistant accessions (102 PIs collected in diverse geographical regions and four U. S. cultivars) that were available as of June 2013 were obtained (Table 1; below). Plants were grown in a growth chamber set at a photocycle of 18/6 hr (day/night), 23/20° C. (day/night), and 50% relative humidity for about 10 days. Young leaf tissue was collected from two individuals for each line and kept individually at −80° C. for genomic DNA isolation.

Quantitative PCR Validation of Copy Number Variation

Genomic DNA extraction was performed as described in a previous study ('Fosmid library construction' section in 'Supplementary Materials' in Cook et al., *Science*, 338, 1206-1209, 2012). A pool of two plants of each germplasm accession was used for the DNA extraction. The presence of the junction between two adjacent copies of the 31.2 kb repeat described by Cook et al. (*Science*, 338, 1206-1209, 2012) was first investigated using tandem repeat site-specific primers that span the junction between two repeat units, and thus only produce a product if the 31.2 kb unit is repeated at least twice (Primer IDs 1 and 2 in Table 2; SEQ ID NOs: 1 and 2, respectively). Having identified lines that contain more than one copy of the 31.2 kb unit, then copy number was investigated. Genomic qPCR (quantitative PCR on the genomic DNA from the locus) was performed on the genomic DNA samples described above using the Brilliant II QPCR Master Mix with Low ROX kit (Agilent Technologies) and the Mx3000P QPCR system (Agilent Technologies). Relative quantification using the $\Delta\Delta C_T$ measurement method (Livak & Schmittgen, *Methods*, 25, 402-408, 2001) was used to measure copy number relative to the soybean reference genome, from the Williams 82 line. Amplification efficiencies of all tested genes were determined by 10× dilution series. A heat shock protein gene (hsp) (Li et al., *Plant Physiology*, 151, 1087-1095, 2009) was used as an endogenous control for all assays. A sequence of Glyma18g02590, one of the Rhg1 genes in the duplicated region, was chosen for primer design (Primer IDs 3 and 4 in Table 2; SEQ ID NOs: 3 and 4, respectively) using PrimerQuest$^{SM}$ (Integrated DNA technologies) based on the reference genome and fosmid clone sequences from Cook et al. (*Science*, 338, 1206-1209, 2012). $C_T$ values for technical replicate(s) of both of the internal control and target genes were obtained from the same plate and run at all times. A minimum of four technical replicates was prepared to generate $\Delta C_T$ values. 95% confidence intervals were calculated to give error bars, and the copy number assigned to the nearest integer value.

TABLE 2

| SEQ ID | Primer | Sequence |
|---|---|---|
| 1 | 1F | AGCCTGCTCCTCACAAATTCTTGC |
| 2 | 9R-1 | TCCTCTTGATCTCGTAGGAAAAGA |
| 3 | 2590-forward | TGGAGTGGGCTGAATCTCTT |
| 4 | 2590-reverse | ATGGAAGCAAGAGCAGCATT |

DNA sequences of oligonucleotide primers used for assays in this example.

Whole-Genome Shotgun Sequencing

DNA extracted as above was treated with RNase (Roche Applied Science, Indianapolis, Ind.) by incubating in 25 µg/ml RNase at 4° C. overnight. Whole-genome shotgun sequencing of nine germplasm accessions was conducted using Illumina technology. 1.5 µg of genomic DNA were sequenced using the Illumina HiSeq 2500 instrument with 150 or 155 bp paired-end sequencing at the University of Illinois Biotechnology Center. A total of nine DNA sequencing libraries were prepared with the Illumina TruSeq DNA Sample Preparation Kit (Illumina, San Diego Calif.). The libraries were loaded into lanes, and sequenced using version one of the Illumina TruSeq SBS sequencing Rapid Kit. A total of 41 to 48 Gb of reads having average quality scores 30 or higher were produced from each lane (Table 3). The data from the accession LD09-15087a was previously published (Cook et al., *Science*, 338, 1206-1209, 2012). Illumina raw reads obtained from independent studies were as follows: 41 lines from SoyNAM founder lines, 31 accessions including W06 (SRR064619) (Lam et al., *Nature Genetics*, 42, 1053-1059, 2010), and PI 437654, PI 90763, PI 89772, PI 548402, PI 548316, PI 209332 (Cook et al., *Plant Physiology*, 165, 630-647, 2014). To avoid biased SNV calling due to low read depth in given sequence regions, two SoyNAM lines (LD00-2817 and LD00-3309) from 41 in total were selected, since they gave coverage evenly across the repeat unit without gaps. Thus, the total whole-genome re-sequenced dataset consists of 88 accessions, of which 18 contain the Rhg1 resistance repeat. Analysis of the repeat sequence was done on the set of 18, while whole-genome population analysis was done on the set of 88.

TABLE 3

Summary of whole-genome shotgun sequencing data of the multiple copy Rhg1 germplasm accessions.

| Strain designation | Number of individuals used for DNA extraction | Library size (bp) | Lane designation | Read length | Read counts* | % Mapped† | % Unique alignment‡ | Haploid coverage§ | NCBI SRA Runs |
|---|---|---|---|---|---|---|---|---|---|
| LD10-30036 | Single plant | 580 | one lane | 150 | 274165110 | 96.73 | 84.40 | 37.39 | SRR1784853 |
| PI 438489 B | Single plant | 600 | barcoded on a lane | 155 | 80082290 | 96.80 | 88.42 | 11.28 | SRR1784855 |
| PI 467332 | Single plant | 600 | barcoded on a lane | 155 | 77425484 | 96.81 | 88.84 | 10.91 | SRR1784857 |
| PI 89008 | Single plant | 600 | barcoded on a lane | 155 | 82525120 | 96.91 | 88.89 | 11.63 | SRR1784856 |
| PI 467327 | Single plant | 600 | barcoded on a lane | 155 | 79049326 | 91.71 | 88.51 | 11.14 | SRR1784858 |

TABLE 3-continued

Summary of whole-genome shotgun sequencing data of the multiple copy Rhg1 germplasm accessions.

| Strain designation | Number of individuals used for DNA extraction | Library size (bp) | Lane designation | Read length | Read counts* | % Mapped[†] | % Unique alignment[‡] | Haploid coverage[§] | NCBI SRA Runs |
|---|---|---|---|---|---|---|---|---|---|
| PI 92720 | Two plants | 600 | barcoded on a lane | 150 | 82547664 | 96.73 | 88.29 | 11.26 | SRR1784896 |
| PI 88788 | Single plant | 600 | barcoded on a lane | 150 | 76832584 | 96.95 | 87.31 | 10.48 | SRR1784885 |
| PI 461509 | Two plants | 600 | barcoded on a lane | 150 | 74607536 | 96.62 | 88.30 | 10.17 | SRR1784859 |
| PI 87631-1 | Two plants | 600 | barcoded on a lane | 150 | 75541238 | 96.88 | 88.12 | 10.30 | SRR1784894 |

*The total read count is provided as the sum of read 1 & read 2 of each cluster during one paired-end read.
[†]% Mapped refers to the total number of reads mapped to the reference genome by Novoalign.
[‡]Unique alignment of reads is reported as % Unique alignment.
[§]Haploid genome length of *G. max* = 1.1 Gb (Schmutz et al., *Nature* 463(7278): 178-183 2010).

Confirmation of Copy Number Variation by Read Depth

To confirm copy number variation within the tandemly duplicated region of the Rhg1 allele, reads from each sample were aligned to the Glyma1.1 version of the soybean genome assembly. Novoalign (v 3.00.03) (on the World Wide Web at novocraft[dot]com) with paired end options was used to align the reads to the reference genome. Only single alignment locations were allowed for reads. The number of reads aligned to the repeat unit reference sequence was counted from a BAM file using SAMtools (v0.1.18). Copy number, C, for a repeat unit (31.2 kb) was calculated by the equation, $C = \text{average } c \pm SD$, $c = rw^{-1}$, where C represents copy number of the repeat unit, c represents copy number relative to the each sequence window, r represents the total number of reads aligning on the repeat unit, w represents the total number of reads aligning on the sequence window, and SD represents standard deviation. The value of C above across six sequence analysis regions (windows) across the 31.2 kb repeat unit were used to calculate the overall copy number of the unit, as described in Cook et al. (*Science*, 338, 1206-1209, 2012), which is incorporated herein in its entirety.

SNV Detection

Figure 9:
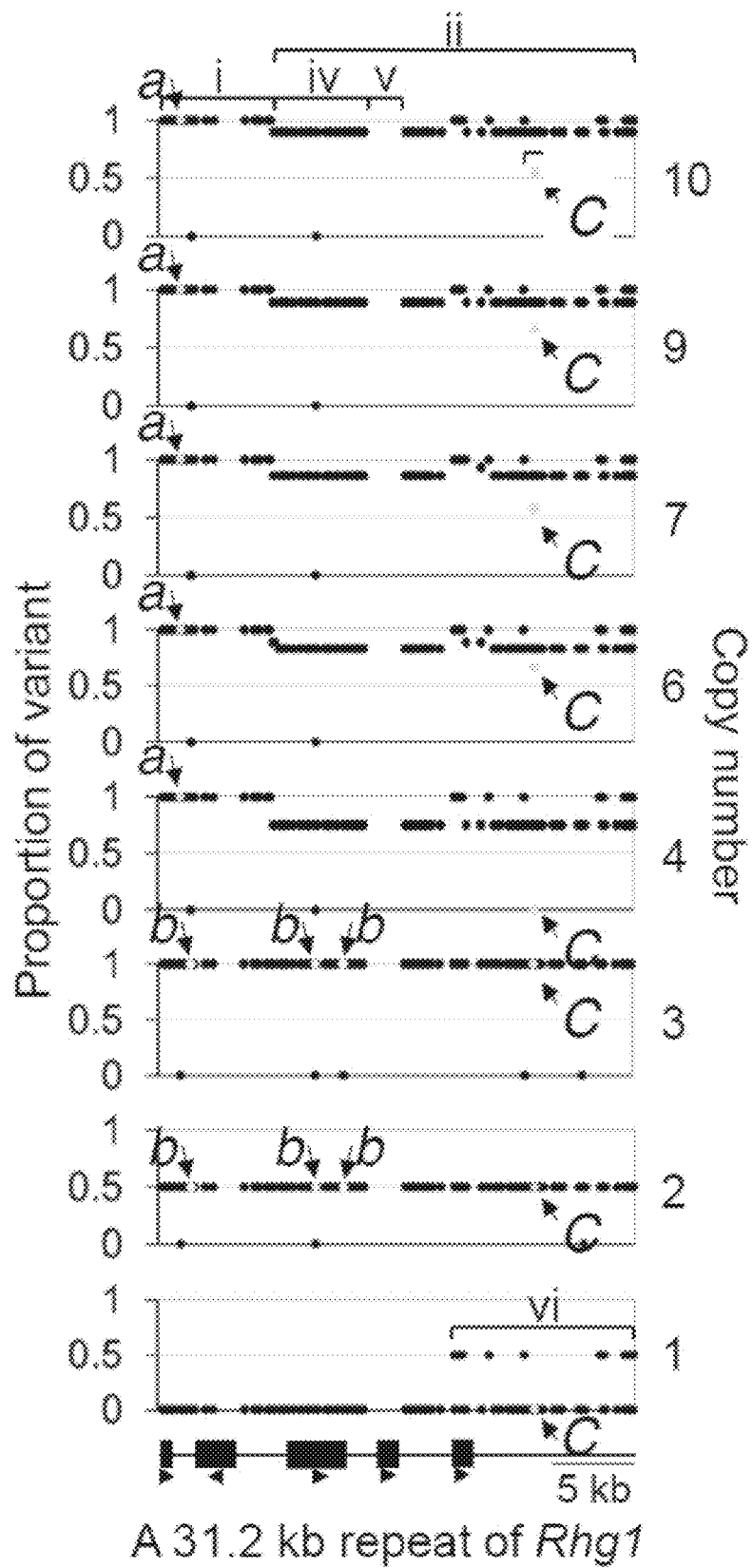
FIG. 9. Sequence variation within the Rhg1 repeat. One hundred forty-nine single nucleotide variants are distributed in an Rhg1 31.2 kb repeat unit. The probability of observing given sequence variants was depicted as separate graphs from top (10 copies) to bottom (single copy). Probability 1 represents 100% of chance of a given nucleotide. 'i' marks a region where all resistant germplasm but the 2 copy variant shows 100% difference from the susceptible variant. a represents a variant shared by all accessions with four or more copies. Region 'ii' shows probability consistent with one copy of the repeat in the lines with 4 or more copies having the same sequence as the reference, others being divergent. b represents variants shared by two and three copy germplasm. c is a single position at 1,657,025 bp, where P varies from 0.5 to 1 depending on copy number. 'iv' marks the Glyma18g02590 gene encoding a predicted $\alpha$-SNAP. 'v' marks a region with no SNVs. 'vi' marks the region with variants to the reference found in one single copy accession. Below the graph, gene models are shown from the Williams 82 reference genome; the final two exons of Glyma18g02570, Glyma18g02580, Glyma18g02590, Glyma18g02600, and Glyma18g02610 (from left to right).

SNVs were predicted from aligned read data using VarScan v2.3.5 (Koboldt et al., *Genome Research*, 22, 568-576, 2012). Command line options are as follows: mpileup2snp--min-coverage [8]--min-ave-qual [20]--min-var-freq [0.01]--p-value [0.01]. For all accessions of a given copy number, the frequency of reads carrying a SNV that differs from the Williams 82 reference divided by the total number of reads (hence, a probability estimate of observing the SNV in any given read) was plotted against position in the 31.2 kb repeat unit (FIG. 9). The frequency of variants at each SNV, and thus the number of repeats present each carrying a given variant, was estimated using alignment of Illumina reads.

Repeat Subunit Assembly and Type Definitions

Phasing analysis using informative bases derived from paired-end reads from single molecules was used to reconstruct the individual repeated sequence units in the Rhg1 locus in a manual process of assembly similar to that used for haplotype reconstruction or phasing. For each germplasm accession, mapped, paired reads that possessed variants from the reference sequence (the Williams 82 single-copy sequence, W) were merged into a single data file using in-house Perl scripts. Only the reads with bases varying from the 31.2 kb single-copy region from Williams 82 with Phred q≥20 were selected for assembly steps. Variants located at the start position of a read or within three bases at the end of read were ignored. Two SNVs that reside on the same read or the corresponding mate in paired-end reads were considered to have originated from the same molecule, and can thus be used to define a given 31.2 kb repeat unit in an Rhg1 repeat genotype. Thus, only reads or mate pairs with two SNVs derived from the same molecule were used for phasing. To obtain accurate and complete phasing of each repeat unit, multiple possible phasing configurations were validated by fosmid clone sequences from our previous study (Cook et al., *Science*, 338, 1206-1209, 2012). Firstly, we configured three different repeat unit subtypes within Rhg1 from PI 88788. Across all SNVs in PI 88788 (with the exception of the SNV at 1,657,025 bp), probabilities of SNVs within Rhg1 are either 1 or ~0.9, indicating either a single type of sequence present in ten copies per haploid genome, or a complete distinguishable repeat with a single copy, and repeats with higher-frequency SNVs. These reads could be assembled consistently across the variable regions of the repeat, including all of the Glyma18g02590 gene. In order to confirm the homogeneity of the repeat units, two fosmid clones, fosmids #2 and #3 in FIG. 1, carried all of the predicted single copy SNVs including 5 positions identical to the reference sequence (FIG. 4A), confirming that the single-copy SNVs are all within a single repeat unit. In addition, fosmid #2 (Cook et al., *Science*, 338, 1206-1209, 2012) spans the last duplicated repeat copy at the centromeric end and the non-duplicated region. This indicates that the single copy (W type) repeat subunit is located at the centromeric end of the repeat in the PI 88788 haplotype. Thirty-three percent of PI 88788 reads are T (thymine) at the 1,657,025 bp SNV (Table 4), suggesting 3 of the 9 repeat units are distinguishable at this location. The 3 copies per haploid genome carrying T at 1,657,025 bp were used to define subtype $F_A$ (Fayette, 10 copies, is directly derived from PI 88788, which carries nine copies of the repeat; the two were previously assumed to carry the same Rhg1 allele). One copy is subtype W. The remaining 5 copies in PI 88788 were identified as subtype $F_B$. Fosmids #4 and #5 in FIG. 1 confirmed complete sequences of repeat subtypes $F_B$ and $F_A$, respectively. Thus, we reconstructed the repeat at Rhg1 from PI 88788 as three subtype $F_A$, five subtype $F_B$, and a single subtype W at the centromeric end. Three-copy type germplasm collections (Peking, PI 90763, PI 437654, PI 467327, PI 89772, & Jidong5) showed only a single genotype at each SNP This sequence is distinctive from W, $F_A$ and $F_B$, resulting a single subtype P (Peking).

Table 4 shows the frequency of sequence variants from the Williams 82 reference at five SNV positions (FIG. 10A). Variant frequency at each position is displayed. The count observed for the two possible bases at each position are displayed above the corresponding graph. A value of greater than 0.6 was considered as 1.0. Copy number of each germplasm is given in parentheses.

TABLE 4

(Part 1)

| | PI 438489 B (2) | PI 467327 (3) | Peking (3) | PI 89772 (3) | LD00-2817 (3) | PI 89008 (4) | PI 87631-1 (6) | PI 467332 (6) | PI 461509 (6) |
|---|---|---|---|---|---|---|---|---|---|
| green | 2 | 0 | 0 | 0 | 0 | 7 | 6 | 13 | 9 |
| red | 16 | 34 | 44 | 34 | 78 | 18 | 33 | 41 | 31 |

(Part 1)

| | PI 92720 (7) | Cloud (7) | PI 88788 (9) | PI 209332 (10) | LD00-3309 (10) | LD02-4485 (10) | LD09-15087a (10) | LD10-30036 (10) | PI 438489 B (2) |
|---|---|---|---|---|---|---|---|---|---|
| green | 7 | 21 | 11 | 10 | 8 | 2 | 59 | 18 | 2 |
| red | 55 | 77 | 66 | 102 | 62 | 36 | 439 | 150 | 11 |

(Part 2)

| | PI 467327 (3) | Peking (3) | PI 89772 (3) | LD00-2817 (3) | PI 89008 (4) | PI 87631-1 (6) | PI 467332 (6) | PI 461509 (6) | PI 92720 (7) |
|---|---|---|---|---|---|---|---|---|---|
| green | 0 | 0 | 0 | 0 | 10 | 4 | 7 | 10 | 6 |
| red | 20 | 47 | 37 | 75 | 23 | 30 | 45 | 42 | 42 |

(Part 2)

| | Cloud (7) | PI 88788 (9) | PI 209332 (10) | LD00-3309 (10) | LD02-4485 (10) | LD09-15087a (10) | LD10-30036 (10) | PI 438489 B (2) | PI 467327 (3) |
|---|---|---|---|---|---|---|---|---|---|
| green | 15 | 11 | 4 | 5 | 1 | 46 | 19 | 3 | 0 |
| red | 74 | 63 | 107 | 57 | 27 | 342 | 160 | 9 | 19 |

(Part 3)

| | Peking (3) | PI 89772 (3) | LD00-2817 (3) | PI 89008 (4) | PI 87631-1 (6) | PI 467332 (6) | PI 461509 (6) | PI 92720 (7) | Cloud (7) |
|---|---|---|---|---|---|---|---|---|---|
| green | 0 | 0 | 0 | 33 | 20 | 37 | 26 | 30 | 56 |
| red | 51 | 56 | 60 | 0 | 12 | 12 | 17 | 20 | 48 |

(Part 3)

| | PI 88788 (9) | PI 209332 (10) | LD00-3309 (10) | LD02-4485 (10) | LD09-15087a (10) | LD10-30036 (10) | PI 438489 B (2) | PI 467327 (3) | Peking (3) |
|---|---|---|---|---|---|---|---|---|---|
| green | 46 | 60 | 29 | 16 | 227 | 100 | 1 | 0 | 0 |
| red | 24 | 55 | 22 | 20 | 260 | 61 | 5 | 32 | 56 |

(Part 4)

| | PI 89772 (3) | LD00-2817 (3) | PI 89008 (4) | PI 87631-1 (6) | PI 467332 (6) | PI 461509 (6) | PI 92720 (7) | Cloud (7) | PI 88788 (9) |
|---|---|---|---|---|---|---|---|---|---|
| green | 0 | 0 | 9 | 5 | 8 | 1 | 9 | 8 | 12 |
| red | 49 | 58 | 26 | 39 | 54 | 25 | 41 | 70 | 48 |

(Part 4)

| | PI 209332 (10) | LD00-3309 (10) | LD02-4485 (10) | LD09-15087a (10) | LD10-30036 (10) | PI 438489 B (2) | PI 467327 (3) | Peking (3) |
|---|---|---|---|---|---|---|---|---|
| green | 12 | 9 | 2 | 44 | 10 | 2 | 0 | 0 |
| red | 99 | 51 | 20 | 414 | 114 | 5 | 31 | 53 |

(Part 5)

| | PI 89772 (3) | LD00-2817 (3) | PI 89008 (4) | PI 87631-1 (6) | PI 467332 (6) | PI 461509 (6) | PI 92720 (7) |
|---|---|---|---|---|---|---|---|
| green | 0 | 0 | 9 | 7 | 8 | 1 | 7 |
| red | 52 | 34 | 26 | 40 | 55 | 29 | 47 |

TABLE 4-continued (Part 5)

|  | Cloud (7) | PI 88788 (9) | PI 209332 (10) | LD00-3309 (10) | LD02-4485 (10) | LD09-15087a (10) | LD10-30036 (10) |
|---|---|---|---|---|---|---|---|
| green | 8 | 12 | 11 | 9 | 3 | 47 | 13 |
| red | 60 | 42 | 102 | 55 | 17 | 438 | 99 |

Phasing steps for other germplasm accessions were performed in the same way described above. Phylogenetic analysis using the parsimony method was conducted on the phased SNP locations in and around Glyma18g02590 in order to validate the classification of four subtypes, once phasing was completed for all of the accessions for which whole-genome sequence data was available (FIG. 4B). Glyma18g02590 gene sequence, including coding DNA sequence (CDS), untranslated region (UTR), and introns from each sequenced accession was used for the parsimony analysis. For each genotype, we were able to manually assemble a set of sequences derived from a single molecule into a contig by phasing of the paired end reads. To identify the subtype located at the very 3' end of the Rhg1 repeat in accessions, a 200 bp region spanning the junction between the end of the repeat and the neighboring, non-repeated sequence was amplified by PCR and sequenced by the Sanger method (Table 5, below; FIG. 4C).

Evolutionary Analysis

Two separate nucleotide sequence datasets were prepared for phylogenetic analysis. Firstly, the informative SNVs in genes surrounding the Rhg1 locus were derived from alignments of Illumina whole genome sequencing reads of 18 germplasm accessions with experimentally validated Rhg1 copy number (hereafter, this dataset is termed WGS data). The germplasm accessions in the WGS data are as follows: three single-copy germplasm accessions (Williams 82, PI 427136, & PI 518751), one 2 copy (PI 438489 B), three 3 copy (PI 467327, Peking, & PI 89772), one 4 copy (PI 89008), three 6 copy (PI 87631-1, PI 461509, & PI 467332), two 7 copy (PI 92720 & Cloud), one 9 copy (PI 88788), and four 10 copy (PI 209332, LD10-30036, LD09-15087a, & LD00-3309). SNPs within coding DNA sequences (CDSs) of 38 genes (a total of 54,771 bp) across a 400 kb region centered on Rhg1 were prepared using the methods from the step "SNV detection" described above. Two genes (Glyma18g02730 & Glyma18g02750) that gave read depth below a minimum threshold (sequence coverage 8) set across genotypes were excluded in this study. Secondly, the complete data set for 19,652 G. max and G. soja germplasm accessions genotyped using the Illumina INFINIUM® II BeadChip array, which carries 52,041 SNPs probes targeting genic and intergenic regions, was obtained from SoyBase (on the World Wide Web at soybase[dot]org). After removing low quality SNPs, 19,548 germplasm accessions with informative, mono-allelic SNP analysis results were prepared (hereafter, INFINIUM®data). One hundred-seventeen SNPs across the 1.5 Mbp region centered on Rhg1 were used for analysis of soybean populations. For WGS data, phylogenetic analysis was performed using the maximum parsimony (MP) method with 10,000 bootstrap replicates to assess reliability of clustering, using MEGA 6.0 (Tamura et al., Molecular Biology and Evolution, 30, 2725-2729, 2013). Clustering of germplasm accessions from the much larger INFINIUM®dataset was performed by using Parsimonator v1.0.2 (github[dot]com/stamatak/Parsimonator-1.0.2). Ten SNPs for each taxon located between 1,620,585 bp and 1,712,832 bp on chromosome 18 were used for the phylogenetic analysis. For SNVs located in the repeat unit, apparent heterozygosity (i.e. diversity between repeat units) was validated by using whole genome sequencing data. SNVs with apparent heterozygosity were removed before analysis. All phylogenetic trees were visualized using Geneious 5.6.5 (available on the World Wide Web at biomatters[dot]com).

Selection Analysis

For both datasets, WGS and INFINIUM®, the nucleotide diversity was quantified as $\pi$ (Nei & Li 1979) and $\theta$ (Watterson 1975). Tajima's test of neutrality (Tajima 1989) was additionally performed for the INFINIUM® data. We used two software packages for these analysis ($\pi$, $\theta$, Tajima's D): MEGA 6.0 (Tamura et al., Molecular Biology and Evolution, 30, 2725-2729, 2013) and VariScan 2.0.3 (Hutter et al., BMC Bioinformatics 7, 409, 2006) for the Linux platform; results were confirmed using both packages. Nucleotide diversity was calculated for each gene (WGS data) or a sliding window (INFINIUM® data: 10 SNPs window size and 5 SNPs window increment). MS (Hudson, Bioinformatics 18, 337-338, 2002) was used to calculate 10,000 replicate simulations of a neutral model with the values of $\theta$ generated by VariScan. Since soybean is known to be subject to recent population bottlenecks as a result of domestication, we ran a range of simulations modeling instantaneous bottlenecks from 10,000 to 100 generations before present in order-of-magnitude increments. This and a similar range of recent population growth models consistent with expansion of a cultivated population over the same timeframe produced lower threshold values than the neutral model. The more stringent neutral model values were used to create a P-value lookup table, P-values were calculated for each window, and a false discovery rate correction applied to the P-values. TASSEL 3.0 (Bradbury et al., Bioinformatics, 23, 2633-2635, 2007) was used to evaluate linkage disequilibrium (LD) for both datasets. The full matrix was selected for comparisons. The fixation index ($F_{ST}$) was calculated for the INFINIUM® data as follows: Two separated populations, the first population with 46 single-copy germplasm accessions and the second with 48 multiple-copy accessions, were selected based on the genomic qPCR and whole-genome shotgun sequencing results.

Significant values of $F_{ST}$ were determined by calculating a P-value using a log-likelihood (G) based significance test and then applying the Bonferroni correction (alpha level 0.01) on P-values obtained for each locus. For comparisons between soybean populations based on their origin, three major countries (China, Japan, and Korea) were selected as potentially geographically distinct populations. The fixation index ($F_{ST}$) was calculated for each SNV using GENEPOP 4.3 (Rousset, Molecular Ecology Resources, 8, 103-106, 2008).

Population Structure Analysis

Using the admixture model (STRUCTURE version 2.3.4; Pritchard et al., Genetics 155, 945-959, 2000; Falush, et al.,

*Genetics* 164, 1567-1587, 2003) we estimated the shared genetic structure of the *Glycine max* & *G. soja* population of 15,452 accessions genotyped using the soybean INFINIUM® array. After removing individuals with ambiguous originality, 15,452 individuals were analyzed across 42,509 INFINIUM® SNPs data for each individual. All structure runs used 10,000 iterations after a burn-in of length 10,000. The number of clusters considered was set from 2-8. The number of individuals in each subpopulation clustered by STRUCTURE is as follows: 5.A (3,776 accessions), 6.A (1,230), 6.B (2,906), 7.A (2,900), 7.B (913), 8.A (2,865), and 8.B (1,115). Each subpopulation was used for the Tajima's test as described above.

Copy Number Variation at Rhg1

We investigated copy number variation of the previously described Rhg1 repeat (Cook et al., *Science,* 338, 1206-1209, 2012) within soybean germplasm accessions (Table 1). While the two genotypes PI 88788 and Peking represent the two main sources of Rhg1-mediated SCN resistance, several other germplasm accessions, not known to be related by pedigree, have been shown to have genetic SCN resistance, possibly mediated by Rhg1 (Concibido et al., *Crop Science,* 44, 1121-1131, 2004). We investigated lines that were previously described to show SCN resistance interactions of any type (Diers et al., *Crop Science,* 37, 1966-1972, 1997; Chen et al., *Genome,* 49, 938-949, 2006). Firstly, we ascertained the presence/absence of the previously described CNV event (Cook et al., *Science,* 338, 1206-1209, 2012) in the SCN-resistant soybean germplasm, by using a PCR assay specific to the fusion site common to the previously characterized repeats. Since we only investigated accessions positive for the canonical repeat junction characteristic of the cloned Rhg1 locus, we cannot rule out the possibility that other copy number variations occur at this locus that do not have the same repeat fusion site. However, from a total of 88 accessions subjected to whole-genome sequencing, all 25 accessions that showed greater than one copy at the Rhg1 locus were also positive in the fusion site assay.

Out of 106 accessions, 62 showed a product in a PCR that targeted the unique fusion site between tandemly duplicated copies at Rhg1. This indicates the presence of the repeat described by Cook et al. (*Science,* 338, 1206-1209, 2012), with the same junction sequence at the Rhg1 locus (Table 1). Secondly, copy number of the Rhg1 repeat in each accession was estimated using genomic quantitative PCR (genomic qPCR). A wide distribution of copy number was found among the accessions, with known copy number variants possessing 3 copies (Peking, PI 89772, PI 437654, PI 90763), 7 (Cloud), 9 (PI 88788), and 10 (Fayette, PI 209332) showing the expected copy numbers (FIG. 3; Cook et al., *Science,* 338, 1206-1209, 2012; Cook et al., *Plant Physiology,* 165, 630-647, 2014). Estimated copy number was then independently confirmed in fourteen selected lines by performing WGS and calculating relative read depths acquired from alignments to the Williams 82 reference genome. A broad diversity of CNV among Rhg1 loci was detected; two, 3, 4, 6, 7, 9, and 10 copies were detected in different *Glycine max* accessions and one three-copy variant in a *G. soja* accession (FIG. 3; Table 1). Notably, despite its pedigree derived from PI 88788, we found that Fayette had 10 copies of the repeat as previously described, but PI 88788 had 9 copies, consistent with Fiber-FISH data (Cook et al., *Plant Physiology,* 165, 630-647, 2014). This suggests that an event that increased copy number by one unit occurred during the process of selection for the Fayette cultivar.

Classification of Repeat Types by Sequence

The WGS data were analyzed for nucleotide sequence variations within Rhg1, and amino-acid variants inferred from the nucleotide sequence. In total, 149 positions that harbor SNVs were identified within the sequence that comprises the Rhg1 repeat across eight separate copy numbers, including the susceptible single copy versions of the sequence (FIG. 9). We detected several patterns of sequence variant within and between copy numbers. Firstly, the patterns of SNVs in each genotype were correlated with copy number of the genotype. For variants with three copies or more, the first 8 kb region was clearly differentiated from the Williams 82 sequence in all copies (region 'i' in FIG. 9). In region 'ii' in FIG. 9 in types with 4-10 copies, all but one copy of the repeat varies from the reference (the exception being the SNV at 1,657,025 bp (labeled 'iii' in FIG. 9) which likely arose after the origin of the repeat). In the three-copy variant, the entire 31.2 kb unit is distinguished from the reference by multiple sequence variations. Variations throughout the Glyma18g02590 gene encoding an α-SNAP protein were observed in all multiple copy lines ('iv' in FIG. 9). No sequence variants, however, were found in the next gene, a protein of unknown function (Glyma18g02600) (region 'v' in FIG. 9). For one genotype with two copies, all of the nucleotide variants showed 0.5 probability of occurring in the shotgun genome sequence, suggesting two distinct repeat sequences, only one of which differs from the Williams 82 reference. In a comparison between the single copy types, 24 SNVs differing from Williams 82 were found ('vi' in FIG. 9). These 24 variants were identified in the accession PI 518751 and, significantly, were also detected in resistant, multiple copy loci (2 through 10 copies). These variants are located in the region labeled 'vi' of FIG. 9, which lies from the 5' end of Glyma18g02610 (a wound-inducible protein) to the end of the repeat.

FIG. 9 reveals the physical distribution of variants in the tandemly duplicated blocks, and thus provides intriguing evidence for specific crossover points during the evolution of the repeat. However, since the reads are far shorter than the length of the repeat, it was unclear whether these sequences represent distinct repeat subtypes, or whether individual repeat units show extensive variation within themselves. A previous study (Cook et al., *Plant Physiology,* 165, 630-647, 2014) also reported SNV heterogeneity between repeats in high-copy Rhg1 loci, but without determining the origin of these SNVs within the structure of the repeat. Therefore, we set out to determine variants that differentiate the multiple repeated loci. To investigate the diversity within the individual copies, we employed a haplotype phasing technique, using paired reads to connect variants that are present in the same copy among multiple copies (FIG. 10A). Four subtype configurations (referred to henceforth as subtypes W, P, $F_A$, and $F_B$) were obtained by phasing 149 SNVs in the repeats from Williams 82 (W), Peking (P), and PI 88788 (F). A SNV located in an intergenic region (1,657,025 bp on the chromosome 18) between two genes, Glyma18g02610 and Glyma18g02620 was useful in developing the hypothesis that there are four general types of repeat (W, P, $F_A$, and $F_B$; FIG. 4A) in the multiple copy versions of the locus. We interpreted the data in FIG. 9 as Williams 82 carrying only a single copy of the W type of the 31.2 kb sequence, Peking having three copies all of the P type, and PI 88788 having eight $F_A$ or $F_B$ copies and a copy of W. Since individual copies could not be definitively linked to the rest of the repeat sequence as a result of zero sequence diversity in the vicinity of Glyma18g02600, we then performed a phylogenetic analysis of the sequences of the Glyma18g02590 gene. The four versions of the repeat present in the previously characterized PI 88788, Peking and Williams 82 genotypes (W, P, $F_A$, and $F_B$) were found to be representative of all of the repeat units in other copy number alleles, all of the repeat units falling into one of these four categories (FIG. 4B). By combining data on the frequency of sequence variants in different germplasm accessions with different repeat composition (Table 4) and using Sanger sequencing (FIG. 10B) to confirm the presence of SNV variants, the composition of repeat subtypes within each Rhg1 allele was estimated (FIG. 4C). The Williams 82 and other single copy genotypes investigated appear to only have the W type present. The three-copy accessions all had only one (P) subtype as in the Peking genotype. The one two-copy accession had one copy of P and one of W. The six, 7, 9, and 10 copy alleles all have the same three subtypes present as PI 88788 ($F_A$, $F_B$, & W), with W always present in one, partial copy. As indicated in FIG. 9, the centromere-proximal repeat copy in these accessions has a 5' (telomere proximal) sequence identical to $F_A$ or $F_B$ up to and including the variant at 8,068 bp. The sequence then becomes highly similar to the W sequence beginning with base 8,114 and continuing to the fusion site at the end of the repeat. Thus, the PI 88788 genome has 9 $F_A$ and $F_B$ type sequences of the Glyma18g02580 gene but eight $F_A$ and $F_B$ copies, and one copy of the W sequence for Glyma18g02590, -2600 and -2610. The germplasm accession PI 89008, with 4 copies, had three copies of subtype $F_B$, again with just one copy of W. By re-analysis of the fosmids previously used to clone the repeat sequence (Cook et al., Science, 338, 1206-1209, 2012), the partial subtype W sequence in the PI 88788 genotype was found to be located at the centromere-proximal end of the repeat. Sanger sequencing was also used on DNA amplified from the very 3' end of the Rhg1 repeat (Table 5) to confirm the presence of the variant at this position. It is therefore likely that the subtype W sequence is also centromere-proximal in the genotypes containing $F_A$ and $F_B$ in multiple copies with one copy of the W subtype of Glyma18g02590 (FIG. 4C).

We then investigated the predicted amino acid sequences of the four genes in the repeat, and how these varied between the duplicated copies. From all available Rhg1 repeat subtypes in all genotypes, the predicted amino acid sequences relative to the Williams 82 reference genome (subtype W) were investigated. No differences in encoded amino acid sequence were identified for Glyma18g02580 (where there were two synonymous substitutions), Glyma18g02600 (no variants at all), or Glyma18g02610 (four synonymous substitutions) (Table 6 However, several variants exist in amino acid sequence of the α-SNAP protein (Glyma18g02590) (FIG. 4D; Table 6). Subtypes $F_A$ and $F_B$ are different from W at several locations. The amino acid sequence is identical between subtypes $F_A$ and $F_B$, except for one variant in some copy number variants (Table 6). Subtype P has a distinctive amino acid sequence for Glyma18g02590, with some amino acids resembling $F_A$ and $F_B$, some resembling W, and some unique to P (FIG. 4D; SEQ ID NOs: 24-26). It is interesting to note that PI 88788-type Rhg1 alleles likely express two different forms of the α-SNAP protein, and that Peking-derived germplasm has a third version of this protein which is distinct from either of the above.

Table 6 (below) shows single nucleotide variations (SNVs) identified at three genes within the Rhg1 repeat in 22 soybean germplasm accessions. Variant sites are numbered relative to the first nucleotide position of each gene (Δ). When multiple genotypes are observed within one accession, detected bases are divided by a vertical line. The repeat subtypes corresponding to each genotype are listed on the right. **S and R indicate susceptible and resistant to SCN, respectively. 'na' means 'data not available'. # S and N indicate Synonymous/Nonsynonymous substitution. All samples are G. max except Jidong 5, which is G. soja.

Relationship Between CNV and SCN Resistance Reactions

Figure 11:
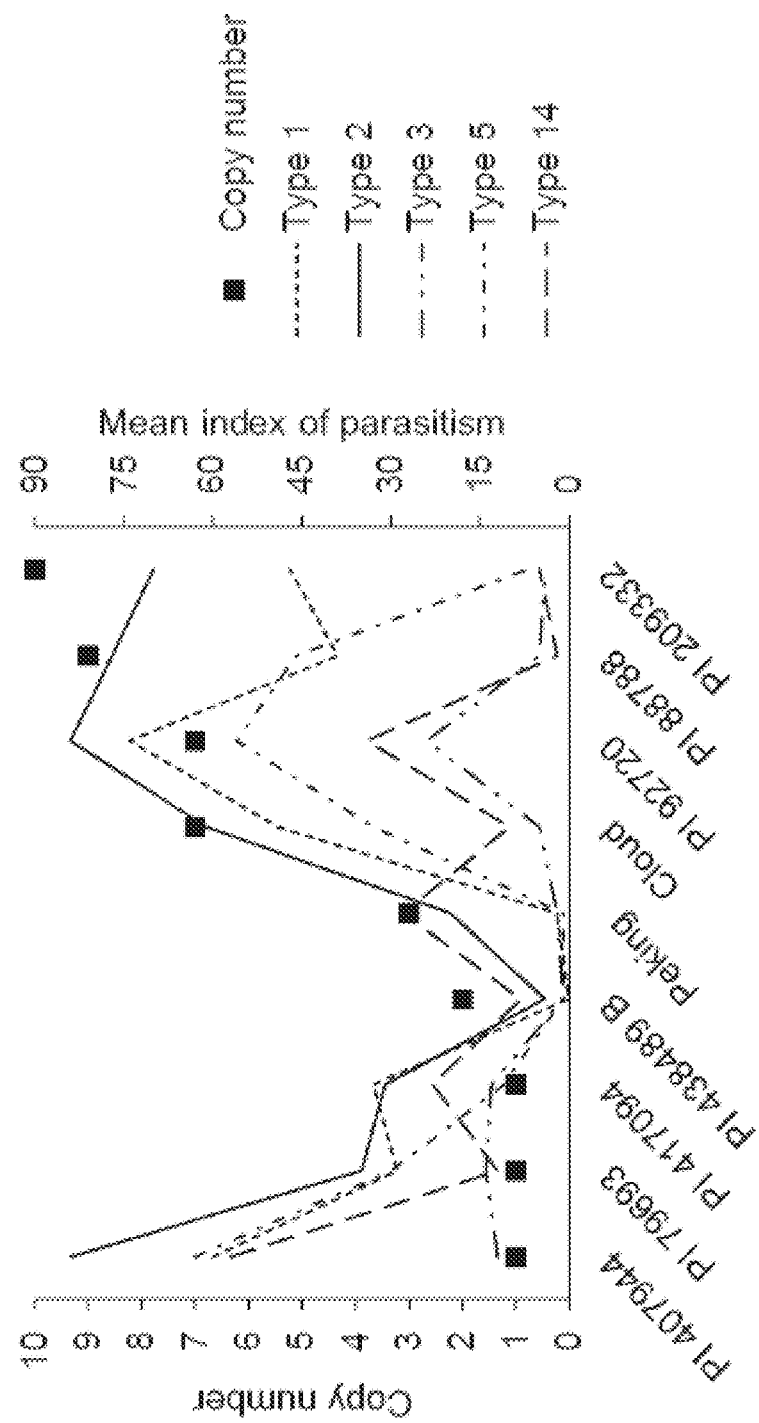
FIG. 11. Soybean cyst nematode (SCN) resistant germplasm with copy number confirmed by two methods, and their resistance reaction to SCN types. Nine SCN resistance germplasms with confirmed copy number at the Rhg1 locus and resistance reactions to five commonly used SCN types are displayed. The mean index of parasitism was obtained from Diers et al. (*Crop Science,* 37, 1966-1972, 1997).

We selected nine germplasm accessions with validated CNVs at the Rhg1 locus where complete data for resistance to diverse SCN types is available (FIG. 11). So far, Rhg1-b is the only SCN resistance locus discovered in PI 88788 (9 copies) (Concibido et al., Crop Science, 44, 1121-1131, 2004; Glover et al., Crop Science, 44, 936-941, 2004). PI 88788 shows resistance to both types 3 and 14. PI 209332 (10 copies), which harbors one more repeat unit than PI 88788, shows a similar resistance reaction to PI 88788 (Niblack et al., Journal of Nematology, 34, 279-288, 2002; Colgrove & Niblack, Journal of Nematology, 40, 39-45, 2008), but this accession also shows resistance to an additional SCN type, 5, to which Peking (3 copies) and PI 438489 B (2 copies) are strongly resistant, likely because of one or more additional loci such as Rhg4 (Concibido et al., Crop Science, 44, 1121-1131, 2004). Surprisingly, since it only has two copies at the Rhg1 locus, PI 438489 B shows strong resistance to all investigated SCN types. It is interesting to note that two seven-copy accessions (Cloud & PI 92720) show non-identical resistance reactions. This result is consistent with previous findings that while Rhg1 is usually necessary for effective nematode resistance, this resistance is modified by other resistance loci.

Diversity and Disequilibrium at Rhg1

Figure 12:
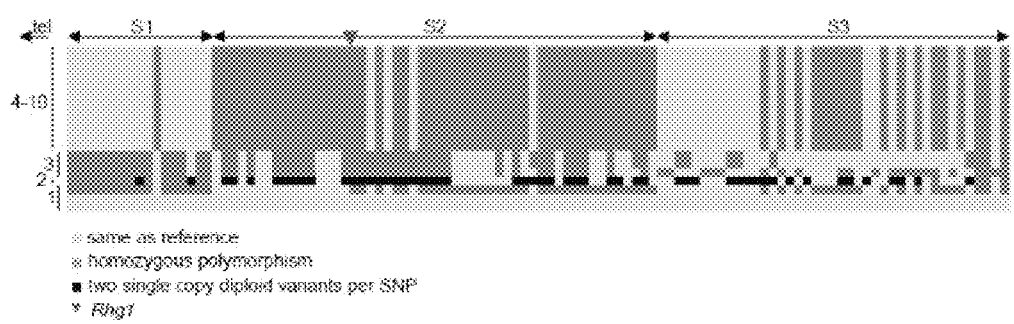
FIG. 12. Sequence variants in the 400 kb region across the Rhg1 locus, displayed according to copy number at Rhg1. Single nucleotide polymorphisms (SNPs) in coding DNA sequence (CDS) of genes in germplasm accessions are represented as colored blocks. Copy number in the accession is denoted on the left. D1, S2, and S3 are from FIG. 5B. 'tel'=telomere.
Figure 13:
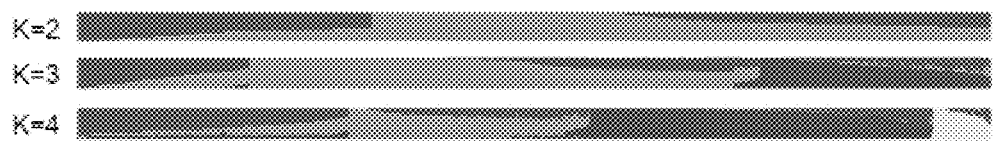
FIG. 13. Population structure estimation using K=2 through 4. Each individual is represented by a thin vertical line, which is partitioned into K colored segments that represent the individual's estimated membership fractions in K clusters.

Previously, network analysis of shared variants was used to investigate relationships between 30 high, low and single copy Rhg1 accessions (Cook et al., Plant Physiology, 165, 630-647, 2014). However, the reconstruction of the repeat sequences using phasing allowed us to use phylogenetic approaches to infer ancestry of the individual repeated units within each Rhg1 locus. We initially analyzed sequence variant data from 18 soybean accessions where we had analyzed WGS data and validated the presence of the repeat in the genome. Since the repeat itself is variable in gene dosage and thus difficult to accurately genotype, coding DNA sequence (CDS) was analyzed for variants in 38 genes flanking Rhg1 in the single-copy 400 kb region either side of the repeat. Nucleotide diversity (π) ranged between zero and 0.00205 in CDS in this region across these accessions. As the location neared the Rhg1 locus, π rose sharply, most notably in the 70-80 kb region closest to the telomere-proximal end of the repeat (top graph in FIG. 5A). The nucleotide diversity rose to almost six times the G. max average, 0.00053 (Zhu et al., Genetics, 163, 1123-1134, 2003) in the Rhg1 flanking regions of accessions with 3, and 9 and 10 copies (middle and bottom respectively in FIG. 5A). In contrast, low and even zero values of sequence diversity were seen at greater distances from the locus. We thus investigated linkage disequilibrium (LD) surrounding the Rhg1 locus. The LD (measured by $R^2$) within the ~150 kb of the S2 region containing the Rhg1 locus is strong and statistically significant (FIG. 5B; FIG. 12). Thus, we concluded that a block of strong LD extended for 70-80 kb either side of the repeat. We then used the apparent boundaries of the LD block, combined with the regions where nucleotide diversity quickly rose or fell (vertical lines in FIG. 5A), to define three linkage blocks (S1, S2 and S3; FIGS. 5A and 5B) surrounding the repeat, with S2 being the block containing the Rhg1 repeat itself.

Evolutionary Analysis of Rhg1 Repeat Units

Figure 5C:
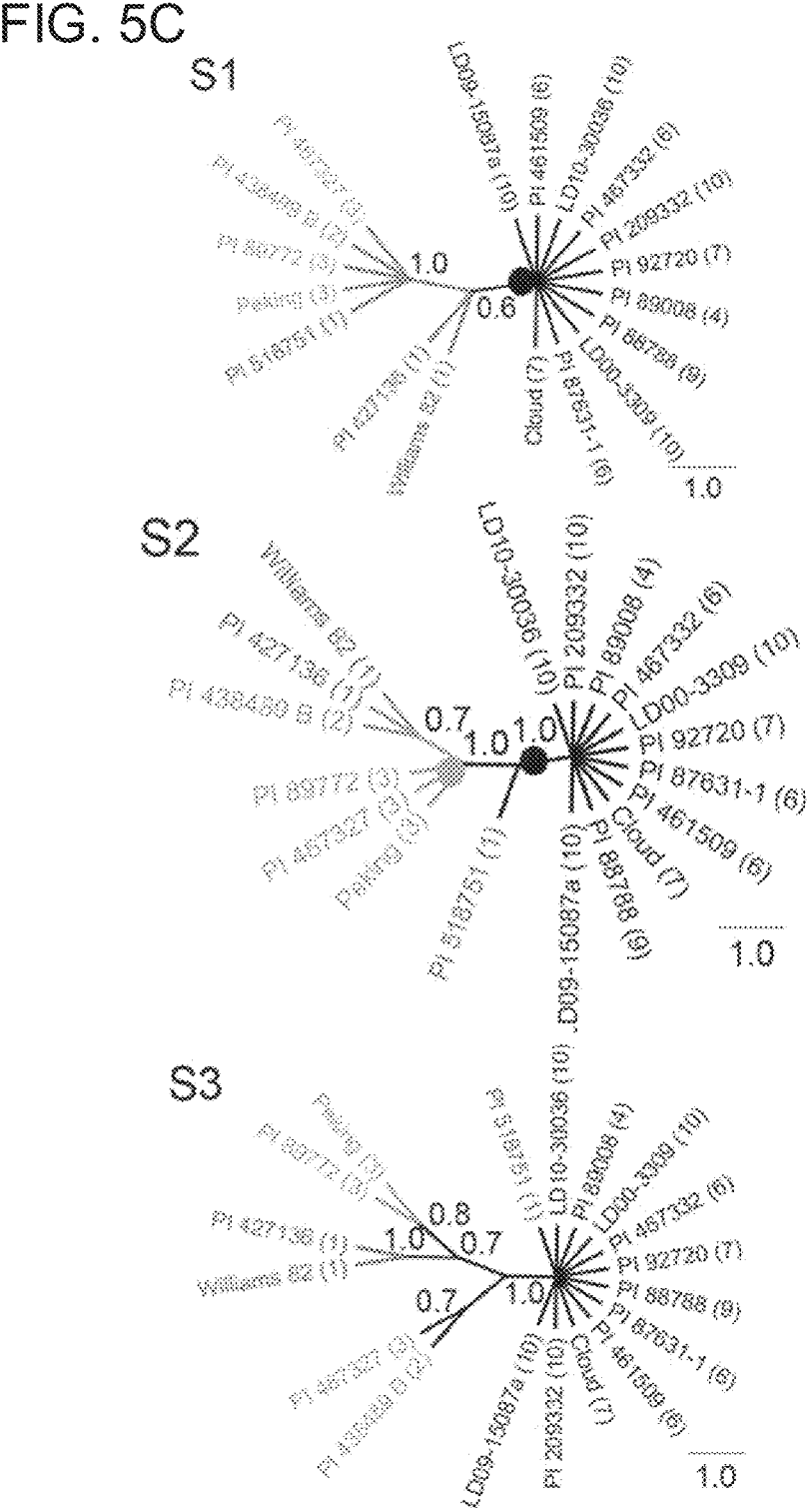

While the Rhg1 repeat itself is polymorphically repetitive and thus not readily amenable to phylogenetic analysis, the surrounding regions, if in strong LD, can be used to determine the relatedness of the Rhg1 genomic regions in the accessions carrying the repeat. Within each of the three regions S1, S2 and S3, we performed phylogenetic analysis of the 18 accessions that underwent WGS using maximum parsimony (MP), in the case of the S2 region using only sequences outside the repeat. The resulting phylogenetic trees clearly showed that three groups were found in the S2 region, (the Rhg1 locus and a ~70 kb region extending either side (FIG. 5C)). The tree for the S2 region, while derived only using the genomic sequence outside the repeat, corresponds well to both the copy number data and the phylogenetic analysis of the repeat subtypes. Accessions with more than three copies (with $F_A+F_B$ and W repeat types) form a distinct Glade, as do all those with three copies (P repeat type) (FIGS. 4B, 4C, and 5C). The single copy types do not cluster into a monophylectic group. We do not see precisely the same clustering in the S1 and S3 regions, which are likely sufficiently distant that LD around the repeat has broken down (FIG. 5C). Nonetheless, genotyping outside the repeat in the S2 region can be used to detect the Rhg1 accessions with either three or more than three copies, which correspond to all the Rhg1 alleles so far found to be useful in plant breeding.

Signatures of Selection at Rhg1

Figure 6A:
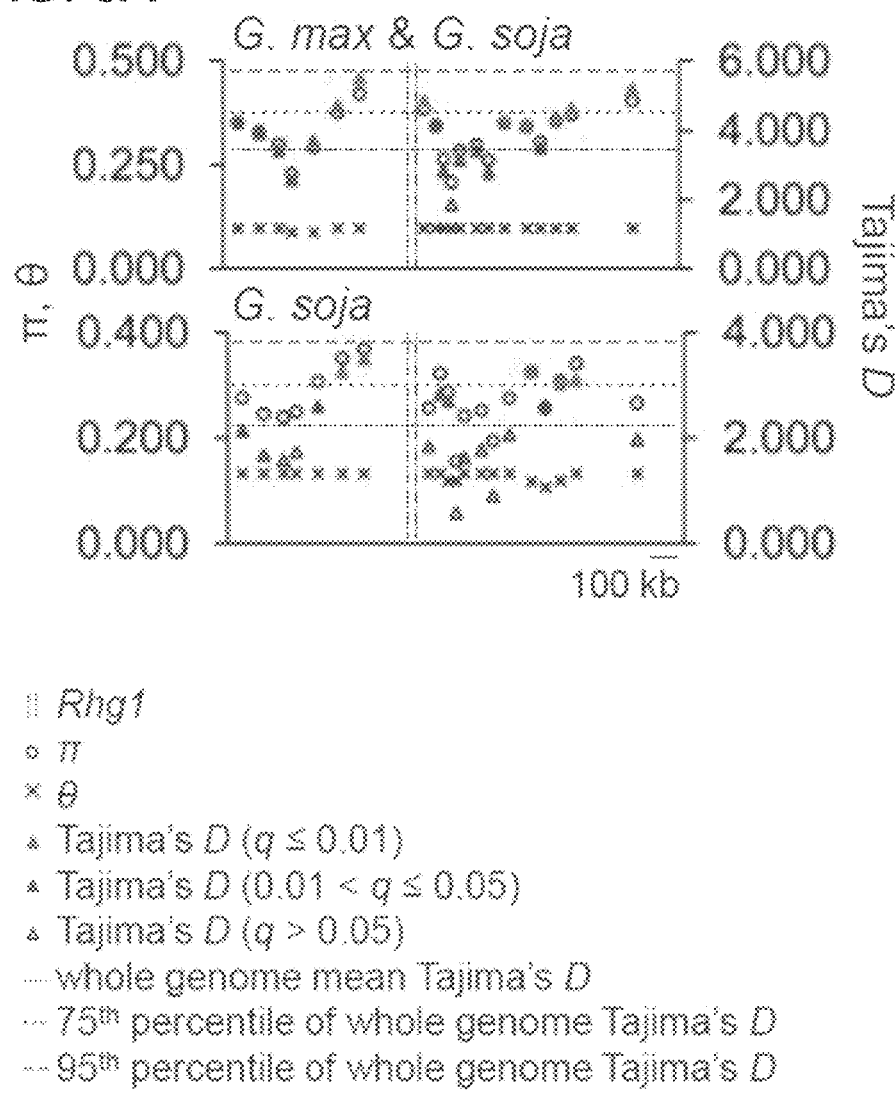

We next investigated signatures of selection for Rhg1 in soybean populations by testing neutrality and population differentiation. Using high-density SNP genotyping data generated using the soybean 50K Illumina SNP array (Song et al., PLoS One, 8, e54985, 2013) for the soybean germplasm collection (available on the World Wide Web at soybase[dot]org), we initially analyzed the entire dataset of currently genotyped accessions (19,548). High nucleotide diversity ($\pi$) and positive Tajima's D (both statistically significant and well above the average for the soybean genome) were apparent near the Rhg1 locus in soybean (Glycine max & G. soja) (top graph in FIG. 6A). Wild soybean, G. soja, also showed a very similar selection signature to the whole population of germplasm accessions (bottom graph in FIG. 6A).

A high fixation index ($F_{ST}$), significantly (P≤0.01) associated with population differentiation near the locus (FIG. 6B), was also observed at Rhg1 when the Rhg1-carrying genotypes were considered as a separate population, to test if Fst is higher within the repeat-carrying genomes than expected if all the polymorphisms were randomly distributed among accessions. This effectively indicates that the repeats are in linkage disequilibrium (LD). LD surrounding the Rhg1 gene was also detected using the $R^2$ method (FIGS. 5B and 6B). Interestingly, the LD around Rhg1 was less marked on the centromere proximal side of the repeat. Thus, four indicators (Tajima's D, $\pi$, LD and $F_{ST}$) suggest that differential selection may have occurred around the Rhg1 locus.

Geographic and Genetic Structure of Nematode-Resistant Populations

To test whether the signatures of selection could be affected by the geographic area of origin for the accessions, the entire soybean germplasm high-density SNP dataset was regrouped according to the origin of each germplasm accession, then three major groups, China (3858 accessions), Korea (3311), and Japan (2466) were selected. The repeat was present in all of these populations, in both the three copy and more than three copy versions. Overall, no significant population differentiation was detected between Korean and Chinese accessions (KR vs CH), and Chinese and Japanese (CH vs JP) (top and bottom graph in FIG. 6C respectively).

A lower degree of population differentiation compared to KR vs CH and CH vs JP was observed between Korean and Japanese accessions (KR vs JP) (middle graph in FIG. 6C).

Figure 7B:
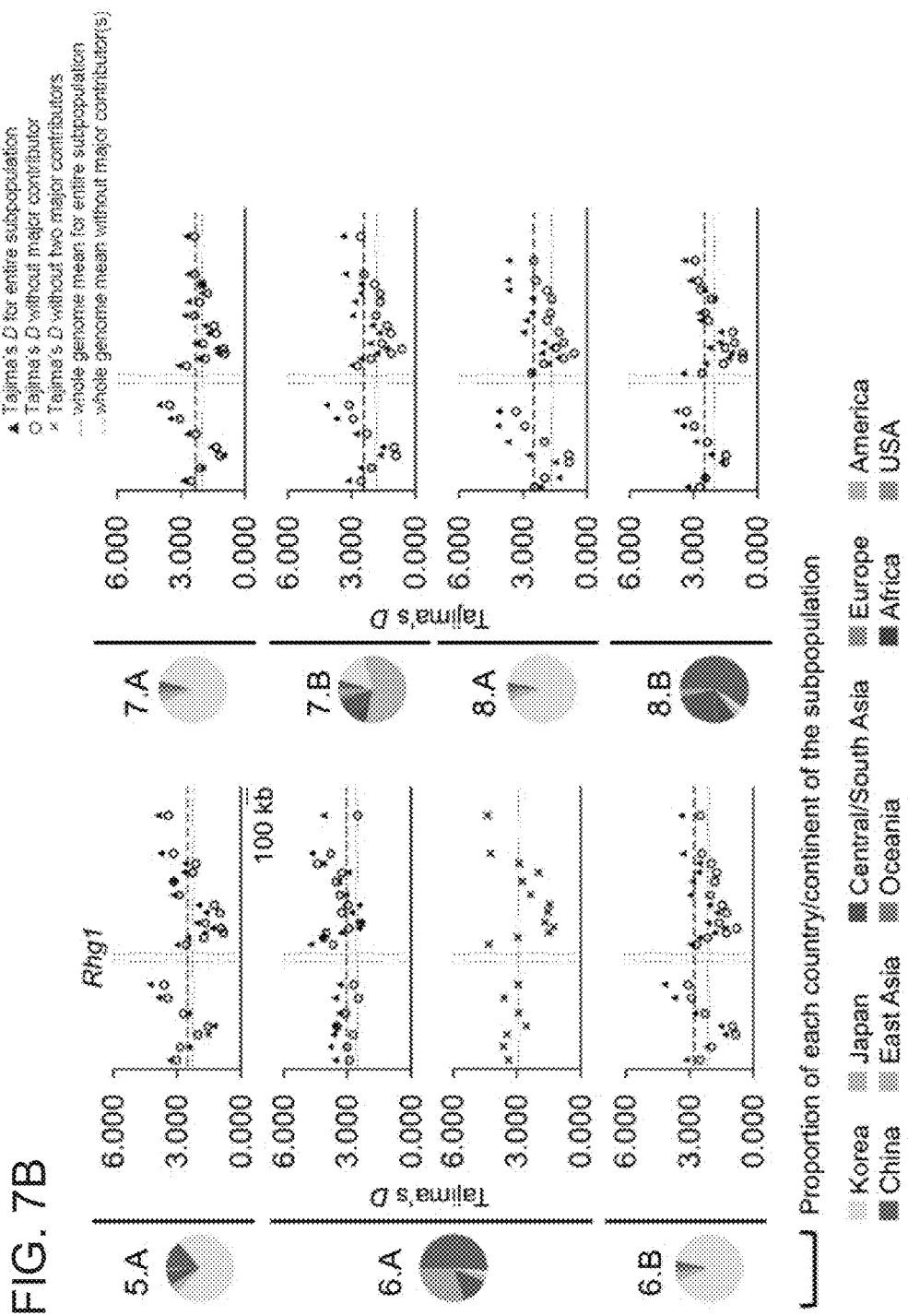
Figure 14:
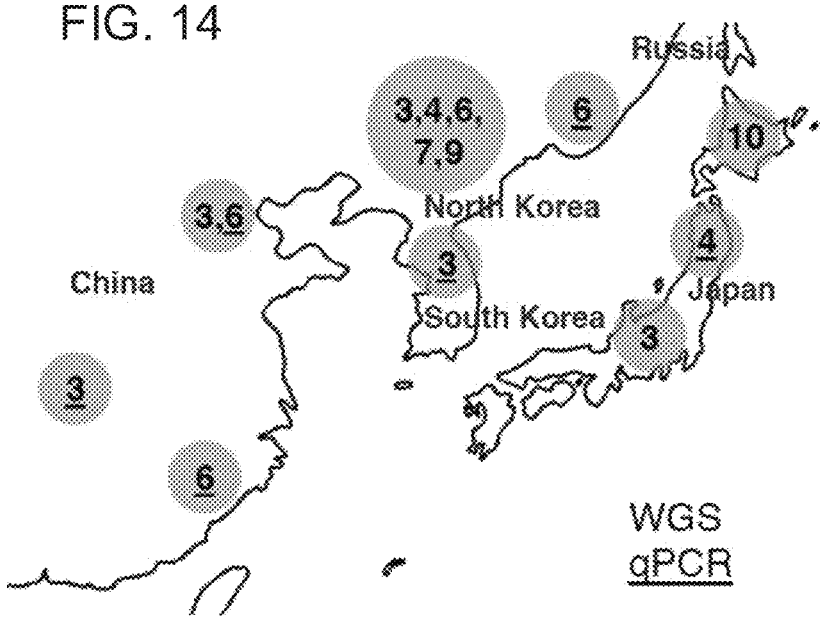
FIG. 14. Map of East Asian collection localities for SCN resistant soybean germplasm, showing copy number variation in the Rhg1 locus. The thirty-eight resistant germplasm accessions with Rhg1 copy number determined are distributed among diverse geographical regions. Germplasm collection coordinates (or city/province) were obtained from the National Plant Germplasm System (on the World Wide Web at ars-grin.gov/npgs). Germplasm accessions without specific localities are as follows: twelve accessions from China, one from Japan, one from Korea, and six with unknown origin. WGS: data supported by whole genome sequencing. qPCR: data supported by genomic qPCR.

Since false signals of selection can be caused by population structure, we evaluated whether the signatures of non-neutral selection at the Rhg1 locus could be related to population demography. We thus clustered the population according to INFINIUM® SNP data (FIG. 7C; FIG. 14). We observed a strongly positive value of Tajima's D (in all cases above the G. max genome average for the population) in all but one subpopulation (6.A in FIG. 7B). The multiple copy accessions are not confined to 6.A but are present in multiple subpopulations. In each case the pattern resembles that obtained from the full population data described in FIG. 6A. Since most subpopulations are dominated by accessions from one country, we tested whether removal of those accessions altered the result; this did not appreciably change the pattern (FIG. 7B). Therefore population structure is not primarily responsible for the observed signature.

Figure 8:
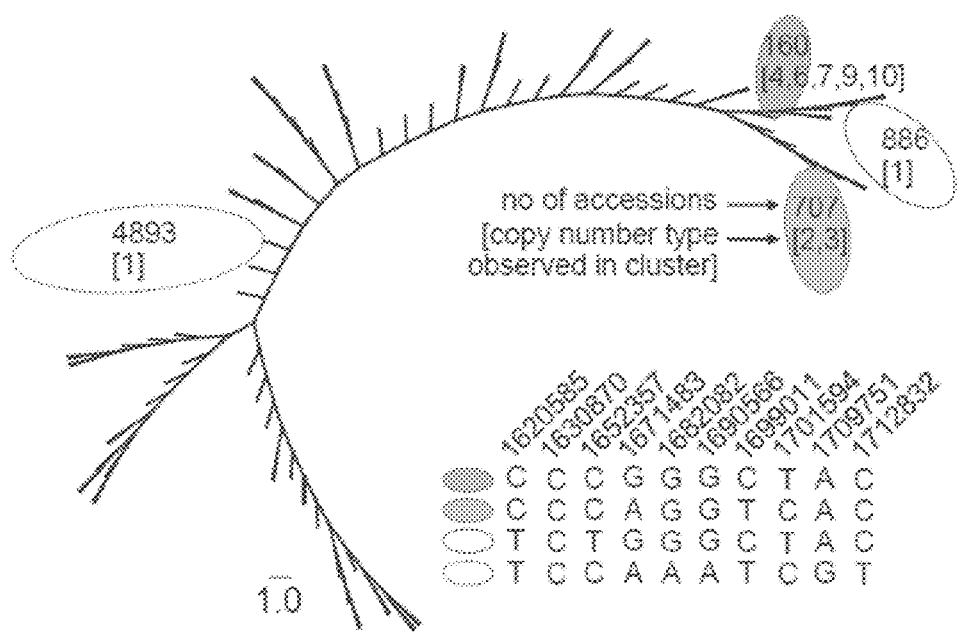
FIG. 8. Parsimony tree of 15,996 soybean accessions at the S2 linkage disequilibrium block surrounding Rhg1. The four terminal branches containing all germplasm accessions described elsewhere in the manuscript are labeled, together with the number of accessions carrying the same combination of SNPs.

The strong LD around the Rhg1 locus, and the shared ancestry of the SNPs within the range of LD, means that high-density genotyping data can potentially be used to classify accessions that likely carry alleles of Rhg1. In order to determine how common the Rhg1 genotype is within the germplasm collection, a maximum parsimony phylogenetic approach was applied to cluster the SNPs informative for copy-number alleles within the S2 LD block across the entire germplasm collection. A total of 10 SNPs, 9 located in sequence region S2 in FIG. 5, and one within the Rhg1 repeat unit, formed 89 distinct combinations among 15,996 germplasm accessions (all accessions bar those that were released as cultivars) (FIG. 8; Table 7). Table 7 (below) shows 15,996 soybean germplasm accessions clustered by maximum parsimony phylogenetic analysis of the sequence region near the Rhg1 allele, indicating germplasm accessions predicted to carry Rhg1.

Four distinct SNP combinations corresponded to the clusters identified in FIG. 5C. Validated multiple copy germplasm fell into one of two clusters, one containing 160 accessions and the other 707. A cluster with 160 accessions in FIG. 8 corresponds to germplasm with 4-10 copies, while a second cluster with 707 accessions corresponds to 2 or 3 copy germplasm. Other clusters, including one that lies on the same branch as the two multi-copy accessions, have either one or an unknown number of copies. Thus, at least 867 accessions have been identified as potential Rhg1 alleles, most of which are likely to represent new sources of the resistance gene, and several divergent but related groups have been identified that may be investigated for the presence of new alleles of Rhg1.

In the present disclosure, several major new findings are provided: (i) Rhg1 is a highly variable repeat region that can be accurately genotyped by genomic qPCR. We add to previous knowledge of the diversity of this repeat, Rhg1 within the lines investigated having two, three, four, 6, 7, 9 or 10 tandem repeats of just over 31 kb each; (ii) the individual repeated units of known Rhg1 alleles can be classified into four types based on sequence. Some Rhg1 loci carry up to three different types of repeat unit; (iii) the Rhg1 locus is in LD with the surrounding region of the genome, (iv) clustering of accessions by flanking sequence matches the phylogenetic analysis of the individual repeat units, and thus existing high density SNP data on flanking regions can be used to classify in silico thousands more accessions for Rhg1 presence and type; and (v) analysis of variants in the region around Rhg1 shows signatures of selection. The implications of these findings are discussed below.

Origin of Rhg1

The cloning of Rhg1 was the first observation that plant disease resistance loci can consist of a multi-gene cluster CNV of non-canonical resistance genes in tandem formation (Cook et al., Science, 338, 1206-1209, 2012). The Rhg1 locus is common among nematode-resistant G. max accessions, because over half (58%; 62 out of 106) of screened SCN-resistant germplasm is positive for the presence of the repeat junction. It is possible that other copy number variations exist at this locus and this number could be higher, but we have found no evidence for repeats at Rhg1 that do not contain the canonical fusion site, despite investigating a total of 88 whole-genome sequences for such repeats.

Soybean originated geographically in East Asia, where wild Glycine grows naturally. The PIs or germplasm accessions carrying Rhg1 (not including lines submitted as U. S. cultivars) used experimentally in this study originate from distributed locations across East Asia (22 from China; 8 from Japan; 7 from Korea; 1 from Russia; FIG. 14). These 62 lines share a common repeat junction, strongly suggesting they share a common origin. Most likely the repeat originally arose as a duplication caused by unequal crossover, with subsequent illegitimate recombination events then giving rise to versions with more than two copies. Taken together, the evidence suggests that the hypothetical duplication event that created the copy number variation in Rhg1 happened sufficiently long ago in soybean evolution for it to be distributed across the area where soybeans are endemic. In contrast to this, it has been reported that the CNV locus conferring the maize aluminum tolerance trait is detected only in maize lines sharing the same geographical origin (Maron et al., Proc Nat Acad Sci USA, 110: 5241-5246, 2013). It has been estimated that the divergence of the progenitors of domesticated G. max and one modern wild G. soja line was 0.27 million years ago (MYA) (Kim et al., Proc Nat Acad Sci USA, 107: 22032-22037, 2010); domestication itself is much more recent, occurring within the last 10,000 years. One of the G. soja accessions analyzed by whole-genome sequencing carries three copies of the tandemly duplicated unit at Rhg1 and shows the same repeat structure as five of the three-copy G. max accessions, and the G. soja population shows the same signature of selection as the G. max population at Rhg1. This provides evidence that the origin of the tandem duplications of the 31.2 kb region at the Rhg1 locus occurred before the divergence of the common ancestors of cultivated soybean and one sequenced G. soja line; i.e. long before domestication. The estimated time of divergence of the ancestors of the G. soja line was investigated previously (Kim et al., Proc Nat Acad Sci USA, 107: 22032-22037, 2010) and G. max-like progenitors were estimated to have been in East Asia some time prior to 0.27 MYA. Since the Rhg1 repeat is distributed in both G. max and G. soja lines throughout East Asia, we postulate that the origin of Rhg1 is likely to predate this divergence.

Selection of Rhg1

Strong LD surrounding the Rhg1 locus in both the SCN resistant accessions and the population of all soybean germplasm accessions are provided. However, the LD extends for less than 100 kb, which implies that the locus has been under selection for a large number of meiotic cycles, many more than are conceivable since purposeful selection for SCN resistance by breeders began. On the other hand, other indicators of selection (such as Tajima's D) extend significantly further from the locus. This strong signature of selection is likely the result of pathogen pressure from SCN. This in turn provides evidence that SCN and resistance to SCN have been a major selective force for some time during evolution and artificial selection of G. max and G. soja.

Others have used clustering methods to show that Rhg1 has distinct sequence, as well as repeat copy number, in different accessions (Cook et al., Plant Physiology, 165, 630-647, 2014). Using phylogenetic analysis of the individual repeat sequences we assembled, and the flanking region in LD, we show that the individual repeat units in Rhg1 can be categorized into three lineages (three, more than three, and two copies; P, $F_A/F_B$, and W repeat types). Evidence for potentially divergent function comes from genes within the repeat, primarily the predicted α-SNAP protein, which also can be classified into three groups according to predicted amino acid sequence. Two of these variants are present together in the most widely used Rhg1 alleles from Fayette and PI 88788.

Population genetic analyses of the SNPs in a 1.5 Mbp region around Rhg1 revealed positive Tajima's D statistics, which along with LD around the locus, high nucleotide diversity and $F_{ST}$, make positive selection likely at this locus. Population structure is unlikely to have resulted in a false signature of selection, since subpopulations derived from genotype-based clustering show the same signature. Just one subpopulation cluster (6.A in FIG. 7B), which is composed of about 45% of U. S. and European accessions, showed very minimal signs of selection on this locus. Since positive selection at this locus is likely the result of pathogen pressure from SCN, the first report of SCN in the US was 1954 (Winstead et al., Plant Disease Reporter 39, 9-11, 1955) and there has been no outbreak of SCN throughout Europe so far, this observation fits the conclusion that positive selection at the locus is a result of SCN pathogen pressure in areas with a longer history of soybean and SCN populations.

The $F_{ST}$ statistic shows fixation around the locus if the lines carrying Rhg1 are regarded as a separate population. This observation amounts to an alternative measurement of LD around the locus, and fits with signatures of positive selection. However, when accessions are compared between countries of origin as separate populations, $F_{ST}$ gives ambiguous results, with some comparisons showing reduced fixation around the locus. Segregation distortion at the Rhg1 locus has been reported in modern soybean breeding populations (Kopisch-Obuch & Diers, Theoretical and Applied Genetics, 112, 199-207, 2006). Significantly fewer homozygous-resistant plants were observed in analyzed $F_4$ populations and seedling emergence was significantly lower for SCN resistant plants, which imply active selection on this locus to stabilize the segregation distortion. Combining the evidence for wide variation in copy number at the locus, high LD and Tajima's D, the selection signature independent of the domestication bottleneck, relatively low or ambiguous $F_{ST}$ between geographic populations, and reduced viability of Rhg1 homozygotes, we conclude that the Rhg1 locus may be subject to balancing selection within populations in East Asia. We also saw that population differentiation in $F_{ST}$ varied across geographic location comparisons. A likely explanation of this is unequal pathogen pressure of SCN in different geographic areas.

Mechanism of Repeat Origin and Variation

Although recent CNV surveys in plants are increasing our knowledge of the extent and patterns of CNV in plant genomes such as soybean (McHale et al., Plant Physiology, 159, 1295-1308, 2012), the mechanisms of CNV generation remain unknown in most cases. All Rhg1 sequences examined so far possess the same junction point between the repeat and the genome, strongly implying a common origin, most likely a single duplication event by unequal crossover. A partial sequence (185 bp) having ~75% identity to the 5' and 3' long terminal repeat (LTR) regions of Ty1/copia-like retrotransposons RTvr1 or RTvr2 is present within 400 bp of the duplication junction across all germplasm investigated. The Rhg1 locus is located close to the telomere (within 3% of the chromosome length) of chromosome 18. It is known that higher rates of recombination occur towards the telomere (Ott et al., *PLoS One*, 6, e22306, 2011). It has been suggested that high levels of CNVs in crop genomes are located preferentially in regions of high recombination (Muñoz-Amatriaín et al., *Genome Biology*, 14, R58, 2013). The source of the first duplication event to arise at Rhg1 could therefore be the result of Ty1/copia-like retrotransposon RTvr1 or RTvr2 activity in a sequence region with high recombination, which provided a similar sequence at the beginning and end of the repeated unit to allow illegitimate crossover. Once two copies of the unit were present, additional copies could readily be generated by slippage at the repeat during meiosis. The high rate of recombination at this locus, combined with strong positive selection pressure for high copy number, then led to the wide range of repeat copy number observed in the population. We found SNVs in a single copy cultivar (PI 518751) that are shared with some multiple copy types, which may represent evidence of recent crossover between repeat-carrying and single-copy lines during natural or artificial crossing and selection.

Implications for Soybean Breeding

Figure 3:
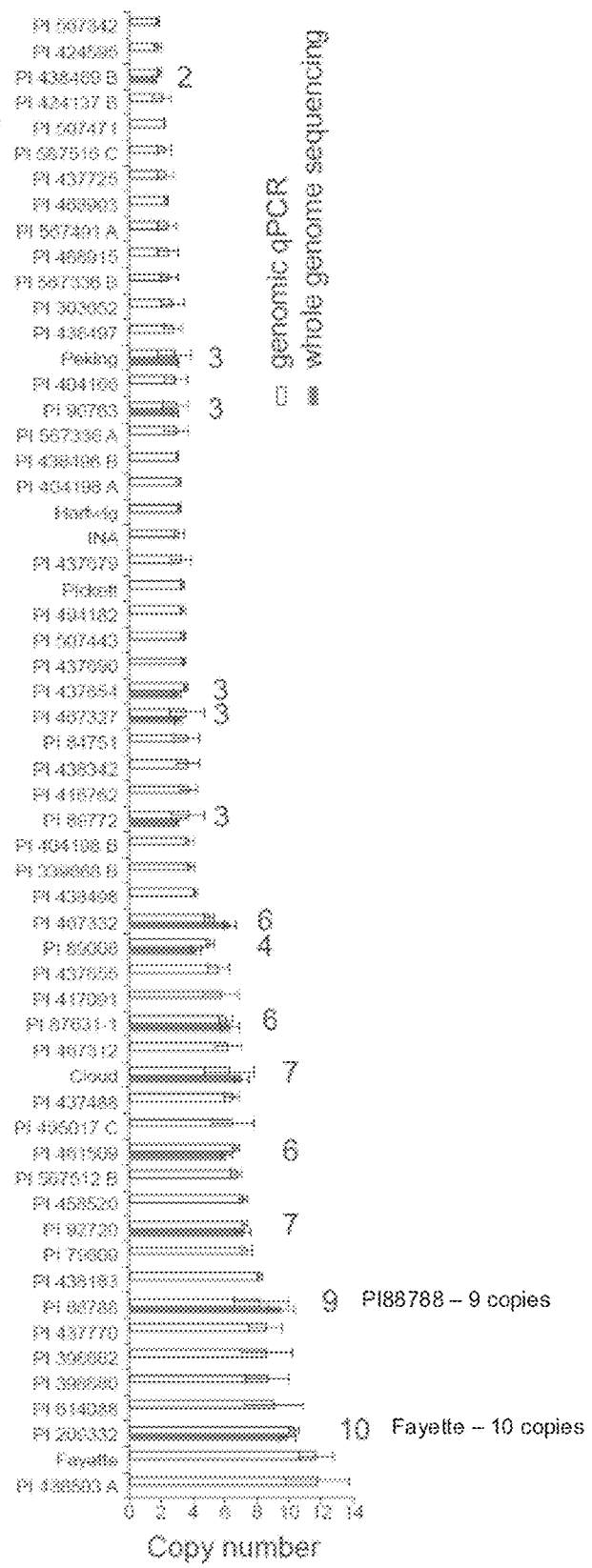
FIG. 3. Distribution of copy number at the Rhg1 locus in soybean accessions with soybean cyst nematode resistance. Estimates of copy number of the tandem duplication at Rhg1 were obtained by using genomic qPCR analysis targeting a gene (Glyma18g02590) in the repeat, and arranged in order of estimated copy number. The mean±95% confidence interval was plotted. A second estimate of the Rhg1 copy number based on read depth of whole genome sequencing was performed where data was available. Data are means±SD. The estimated copy number for lines with both types of data available (based on the whole genome data coverage) is to the right of the bars.

Fayette (10 copies) is a cultivar developed from Williams (2)×PI 88788, with the objective of transferring the SCN resistance of PI 88788 (9 copies at Rhg1; FIG. 3) to a U.S. adapted cultivar (Bernard et al., *Crop Science*, 28, 1028-1029. 1988). Given the wide range of observed copy number and this observed change during a soybean-breeding program, we speculate that alteration of the copy number at Rhg1 is rapid and continual. This suggests that manipulation of the repeat by artificial crossing and marker-assisted selection to obtain other repeat architectures is possible. For example, it may be possible to combine two different Rhg1 subtypes (e.g. subtype P and subtypes $F_A/F_B$) in a single line, if enough progeny are screened from an appropriate cross. Considering that variation in copy number has been observed within a population derived from a single Rhg1 allele (Fayette/PI 88788), it is possible that changes of copy number at Rhg1 may be a cause of variation in the effectiveness of nematode resistance observed in soybean breeding lines.

This data also gives molecular evidence to support correlation between Rhg1 copy number and female Indices (FI) observed from virulence assays. It has previously been shown that FIs from Cloud (7 copies), PI 88788 (9), and PI 209332 (10) were highly correlated, as were those of PI 438489 B (2), PI 90763 (3), PI 89772 (3), and Peking (3) (Colgrove & Niblack, *Journal of Nematology*, 40, 39-45, 2008). It is now clear from the data presented here that the first three germplasm accessions have relatively high copy numbers compared to the second four, and carry three repeat sequence subtypes ($F_A$, $F_B$, and W) corresponding to two distinct types of α-SNAP protein. On the contrary, the second four germplasm accessions have a different subtype (P), which has a third type of the α-SNAP protein. This finding strongly suggests that either the number of copies in the Rhg1 haplotype, the sequence of the α-SNAP protein, or both have a strong effect on SCN type-specific resistance. The accession PI 438489 B possesses just two copies of the Rhg1 repeat. Its repeat is composed of subtype W, which is nearly identical in sequence to susceptible single copy germplasm, and subtype P, which encodes an α-SNAP protein identical to that found in three copy alleles of Rhg1 such as Peking. Thus, only two copies are present at Rhg1 in the line, with a single copy of repeat type P. Nonetheless, the resistance spectrum is similar to that observed in germplasm with three copies of subtype P (Colgrove & Niblack, *Journal of Nematology*, 40, 39-45, 2008). This suggests that the sequence of the individual repeat units, as well as copy number, plays a role in the type specificity of Rhg1-mediated nematode resistance.

CNV at the Rhg1 locus has been selected for and retained within the population of wild soybean for some time prior to domestication. High levels of sequence and copy number diversity exist within the repeat, but surrounding SNPs are strongly linked to different repeat types. The strong LD around the locus allows classification of many soybean germplasm accessions as likely Rhg1 alleles according to the public high density SNP genotyping data. The complex sequence and structural diversity at this locus likely has had a large impact on population-level nematode resistance, potentially allowing the rapid evolution of the repeat to compete with the evolution of virulence genes within the nematode. However, previously observed fitness penalties of the Rhg1 locus combined with our observations of limited fixation within individual populations imply that the susceptible alleles may be maintained in the population by balancing selection.

Example 2: Selection for Copy Number at a Resistance Locus Improves Resistance to a Crop Pathogen Copy number variation (CNV) is implicated in important traits in multiple crop plants, but can be unstable and thus challenging to genotype using conventional genetic linkage. The Rhg1 allele of soybean conferring resistance to soybean cyst nematode (SCN) is a CNV of a 31.2 kb genomic region containing four genes. Here, we develop reliable, high throughput methods to quantify Rhg1 and other CNV for selective breeding based on the TAQMAN® PCR assay, using closing related genomic sequences as internal controls. These controls can be derived from either homeologous chromosome regions, or sequence differences between repeat units within the CNV region itself. Using these methods we were able to track CNV through genetic crosses. We show that extensive CNV exists within Fayette, a single inbred SCN-resistant soybean cultivar with a high copy number. Copy number at Rhg1 is therefore unstable within a released variety over a relatively small number of generations. Using our assay to select for individuals with altered copy number, we obtained plants with both increased copy number and increased SCN resistance relative to control plants. Thus, CNV genotyping technologies represent a new type of marker-assisted selection to select for desirable traits in breeding populations, and to control for variation within cultivars.

Introduction

Artificial selection of traits, by phenotype and/or genotype, is the basis of all breeding programs. Genotyping using molecular markers or sequencing has become widely used in plant breeding, for characterizing existing genetic variation within species, for marker-assisted selection and for genomic breeding to produce improved cultivars or (Moose and Mumm, *Plant Physiol* 147:969-977, 2008). Soybean cyst nematode (SCN, *Heterodera glycines* Ichinohe) is the most damaging pest of soybean *Glycine max* L. Merr.) in the USA in yield loss terms, and the PI 88788-derived version of the Rhg1 locus was found to confer the strongest and most useful SCN resistance known (Concibido et al., *Crop Sci.* 44:1121-1131, 2004; Kim et al., *Plant Genome* 3:81-89, 2010). Two simple sequence repeat (SSR) markers (Cregan et al., *Theor. Appl. Genet.* 99:811-818, 1999) have been widely used for marker assisted selection for SCN resistance conferred by Rhg1 since the 1990s (e.g. fine-mapping of Rhg1; Kim et al., *Plant Genome* 3:81-89, 2010). Since this time it has been known that multiple alleles of Rhg1 exist that have different profiles of resistance against SCN types.

Recent progress in understanding the genetic structure of Rhg1 has revealed that SCN resistance is mediated by CNV at the Rhg1 locus (Cook et al., *Science* 338:1206-1209, 2012). Allelic variation at Rhg1 is now can be understood to reflect both sequence and copy number of the locus, with copy number playing a dominant role (Cook et al., *Science* 338:1206-1209, 2012; Lee et al., *Mol. Ecol.* 24:1774-1791, 2015). The CNV at Rhg1 contains from one to ten copies per haploid genome of a tandemly duplicated 31.2 kb unit containing four genes (Lee et al., *Mol. Ecol.* 24:1774-1791, 2015) (all copy numbers stated henceforth in this example are per haploid genome). The current molecular markers (e.g. SSR markers, Cregan et al., *Theor. Appl. Genet.* 99:811-818, 1999; KASP assays (Kadam et al., *Plant Sci.* 242:342-250, 2016; epublished August 2015) and Shi et al., *BMC Genomics* 16:314, 2015) used to select the Rhg1 locus do so via genetic linkage to different repeat alleles, and are not capable of directly measuring CNV.

Currently, the only ways to determine copy number at the Rhg1 locus are slow and costly methods, for example whole genome sequencing (WGS) (Cook et al., *Science* 338:1206-1209, 2012; Cook et al., *Plant Physiol.* 165:630-647, 2014; and Lee et al., *Mol. Ecol.* 24:1774-1791, 2015) or fiber-fluorescence in situ hybridization (Fiber-FISH) (Cook et al., *Science* 338:1206-1209, 2012; Cook et al., *Plant Physiol.* 165:630-647, 2014). Other than Fiber-FISH, which is particularly expensive and challenging, these assays generally have insufficient accuracy to discriminate a single copy difference between high-copy genotypes (e.g. comparative genomic hybridization (CGH); Anderson et al., *G3 (Bethesda)* 4:1307-1318, 2014). The quantitative polymerase chain reaction (qPCR) method described by Lee et al. (*Mol. Ecol.* 24:1774-1791, 2015) cannot be used with sufficient throughput to genotype breeding populations. As a result, a faster and simpler marker technology is needed.

The TAQMAN® PCR assay (Holland et al., *Proc. Natl Acad. Sci. USA* 88:7276-80, 1991) has been applied to many applications including the analysis of CNV (Ingham et al., *Biotechniques* 31:132-134, 136-40, 2001; Anhuf et al., *Hum. Mutat.* 22:74-78, 2003; Schaeffeler et al. *Hum. Mutat.* 22:476-485, 2003). However, the current implementation of the TAQMAN® PCR technology for copy number analysis has two major disadvantages: (i) two sets of primers and probes, one for a target sequence and one for a reference sequence, which often have an unequal amplification efficiency and reduce accuracy and (ii) two assays are needed in separate tubes to measure the copy number of a single target, doubling the cost. The ultimate result of these disadvantages is to make the assay generally too costly for an application such as plant breeding. Here we report an adaptation of TAQMAN® PCR for the measurement of copy number that is fast, accurate and lower in cost.

The soybean genome shows clear evidence of a recent allopolyploidization event, leading to two or more homeologous, syntenic copies of the majority of the genome with small sequence differences (Gill et al., *Plant Physiol.* 151:1167-1174, 2009; Schmutz et al. *Nature* 463:178-83, 2010). The Rhg1 locus on chromosome 18 has two clear homeologs, present on chromosomes 11 and 2 (Cook et al., *Science* 338:1206-1209, 2012). Investigation of a large number of soybean germplasm accessions revealed that rapid evolution and selection of Rhg1 resulted in high levels of sequence and copy number diversity at the chromosome 18 locus (Lee et al., *Mol. Ecol.* 24:1774-1791, 2015), but there is no evidence of linkage of SCN resistance to the chromosome 2 or 11 loci, nor is there evidence of CNV at these sites. We applied this evolutionary and genomic evidence to the development of molecular genotyping markers for the Rhg1 CNV. We demonstrate the marker's capability of identifying diverse copy number types with distinct repeat units. Using data that reveal the diversity of copy number variants within a population of an SCN resistance cultivar, we select plants that have enhanced SCN resistance.

Methods

Plant Samples and Genomic DNA Preparation.

Soybean seed, including plant introductions (PIs) and cultivars, was obtained from the United States Department of Agriculture (USDA) soybean germplasm collection (Urbana, Ill.). Eight soybean germplasm lines (LD10-10198, LD10-8238, LD10-9785, LD10-9816, LD10-6923, LD10-382, LD10-1249, & LD10-3337) with available SCN phenotype data for HG types 0 and 2.5.7 and pedigree records were selected from the 2013 Northern Regional Soybean Cyst Nematode Tests. A population of Fayette (PI 518674), carrying the Rhg1 allele from PI 88788, was derived from seed stocks held at the University of Illinois in Urbana, Ill., US. A mapping population used in the 'Selective breeding for copy number' section in 'Results' was developed from a cross between the germplasm lines LD00-3309 and IA 3023 in the lab of Dr. Brian W. Diers at the University of Illinois in Urbana, Ill., US. LD00-3309 carries the Rhg1 allele from PI 88788. Plants were grown in a growth chamber set at a photocycle of 18/6 hr (day/night), 23/20° C. (day/night), and 50% relative humidity for about 10 days. Young leaf tissue was collected for each plant and kept at −80° C. until genomic DNA isolation. Genomic DNA was extracted as described in our previous study ('Fosmid library construction' section in 'Supplementary Materials' in Cook et al., *Science* 338:1206-1209, 2012) with modifications in sample homogenization steps: tissue samples were collected in Collection Microtubes (Qiagen) for a 96-well rack, then the frozen samples were homogenized using the 2000 Geno/Grinder (SPEX SamplePrep) set for 30 sec at 1,500 rpm (setting 500 at 1× rate). The final concentration of genomic DNA was 5 ng/μL.

SNV Detection.

Single nucleotide variants (SNVs) used for copy differentiation were determined in a previous study (Lee et al., *Mol. Ecol.* 24:1774-1791, 2015). Single copy number of the homeologous regions on chromosomes 11 and 2 was confirmed using WGS as previously described (Cook et al., *Science* 338:1206-1209, 2012). Sequence homozygosity for both homeologous sequence regions in *G. max* was confirmed in diverse copy number accessions. WGS for eleven accessions acting as copy number controls were obtained in previous studies: from Lee et al., *Mol. Ecol.* 24:1774-1791, 2015, PI 438489 B (2 copies), PI 89008 (4 copies), PI 461509 and PI 467332 (6 copies, copy number genotyping assay only), and PI 87631-1 (6 copies, subtype genotyping assays only), and PI 88788 (9 copies); from Cook et al. 2014, Peking (PI 548402), PI 437654 (3 copies, copy number assay only) and PI 89772 (3 copies, subtype assay only), Cloud (PI 548316) (7 copies), and PI 209332 (10 copies). The Williams 82 line was used the reference single copy accession.

Development of Genotyping Assays.

Primers listed in Table 8 were designed so that there are no sequence polymorphisms between Rhg1 (on chromosome 18) and the homeolog gene (on chromosome 11) where the primers anneal, and 2) there are sequence polymorphisms between Rhg1 and non-target homeologs on other (non-11) chromosomes (such as chromosome 2). The probes were designed so there was a single nucleotide mismatch between probe sequences. Proposed primer/probe sequences that passed the Applied Biosystems' quality control check system were ordered and used for the described work, using Custom SNP Genotyping Assays (Applied Biosystems). Two probes were designed to anneal specifically to two sequences with a single nucleotide mismatch, and labeled with VIC® or FAM™ dye. For the copy number genotyping assay (homeolog-controlled TAQMAN® PCR assay; hcTaqMan), the primer sequences were designed to amplify two genomic loci, Glyma.18G022600, one of the Rhg1 genes present in multiple copies in Rhg1 resistant lines, and a near-identical homeologous gene, Glyma.11G234400. Probe sequences were designed to anneal specifically to a sequence region where a single nucleotide mismatch exists between these two loci. We confirmed using WGS data that Glyma.11G234400 is present in one copy on chromosome 11 in all available Rhg1 copy variants. Probe 1, which generates VIC-dye fluorescence, anneals specifically to the repeat unit in the Rhg1 locus (possessing T at 1,648,291 bp on Chromosome 18). Probe 2, which generates FAM-dye fluorescence, anneals to the single copy homeologous sequence (C at 37,413,212 bp on Chromosome 11). Therefore, probe 1 generates altered amounts of reporter dye as the number of repeat units changes in multiple copy loci, while probe 2 provides a constant reference signal, thus the ratio of the two dyes is proportional to copy number.

TABLE 8

Sequence information for probes and primers used in homeolog- or tandem repeat-controlled TAQMAN ® PCR assays.

| Assay name | Sequence type | Sequence | SEQ ID NO: |
|---|---|---|---|
| hcTaqMan | Forward primer | GCAGCTGTTGGAATCATTCTTTGTT | 5 |
| | Reverse primer | AGGATCCAAATGAGAAAGAGGTTCA ATTT | 6 |
| | Probe 1 (VIC) | GGTTTATTGTATGGTG | 7 |
| | Probe 2 (FAM) | GGTTTACTGTATGGTG | 8 |
| trcTaqMan-f | Forward primer | CTGAAGTATGGAGTTAAAGGACACC TT | 9 |
| | Reverse primer | CGTTCTAATGCATTGGTTATAGCAA CAA | 10 |
| | Probe 1 (VIC) | CAGAGTTGGCAGATGC | 11 |
| | Probe 2 (FAM) | CAGAGTTTGCAGATGC | 12 |
| trcTaqMan-p | Forward primer | CACCTTCTTAATGCTGGCATCTG | 13 |
| | Reverse primer | CTGATATCGTTCTAATGCATTGGTT | 14 |

TABLE 8 -continued

Sequence information for probes and primers used in homeolog- or tandem repeat-controlled TAQMAN ® PCR assays.

| Assay name | Sequence type | Sequence | SEQ ID NO: |
|---|---|---|---|
| | Probe 1 (VIC) | TAGCAACAACGTCCTCTT | 15 |
| | Probe 2 (FAM) | TAGCAACAACCTCCTCTT | 16 |
| trcTaqMan-w | Forward primer | GGTTCGTTTAGAAGGGATGAAAATG C | 17 |
| | Reverse primer | TTCACAATGTTTCAGGTGTGTTGAA AG | 18 |
| | Probe 1 (VIC) | AGCACCGTCATCTAA | 19 |
| | Probe 2 (FAM) | CAGCACCGTTATCTAA | 20 |

For trcTaqMan (tandem repeat-controlled TAQMAN® PCR assays) distinguishing one repeat subtype from others, the probe sequences were designed to anneal specifically to a sequence region where a single nucleotide mismatch exists between one of the repeat subtypes (F, P and w) and the two others at the Rhg1 locus. Since the W subtype exists in one copy in all characterized repeat loci, this can also be used to determine copy number. To find the fluorescence ratio from hcTaqMan, a final value equals to $vf^{-1}$, where v represents VIC-dye fluorescence value, and f represents FAM-dye fluorescence value. The formula for trcTaqMan was as follows: $fv^{-1}$ (trcTaqMan-f), $vf^{-1}$ (trcTaqMan-p), and $vf^{-1}$ (trcTaqMan-w).

Figures 15A, 15B:
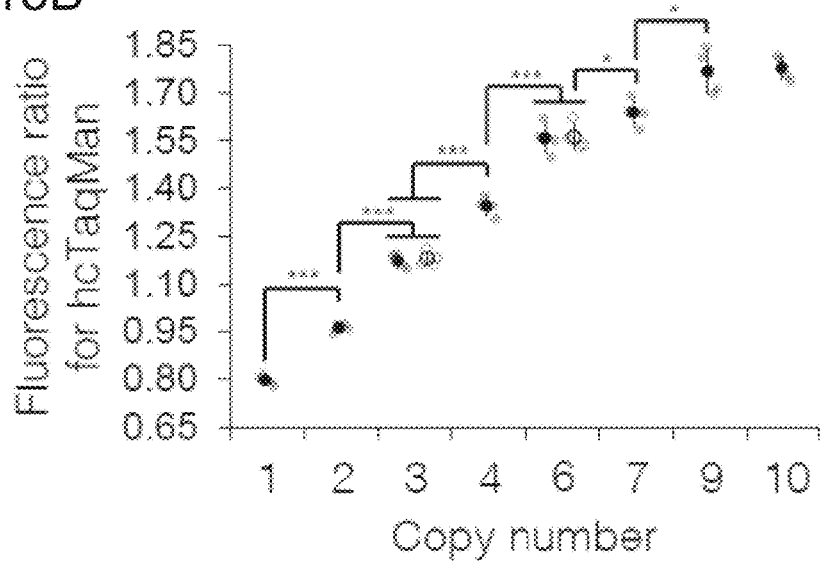
FIG. 15A-15B. A homeolog-controlled assay to genotype copy number variants.
Figure 16A:
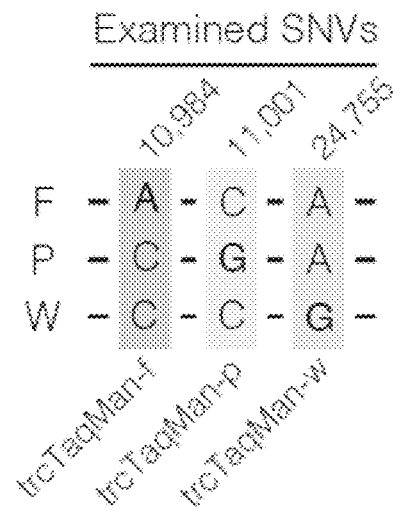
FIG. 16A-16B. Tandem repeat-controlled assays to genotype repeat unit variants within copy number alleles.
Figure 16B:
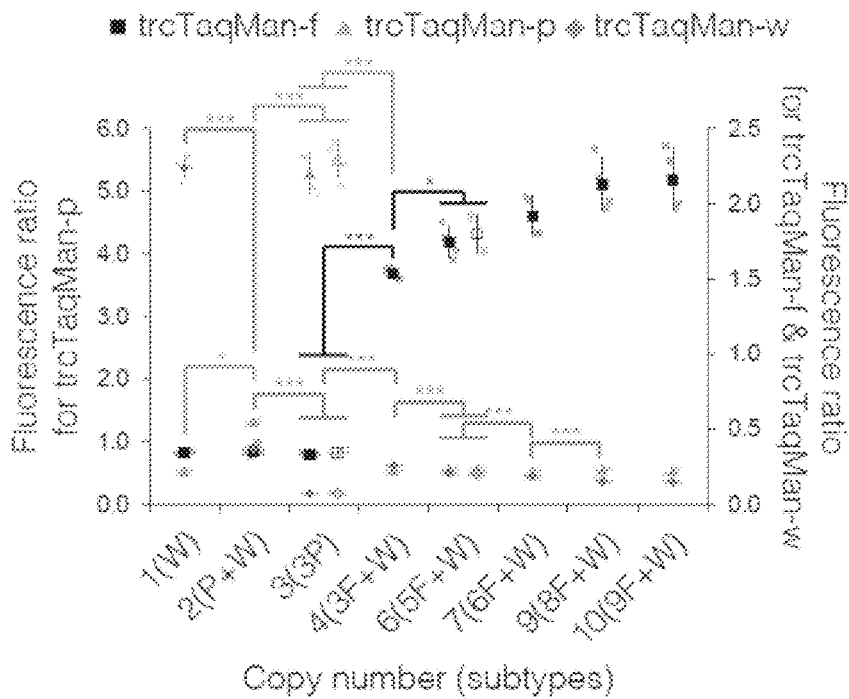

Fluorescence signals were measured using the Roche LightCycler 480 System (Roche) with TAQMAN® Universal PCR Master Mix (Applied Biosystems) together with the Custom TAQMAN® SNP Genotyping assay (Applied Biosystems) according to the manufacturer's instructions. LightCycler 480 Multiwell plates (384 well white) and LightCycler 480 Sealing Foil were used for runs. For each 5 µl of PCR reaction, 12 ng of genomic DNA template was added. A minimum of three independent experiments were performed to generate fluorescence ratio values. Each experiment has four (assay development steps; FIGS. 15B and 16B) or seven (intensive genotyping in Fayette cultivar; FIG. 17B) technical replicates unless otherwise noted. Fluorescence signal values for technical replicates were obtained from the same plate and run at all times. Data from one experiment are presented as figures. The results were analysed for statistical significance by the two-tailed unpaired t-test or one-way analysis of variance (ANOVA) in conjunction with a two-tailed Tukey's multiple comparison test. 95% confidence intervals were calculated to give error bars.

Validation of Copy Number Variation by Read Depth.

To validate copy number within the tandemly duplicated 31.2 kb region of the Rhg1 allele in variant lines detected using qPCR, a WGS read depth-based approach (Lee et al., Mol. Ecol. 24:1774-1791, 201) was used. Whole-genome shotgun sequencing of two soybean cultivar Fayette plants was conducted using Illumina technology. 2.0 µg of genomic DNA was sequenced using the Illumina HiSeq 2500 instrument with 160 bp paired-end sequencing at the Roy J. Carver Biotechnology Center at the University of Illinois (Urbana, Ill.). The DNA fragment size for the soybean whole-genome shotgun sequencing library was 550 bp. A total of two DNA sequencing libraries were prepared with the Hyper library construction kit (Kapa Biosystems); the library was loaded onto one lane of a flow cell and sequenced using version 4 of a TruSeq SBS sequencing kit (Illumina) and bcl2fastq v1.8.4 conversion software (Illumina) was used to demultiplex fastq files. The quality scores in fastq files were processed with Casava 1.8.2 (Illumina). A total of 434,371,178 reads (220,599,252 for Fayette #99 and 213,771,926 for #102; about 32× coverage of the 1.1 gb soybean genome for each plant sample sequenced) having average quality scores 30 or higher were produced. Based on our previous study (Lee et al., *Mol. Ecol.* 24:1774-1791, 2015), the depth of the coverage within the duplicated region was calculated. Novoalign (v 3.02.08) (on the World Wide Web at novocraft[dot]com) with paired end options was used to align the reads to the soybean reference genome assembly. After alignment of Illumina reads, SAMtools (v1.2) (Li et al., *Bioinformatics*, 25:2078-2079, 2009) was used to manipulate output files. To identify the number of subtype F in Fayette, the frequency of sequence variants from the Williams 82 reference at SNV positions was determined as described in our previous study (Lee et al., *Mol. Ecol.* 24:1774-1791, 2015). Statistical was determined by one-way ANOVA in conjunction with a two-tailed Tukey's multiple comparison test.

Soybean Cyst Nematode Greenhouse Test.

Standardized testing protocols were used to reduce potential causes of variability in cyst development. Test protocols were as follows: Seeds of each soybean (Macon, susceptible control; PI 88788, resistance allele donor; and Fayette plants that were the progeny of copy number variant individuals #19, #86, #99 and #102 selected using marker technologies) were pre-germinated in moist filter paper for 48 hr at 27° C. or until seedlings were about 3 cm long, to ensure that similar seedlings can be selected for planting. The number of pre-germinated seeds was about 3× the number needed for planting; 30 seeds for Fayette plant #19, 40 for #86, 40 for #99, 40 for #102. Prepared pots were closed-bottomed polypropylene crocks containing polyvinyl chloride (PVC) tubes (22 each) filled with a 70% sandy loam soil with a hole about 3 cm deep made with a pencil sized dowel in the center of each tube for infestation of soil with SCN eggs (HG type 2.5.7) and planting of seedlings. Prepared inoculum of SCN eggs was carefully pipetted into the soil at the edge of each hole (1 ml per tube at desired concentration level of 2000 eggs per ml). One seedling each was planted into a hole adjacent to the inoculum; holes were carefully closed by gently pressing in soil, a pre-labeled pot tag was inserted into the tube, and each tube was carefully watered with a small amount of water. Closed-bottomed crocks were transferred to 27° C. water tables in the greenhouse and maintained for 30 days under 16 hr light regimen with daily watering amounts per tube dependent on the growth stage of the plants so that only an adequate amount of water was added. After 30 days, crocks were removed from the greenhouse and soaked in buckets for easy removal of roots from tubes. Roots were briefly soaked in water to remove remaining soil and transferred to water-filled cups with a corresponding labeled tag. Each root was then processed to remove and collect cysts from roots by spraying roots with water over nested sieves (20/60 mesh). Cysts were carefully collected from the bottom (60 mesh) sieve by rinsing into counting dishes (petri dish bottoms) and then were enumerated under a stereomicroscope. The number of cysts on each root system was counted under a stereomicroscope. Statistical significance was determined by one-way analysis of variance (ANOVA) followed by the two-tailed Dunnett's test (for multiple comparisons) or the two-tailed t-test.

Results

Copy Number Genotyping Using a Homeologous Sequence Control.

In many plant genomes, including soybean, a homeologous region exists with a very similar sequence to any given gene, as a result of recent whole-genome duplication. Since CNV occurs usually at a specific point in the genome, the homeologous locus can generally be assumed to be present in a single copy. To overcome the limitations of current genotyping methods and measure the number of tandemly duplicated repeat units at Rhg1, we developed a marker assay that compares the abundance of a target sequence with that of a homeologous sequence region as an internal control.

The TAQMANN® PCR chemistry (Holland et al., *Proc. Natl Acad. Sci. USA* 88:7276-80, 1991) is usually used to measure the ratio between two polymorphic nucleotides at the same locus, but here we use it to measure the ratio between a sequence and its homeolog; we refer to this as homeolog-controlled TAQMAN® PCR (hereafter, hcTaqMan). We developed an hcTaqMan marker that measures the abundance of Glyma.18G022600, one of the duplicated Rhg1 genes on chromosome 18, with respect to its single-copy homeolog on chromosome 11 (FIG. 15A, Table 8). As a control, we measured eight separate known CNVs at Rhg1 (1 to 10 copy; Lee et al., *Mol. Ecol.* 24:1774-1791, 2015) (FIG. 15B). As the copy number increased, the fluorescence ratio from hcTaqMan rose accordingly. The differences in fluorescence ratio between copy number types were highly significant (P<0.001) up to 6 copies. Statistical significance (P<0.05) between accessions with incremental copy numbers was observed up to 9 copies.

Genotyping of the Rhg1 CNV Internal Sequence Variants.

Using a similar approach, we then developed TAQMAN® PCR assays to measure the ratios between known sequence variants within the repeat. The repeat units in the Rhg1 locus can be classified into four subtypes ($F_A$, $F_B$, P and W) based on sequence polymorphisms, with some Rhg1 alleles carrying up to three different sequence subtypes of the repeat unit (Lee et al., *Mol. Ecol.* 24:1774-1791, 2015). The $F_A$ and $F_B$ variants are only differentiated by one nucleotide; we did not attempt to differentiate between these two and refer to them herein as F. Of the two main sources of Rhg1-mediated SCN resistance, PI 88788 has subtype F in 8 tandem copies and subtype W in one copy at the Rhg1 locus, and Peking possesses subtype P in 3 tandem copies (Lee et al., *Mol. Ecol.* 24:1774-1791, 2015). Since PI 88788 and Peking have widely different resistance reactions (Niblack et al., *J. Nematol.* 34:279-288, 2002), discrimination between the repeat unit sequences is likely also crucial for the success of correlation between genotyping and resistance reaction-based phenotypes. We developed tandem repeat-controlled TAQMAN® assays (hereafter, trcTaqMan composed of three assays, trcTaqMan-f, trcTaqMan-p & trcTaqMan-w) that each measure the ratio of one subtype to the other two (FIG. 16A, Table 8). In the higher copy versions of the Rhg1 locus studied so far (4 or more copies, Lee et al., *Mol. Ecol.* 24:1774-1791, 2015), the W type repeat is present in one copy, and the F subtype in a variable number of copies, the number of which are clearly resolved by the trcTaqMan-f assay (FIG. 16B). Subtype P-containing loci were clearly distinguished from others by trcTaqMan-p (FIG. 16B). Most accessions contain either three or zero P repeats, however one accession PI 438489 B assayed has one copy of P and one of W (Lee et al., *Mol. Ecol.* 24:1774-1791, 2015), and is clearly differentiated. The SCN susceptible Williams 82 has one copy of subtype W, as do other single copy genotypes investigated (Lee et al., *Mol. Ecol.* 24:1774-1791, 2015). The differences in the ratio were statistically significant (P <0.001) for each single copy increment up to 9 copies (trcTaqMan-w in FIG. 16B). Since the W repeat is only present in one copy in currently characterized lines, trcTaqMan-w or trcTaqMan-f therefore represents an alternative means for characterizing copy number in lines that contain the W and F repeat subtypes.

Selective Breeding for Copy Number.

Figure 20:
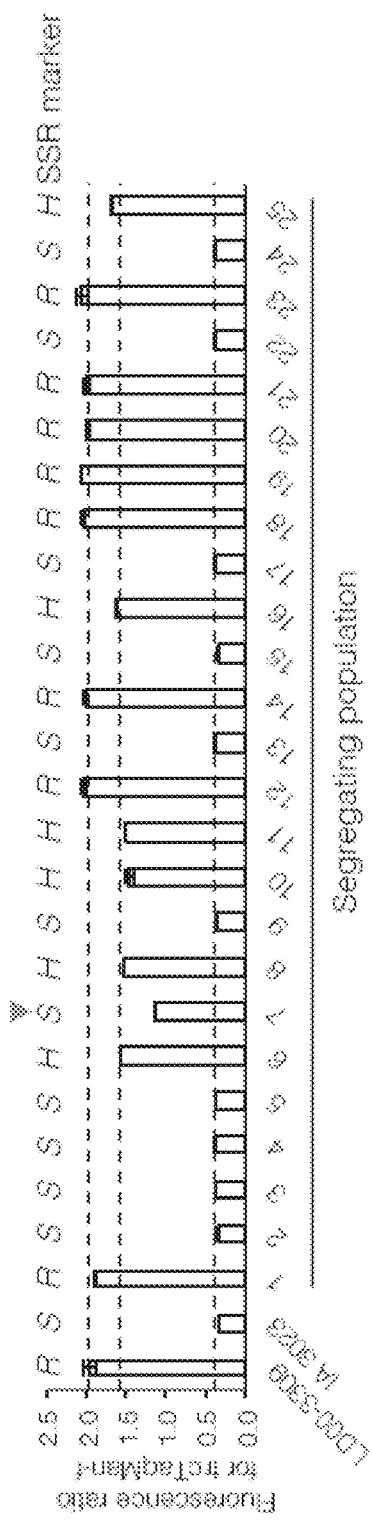
FIG. 20. Genotyping a population segregating for the Rhg1 locus. A segregating population was assayed using the trcTaqMan-f probe set. LD00-3309 carries the Rhg1 allele from PI 88788 (9 copies; 8 of subtype F and one of W), while IA 3023 is susceptible (one copy of W). The population was developed from a cross between these two parental lines. The SSR marker genotyping was grouped into three genotypes, the resistance donor parent type homozygous for the resistance allele (R), the recipient parent type homozygous for the susceptible allele (S), and plants heterozygous for the locus (H). Segregating SSR marker data (R, S or H types) was labeled on the top of parental lines and progenies (1 through 25). Three technical replicates were prepared to generate fluorescence signal values for each individual. The mean±95% confidence interval was plotted.
Figure 21:
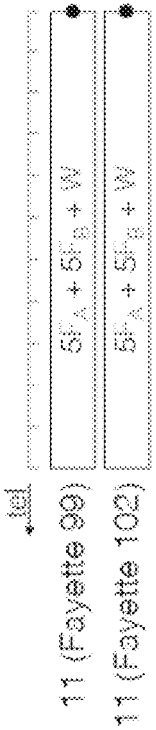
FIG. 21. trcTaqMan-f distinguishes simulated heterozygous alleles using mixed DNA. trcTaqMan-f was applied on mixed DNA samples (e.g. PI 88788+Williams 82 on x-axis means equimolar quantities of genomic DNAs from PI 88788 and Williams 82 were pooled, creating simulated DNA for a heterozygous allele). A red triangle represents a decrease in fluoresce ratio for a pool of PI 88788 and Williams 82 compared to the homozygous resistance allele in PI 88788. Three technical replicates were prepared to generate fluorescence signal values for each individual. The mean±95% confidence interval was plotted. Significant difference (*$P<0.05$, **$P<0.01$ based on a two-tailed unpaired t-test) was indicated between the PI 88788 and mixed DNA containing PI 88788.

To investigate the utility of copy number analysis in soybean genetics and breeding, trcTaqMan-f was applied in a breeding population segregating for the Rhg1 allele from PI 88788. (FIG. 20). The marker specifically distinguishes subtype F that is only from allelic donor LD00-3309. The marker is co-dominant: progeny with high fluorescence ratio values could be divided into two groups, a value close to the donor parent and a value discernably lower than the donor parent's value. The population was conventionally genotyped using the SSR marker Satt309 (Cregan et al., *Theor. Appl. Genet.* 99:811-818, 1999) (three groups, R, S and H, on the top of each bar in FIG. 20). All progeny with low fluorescence ratio values (below 0.5) corresponded with the susceptible parent genotype (IA 3023; SSR marker group S). Progeny with donor parent copy number corresponded to the SSR marker R without exception, showing homozygosity for Rhg1. Progeny with copy number values different from either of the two parents were heterozygous alleles, as validated using mixed genomic DNA sample tests (triangle in FIG. 21) with one exception, segregant number 7 (triangle in FIG. 20). Segregant 7 was homozygous for the susceptible parent genotype. However, our results showed the presence of subtype F and suggested a reduced number of subtype F copies compared to other heterozygous progeny, indicating a possibility of instability or crossover at the Rhg1 locus.

We then investigated the capability of copy number analysis and repeat genotyping technologies to predict SCN resistance phenotypes in breeding lines (FIG. 22A-22D; Peking and PI 437654 were assumed to carry the same Rhg1 allele). PI 88788 and PI 437654 are resistant to nematode biotypes HG 0 and HG 2.5.7 respectively (Niblack et al., *J. Nematol.* 34:279-288, 2002). Five lines (LD10-10198, LD10-8238, LD10-9785, LD10-9816 & LD10-6923) showed identical copy number and repeat analysis results. All those lines have high copy number (9 or 10) at Rhg1 (FIG. 22A) and nearly identical genotyping results as those for PI 88788 (FIG. 22B). While LD10-6923 has both PI 88788 and PI 437654 in its pedigree, no marker evidence was found for the presence of the PI 437654-derived resistance allele (FIG. 22C), which corresponds to susceptibility to HG 2.5.7. In contrast, another line, LD10-3337, descended from both resistance sources showed resistance to HG 2.5.7, not HG 0. Genotyping data indicated that this line has three repeat copies (FIG. 22A) and shares the same repeat unit composition only with PI 437654-derived allele (FIG. 22C), not PI 88788 (FIG. 22B).

Copy Number Variability within an SCN Resistant Soybean Variety.

In response to the evidence of instability of copy number at the Rhg1 locus described above, we investigated copy number in a population of the soybean cultivar Fayette (a cultivar developed with the objective of transferring the SCN resistance of PI 88788; Bernard et al., *Crop Sci.* 28:1028-1029, 1988). Fayette was previously shown to carry ten tandem repeats at the Rhg1 allele (Cook et al., *Science* 338:1206-1209, 2012). Interestingly, this variety has Rhg1 derived from PI 88788, which has only nine copies (Cook et al., *Plant Physiol.* 165:630-647, 2014; Lee et al., *Mol. Ecol.* 24:1774-1791, 2015).

One hundred and two plants of Fayette were genotyped by using hcTaqMan (FIG. 17A). Surprisingly, a wide distribution of predicted copy number was found compared to the nine-copy control PI 88788, which is the allelic source of SCN resistance in Fayette. The plants that showed the lowest and highest fluorescence level were selected for further genotyping. While there were no statistically significant differences in the copy number/subtype composition between the individual with the lowest predicted copy number and the PI 88788 individual validated as nine copy (FIG. 17B), the fluorescence ratio of individual 102 (highest predicted copy number) was significantly higher than the known ten-copy accession PI 209332 (FIG. 17B, left). The presence of an additional copy of subtype F in 102 compared to the ten copy accession was predicted (FIG. 17B, center and right).

Figure 23:
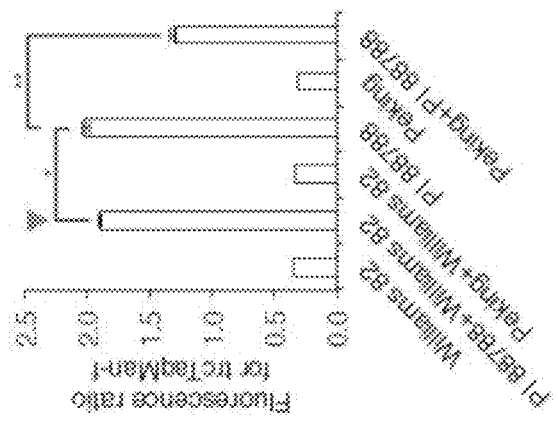
FIG. 23. Repeat structure of 11-copy number variants. The composition of repeat subtypes in the 11 copy variant lines was determined using whole genome sequencing. Rhg1 copy number of each plant was denoted on the left. The label of each individual plant samples as FIG. 17A was in a parenthesis. Black-filled circles indicate the PI 88788 sequence at the end of the repeat. The centromere-proximal end is marked by. Tel: telomere.

Copy number of two predicted high-copy individuals (numbers 99 and 102) was then assayed using WGS, using relative read depths acquired from alignments to the Williams 82 reference genome. We confirmed that both plants have eleven copies of the repeat (the highest Rhg1 copy number in soybean found to date; color-filled bars in FIG. 17C). These plants had an additional two-copies of a subtype F based on the sequence information (open bars in FIG. 17C), which we could identify as the $F_A$ version of the repeat (FIG. 23), relative to the previously assayed nine-copy source Lee et al., *Mol. Ecol.* 24:1774-1791, 2015). Thus, population of the released, inbred cultivar Fayette is heterogeneous for Rhg1 copy number, with individuals showing 9, 10 and 11 copies of the repeat per haploid genome.

Increased Nematode Resistance in High Copy Number Individuals.

Figure 18:
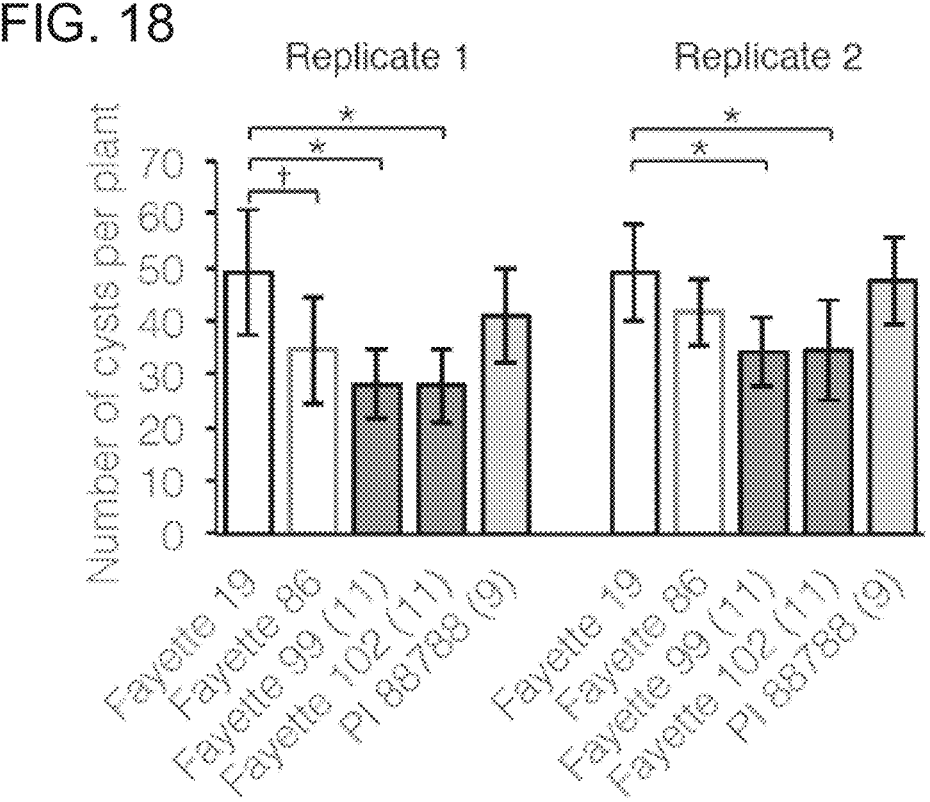
FIG. 18. Increased SCN resistance in plants selected for increased copy number. The mean number of cysts on the roots of each plant is shown for selected Fayette individuals (the descendants of confirmed eleven copy individuals 99 and 102, and lines 19 and 86, control lines that do not show significant changes in copy number) selected in FIG. 17, and PI 88788 (the nine copy donor genotype for Rhg1 of Fayette). *$P<0.05$ using a one-way ANOVA followed by a two-tailed Dunnett's test to compare with Fayette line 19. †$P<0.05$ for a comparison between Fayette 19 and 86 by one-way ANOVA followed by a two-tailed t-test. n=10 except for Fayette 86 replicate 2 (n=9) and Fayette 102 replicate 2 (n=8). Confirmed copy number by whole-genome sequencing is in parentheses on x-axis.
Figure 19:
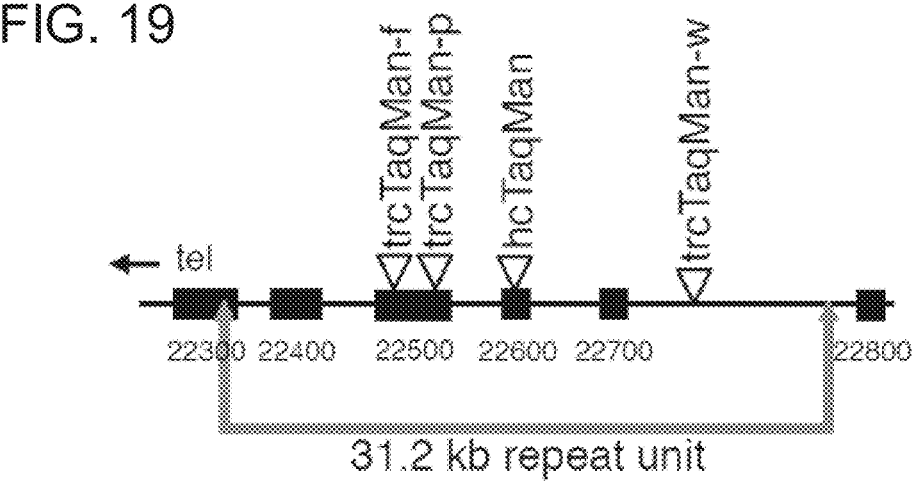
FIG. 19. Diagram of a 31.2 kb repeat unit of single copy Williams 82 genome at the Rhg1 locus and homeolog- or tandem repeat-controlled assays. Gene models from the Williams 82 soybean reference genome annotation V. 2.0 are shown as black blocks. The 31.2 kb repeat unit (red color arrows) extends from the final two exons of Glyma.18G022300 through the intergenic region between Glyma.18G022700 and Glyma.18G022800. Gene names are given below the gene model (e.g. 22300 means Glyma.18G022300). Direction of telomere indicated by "tel".

SCN resistance was tested in the eleven-copy individuals selected from the Fayette pool compared to control plants from the same pool (Fayette 19 & 86, $19^{th}$ and $86^{th}$ in order of estimated copy number in FIG. 17A, respectively). In two separate SCN bioassays, resistance to SCN was significantly (P<0.05) increased in eleven-copy plants relative to Fayette 19 (FIG. 18). While not statistically significant, the mean level of resistance was also higher in the eleven copy lines relative to Fayette 86.

Discussion

Molecular markers were developed in this study that can accurately determine copy number up to nine copies in a single two-primer PCR reaction. This can be achieved by using internal sequence controls, which can be either a homeologous copy of the sequence present in many crop genomes at a genetically distinct locus, or by utilizing single nucleotide variants between the copies at the same locus. Our data show that these marker technologies can effectively genotype allelic variation in copy number, up to nine copies. Above nine copies the selection method is insufficiently precise for exact copy number genotyping with a single assay, however with technical replication it can yield reproducible results, or it can be used in a screen for higher copy individuals to use as donor parents. The lower level of accuracy causes some ambiguity; for example the intermediate level of resistance found in the Fayette 86 line (FIG. 18) may reflect heterozygosity for 10 and 11 copy alleles (see intermediate assay result in FIG. 17), explaining why this line does not show statistically significant differences in resistance with the WGS-confirmed 11-copy lines 99 and 102. Nonetheless, lines selected from large numbers of plants in this manner can be phenotyped and used directly, or reliably characterized using previously described, labor intensive methods such as whole-genome sequencing or Fiber-FISH.

Advantages of internally-controlled TaqMan® assays over currently existing methods are: (i) markers are sensitive to small changes in the number or sequence of repeats; (ii) markers do not need separate controls, thus multiple reaction tubes per sample, which reduces costs and increases throughput; (iii) markers are directly situated at the causative locus and linkage cannot be broken; and (iv) sequence variation and copy number variation can be assayed simultaneously.

SCN resistance mediated by Rhg1 is known to be highly variable, even in varieties where the Rhg1 allele is derived from the same resistance source (Niblack et al., *Plant Health Prog.* doi:10.1094/PHP-2009-0513-01-RV). Several competing hypotheses have existed to explain this variation, the leading explanation previously being a complex genetic system where many second-site modifier loci exist for Rhg1. While it is now well established that some second-site loci (such as Rhg4) can explain some line-to-line variability (Meksem et al., *Appl. Genet.* 103:710-717, 2001; Glover et al., *J. Crop Sci.* 44:936-94, 2004; Brucker et al., *Appl. Genet.* 111:44-49, 2005), our data provide an additional, alternative explanation. Since the Fayette population used in this study likely contains individuals heterozygous and homozygous for sequences of 9 to 11 copies, and the resolution of single-copy differences in individuals with more than 9 copies is at the limits of the assay, the result appears as a continuum of ratio measurements (FIG. 17). Based on the data presented here, we conclude that copy number and thus SCN resistance is variable within in a cultivar with a large number of repeats at Rhg1. Genetic variation, even in an inbred cultivar, is present at Rhg1 and can be selected for CNVs. The most likely explanation for this is instability of the repeat, which is likely to be increasingly subject to illegitimate recombination as the number of copies increases.

The current widespread use of PI 88788-derived Rhg1 is because breeders have successfully combined high yield with this source of resistance (Kim et al., *Crop Sciences*, 51, 934-943, 2011). Peking-derived SCN resistance has proved harder to translate into high-yielding varieties. In addition, two other Rhg1 sources (Peking and PI 437654) used in commercial cultivars are notably less effective against SCN than Rhg1 derived from PI 88788 without help from other SCN resistance loci (Niblack et al., *J. Nematol.* 34:279-288, 2002; Concibido et al., *Crop Sci.* 44:1121-1131, 20044; Colgrove & Niblack, *J Nematol*, 40:39-45, 2008). Selection of a high copy number donor parent from within a population of plants from an inbred line, as described here, may allow greater nematode resistance to be incorporated into soybean breeding lines. Additionally, by using the variant-specific markers to select from large populations of crosses between different Rhg1 alleles, it may be possible to combine the Peking and PI88788 repeat types in a single line by finding a rare recombinant. The sequence of the tandem repeat (Cook et al., *Science* 338:1206-1209, 2012) and reconstruction of individual repeat units (Lee et al., *Mol. Ecol.* 24:1774-1791, 2015) in the Rhg1 alleles strongly suggest that the presence of multiple nucleotide variants may contribute, along with copy number variation, to the difference in SCN race-specificity between the Peking and PI88788 alleles.

Since other valuable traits have been shown to be mediated by copy number polymorphisms (e.g. aluminum tolerance, Maron et al., *Proc Natl Acad Sci USA* 110:5241-5246, 2013; boron-toxicity tolerance, Sutton et al., *Science*, 318: 1446-1449, 2007; flowering, Díaz et al., *PLoS ONE* 7(3): e33234, 2012, and Würschum et al., *BMC Genet.* 16:96, 2015; grain size, Wang et al., *Nat Genet.* 47(8):944-948, 2015), and it is now possible to select for copy number, CNV selection has promise for the improvement of several traits in plant breeding approaches. In addition, the methods we describe here may be useful for measuring other CNVs, in diverse areas such as animal breeding, differentiation of closely related strains of pathogens, or cancer diagnostics.

Example 3: A Genetic Marker System to Reduce Variation in Soybean Cyst Nematode Resistance within Commercial Varieties Copy number variations of DNA segments (CNV) mediate a number of valuable crop traits. Reliable methods to measure high genomic copy numbers of copy number variant sites are needed for many applications, one of which is to genotype the soybean cyst nematode (SCN) resistance Rhg1 allele of soybean. The Rhg1 is a copy number polymorphism of a 31.2 kb unit, widely used for resistance SCN, especially in the major soybean producing areas in the U.S. Here we develop a genetic marker technology that measures copy number of the soybean Rhg1 genes as a method to rapidly and accurately measure the variability we have shown to be present in this gene within breeding populations. This is likely the source of variability in SCN resistance reported in current commercial soybean seed varieties that can result in yield deficiencies.

This marker technology works by comparing the number of copies of the resistance gene to the number of copies of a homeologous gene (a nearly identical gene on another chromosome, which can be assumed to be present in one copy per haploid genome). The method is based on probe hybridization that discriminates a single nucleotide variation (SNV) between the target and homeologous sequence, and generates fluorescence signal in a quantitative PCR (qPCR) assay similar to the established TaqMan® method. The assay targets one of the Rhg1 genes in the duplicated region in the locus. The ultimate result of these hybridizations is that as the copy number increases, the fluorescence ratio from the PCR assay rises accordingly.

Our findings indicate that not only does this technology predict how effective a given SCN resistance gene will be against different nematode types, it also shows that variation exists within existing soybean varieties (different plants have different copy number). For some time, variation in SCN resistance in "resistant" varieties has been observed and has been a mystery to geneticists and breeders. Thus, our assay provides a means for soybean breeders and seed companies to increase the effectiveness and uniformity of genetic resistance to SCN in commercial soybean seed.

Prior implementations of TaqMan® technology for copy number analysis requires two sets of primers and probes, doubling costs, and reducing accuracy and reproducibility. Thus the assay is cost prohibitive for an application such as plant breeding. The system exemplified herein, in contrast, can employ the same amplification and detection chemistry, but measures a ratio between two loci in the same genome directly with the same two primers and probes tailored for the test and control versions of the target sequence. The assay produces results quickly: given genomic DNA samples, the assay returns results in around two hours. It has an internal control and needs no reference reaction, and is more accurate and less sensitive to DNA quality, as well as being significantly less expensive and faster.

Example 4: Analysis of Known Copy Number Soybean Variants to Determine Accuracy and Reproducibility We used selected sixteen soybean germplasm accessions with previously validated copy number variations at the Rhg1 locus (Cook et al., *Science* 338:1206-1209, 2012; Cook et al., *Plant Phys* 165:630-647, 2014, Lee et al., 2015) in order to determine the accuracy and reproducibility of the homeolog-controlled TAQMAN® PCR method. A minimum of four technical replicates was prepared to generate fluorescence signal values. 95% confidence intervals were calculated to give error bars. As the copy number increased, the fluorescence ratio of the target to the control probe from the assay (hcTaqMan) rose accordingly (see FIG. 15B), with clear proportionality to copy number.

Fayette (PI 518674) is a SCN resistant U.S. soybean cultivar derived from PI 88788 and its Rhg1 allele has been successfully introgressed into high yielding soybean cultivars. Unlike its resistance source PI 88788 (9 copy accession), Fayette carries 10 tandem repeats at the Rhg1 locus (Cook et al., *Science* 338:1206-1209, 2012; Cook et al., *Plant Phys* 165:630-647, 2014) implying that the repeat is unstable in the breeding population that gave rise to this line. Interestingly, it has previously been observed that SCN resistance varies in a soybean population developed by crossing the same resistance donor with recipient parents. In order to test whether this type of variation could be the result of variation in copy number, eighty-eight individuals of Fayette were genotyped by using the TAQMAN® copy number genotyping assay described herein (see FIG. 17). A wide distribution of copy number was found among individuals and several of them showed distinguishably higher fluorescence signals compared to the rest of the population.

Figure 24:
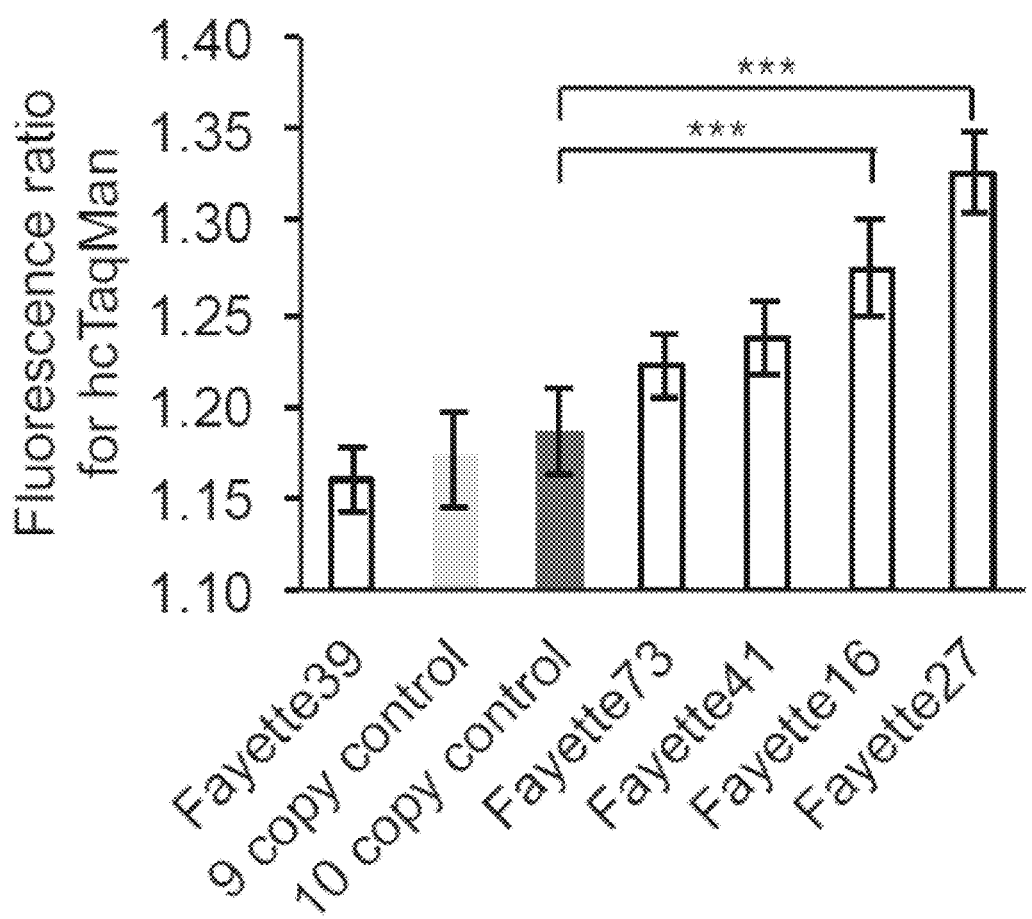
FIG. 24. Four and one individuals, which showed higher and lower signals than PI 88788, respectively, were selected for intensive genotyping including three independent experiments and seven technical replicates for each experiment. Copy number estimations of two individuals (Fayette 16 & 27) were significantly different from either 9 or 10 copy germplasm accessions. Significant differences (P<0.001 based on ANOVA Bonferroni-Holm test) between the 10 copy control and individual Fayette lines are indicated. Data from one experiment are presented.

Four and one individuals, which showed higher and lower signals than PI 88788, respectively, were selected for intensive genotyping including three independent experiments and seven technical replicates for each experiment. Copy number estimations of two individuals (Fayette 16 & 27) were significantly different from either 9 or 10 copy germplasm accessions (see FIG. 24. Significant differences (P<0.001 based on ANOVA Bonferroni-Holm test) between the 10 copy control and individual Fayette lines are indicated. Data from one experiment are presented.

In summary, data provided herein shows that copy number of Rhg1 is variable within an inbred population of an existing cultivar. This variation is likely to cause variation in SCN resistance, which could either become problematic for breeding lines if altered copy number leads to reduced resistance, or could be exploited by selecting lines with more/more optimal (including, in some instances, fewer) copy number for bulking and/or as breeding parents. The TAQMAN® PCR Rhg1 copy number assay described here can be used as a means of either controlling for this type of variation or of selecting for useful variants such as those with increased or decreased copy number.

This disclosure provides methods of determining the copy number of a variable copy number sequence in a genome, using a very similar sequence in the same genome as an internal control (that is, in the same reaction as the target/variable sequence) in a quantitative PCR analysis. The disclosure further provides specific systems and methods for using the described copy number determination methods in various context, including specifically in plant breeding programs to select for copy number of a variable copy number gene, including in high-throughput systems. It will be apparent that the precise details of the methods described may be varied or modified without departing from the spirit of the described invention. We claim all such modifications and variations that fall within the scope and spirit of the claims.

TABLE 1

Presence/absence of repeat junction(s) and copy number estimation using whole genome sequencing (WGS) or genomic qPCR amplification of the gene Glyma18g02590 in Rhg1.

| Strain designation | Cultivar name | Taxonomy | Origin* | Tandem duplict'n[†] | Copy number variation | |
|---|---|---|---|---|---|---|
| | | | | | WGS[‡] | Glyma18g02590[§] |
| PI 200495 | | G. max | Japan | N | — | — |
| PI 209332 | | G. max | Japan | Y | 9.8 ± 0.47 | 10.3 ± 0.25 |
| PI 303652 | | G. max | China | Y | — | 2.7 ± 0.81 |
| PI 339868 B | Yuwoltae | G. max | Korea | Y | — | 3.9 ± 0.68 |
| PI 398680 | | G. max | Korea | Y | — | 8.7 ± 2.01 |
| PI 398682 | | G. max | Korea | Y | — | 8.6 ± 1.05 |
| PI 399061 | | G. max | Korea | Y | — | 1.3 ± 0.53 |
| PI 404166 | | G. max | China | Y | — | 2.9 ± 0.19 |
| PI 404198 A | | G. max | China | Y | — | 3.1 ± 0.10 |
| PI 404198 B | | G. max | China | Y | — | 3.8 ± 0.22 |
| PI 407729 | | G. max | China | N | — | — |
| PI 407944 | | G. max | Korea | N | — | — |
| PI 416762 | | G. max | Japan | Y | — | 3.7 ± 0.09 |
| PI 417091 | | G. max | Japan | Y | — | 5.7 ± 0.45 |
| PI 417094 | | G. max | China | N | — | — |
| PI 424137 B | | G. max | Korea | Y | — | 2.0 ± 0.16 |
| PI 424595 | | G. max | Korea | Y | — | 1.8 ± 0.43 |
| PI 437488 | | G. max | Russia | Y | — | 6.4 ± 0.23 |
| PI 437654 | | G. max | China | Y | 2.9 ± 0.12 | 3.6 ± 0.54 |
| PI 437655 | | G. max | China | Y | — | 5.6 ± 1.53 |
| PI 437679 | | G. max | China | Y | — | 3.2 ± 0.08 |
| PI 437690 | | G. max | China | Y | — | 3.4 ± 0.73 |
| PI 437725 | | G. max | China | Y | — | 2.3 ± 0.56 |
| PI 437770 | | G. max | China | Y | — | 8.5 ± 0.30 |
| PI 437908 | | G. max | China | N | — | — |
| PI 438183 | | G. max | China | Y | — | 8.2 ± 1.35 |

TABLE 1-continued

Presence/absence of repeat junction(s) and copy number estimation using whole genome sequencing (WGS) or genomic qPCR amplification of the gene Glyma18g02590 in Rhg1.

| Strain designation | Cultivar name | Taxonomy | Origin* | Tandem duplict'n[†] | Copy number variation WGS[‡] | Glyma18g02590[§] |
|---|---|---|---|---|---|---|
| PI 438342 | | G. max | Unknown | Y | — | 3.7 ± 0.27 |
| PI 438489 B | | G. max | Unknown | Y | 1.6 ± 0.11 | 1.9 ± 0.51 |
| PI 438496 B | | G. max | Unknown | Y | — | 3.0 ± 0.65 |
| PI 438497 | | G. max | Unknown | Y | — | 2.7 ± 0.79 |
| PI 438498 | | G. max | Unknown | Y | — | 4.1 ± 1.08 |
| PI 438503 A | | G. max | Unknown | Y | — | 11.7 ± 0.33 |
| PI 458519 AH | | G. max | China | N | — | — |
| PI 458520 | | G. max | China | Y | — | 7.2 ± 1.67 |
| PI 461509 | | G. max | China | Y | 6.0 ± 0.36 | 6.7 ± 0.37 |
| PI 467310 | | G. max | China | N | — | — |
| PI 467312 | | G. max | China | Y | — | 6.2 ± 0.25 |
| PI 467327 | | G. max | China | Y | 3.1 ± 0.27 | 3.6 ± 1.02 |
| PI 467332 | | G. max | China | Y | 6.3 ± 0.38 | 5.0 ± 0.39 |
| PI 468903 | | G. max | China | Y | — | 2.3 ± 0.74 |
| PI 468915 | | G. max | China | Y | — | 2.4 ± 1.10 |
| PI 468916 | | G. soja | China | N | — | — |
| PI 475810 | | G. max | China | N | — | — |
| PI 490769 | | G. max | China | N | — | — |
| PI 494182 | | G. max | Japan | Y | — | 3.4 ± 1.08 |
| PI 495017 C | | G. max | China | Y | — | 6.5 ± 0.22 |
| PI 507422 | | G. max | Japan | Y | — | 0.5 ± 0.07 |
| PI 507443 | | G. max | Japan | Y | — | 3.4 ± 0.82 |
| PI 507471 | | G. max | Japan | Y | — | 2.2 ± 0.59 |
| PI 507476 | | G. max | Japan | Y | — | 0.6 ± 0.26 |
| PI 509100 | | G. max | Korea | Y | — | 1.1 ± 0.14 |
| PI 518671 | Williams 82 | G. max | — | N | 1[¶] | — |
| PI 518674 | Fayette | G. max | — | Y | 10[¶] | 11.7 ± 0.53 |
| PI 532434 | | G. max | China | N | — | — |
| PI 532444 A | | G. max | China | N | — | — |
| PI 532444 B | | G. max | China | N | — | — |
| PI 543795 | Hartwig | G. max | — | Y | — | 3.1 ± 0.16 |
| PI 548316 | Cloud | G. max | China | Y | 6.9 ± 0.48 | 6.2 ± 0.38 |
| PI 548317 | Columbia | G. max | China | N | — | — |
| PI 548402 | Peking | G. max | China | Y | 3[¶] | 2.8 ± 0.05 |
| PI 548415 | Sooty | G. max | China | N | — | — |
| PI 548988 | Pickett | G. max | — | Y | — | 3.3 ± 0.10 |
| PI 567285 | | G. max | China | N | — | — |
| PI 567286 | | G. max | China | N | — | — |
| PI 567303 A | | G. max | China | N | — | — |
| PI 567325 A | | G. max | China | N | — | — |
| PI 567325 B | | G. max | China | N | — | — |
| PI 567328 | | G. max | China | N | — | — |
| PI 567336 A | | G. max | China | Y | — | 3.0 ± 0.27 |
| PI 567336 B | | G. max | China | Y | — | 2.5 ± 0.74 |
| PI 567342 | | G. max | China | Y | — | 1.8 ± 0.07 |
| PI 567363 B | | G. max | China | N | — | — |
| PI 567364 | | G. max | China | N | — | — |
| PI 567365 | | G. max | China | N | — | — |
| PI 567373 A | | G. max | China | N | — | — |
| PI 567373 B | | G. max | China | N | — | — |
| PI 567400 | | G. max | China | N | — | — |
| PI 567415 A | | G. max | China | N | — | — |
| PI 567418 A | | G. max | China | N | — | — |
| PI 567421 | | G. max | China | N | — | — |
| PI 567445 B | | G. max | China | N | — | — |
| PI 567491 A | | G. max | China | Y | — | 2.4 ± 0.58 |
| PI 567492 | | G. max | China | N | — | — |
| PI 567507 B | | G. max | China | N | — | — |
| PI 567510 A | | G. max | China | N | — | — |
| PI 567512 B | | G. max | China | Y | — | 6.7 ± 0.23 |
| PI 567516 C | | G. max | China | Y | — | 2.2 ± 0.61 |
| PI 567535 A | | G. max | China | N | — | — |
| PI 567562 A | | G. max | China | N | — | — |
| PI 567568 A | | G. max | China | N | — | — |
| PI 567577 | | G. max | China | N | — | — |
| PI 567581 | | G. max | China | N | — | — |
| PI 567583 C | | G. max | China | N | — | — |
| PI 567583 D | | G. max | China | N | — | — |
| PI 567636 | | G. max | China | N | — | — |
| PI 567660 B | | G. max | China | N | — | — |
| PI 606749 | INA | G. max | — | Y | — | 3.1 ± 0.14 |
| PI 614088 | Loda | G. max | — | Y | — | 9.0 ± 1.86 |
| PI 79609 | | G. max | China | Y | — | 7.4 ± 1.57 |

TABLE 1-continued

Presence/absence of repeat junction(s) and copy number estimation using whole genome sequencing (WGS) or genomic qPCR amplification of the gene Glyma18g02590 in Rhg1.

| Strain designation | Cultivar name | Taxonomy | Origin* | Tandem duplict'n[†] | Copy number variation WGS[‡] | Glyma18g02590[§] |
|---|---|---|---|---|---|---|
| PI 79693 | | G. max | China | N | — | — |
| PI 84751 | | G. max | Korea | Y | — | 3.6 ± 0.25 |
| PI 87631-1 | | G. max | Japan | Y | 6.2 ± 0.61 | 6.0 ± 1.31 |
| PI 88788 | | G. max | China | Y | 9.4 ± 0.78 | 8.2 ± 1.86 |
| PI 89008 | | G. max | China | Y | 4.2 ± 0.34 | 5.0 ± 0.82 |
| PI 89772 | | G. max | China | Y | 3.0 ± 0.11 | 3.7 ± 0.26 |
| PI 90763 | | G. max | China | Y | 2.9 ± 0.12 | 2.9 ± 0.12 |
| PI 92720 | | G. max | China | Y | 7.0 ± 0.50 | 7.2 ± 1.02 |
| W06 | Jidong5 | G. soja | China | Y | 3.0 ± 0.10 | — |
| LD00-2817 | breeding line | G. max | — | Y | 3.1 ± 0.15 | — |
| LD00-3309 | breeding line | G. max | — | Y | 9.7 ± 0.75 | — |
| LD09-15087a | breeding line | G. max | — | Y | 10.5 ± 1.46 | — |
| LD10-30036 | breeding line | G. max | — | Y | 10.6 ± 1.44 | — |

*Based on National Plant Germplasm System (on the World Wide Web at ars-grin.gov/npgs).
[†]Positive to the presence of the DNA junction indicative of a repeat within the Rhg1 locus. Data is based on PCR targeting the unique fusion site between repeats. Y: positive, N: negative.
[‡]Copy number validated by whole genome sequencing method. Mean ± standard deviation.
[§]Copy number estimation by genomic qPCR. Mean ± confidence interval (95%).
[¶]According to Cook et al., *Science*, 338, 1206-1209, 2012.

TABLE 5

Sequence variants in the repeat junction: the sequence region that spans the centromere-proximal repeat and the adjoining non-duplicated region of the genome adjacent to Rhg1.

| Strain designation | Cultivar name | CNV[†] | −198 | −153 | −149 | −79~−80 | +31 | +38 | +53 | +63~+64[Δ] | +86 | +87 | 105 | +116 |
|---|---|---|---|---|---|---|---|---|---|---|---|---|---|---|
| PI 209332 | | 10 | G | C | G | — | G | A | T | AATTTTTTGAATGGTGATAACGGCCAATATT | A | T | T | A |
| PI 518674 | Fayette, derivative of PI 88788 | 10 | G | C | G | — | G | A | T | AATTTTTTGAATGGTGATAACGGCCAATAAT | A | T | T | A |
| LD09-15087a | breeding line; derivative of PI 88788 | 10 | G | C | G | — | G | A | T | AATTTTTTGAATGGTGATAACGGCCAATATT | A | T | T | A |
| PI 88788 | | 9 | G | C | G | — | G | A | T | AATTTTTTGAATGGTGATAACGGCCAATATT | A | T | T | A |
| PI 548316 | Cloud | 7 | G | C | G | — | G | A | T | AATTTTTTGAATGGTGATAACGGCCAATAAT | A | T | T | A |
| PI 87631-1 | | 6 | G | C | G | — | G | A | T | AATTTTTTGAATGGTGATAACGGCCAATATT | A | T | T | A |
| PI 89008 | | 4 | G | C | G | — | G | A | T | AATTTTTTGAATGGTGATAACGGCCAATAAT | A | T | T | A |
| PI 548402 | Peking | 3 | A | C | G | G[‡] | G | G | C | AATTTTTTGAATGGTGATAACGGCCAATATT | G | C | C | G |
| PI 90763 | | 3 | A | C | G | G | G | G | C | AATTTTTTGAATGGTGATAACGGCCAATAAT | G | C | C | G |
| PI 437654 | | 3 | A | C | G | G | G | G | C | AATTTTTTGAATGGTGATAACGGCCAATATT | G | C | C | G |

TABLE 5 -continued

Sequence variants in the repeat junction: the sequence region that spans the centromere-proximal repeat and the adjoining non-duplicated region of the genome adjacent to Rhg1.

| Strain designation | Cultivar name | CNV† | Sequence variants* (-1, end of tandem repeat, 1663442 bp on chromosome 18) | | | | | | | | | | |
|---|---|---|---|---|---|---|---|---|---|---|---|---|---|
| | | | -198 | -153 | -149 | -79~-80 | +31 | +38 | +53 | +63~+64^Δ | +86 | +87 | 105 +116 |
| PI 467327 | | 3 | A | C | G | G | G | G | C | AATTTTTTGAATGGTG ATAACGGCCAATAAT | G | C | T A |
| PI 89772 | | 3 | A | C | G | G | G | G | C | AATTTTTTGAATGGTG ATAACGGCCAATATT | G | C | C G |
| PI 438489 B | | 2 | G | A | A | G | A | G | C | ---------------- ---------------- | G | T | T A |
| PI 518671 | Williams 82 | 1 | G | A | A | G | A | G | C | ---------------- ---------------- | G | T | T A |

*Variants were confirmed by Sanger sequencing method.
†Copy number variation (FIG. 3)
‡DNA sequence insertions based on Williams 82 genome assembly (online at phytozome.net).
^Δ SEQ ID NO: 23

TABLE 6 part 1

| | | | Copy # | 1 | 1 | 1 | 2 | 3 | 3 | 3 | 3 | 3 | 3 | 3 |
|---|---|---|---|---|---|---|---|---|---|---|---|---|---|---|
| | | | Strain designation | Williams 82 | PI 427136 | PI 518751 | PI 438489 B | Peking | PI 90763 | PI 437654 | PI 467327 | PI 89772 | LD00-2817 | Jidong 5 |
| | | | Subtype | W | W | W | P\|W* | P | P | P | P | P | P | P |
| | | | Phenotype** | S | S | S | R | R | R | R | R | R | R | na |
| Gene ID: Glyma18g | Position (bp) Δ | Exon/Intron | # | | | | | | | | | | | |
| 02580 | 335 | Exon | S | C | C | C | T\|C* | T | T | T | T | T | T | T |
| 02580 | 796 | Intron | | T | T | T | C\|T | C | C | C | C | C | C | C |
| 02580 | 2747 | Exon | S | T | T | T | C\|T | C | C | C | C | C | C | C |
| 02590 | 9 | Exon | S | C | C | C | T\|C | T | T | T | T | T | T | T |
| 02590 | 391 | Intron | | C | C | C | T\|C | T | T | T | T | T | T | T |
| 02590 | 558 | Intron | | T | T | T | G\|T | G | G | G | G | G | G | G |
| 02590 | 636 | Intron | | G | G | G | A\|G | A | A | A | A | A | A | A |
| 02590 | 870 | Intron | | A | A | A | G\|A | G | G | G | G | G | G | G |
| 02590 | 1228 | Intron | | C | C | C | A\|C | A | A | A | A | A | A | A |
| 02590 | 1664 | Intron | | T | T | T | C\|T | C | C | C | C | C | C | C |
| 02590 | 1694 | Intron | | G | G | G | T\|G | T | T | T | T | T | T | T |
| 02590 | 1695 | Intron | | C | C | C | T\|C | T | T | T | T | T | T | T |
| 02590 | 1735 | Intron | | C | C | C | T\|C | T | T | T | T | T | T | T |
| 02590 | 2100 | Intron | | C | C | C | G\|C | G | G | G | G | G | G | G |
| 02590 | 2276 | Intron | | G | G | G | A\|G | A | A | A | A | A | A | A |
| 02590 | 2636 | Exon | N | C | C | C | C | C | C | C | C | C | C | C |
| 02590 | 2653 | Exon | N | C | C | C | G\|C | G | G | G | G | G | G | G |
| 02590 | 2752 | Intron | | C | C | C | T\|C | T | T | T | T | T | T | T |
| 02590 | 3277 | Intron | | T | T | T | A\|T | A | A | A | A | A | A | A |
| 02590 | 3439 | Intron | | C | C | C | T\|C | T | T | T | T | T | T | T |
| 02590 | 3504 | Intron | | G | G | G | C\|G | C | C | C | C | C | C | C |
| 02590 | 3517 | Intron | | G | G | G | A\|G | A | A | A | A | A | A | A |
| 02590 | 3921 | Intron | | C | C | C | T\|C | T | T | T | T | T | T | T |
| 02590 | 3953 | Intron | | T | T | T | C\|T | C | C | C | C | C | C | C |
| 02590 | 4005 | Intron | | T | T | T | G\|T | G | G | G | G | G | G | G |
| 02590 | 4393 | Exon | N | G | G | G | T\|G | G | G | G | G | G | G | G |
| 02590 | 4396 | Exon | N | G | G | G | T\|G | T | T | T | T | T | T | T |
| 02590 | 4402 | Exon | N | C | C | C | A\|C | A | A | A | A | A | A | A |
| 02590 | 4646 | Exon | N | A | A | A | T\|A | T | T | T | T | T | T | T |
| 02610 | 2 | Exon | S | A | A | C | C\|A | C | C | C | C | C | C | C |
| 02610 | 150 | Exon | S | T | T | T | C\|T | C | C | C | C | C | C | C |
| 02610 | 202 | Exon | S | A | A | G | G\|A | G | G | G | G | G | G | G |

TABLE 6-continued

Part 2

| | | | Copy # | 4 | 6 | 6 | 6 | 7 | 7 | 9 | 10 | 10 | 10 | 10 |
|---|---|---|---|---|---|---|---|---|---|---|---|---|---|---|
| | | | Strain designation Subtype Phenotype** | PI 89008 $F_B$\|W R | PI 467332 $F_AF_B$\|W R | PI 87631-1 $F_AF_B$\|W R | PI 461509 $F_AF_B$\|W R | Cloud $F_AF_B$\|W R | PI 92720 $F_AF_B$\|W R | PI 88788 $F_AF_B$\|W R | PI 209332 $F_AF_B$\|W R | LD10- 30036 $F_AF_B$\|W R | LD09- 15087a $F_AF_B$\|W R | LD00- 3309 $F_AF_B$\|W R |
| Gene ID: Glyma18g | Position (bp)Δ | Exon/ Intron | S/N # | | | | | | | | | | | |
| 02580 | 335 | Exon | S | T | T | T | T | T | T | T | T | T | T | T |
| 02580 | 796 | Intron | | C | C | C | C | C | C | C | C | C | C | C |
| 02580 | 2747 | Exon | S | C | C | C | C | C | C | C | C | C | C | C |
| 02590 | 9 | Exon | S | T\|C | T\|C | T\|C | T | T\|C | T\|C | T\|C | T\|C | T\|C | T\|C | T\|C |
| 02590 | 391 | Intron | | T\|C | T\|C | T\|C | T\|C | T\|C | T\|C | T\|C | T\|C | T\|C | T\|C | T\|C |
| 02590 | 558 | Intron | | G\|T | G\|T | G\|T | G\|T | G\|T | G\|T | G\|T | G\|T | G\|T | G\|T | G\|T |
| 02590 | 636 | Intron | | A\|G | A\|G | A\|G | A\|G | A\|G | A\|G | A\|G | A\|G | A\|G | A\|G | A\|G |
| 02590 | 870 | Intron | | G\|A | G\|A | G\|A | G\|A | G\|A | G\|A | G\|A | G\|A | G\|A | G\|A | G\|A |
| 02590 | 1228 | Intron | | A\|C | A\|C | A\|C | A\|C | A\|C | A\|C | A\|C | A\|C | A\|C | A\|C | A\|C |
| 02590 | 1664 | Intron | | C\|T | C\|T | C\|T | C\|T | C\|T | C\|T | C\|T | C\|T | C\|T | C\|T | C\|T |
| 02590 | 1694 | Intron | | T\|G | T\|G | T\|G | T\|G | T\|G | T\|G | T\|G | T\|G | T\|G | T\|G | T\|G |
| 02590 | 1695 | Intron | | T\|C | T\|C | T\|C | T\|C | T\|C | T\|C | T\|C | T\|C | T\|C | T\|C | T\|C |
| 02590 | 1735 | Intron | | T\|C | T\|C | T\|C | T\|C | T\|C | T\|C | T\|C | T\|C | T\|C | T\|C | T\|C |
| 02590 | 2100 | Intron | | G\|C | G\|C | G\|C | G\|C | G\|C | G\|C | G\|C | G\|C | G\|C | G\|C | G\|C |
| 02590 | 2276 | Intron | | A\|G | A\|G | A\|G | A\|G | A\|G | A\|G | A\|G | A\|G | A\|G | A\|G | A\|G |
| 02590 | 2636 | Exon | N | A\|C | A\|C | A\|C | A\|C | A\|C | A\|C | A\|C | A\|C | A\|C | A\|C | A\|C |
| 02590 | 2653 | Exon | N | C | C | C | C | C | C | C | C | C | C | C |
| 02590 | 2752 | Intron | | T\|C | T\|C | T\|C | T\|C | T\|C | T\|C | T\|C | T\|C | T\|C | T\|C | T\|C |
| 02590 | 3277 | Intron | | A\|T | A\|T | A\|T | A\|T | A\|T | A\|T | A\|T | A\|T | A\|T | A\|T | A\|T |
| 02590 | 3439 | Intron | | T\|C | T\|C | T\|C | T\|C | T\|C | T\|C | T\|C | T\|C | T\|C | T\|C | T\|C |
| 02590 | 3504 | Intron | | C\|G | C\|G | C\|G | C\|G | C\|G | C\|G | C\|G | C\|G | C\|G | C\|G | C\|G |
| 02590 | 3517 | Intron | | A\|G | A\|G | A\|G | A\|G | A\|G | A\|G | A\|G | A\|G | A\|G | A\|G | A\|G |
| 02590 | 3921 | Intron | | T\|C | T\|C | T\|C | T\|C | T\|C | T\|C | T\|C | T\|C | T\|C | T\|C | T\|C |
| 02590 | 3953 | Intron | | C\|T | C\|T | C\|T | C\|T | C\|T | C\|T | C\|T | C\|T | C\|T | C\|T | C\|T |
| 02590 | 4005 | Intron | | G\|T | G\|T | G\|T | G\|T | G\|T | G\|T | G\|T | G\|T | G\|T | G\|T | G\|T |
| 02590 | 4393 | Exon | N | C\|G | C\|G | C\|G | C\|G | C\|G | C\|G | C\|G | C\|G | C\|G | C\|G | C\|G |
| 02590 | 4396 | Exon | N | C\|G | C\|G | C\|G | C\|G | C\|G | C\|G | C\|G | C\|G | C\|G | C\|G | C\|G |
| 02590 | 4402 | Exon | N | A\|C | A\|C | A\|C | A\|C | A\|C | A\|C | A\|C | A\|C | A\|C | A\|C | A\|C |
| 02590 | 4646 | Exon | N | T\|A | T\|A | T\|A | T\|A | T\|A | T\|A | T\|A | T\|A | T\|A | T\|A | T\|A |
| 02610 | 2 | Exon | S | C | C | C | C | C | C | C | C | C | C | C |
| 02610 | 150 | Exon | S | C | C | C | C | C | C | C | C | C | C | C |
| 02610 | 202 | Exon | S | G | G | G | G | G | G | G | G | G | G | G |

TABLE 7

15,996 soybean germplasm accessions clustered by maximum parsimony phylogenetic analysis of the sequence region near the Rhg1 allele, indicating germplasm accessions predicted to carry Rhg1.

| | No of germ-plasm | Copy number type observed | Germplasm designation |
|---|---|---|---|
| Cluster1 | 707 | 2, 3 | PI656647, PI654356, PI644046, PI644045, PI644044, PI644043, PI644042, PI639540, PI636694, PI635039, PI634335, PI633736, PI633620, PI629015, PI629013, PI619232, PI617041, PI613560, PI613559A, PI612614, PI612611, PI612146, PI606749, PI605779D, PI604100, PI603953, PI603914, PI603910C, PI603585B, PI603585A, PI603555, PI603547, PI603527B, PI603527A, PI603497, PI603453, PI603445B, PI603443C, PI603443A, PI603438B, PI603421B, PI603411, PI603404, PI603402, PI603384, PI603218, PI603176B, PI603176A, PI603168, PI603161, PI603152, PI602597, PI602492, PI597475B, PI597475A, PI595645, PI594847, PI594314, PI594301, PI594286, PI594283, PI594280E, PI594280D, PI594280C, PI594280A, PI594227B, PI594191, PI594170B, PI594170A, PI594160, PI594023A, PI594001, PI593999B, PI593995A, PI593970, PI592903, PI578376, PI576154, PI568262, PI568236, PI567606, PI567605, PI567521, PI567516C, PI567491A, PI567424B, PI567421, PI567420, PI567419A, PI567398, PI567388, PI567387, PI567386, PI567342, PI567336B, PI567336A, PI567319B, PI567305, PI567304, PI567234B, PI567234A, PI564276, PI561570, PI561470, PI561401, PI561400, PI561395, PI561361, PI561310, PI559934, PI559932, PI559370, PI556949, PI555453, PI553047, PI548991, PI548988, PI548970, PI548665, PI548655, PI548645, PI548563, PI548546, PI548484, PI548467, PI548440, PI548438, PI548402S, PI548402, PI548290, PI548246, PI548205, PI548171, PI544354, PI543855, PI543795, PI543794, PI542712, PI533605, PI522236, PI518772, PI518677, PI518676, PI518665, PI511813, PI510675, PI509109, PI509092, PI509089, PI509077, PI508296G, PI508296E, PI507476, PI507475, PI507474, PI507473, PI507472, PI507470, PI507454, PI507443, PI507439, PI507435, PI507426, PI507423, PI507422, PI507420, PI507417, PI507416, PI507403, PI507395, PI507390, PI507387, PI507382, PI507378, PI507368, PI507367, PI507366, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI507365, PI507364, PI507362, PI507361, PI507354, PI507349, PI507167A, PI507148, PI507132A, PI507079, PI506908, PI506870, PI506868, PI506862, PI506856, PI506827, PI506503, PI497966, PI494182, PI468915, PI468903, PI468384, PI467327, PI467316, PI464910, PI458306B, PI458298, PI458292, PI458287, PI458282, PI458269, PI458243, PI458236B, PI458231, PI458212, PI458175B, PI458130, PI458102, PI458094, PI458085B, PI458085A, PI458077, PI458050, PI458032, PI458030, PI458020, PI458018, PI442014, PI442012A, PI442009A, PI442008, PI442006, PI442005, PI438498, PI438496B, PI438491, PI438489B, PI438343, PI438342, PI438311, PI438307, PI438306, PI438250A, PI438241, PI438240, PI438239B, PI438239A, PI438218, PI438183, PI438169, PI438031, PI437950, PI437905, PI437868, PI437840B, PI437828, PI437825, PI437786, PI437781, PI437725, PI437703, PI437690, PI437679, PI437664, PI437572, PI437568, PI424617, PI424596, PI424580, PI424578, PI424577, PI424555B, PI424553, PI424551, PI424549B, PI424549A, PI424545, PI424542, PI424535B, PI424523B, PI424504B, PI424503, PI424496, PI424484B, PI424484A, PI424480, PI424476, PI424461, PI424457, PI424454, PI424452, PI424433, PI424413, PI424394, PI424393, PI424392, PI424361, PI424360, PI424348B, PI424345, PI424344, PI424338, PI424335B, PI424335A, PI424332, PI424331, PI424318, PI424310, PI424309A, PI424298, PI424294A, PI424286, PI424278A, PI424276, PI424270A, PI424255C, PI424254, PI424251B, PI424248, PI424229B, PI424222B, PI424214A, PI424187, PI424182C, PI424182B, PI424172B, PI424169A, PI424167, PI424164A, PI424163, PI424159C, PI424151, PI424137B, PI423960B, PI423927, PI423926, PI423915, PI423888, PI423885, PI423883, PI423882B, PI423882A, PI423881, PI423880, PI423871, PI423862, PI423859, PI423856, PI423851, PI423832, PI423827B, PI423825, PI423821, PI423813, PI423811, PI423808B, PI423799B, PI423792, PI423760, PI423756A, PI423738, PI423729, PI423724, PI423722, PI417579, PI417441, PI417426, PI417415, PI417395, PI417394, PI417377, PI417247, PI417245, PI417103, PI417041, PI417005, PI416940, PI416877, PI416861, PI416839, PI408335A, PI408328, PI408320, PI408316, PI408310B, PI408304, PI408302, PI408300, PI408294B, PI408281A, PI408275, PI408272B, PI408272A, PI408269D, PI408269C, PI408268, PI408246_1, PI408233B, PI408229C, PI408228B, PI408225A, PI408222C, PI408208, PI408202, PI408200A, PI408193, PI408192_2, PI408191B, PI408191A, PI408168, PI408167A, PI408157, PI408152, PI408143, PI408142, PI408140B, PI408137B, PI408134A, PI408124D, PI408120, PI408096, PI408085, PI408084C, PI408084A, PI408063, PI408055D, PI408055C, PI408054, PI408053, PI408048B, PI408041, PI408037, PI408030, PI408029, PI408020D, PI408020A, PI408019C, PI408015, PI408014, PI408013, PI408012, PI408010_1, PI408002, PI408001, PI407998D, PI407998A, PI407996, PI407986B, PI407977, PI407975A, PI407974B, PI407972A, PI407960B, PI407957, PI407949, PI407943, PI407941B, PI407940, PI407937_1, PI407935, PI407923, PI407920, PI407919, PI407915, PI407913B, PI407911, PI407910, PI407909, PI407907B, PI407906, PI407900, PI407899, PI407892A, PI407886, PI407877C, PI407874_1, PI407868B, PI407859_1, PI407857, PI407852, PI407839_2, PI407833C, PI407833B, PI407833A, PI407832B, PI407823, PI407817, PI407806B, PI407806A, PI407805C, PI407805B, PI407805A, PI407795B, PI407795A, PI407788A, PI407771, PI407770, PI407302, PI407301, PI404198B, PI404198A, PI404167, PI404166, PI399122, PI399108, PI399100, PI399098, PI399097, PI399095, PI399082, PI399078, PI399071, PI399070, PI399065, PI399064, PI399062, PI399061, PI399057, PI399056, PI399041, PI399033, PI399023, PI399022, PI398999, PI398987, PI398978, PI398967, PI398964, PI398958, PI398952, PI398950, PI398949, PI398947, PI398941, PI398940, PI398932, PI398926, PI398922, PI398896, PI398874, PI398854, PI398828, PI398827, PI398823, PI398803, PI398802, PI398768, PI398767, PI398755, PI398744, PI398742, PI398738, PI398737, PI398720, PI398706, PI398705, PI398704, PI398692, PI398690, PI398688, PI398683, PI398682, PI398668, PI398657, PI398643, PI398635, PI398633, PI398631, PI398619, PI398618, PI398612, PI398610, PI398609, PI398606, PI398603, PI398598, PI398593, PI398592, PI398587, PI398555, PI398550, PI398547, PI398545, PI398540, PI398537, PI398535, PI398533, PI398529, PI398527, PI398524, PI398516, PI398514, PI398500, PI398499, PI398480, PI398474, PI398473, PI398471, PI398429, PI398427, PI398419, PI398411, PI398398, PI398394, PI398390, PI398388, PI398382, PI398375, PI398372, PI398371, PI398353, PI398343, PI398342, PI398322, PI398317, PI398316, PI398309, PI398306, PI398304, PI398299, PI398298, PI398287, PI398286, PI398282, PI398280, PI398259, PI398248, PI398227, PI398224, PI398223, PI398218, PI398214, PI398213, PI398210, PI398187, PI398183, PI398181, PI391589A, PI391581A, PI381683, PI342002, PI340050, PI340042, PI340040, PI340039, PI340037, PI340034, PI340031B, PI340029, PI340025, PI340022, PI340014, PI340010, PI340000, PI339868E, PI339863A, PI315701, PI304217, PI303652, PI291310B, PI291274B, PI273483C, PI243533, PI227557, PI209334, PI209331, PI201421, PI200503, PI200490, PI196175, PI196171, PI196170, PI187156, PI175182, PI174863, PI171441, PI170896, PI157484, PI157483, PI157441, PI157405, PI103088, PI097094, PI096280, PI096035, PI092698, PI091734, PI091679, PI090763, PI089775, PI089772, PI089146, PI089003_1, PI088508, PI087047, PI085465, PI084960, PI084751, PI084611, PI084609, PI082286, PI079756, PI070507, PI068465_1, PI063468, PI061947, PI061944, PI054859, Peking |
| Cluster2 | 98 | PI639635, PI612762, PI603146, PI597457A, PI597452A, PI597448C, PI578350B, PI578350A, PI578346C, PI578344A, PI578341, PI578339B, PI578339A, PI578337, PI562536, PI549043, PI549040, PI522231B, PI522230C, PI522230B, PI522228, PI522227, PI522226, PI522225B, PI522225A, PI522224B, PI522224A, PI522222, PI522221, PI522220A, PI522219A, PI522219A, PI522218, PI522214A, PI522213B, PI522212B, PI522209B, PI522205A, PI522204, PI522199, PI522198C, PI522194B, PI522194A, PI507847, PI507841B, PI507819, PI507801, PI507800B, PI507795, PI507781, PI507773, PI507764, PI507762, PI507757, PI507749, PI507748, PI507746, PI507739B, PI507738, PI507727, PI507723B, PI507723A, PI507667, PI507663, PI507659, PI507629, PI507628, PI507604, PI479768, PI479750, PI468918, PI468917, PI468916, PI464891C, PI447003B, PI440913B, PI440913A, PI437662, PI424120, PI424093, PI424008B, PI424007, PI424004A, PI423994, PI407235, PI407167, PI407118, PI407112, PI407077, PI407073, PI407072, PI407071, PI342622A, PI342620A, PI342619B, PI342619A, PI326582A, PI324622B |

TABLE 7-continued 15,996 soybean germplasm accessions clustered by maximum parsimony phylogenetic analysis of the sequence region near the Rhg1 allele, indicating germplasm accessions predicted to carry Rhg1.

| | No of germ-plasm | Copy number type observed | Germplasm designation |
|---|---|---|---|
| Cluster3 | 15 | | PI654355, PI640433, PI640432, PI615695, PI596540, PI583367, PI553044, PI547831, PI539861, PI424008A, PI135624, PI101404B, PI101404A, PI081762, PI065549 |
| Cluster4 | 1 | | PI424089 |
| Cluster5 | 33 | | PI628963, PI628939, PI628930, PI628903, PI628844, PI628813, PI615502, PI614702, PI603713, PI603634, PI594431, PI594307, PI587972, PI567773, PI548986, PI507576, PI507504, PI507329, PI506712, PI506621, PI506565, PI506535, PI458213, PI437428A, PI423857, PI417494, PI417428, PI417330, PI417123, PI407055, PI398812, PI378694, PI248510 |
| Cluster6 | 2 | | PI507597, PI507583 |
| Cluster7 | 2 | | PI464939B, PI464939A |
| Cluster8 | 239 | | PI632941, PI605801B, PI605800B, PI605779A, PI603781, PI603774, PI603740A, PI603737A, PI603706B, PI603706A, PI603667A, PI603580, PI603540B, PI603538B, PI603538A, PI603505, PI603406, PI597479, PI594882B, PI594882A, PI594872, PI594861, PI594859, PI594853, PI594818, PI594817, PI594811, PI594802D, PI594763B, PI594760B, PI594745B, PI594745A, PI594735, PI594734, PI594729, PI594624, PI594623, PI594599, PI594511C, PI594510A, PI594494A, PI594470D, PI594470C, PI594470B, PI594447, PI594445, PI594247, PI594233B, PI594233A, PI588011B, PI588011A, PI587996D, PI587996C, PI587988B, PI587915C, PI587912, PI587900D, PI587900C, PI587898, PI587750, PI578475, PI567402, PI567375D, PI567375B, PI567375A, PI567318, PI567279B, PI567279A, PI561290, PI548369, PI548337, PI548189, PI507569, PI507541, PI507513, PI507505, PI507455, PI507432, PI507408, PI507407, PI507374, PI507356, PI507321, PI507290, PI507256, PI507250, PI507190, PI507171, PI507161, PI507141, PI507090, PI507084, PI507078, PI507062B, PI507062A, PI507037, PI507029, PI507027, PI507013, PI506993, PI506992, PI506984, PI506981, PI506971, PI506969, PI506968, PI506967, PI506963, PI506958, PI506957, PI506954, PI506951, PI506936, PI506907, PI506904, PI506902, PI506874, PI506822, PI506797, PI506787, PI506769, PI506731, PI506691, PI506658, PI506652, PI506590E, PI506590C, PI506581C, PI506568, PI506567, PI506566, PI506547, PI506536, PI506532, PI459025F, PI459025D, PI459025B, PI459025A, PI458254, PI458252, PI458249, PI458248, PI458247, PI458232, PI458220, PI458095, PI458034, PI437832, PI424495, PI424494, PI423913, PI423896, PI423757, PI423735, PI423732, PI417561, PI417491, PI417469, PI417448, PI417418, PI417390, PI417374, PI417320, PI417222, PI417203, PI417191, PI417168, PI417166, PI417152, PI417098, PI417055, PI416990, PI416988, PI416939, PI416913, PI416904C, PI416890, PI416867, PI416866, PI416862, PI416859, PI416832, PI416831, PI416829, PI416801, PI416789, PI416779, PI416760, PI416754, PI408255B, PI408238_1, PI408187, PI408186C, PI408186B, PI408170, PI408166A, PI408105A, PI408061, PI408032B, PI407965, PI407896, PI399079, PI398225, PI378682C, PI378682A, PI261272C, PI246368, PI243537, PI243519, PI243518, PI229351, PI229324, PI229317, PI229313, PI224272, PI219787, PI205088, PI200536, PI200501, PI200496, PI196172, PI181549, PI181542, PI091349, PI089009_2, PI088312, PI087968, PI087620_1, PI087619, PI086737, PI086452, PI086091_1, PI085252, PI084967, PI084957_1, PI084642, PI080825, FC031943, FC030282 |
| Cluster9 | 26 | | PI603444A, PI603429D, PI603428D, PI603424D, PI594152, PI548496, PI518290, PI507002, PI458180, PI458037, PI423753A, PI417386, PI417376, PI417254, PI417084B, PI417063, PI408217B, PI408217A, PI407956, PI407955, PI407954, PI398604, PI200459, PI179935, PI091343, PI085476 |
| Cluster10 | 1 | | PI424031 |
| Cluster11 | 1 | | PI423884 |
| Cluster12 | 3 | | PI612723, PI578329A, PI436619 |
| Cluster13 | 60 | | PI612724, PI612720B, PI612720A, PI603744, PI603175, PI603170, PI594014A, PI594010, PI594004C, PI594004B, PI594004A, PI561319A, PI538387, PI508295, PI507312, PI468914, PI464922, PI464904, PI458184, PI458106, PI458082, PI424458, PI424409, PI424258, PI424234B, PI423789, PI423747A, PI415074, PI415073B, PI415073A, PI408269B, PI408269A, PI408068A, PI407938, PI407916, PI407830, PI407829, PI407827, PI407783, PI407781B, PI398892, PI398878, PI398877, PI398873, PI398495, PI398479, PI398478, PI398395, PI398386, PI398385, PI398374, PI398228, PI339984, PI243516, PI200447, PI196177, PI157457, PI157436, PI157404, PI085505 |
| Cluster14 | 6 | | PI507590A, PI407248, PI407040, PI407024, PI407023, PI407021 |
| Cluster15 | 4893 | 1 | PI648270, PI647961, PI647085, PI644025, PI644024, PI643146, PI641156, PI640911, PI639637, PI639633B, PI639633A, PI639632C, PI639632B, PI639632A, PI639629, PI639628, PI639627, PI639626, PI639624, PI639623B, PI639623A, PI639622, PI639621, PI639614, PI639612B, PI639596, PI639595, PI639587, PI639586, PI639584, PI639580A, PI639576, PI639572, PI639571A, PI639568, PI639567, PI639560B, PI639554, PI639553, PI639550C, PI639546A, PI639542A, PI639537, PI639535, PI639531, PI639528A, PI639285, PI639284, PI638511, PI636696, PI636695, PI636691, PI634912, PI634911, PI634910, PI634909, PI634908, PI634907, PI634906, PI634905, PI634904, PI634902, PI634901, PI634900, PI634899, PI634898, PI634897, PI634896, PI634895, PI634893, PI634892, PI634890, PI634888, PI634887, PI634882, PI634880, PI634878, PI634877, PI634876, PI634875, PI634874, PI634869, PI634867, PI634813, PI634765, PI634764, PI634763, PI634762, PI634761, PI634760, PI634758, PI634193, PI633983, PI633970, PI633729, PI633608, PI633541, PI633424, PI633049, PI632961, PI632950, PI632945B, PI632943B, PI632905, PI632668, PI632666, PI632665, PI632661B, PI632661A, PI632658, PI632656B, PI632648, PI632636B, PI632431, PI632430, PI632429, PI632428, PI632427, PI632426, PI632425, PI632424, PI632423, PI632405, PI632402, PI632401, PI631438, PI631437, PI629004, PI628951, PI628945, PI628820, PI628811, PI615694, PI615586, PI615585, PI615555, PI615508, PI615507, PI615457, PI615456, PI615455, PI615444, PI614833, PI614831, PI614808, PI614806, PI614673, PI614153, PI613562, PI613558B, PI613558A, PI612932, PI612930, PI612764, PI612763, PI612755, PI612754, PI612753B, PI612753A, PI612750, PI612749, PI612748, PI612747, PI612746, PI612744, PI612743, PI612742, PI612741, PI612737, PI612736, PI612734, PI612731, PI612729, PI612725, PI612719, PI612717, PI612716, PI612714A, PI612712, PI612711B, PI612711A, PI612710, PI612709C, PI612707B, PI612706B, PI612622B, PI612621, PI612620, PI612617B, PI612617A, PI612615, PI612594, PI611112, PI610670, PI608438, PI606442, PI606428, PI606426, PI606410, PI606394, PI606370, PI606364, PI605886E, PI605877A, PI605869B, PI605862B, PI605849, PI605845C, PI605845A, PI605844B, PI605844A, PI605843, PI605841B, PI605839A, PI605838, PI605837C, PI605835, PI605829, PI605817D, PI605817B, PI605792A, PI605765B, PI605765A, PI605758D, PI605750, PI605411, PI604464, PI603915D, PI603910A, PI603900, PI603772, PI603747, PI603738, PI603735A, PI603733, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI603731A, PI603730B, PI603730A, PI603726, PI603720, PI603698I, PI603698H, PI603698G, PI603698D, PI603698C, PI603698B, PI603698A, PI603694B, PI603691, PI603675, PI603674, PI603637A, PI603630, PI603593, PI603582, PI603581, PI603576A, PI603573B, PI603573A, PI603571C, PI603571B, PI603571A, PI603570C, PI603570A, PI603569B, PI603566, PI603563B, PI603554B, PI603554A, PI603549, PI603546B, PI603546A, PI603544A, PI603542, PI603541A, PI603540A, PI603537A, PI603533, PI603529, PI603526, PI603525, PI603515, PI603514, PI603507, PI603506, PI603500, PI603496B, PI603492, PI603476, PI603472D, PI603472B, PI603469, PI603455B, PI603454, PI603447, PI603445A, PI603444E, PI603444D, PI603444C, PI603444B, PI603443B, PI603442, PI603441, PI603440C, PI603440B, PI603440A, PI603437B, PI603434, PI603433B, PI603433A, PI603432B, PI603432A, PI603430A, PI603429C, PI603429B, PI603429A, PI603428C, PI603428B, PI603428A, PI603427A, PI603426G, PI603426F, PI603426E, PI603426A, PI603425, PI603424C, PI603424B, PI603423A, PI603412B, PI603408, PI603405B, PI603398A, PI603383, PI603382A, PI603380, PI603378A, PI603376, PI603373, PI603371, PI603367, PI603358A, PI603357, PI603356, PI603354, PI603341, PI603340, PI600339B, PI603338, PI603337B, PI603337A, PI603335B, PI603334, PI603330, PI603329, PI603327, PI603326, PI603324A, PI603323, PI603320, PI603316, PI603308A, PI603306, PI603300, PI603299, PI603297, PI603296, PI603295, PI603294, PI603203, PI603201, PI603199, PI603197, PI603195, PI603194, PI603193, PI603192, PI603189, PI603187, PI603186, PI603185, PI603182, PI603181, PI603180, PI603174B, PI603174A, PI603165B, PI603165A, PI603153, PI603151B, PI603151A, PI603150, PI603149, PI603148, PI603147, PI602897, PI602896, PI602594, PI602500B, PI602500A, PI602450, PI602449, PI602060, PI599509, PI599300, PI599299, PI597662, PI597661, PI597660, PI597659, PI597658, PI597657, PI597656, PI597655, PI597654, PI597653, PI597482, PI597481, PI597447, PI597446, PI597445, PI597444, PI597441, PI597440C, PI597440B, PI597440A, PI597439, PI597434, PI597433, PI597432, PI597430B, PI597426, PI597425, PI597423, PI597420, PI597416, PI597415, PI597406, PI597405D, PI597405C, PI597405B, PI597405A, PI597404, PI597403B, PI597403A, PI597402, PI597400, PI597399, PI597397A, PI597395, PI597394, PI597393, PI597391C, PI597391B, PI597391A, PI597390, PI597384, PI597383, PI597382, PI596541, PI596526, PI596413, PI596412, PI595843, PI595754, PI595081, PI594922, PI594892, PI594891, PI594885B, PI594885A, PI594884, PI594883, PI594880, PI594873, PI594866, PI594865, PI594839A, PI594838, PI594825, PI594824, PI594815, PI594813, PI594812, PI594805A, PI594800, PI594797, PI594792B, PI594792A, PI594790C, PI594787, PI594778, PI594772A, PI594759C, PI594759, PI594753B, PI594740C, PI594739A, PI594714, PI594709, PI594695, PI594692, PI594683C, PI594670C, PI594670A, PI594669, PI594663, PI594662B, PI594660A, PI594659A, PI594658, PI594654, PI594643, PI594642, PI594637, PI594631B, PI594629, PI594627B, PI594626, PI594618A, PI594598B, PI594591A, PI594546, PI594538B, PI594538A, PI594537, PI594536, PI594535, PI594534, PI594533B, PI594525, PI594522, PI594515, PI594513, PI594512D, PI594512C, PI594512B, PI594511B, PI594511A, PI594510C, PI594510B, PI594509B, PI594506, PI594502, PI594500D, PI594500C, PI594500B, PI594498B, PI594497, PI594494B, PI594491, PI594490, PI594471D, PI594470A, PI594469A, PI594458B, PI594452, PI594449, PI594448B, PI594446, PI594442A, PI594440, PI594436, PI594412, PI594411, PI594406, PI594319, PI594297, PI594296, PI594279, PI594261, PI594245B, PI594245A, PI594200, PI594198, PI594196, PI594178, PI594166, PI594158, PI594022, PI593999A, PI593998, PI593979, PI593976, PI593971, PI593963, PI593962, PI593960, PI593959, PI593957, PI593956E, PI593956D, PI593956C, PI593956B, PI593956A, PI593951, PI593950B, PI593950A, PI593949B, PI593949A, PI593946, PI593943, PI593940, PI593655, PI593463, PI593258, PI592977, PI592976, PI592970, PI592968, PI592962B, PI592962A, PI592959, PI592958, PI592957, PI592956C, PI592956B, PI592956A, PI592948, PI592947, PI592946, PI592945, PI592939, PI592936, PI592921, PI592918, PI592916, PI592912B, PI592912A, PI592908, PI592907D, PI592907B, PI592905, PI592899, PI592560, PI592524, PI592523, PI591561, PI591548, PI591547, PI591546, PI591545, PI591544, PI591543, PI591542, PI591541, PI591540, PI591539, PI591538, PI591537, PI591536, PI591535, PI591534, PI591533, PI591532, PI591531, PI591530, PI591528, PI591527, PI591526, PI591525, PI591524, PI591523, PI591522, PI591521, PI591519, PI591518, PI591517, PI591516, PI591515, PI591514, PI591513, PI591512, PI591510, PI591509, PI591508, PI591507, PI591506, PI591505, PI591504, PI591503, PI591499, PI591498, PI591497, PI591496, PI591495, PI591494, PI591493, PI591492, PI591491, PI591490, PI591488, PI591487, PI591484, PI591435, PI591434, PI591433, PI591431, PI591430, PI591429, PI590932, PI590931, PI588049, PI588047, PI588022B, PI588014A, PI588014A, PI587999D, PI587998G, PI587998E, PI587996B, PI587996A, PI587993, PI587992F, PI587992D, PI587992C, PI587992A, PI587989B, PI587987A, PI587981, PI587980B, PI587978B, PI587978A, PI587977, PI587976B, PI587976A, PI587968B, PI587967, PI587954, PI587952, PI587941, PI587926, PI587924, PI587915B, PI587913A, PI587895, PI587882, PI587872, PI587862C, PI587843, PI587840, PI587780, PI587768, PI587703B, PI587703A, PI587692A, PI587683, PI587671, PI587659B, PI587598A, PI587588B, PI587185, PI587091, PI586980, PI583837, PI583835, PI583365, PI578495, PI578494A, PI578492, PI578490, PI578477C, PI578477B, PI578471A, PI578437B, PI578437A, PI578432B, PI578426, PI578425, PI578422, PI578417B, PI578415, PI578414, PI578412, PI578411, PI578404, PI578400, PI578392A, PI578389, PI578388B, PI578388A, PI578387, PI578386, PI578383, PI578382, PI578380B, PI578380A, PI578378, PI578375B, PI578374, PI578373, PI578371, PI578357, PI578356, PI578335B, PI578335A, PI578319F, PI578319E, PI578319D, PI578319B, PI578318E, PI578318D, PI578318B, PI578311B, PI578310, PI578305A, PI576166, PI576160, PI576146, PI576145, PI574534, PI572294, PI572265C, PI572265B, PI572265A, PI572244, PI572239, PI568254, PI568245, PI567902, PI567791, PI567787, PI567785, PI567782, PI567779C, PI567779B, PI567776, PI567767D, PI567767B, PI567765C, PI567756B, PI567756A, PI567751A, PI567749B, PI567733, PI567731, PI567725, PI567707, PI567703, PI567701, PI567698A, PI567679C, PI567662, PI567647A, PI567631, PI567630B, PI567614B, PI567614A, PI567585B, PI567573A, PI567547, PI567514A, PI567512C, PI567511, PI567510B, PI567510A, PI567486A, PI567481, PI567478, PI567476, PI567474, PI567473D, PI567473C, PI567471, PI567469B, PI567469A, PI567468, PI567467, PI567466A, PI567459, PI567458, PI567457, PI567456, PI567453, PI567447D, PI567447B, PI567447A, PI567445C, PI567445B, PI567445A, PI567441C, PI567441B, PI567441A, PI567439, PI567438, PI567436, PI567435A, PI567433B, PI567433A, PI567428, PI567423, PI567422, PI567418C, PI567418B, PI567418A, PI567417C, PI567417A, PI567416, PI567415B, PI567415A, PI567414, PI567413, PI567412, PI567410A, PI567409B, PI567409A, PI567408, PI567407, PI567405, PI567404A, PI567403A, PI567400, PI567399, PI567397, PI567390, PI567383, PI567382C, PI567380, PI567379B, PI567377B, PI567374, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI567373B, PI567373A, PI567372B, PI567371A, PI567370A, PI567369B, PI567368, PI567365, PI567364, PI567363B, PI567363A, PI567362A, PI567360, PI567359, PI567358, PI567357, PI567352A, PI567351A, PI567347, PI567344A, PI567343, PI567325A, PI567323B, PI567321A, PI567317, PI567316B, PI567315, PI567313, PI567311B, PI567309, PI567306B, PI567302, PI567293, PI567288B, PI567288A, PI567282A, PI567278, PI567277, PI567270B, PI567243, PI567235B, PI567229B, PI567229A, PI567228, PI567226, PI567225, PI567224D, PI567224C, PI567224B, PI567220C, PI567220B, PI567220A, PI567218, PI567217C, PI567217B, PI567216B, PI567216A, PI567215C, PI567215B, PI567215A, PI567214B, PI567214A, PI567213D, PI567213A, PI567212D, PI567212C, PI567212B, PI567212A, PI567211A, PI567209A, PI567208, PI567206, PI567202, PI567201D, PI567201C, PI567201B, PI567200A, PI567199, PI567198, PI567197, PI567193, PI567177, PI567174C, PI567171, PI567169, PI567165, PI567161, PI567156B, PI567153, PI567145B, PI567139A, PI567135A, PI567133B, PI567132C, PI567129, PI567128B, PI567128A, PI567127B, PI567125, PI567107A, PI567106B, PI567104B, PI567103, PI567102B, PI567101, PI567097B, PI567095B, PI567090, PI567089A, PI567088B, PI567088A, PI567086B, PI567082C, PI567082A, PI567075A, PI567074A, PI567072A, PI567069B, PI567069A, PI567060B, PI567060A, PI567058A, PI567057, PI567054C, PI567047A, PI567046B, PI567046A, PI567039, PI567038, PI567037, PI567035B, PI567035A, PI567033B, PI567031C, PI567030, PI567029B, PI567029A, PI567028, PI567026, PI567025B, PI567025A, PI567024, PI567022A, PI567021, PI567020B, PI567020A, PI567011B, PI567003B, PI566999B, PI566998B, PI566998A, PI566989B, PI566989A, PI566983, PI566982, PI566978, PI566974, PI564718, PI562387, PI562373, PI561860, PI561717, PI561389B, PI561371, PI561369, PI561364, PI561351, PI561348, PI561347, PI561340, PI561338B, PI561332, PI561331, PI561330B, PI561330A, PI561322, PI561321, PI561320, PI561319B, PI561314B, PI561314A, PI561312, PI561311B, PI561308, PI561306, PI561301, PI561296C, PI561296A, PI561288, PI561287B, PI561287A, PI561284, PI561283, PI561282D, PI561282C, PI561282B, PI561280, PI561277, PI561275, PI561273, PI561272, PI561271, PI561201, PI559931, PI557535, PI557011, PI557010, PI556989, PI556950, PI556948, PI556931, PI556929, PI556928, PI556888, PI556850, PI556816, PI556780, PI556779, PI556778, PI556776, PI556729, PI556689, PI556687, PI556637, PI556572, PI556511, PI555396, PI553051, PI552538, PI549072, PI549068, PI549067, PI549064, PI549058, PI549057A, PI549050, PI549049A, PI549022, PI549019, PI548989, PI548973, PI548969, PI548779, PI548698, PI548690, PI548689, PI548686, PI548684, PI548683, PI548681, PI548680, PI548679, PI548676, PI548674, PI548672, PI548671, PI548670, PI548668, PI548652, PI548650, PI548648, PI548646, PI548644, PI548643, PI548642, PI548641, PI548640, PI548637, PI548636, PI548635, PI548634, PI548633, PI548632, PI548631, PI548629, PI548626, PI548623, PI548621, PI548617, PI548616, PI548611, PI548609, PI548607, PI548603, PI548600, PI548598, PI548597, PI548596, PI548595, PI548594, PI548593, PI548592, PI548591, PI548590, PI548589, PI548587, PI548586, PI548585, PI548584, PI548582, PI548581, PI548580, PI548576, PI548575, PI548574, PI548573, PI548571, PI548570, PI548569, PI548568, PI548566, PI548565, PI548562, PI548561, PI548558, PI548556, PI548555, PI548551, PI548549, PI548547, PI548544, PI548542, PI548541, PI548540, PI548539, PI548538, PI548537, PI548535, PI548534, PI548533, PI548532, PI548531, PI548530, PI548524, PI548522, PI548520, PI548518, PI548517, PI548515, PI548513, PI548509, PI548507, PI548506, PI548505, PI548504, PI548503, PI548502, PI548501, PI548500, PI548499, PI548487, PI548486, PI548475, PI548470, PI548468, PI548465, PI548464, PI548460, PI548458, PI548452, PI548451, PI548441, PI548439, PI548434, PI548433, PI548431, PI548430, PI548429, PI548428, PI548427, PI548422S, PI548422, PI548421, PI548420, PI548418, PI548417, PI548415, PI548414, PI548410, PI548407, PI548405, PI548404, PI548403, PI548399, PI548398, PI548396, PI548394, PI548393, PI548389, PI548386, PI548384, PI548383, PI548381, PI548380, PI548379, PI548378, PI548375, PI548374, PI548373, PI548372, PI548371, PI548370, PI548368, PI548367, PI548366, PI548365, PI548363, PI548362, PI548361, PI548359, PI548355, PI548353, PI548352, PI548349, PI548345, PI548341, PI548340, PI548338, PI548336, PI548333, PI548332, PI548329, PI548328, PI548322, PI548317, PI548313, PI548311, PI548310, PI548307, PI548306, PI548305, PI548304, PI548300, PI548298, PI548293, PI548286, PI548285, PI548284, PI548281, PI548280, PI548279, PI548275, PI548270, PI548268, PI548264, PI548263, PI548262, PI548259, PI548255, PI548253, PI548252, PI548251, PI548249, PI548245, PI548244, PI548243, PI548242, PI548239, PI548238, PI548236, PI548235, PI548233, PI548230, PI548229, PI548228, PI548227, PI548225, PI548222, PI548221, PI548217, PI548214, PI548213, PI548211, PI548208, PI548204, PI548202, PI548198, PI548194, PI548193, PI548192, PI548191, PI548187, PI548185, PI548184, PI548180, PI548179, PI548177, PI548174, PI548167, PI548166, PI548165, PI548163, PI548162, PI548159, PI547894, PI547893, PI547892, PI547891, PI547890, PI547889, PI547888, PI547887, PI547886, PI547885, PI547884, PI547883, PI547882, PI547881, PI547880, PI547879, PI547878, PI547877, PI547876, PI547875, PI547874, PI547873, PI547872, PI547871, PI547870, PI547869, PI547868, PI547867, PI547866, PI547865, PI547864, PI547863, PI547862, PI547861, PI547860, PI547859, PI547858, PI547857, PI547856, PI547855, PI547854, PI547853, PI547852, PI547851, PI547850, PI547849, PI547848, PI547847, PI547846, PI547845, PI547844, PI547842, PI547840, PI547839, PI547838, PI547837, PI547836, PI547835, PI547834, PI547832, PI547828, PI547826, PI547825, PI547824, PI547823, PI547817, PI547816, PI547815, PI547814, PI547813, PI547811, PI547810, PI547808, PI547803, PI547802, PI547801, PI547800, PI547798, PI547794, PI547792, PI547789, PI547787, PI547786, PI547785, PI547784, PI547783, PI547782, PI547781, PI547780, PI547779, PI547778, PI547777, PI547776, PI547775, PI547774, PI547773, PI547772, PI547771, PI547770, PI547769, PI547768, PI547767, PI547766, PI547765, PI547764, PI547762, PI547761, PI547760, PI547759, PI547758, PI547757, PI547756, PI547755, PI547754, PI547753, PI547752, PI547751, PI547750, PI547749, PI547748, PI547746, PI547745, PI547744, PI547743, PI547741, PI547740, PI547739, PI547738, PI547737, PI547736, PI547735, PI547734, PI547733, PI547732, PI547731, PI547730, PI547729, PI547728, PI547727, PI547726, PI547725, PI547723, PI547721, PI547720, PI547719, PI547718, PI547717, PI547715, PI547712, PI547711, PI547709, PI547708, PI547707, PI547706, PI547705, PI547704, PI547703, PI547702, PI547701, PI547700, PI547699, PI547698, PI547697, PI547696, PI547695, PI547694, PI547693, PI547692, PI547691, PI547690, PI547689, PI547688, PI547687, PI547686, PI547685, PI547684, PI547683, PI547682, PI547681, PI547680, PI547679, PI547678, PI547676, PI547675, PI547673, PI547672, PI547669, PI547668, PI547665, PI547664, PI547663, PI547662, PI547659, PI547657, PI547656, PI547655, PI547654, PI547652, PI547651, PI547650, PI547649, PI547648, PI547647, PI547645, PI547644, PI547643, PI547642, PI547641, PI547640, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI547638, PI547637, PI547636, PI547635, PI547633, PI547632, PI547631, PI547630, PI547629, PI547628, PI547627, PI547626, PI547625, PI547623, PI547622, PI547621, PI547620, PI547619, PI547618, PI547617, PI547616, PI547615, PI547614, PI547613, PI547612, PI547611, PI547609, PI547608, PI547607, PI547606, PI547605, PI547604, PI547603, PI547602, PI547601, PI547600, PI547599, PI547598, PI547597, PI547596, PI547595, PI547594, PI547593, PI547592, PI547591, PI547590, PI547589, PI547588, PI547587, PI547586, PI547585, PI547584, PI547583, PI547582, PI547581, PI547580, PI547579, PI547578, PI547577, PI547576, PI547575, PI547574, PI547570, PI547569, PI547566, PI547565, PI547564, PI547563, PI547562, PI547561, PI547560, PI547559, PI547558, PI547557, PI547556, PI547555, PI547554, PI547553, PI547552, PI547551, PI547549, PI547548, PI547547, PI547546, PI547545, PI547544, PI547543, PI547542, PI547541, PI547540, PI547539, PI547538, PI547537, PI547536, PI547535, PI547534, PI547533, PI547532, PI547531, PI547530, PI547529, PI547528, PI547527, PI547526, PI547525, PI547524, PI547523, PI547522, PI547521, PI547520, PI547518, PI547517, PI547516, PI547515, PI547514, PI547513, PI547512, PI547511, PI547510, PI547509, PI547508, PI547507, PI547505, PI547504, PI547503, PI547502, PI547501, PI547500, PI547499, PI547498, PI547496, PI547495, PI547494, PI547492, PI547491, PI547490, PI547488, PI547487, PI547486, PI547485, PI547484, PI547483, PI547482, PI547481, PI547480, PI547479, PI547477, PI547476, PI547475, PI547474, PI547473, PI547472, PI547471, PI547470, PI547469, PI547468, PI547467, PI547466, PI547465, PI547464, PI547463, PI547462, PI547461, PI547460, PI547459, PI547458, PI547456, PI547455, PI547453, PI547451, PI547450, PI547449, PI547448, PI547447, PI547446, PI547444, PI547443, PI547442, PI547441, PI547438, PI547437, PI547436, PI547435, PI547434, PI547432, PI547431, PI547429, PI547428, PI547427, PI547425, PI547424, PI547423, PI547422, PI547421, PI547420, PI547419, PI547418, PI547417, PI547416, PI547415, PI547414, PI547413, PI547412, PI547411, PI547410, PI547409, PI547408, PI547407, PI547406, PI547403, PI547402, PI547094, PI546375, PI546374, PI546373, PI546053, PI546052, PI546049, PI546047, PI546045, PI546044, PI546043, PI546040, PI546038, PI543857, PI542972, PI542769, PI542768, PI542711, PI542710, PI542404, PI542403, PI542046, PI542045, PI542044, PI540740, PI540739, PI540555, PI540552, PI540551, PI538410B, PI538409, PI538407, PI538405, PI538401B, PI538395, PI538392, PI538388, PI537096, PI537095, PI537094, PI536635, PI534648, PI534646, PI534645, PI533657, PI533654, PI532473, PI532469, PI532467, PI532465, PI532464, PI532444B, PI532444A, PI532441A, PI532436A, PI531519, PI525492, PI525454, PI525453, PI524993, PI522191, PI522190, PI522186, PI518830, PI518771, PI518758, PI518754, PI518752, PI518750, PI518719, PI518718B, PI518718A, PI518716, PI518710, PI518706C, PI518706B, PI518702, PI518673, PI518672, PI518671, PI518669, PI518667, PI514672, PI514671, PI513382, PI512324, PI512323, PI512322D, PI512322C, PI512322B, PI512322A, PI511361, PI511357, PI511356, PI509112, PI509087, PI509084, PI509044, PI508269, PI508083, PI507841A, PI507840, PI507835, PI507834, PI507831, PI507830B, PI507829, PI507827, PI507826, PI507825, PI507824, PI507821, PI507812B, PI507767, PI507766, PI507765, PI507756, PI507755, PI507752, PI507751, PI507741B, PI507741A, PI507717, PI507716, PI507715B, PI507715A, PI507714, PI507713, PI507710, PI507709, PI507707, PI507706, PI507704A, PI507703, PI507702, PI507698, PI507696C, PI507695, PI507693, PI507689, PI507688, PI507687B, PI507686C, PI507682, PI507681A, PI507680, PI507679B, PI507679A, PI507677, PI507676, PI507674, PI507673, PI507671, PI507670, PI507565, PI507547, PI507545, PI507525B, PI507525A, PI507524, PI507522, PI507503, PI507500, PI507496, PI507493, PI507490, PI507479, PI507478, PI507462, PI507461, PI507440, PI507429, PI507400, PI507391, PI507380, PI507353, PI507352, PI507350, PI507338, PI507335, PI507319, PI507305, PI507283, PI507281, PI507277, PI507276, PI507273, PI507251, PI507227, PI507226B, PI507191, PI507188, PI507167B, PI507162, PI507137, PI507106, PI507071B, PI507059, PI507023, PI507012, PI506987, PI506982, PI506977, PI506960, PI506944, PI506924, PI506923, PI506922, PI506901, PI506877, PI506805, PI506775, PI506774, PI506757, PI506745, PI506719, PI506705, PI506701, PI506700, PI506697, PI506673, PI506637, PI506632, PI506628, PI506607, PI506598, PI506560, PI506551, PI506487, PI506486, PI506476, PI506420, PI505650, PI504509, PI504505, PI504503, PI504498, PI504497, PI504493, PI504492, PI504490, PI504489, PI504486, PI504483A, PI504480, PI503340, PI503339B, PI497970, PI497964C, PI497964B, PI497956, PI497955, PI497953, PI497952, PI495832, PI495017B, PI494526, PI490765, PI486329, PI481691, PI481688, PI481683, PI481676, PI479743, PI479742, PI479736, PI479735, PI479734, PI479731, PI479728B, PI479728A, PI479726, PI479725A, PI479724A, PI479722, PI479712, PI479710, PI479709, PI476933, PI476932, PI476928, PI476925, PI476924, PI476921, PI476914, PI476911, PI476908, PI476891, PI476890, PI476889, PI476884, PI476352B, PI476352A, PI476351, PI476350C, PI476350A, PI476349, PI476347, PI476345, PI476344, PI475828, PI475826, PI475824B, PI475824A, PI475823, PI475822C, PI475822A, PI475821, PI475819, PI475818, PI475817, PI475816, PI475815, PI475814, PI475813B, PI475813A, PI475812B, PI475812A, PI475811B, PI475811A, PI475810, PI475783B, PI473573, PI471929B, PI471927, PI471926, PI471904, PI470930, PI470929, PI470226, PI468923, PI468922, PI468921, PI468913, PI468907, PI468383, PI468382, PI468381, PI468374B, PI468374A, PI467344, PI467341, PI467340, PI467339, PI467337, PI467335B, PI467335A, PI467331, PI467324, PI467313, PI467309, PI467308A, PI467307, PI464916, PI464915A, PI464911, PI464896, PI464887, PI464886, PI464882, PI464877, PI464875B, PI458827, PI458825B, PI458825A, PI458546, PI458532B, PI458525, PI458521, PI458519A, PI458299, PI458281B, PI458281A, PI458261, PI458242, PI458198, PI458192, PI458122, PI458093, PI458073, PI458026, PI449457, PI446893, PI445843, PI445837, PI445836, PI445835, PI445834, PI445833, PI445832, PI445831, PI445830, PI445829B, PI445829A, PI445828, PI445825, PI445824B, PI445824A, PI445823, PI445822, PI445820A, PI445819, PI445818B, PI445816B, PI445814, PI445813, PI445812, PI445811, PI445808B, PI445807B, PI445806, PI445805, PI445803, PI445802, PI445800, PI445799, PI445796, PI445795, PI445792, PI445791, PI445790, PI445788, PI445787, PI445682, PI445681, PI445680, PI442045, PI442044, PI442043, PI442041, PI442040, PI442038B, PI442037, PI442035, PI442034, PI442033, PI442032, PI442031, PI442030, PI442029, PI442027, PI442026, PI442024, PI442023, PI442022, PI442004, PI441373B, PI441352, PI438513, PI438510, PI438509B, PI438509A, PI438507C, PI438507B, PI438507A, PI438506, PI438505, PI438504B, PI438504A, PI438503C, PI438500, PI438496C, PI438496A, PI438492, PI438490B, PI438490A, PI438484, PI438483, PI438481, PI438479, PI438478, PI438476, PI438475B, PI438475A, PI438473, PI438472, PI438470, PI438467, PI438466, PI438464, PI438462, PI438461, PI438460, PI438459, PI438458, PI438456, PI438455, PI438454, PI438450, PI438449, PI438448, PI438446B, PI438446A, PI438445, PI438444, PI438443, PI438434, PI438433, PI438432, PI438427, PI438421, PI438420, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI438418, PI438417, PI438415, PI438412, PI438410, PI438409, PI438407, PI438406, PI438404, PI438401, PI438400, PI438398, PI438397, PI438395, PI438394, PI438393, PI438391, PI438389, PI438387, PI438384, PI438383, PI438382, PI438381, PI438380, PI438379, PI438378, PI438375B, PI438375A, PI438374, PI438373, PI438372, PI438371, PI438370, PI438369B, PI438369A, PI438368, PI438367, PI438366, PI438364, PI438363, PI438361, PI438360B, PI438360A, PI438358B, PI438358A, PI438353, PI438352, PI438351, PI438350B, PI438350A, PI438346, PI438339B, PI438338, PI438337, PI438336, PI438334B, PI438334A, PI438333, PI438330B, PI438330A, PI438327, PI438324, PI438322, PI438321, PI438317, PI438313, PI438310, PI438309, PI438305, PI438301, PI438291, PI438290, PI438279, PI438276, PI438272, PI438271B, PI438271A, PI438270, PI438269, PI438268, PI438259A, PI438258, PI438252C, PI438252B, PI438252A, PI438250B, PI438249B, PI438245, PI438238B, PI438238A, PI438237, PI438236, PI438235, PI438234B, PI438234A, PI438233C, PI438233A, PI438232, PI438230A, PI438229, PI438226, PI438225, PI438224, PI438223, PI438222, PI438221, PI438220, PI438219, PI438217, PI438216, PI438212B, PI438212A, PI438211B, PI438211A, PI438210, PI438207A, PI438206, PI438205, PI438204, PI438202, PI438200, PI438196, PI438195, PI438184, PI438182, PI438181B, PI438181A, PI438180, PI438174, PI438171, PI438170, PI438166B, PI438162, PI438160C, PI438160B, PI438160A, PI438159, PI438158A, PI438157, PI438155, PI438154, PI438149, PI438148, PI438147, PI438145, PI438144, PI438142, PI438141B, PI438140, PI438138B, PI438138A, PI438137B, PI438137A, PI438134, PI438131, PI438128B, PI438128A, PI438127, PI438126, PI438125, PI438122, PI438121, PI438120, PI438119, PI438117, PI438116, PI438114, PI438113, PI438112B, PI438112A, PI438111A, PI438110, PI438109C, PI438109B, PI438109A, PI438107, PI438105B, PI438105A, PI438104, PI438102, PI438101, PI438100, PI438098, PI438097, PI438094B, PI438094A, PI438093, PI438092, PI438091, PI438088, PI438087, PI438083, PI438082, PI438081, PI438078, PI438076, PI438075, PI438074, PI438072, PI438071, PI438068, PI438066, PI438061, PI438059, PI438058, PI438057, PI438056, PI438055B, PI438055A, PI438054, PI438053, PI438052, PI438050B, PI438049, PI438048B, PI438048A, PI438047, PI438045, PI438042, PI438041, PI438040, PI438039, PI438038, PI438037, PI438036, PI438035, PI438034, PI438033, PI438030, PI438029, PI438028, PI438027B, PI438026, PI438025, PI438024, PI438022, PI438021, PI438020, PI438019B, PI438019A, PI438015, PI437996C, PI437996B, PI437996A, PI437995B, PI437995A, PI437992, PI437991B, PI437991A, PI437990, PI437989, PI437988, PI437987, PI437984, PI437983, PI437982, PI437981, PI437977, PI437975B, PI437975A, PI437974B, PI437973, PI437972, PI437968, PI437967, PI437965, PI437964B, PI437963, PI437962, PI437961, PI437960, PI437958, PI437957B, PI437956B, PI437956A, PI437955A, PI437954, PI437953B, PI437953A, PI437952, PI437951, PI437949, PI437948, PI437947, PI437946B, PI437946A, PI437945B, PI437945A, PI437943, PI437920B, PI437920A, PI437919, PI437917, PI437916, PI437915B, PI437915A, PI437914, PI437913, PI437912, PI437911, PI437910B, PI437910A, PI437908, PI437907, PI437903, PI437902D, PI437902B, PI437902A, PI437899, PI437898, PI437897, PI437896, PI437895B, PI437893, PI437892, PI437890B, PI437890A, PI437888B, PI437887B, PI437887A, PI437886B, PI437884, PI437883, PI437880, PI437878B, PI437877A, PI437876, PI437875A, PI437871, PI437869, PI437865, PI437862, PI437861, PI437860A, PI437859, PI437857A, PI437855, PI437851B, PI437850, PI437849, PI437844B, PI437843B, PI437843A, PI437841, PI437839B, PI437839A, PI437838, PI437837A, PI437836, PI437835, PI437834B, PI437834A, PI437833, PI437831, PI437830, PI437829, PI437827, PI437826, PI437824, PI437822, PI437820, PI437819, PI437818B, PI437818A, PI437817, PI437814B, PI437814A, PI437812, PI437810, PI437809, PI437808, PI437805, PI437804, PI437803, PI437802, PI437801, PI437799, PI437798, PI437797, PI437796, PI437795, PI437793, PI437788B, PI437788A, PI437787, PI437785, PI437782, PI437780, PI437779, PI437778, PI437777, PI437776, PI437775, PI437774C, PI437774B, PI437774A, PI437773, PI437772B, PI437772A, PI437771, PI437769, PI437768, PI437766, PI437764, PI437762, PI437759, PI437758, PI437756A, PI437755, PI437754, PI437753B, PI437753A, PI437752A, PI437742, PI437740B, PI437740A, PI437735, PI437733, PI437731, PI437713, PI437711B, PI437707, PI437706, PI437705, PI437699, PI437695B, PI437695A, PI437689, PI437685A, PI437681, PI437680B, PI437680A, PI437676B, PI437669, PI437668, PI437660, PI437657, PI437653, PI437649A, PI437648B, PI437647, PI437646A, PI437645B, PI437645A, PI437644, PI437643A, PI437641A, PI437640A, PI437638, PI437637, PI437635D, PI437635C, PI437635B, PI437635A, PI437633D, PI437633C, PI437633B, PI437632B, PI437632A, PI437630D, PI437630C, PI437627, PI437624, PI437623, PI437622B, PI437622A, PI437621B, PI437621A, PI437618, PI437617, PI437615C, PI437614A, PI437613, PI437611B, PI437610B, PI437610A, PI437608, PI437606, PI437605C, PI437605B, PI437605A, PI437604, PI437603, PI437601, PI437600, PI437599, PI437598A, PI437597B, PI437597A, PI437593A, PI437587, PI437583, PI437582, PI437579, PI437578, PI437577, PI437573A, PI437569, PI437566, PI437564, PI437560, PI437557, PI437553, PI437550C, PI437549, PI437548, PI437547, PI437546, PI437543, PI437542, PI437540, PI437539, PI437538, PI437537, PI437536, PI437535, PI437534, PI437533B, PI437533A, PI437532, PI437531, PI437530, PI437529, PI437528, PI437527, PI437526A, PI437524, PI437520A, PI437519, PI437518, PI437515B, PI437515A, PI437513, PI437512, PI437511, PI437510, PI437508B, PI437508A, PI437507, PI437506, PI437504, PI437503, PI437501B, PI437501A, PI437500B, PI437500A, PI437499, PI437498, PI437497, PI437496, PI437495, PI437493, PI437492, PI437491, PI437490, PI437489, PI437484, PI437483, PI437482, PI437480, PI437479, PI437477B, PI437477A, PI437473, PI437471, PI437470, PI437469B, PI437469A, PI437468, PI437467, PI437466, PI437465, PI437464, PI437463B, PI437463A, PI437462D, PI437462C, PI437462B, PI437462A, PI437461, PI437460, PI437459, PI437458B, PI437458A, PI437454, PI437453, PI437452B, PI437451, PI437450, PI437446, PI437445, PI437443, PI437442, PI437441, PI437439, PI437438, PI437437B, PI437437A, PI437436B, PI437436A, PI437434B, PI437434A, PI437433, PI437432B, PI437432A, PI437431, PI437429B, PI437429A, PI437427A, PI437426, PI437425, PI437422, PI437421, PI437420B, PI437420A, PI437419B, PI437419A, PI437418, PI437417, PI437416, PI437415, PI437414, PI437413, PI437412, PI437411, PI437409, PI437408C, PI437408B, PI437408A, PI437406, PI437403, PI437402, PI437401, PI437400, PI437398, PI437397, PI437396, PI437395B, PI437395A, PI437394, PI437393, PI437392, PI437391, PI437390, PI437389C, PI437389B, PI437389A, PI437388, PI437387, PI437386, PI437384, PI437383, PI437381D, PI437381C, PI437381B, PI437381A, PI437380, PI437379, PI437378C, PI437378B, PI437378A, PI437377, PI437376B, PI437376A, PI437374, PI437373, PI437372, PI437371, PI437370, PI437369, PI437368, PI437366, PI437365, PI437364, PI437363B, PI437363A, PI437362, PI437361, PI437360, PI437359, PI437358, PI437357, PI437354, PI437353, PI437352, PI437348, PI437344B, PI437343, PI437341, PI437340B, PI437340A, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI437339C, PI437338, PI437337, PI437334, PI437333, PI437331, PI437330B, PI437330A, PI437329, PI437328, PI437325, PI437324, PI437323, PI437322, PI437321, PI437318, PI437317, PI437316, PI437314, PI437313, PI437312, PI437311B, PI437310, PI437306B, PI437306A, PI437305, PI437303, PI437302, PI437301, PI437300, PI437299, PI437298, PI437297, PI437296, PI437295, PI437294B, PI437294A, PI437293, PI437292B, PI437292A, PI437291, PI437290, PI437289, PI437288, PI437286, PI437285, PI437287, PI437284, PI437283, PI437282, PI437281, PI437280, PI437279, PI437276, PI437274, PI437273A, PI437272, PI437271, PI437270B, PI437270A, PI437269, PI437268, PI437267, PI437266, PI437265D, PI437265B, PI437265A, PI437264, PI437263, PI437262, PI437261D, PI437261C, PI437261B, PI437261A, PI437260B, PI437260A, PI437259, PI437258, PI437257, PI437256, PI437255, PI437254, PI437253, PI437252, PI437251B, PI437251A, PI437249, PI437248, PI437247, PI437246C, PI437246B, PI437246A, PI437245, PI437244, PI437243, PI437242, PI437241, PI437240, PI437239, PI437238, PI437237, PI437236, PI437234, PI437233, PI437231, PI437230, PI437229, PI437228, PI437227, PI437226, PI437225, PI437223B, PI437223A, PI437221, PI437220, PI437219, PI437217, PI437216, PI437215, PI437214, PI437212, PI437211A, PI437210, PI437209, PI437208, PI437207, PI437206, PI437205B, PI437205A, PI437204, PI437203, PI437202, PI437201, PI437200B, PI437200A, PI437199, PI437198, PI437197, PI437196, PI437195, PI437194, PI437193, PI437192, PI437191, PI437190, PI437189B, PI437189A, PI437187, PI437185, PI437181, PI437180, PI437176, PI437174B, PI437174A, PI437173, PI437168C, PI437168A, PI437167C, PI437167B, PI437166B, PI437165B, PI437164, PI437163, PI437162, PI437161, PI437160, PI437159, PI437158, PI437157, PI437156A, PI437154, PI437153B, PI437153A, PI437152, PI437151, PI437150, PI437149, PI437148, PI437147, PI437145A, PI437144, PI437140, PI437139, PI437137, PI437135B, PI437135A, PI437134, PI437132B, PI437132A, PI437129B, PI437129A, PI437127B, PI437127A, PI437126C, PI437126A, PI437124, PI437123, PI437122, PI437121B, PI437121A, PI437120, PI437119, PI437118B, PI437118A, PI437117, PI437115, PI437113, PI437112B, PI437112A, PI437111, PI437109A, PI437108, PI437107, PI437105C, PI437105B, PI437105A, PI437101, PI437099, PI437098, PI437093, PI437091, PI437088A, PI437084, PI437082, PI437081B, PI437081A, PI437080, PI437079B, PI437079A, PI437078B, PI437077, PI437076, PI437075, PI437074, PI437072, PI437071, PI437070, PI437069, PI436612, PI434982, PI434980B, PI432359, PI430600A, PI430594, PI430536, PI429329, PI427143, PI427139, PI427136, PI427107C, PI427088J, PI427088F, PI427088C, PI424613, PI424611B, PI424611A, PI424610, PI424609, PI424594, PI424560, PI424555A, PI424514, PI424506, PI424472B, PI424468, PI424453, PI424448, PI424447, PI424441, PI424418, PI424411, PI424405B, PI424405A, PI424378, PI424340B, PI424320, PI424304, PI424274B, PI424274A, PI424272A, PI424232B, PI424232A, PI424222A, PI424212, PI424210, PI424208, PI424204, PI424199, PI424198, PI424197, PI424196, PI424195B, PI424195A, PI424194, PI424193, PI424191, PI424190, PI424188A, PI424183, PI424178C, PI424137A, PI424131, PI424078, PI424001, PI423980, PI423952, PI423937, PI423924, PI423899, PI423872, PI423869, PI423866, PI423865, PI423864, PI423852, PI423850, PI423837A, PI423831, PI423822, PI423752A, PI423746, PI423744, PI423742, PI423741, PI423736B, PI423731, PI423719, PI423718, PI423717, PI423714, PI423713, PI423712, PI423711, PI423710, PI423709, PI423708B, PI423708A, PI423707, PI423706, PI423705, PI420338, PI417581, PI417578, PI417577, PI417576, PI417575, PI417574, PI417573, PI417572A, PI417566, PI417565, PI417564, PI417558, PI417557, PI417556, PI417555, PI417554, PI417553, PI417551, PI417550, PI417548, PI417547, PI417546, PI417545, PI417544B, PI417544A, PI417543, PI417540, PI417539, PI417538, PI417537B, PI417535, PI417534, PI417533, PI417532, PI417531, PI417530, PI417528, PI417527, PI417526, PI417525, PI417524, PI417523, PI417522, PI417521, PI417519B, PI417519A, PI417517, PI417516, PI417515, PI417513C, PI417513A, PI417512B, PI417512A, PI417510, PI417509, PI417507, PI417506, PI417483, PI417478, PI417461, PI417455, PI417433, PI417432, PI417419, PI417416, PI417412, PI417385, PI417381, PI417375, PI417363, PI417360, PI417358, PI417350, PI417349, PI417335, PI417324B, PI417324A, PI417310, PI417300, PI417299, PI417295, PI417294, PI417292, PI417291, PI417280, PI417273, PI417264, PI417258, PI417240, PI417235, PI417228, PI417227, PI417226, PI417217, PI417210, PI417206, PI417187, PI417163, PI417153, PI417135B, PI417135A, PI417134, PI417094, PI417087, PI417086A, PI417080, PI417078, PI417076, PI417029, PI417025, PI417007, PI417006, PI416972, PI416959, PI416950, PI416941, PI416934, PI416930, PI416929, PI416923, PI416912, PI416908, PI416886, PI416858, PI416852, PI416840, PI416836, PI416835, PI416828, PI416823, PI416813, PI416805, PI416802, PI416799, PI416793, PI416786, PI416776, PI416772, PI416746, PI415701A, PI408344, PI408343, PI408335B, PI408333, PI408318B, PI408311_1, PI408294A, PI408285A, PI408274, PI408259B, PI408237, PI408236, PI408235, PI408204, PI408201A, PI408190, PI408184A, PI408182, PI408180_2, PI408141, PI408134C, PI408117 |
| Cluster16 | 823 | PI639575, PI639569, PI636000, PI632945A, PI632944D, PI632944B, PI632657, PI632655, PI632645, PI632643, PI632642, PI632641B, PI632640C, PI632640B, PI632640A, PI632639C, PI632639B, PI632639A, PI632637, PI628961, PI628960, PI628943, PI628897, PI628895, PI628857, PI615516, PI615513, PI615512, PI615505, PI615501, PI615498, PI615494, PI615484, PI615481, PI615478, PI615471B, PI615469, PI615451A, PI615449, PI615448, PI615445, PI615438, PI615437, PI615436, PI615435, PI606440B, PI606439, PI606438A, PI606435, PI606432A, PI606430, PI606429, PI606427, PI606424, PI606423, PI606422, PI606420, PI606418A, PI606416B, PI606416A, PI606414, PI606413, PI606406, PI606404, PI606401, PI606399, PI606397B, PI606397A, PI606393, PI606392, PI606390B, PI606390A, PI606388, PI606387, PI606382B, PI606382A, PI606380B, PI606380A, PI606379, PI606378, PI606373, PI606372, PI606368, PI606365, PI606363, PI606362, PI605909B, PI605909A, PI605897C, PI605895, PI605894, PI605893, PI605892, PI605891C, PI605891B, PI605891A, PI605890B, PI605890A, PI605889, PI605885C, PI605883, PI605882B, PI605881, PI605877F, PI605877E, PI605877D, PI605877C, PI605876E, PI605876D, PI605875, PI605874A, PI605873, PI605865B, PI605863B, PI605861B, PI605861A, PI605857B, PI605854B, PI605848, PI605842C, PI605842A, PI605840E, PI605840C, PI605840B, PI605837B, PI605837A, PI605828B, PI605822, PI605820, PI605818B, PI605816, PI605815, PI605814, PI605813, PI605812, PI605811, PI605807, PI605803, PI605801A, PI605800A, PI605796, PI605795, PI605786D, PI605786B, PI605781D, PI605779C, PI605777, PI605776, PI605775, PI605774, PI605770, PI605769, PI605768, PI605764A, PI605763, PI605761, PI605760, PI605759, PI605757, PI605752, PI605751, PI605745C, PI605745B, PI605745A, PI605744, PI605743B, PI605743A, PI603784, PI603783, PI603782, PI603776, PI603764C, PI603760, PI603758E, PI603758C, PI603758B, PI603758A, PI603757A, PI603755C, PI603755B, PI603755A, PI603751B, PI603748, PI603745, PI603742B, PI603732B, PI603732A, PI603730E, PI603730D, |

US 10,337,072 B2
91 92

TABLE 7-continued 15,996 soybean germplasm accessions clustered by maximum parsimony phylogenetic analysis of the
sequence region near the Rhg1 allele, indicating germplasm accessions predicted to carry Rhg1.

| No of germ-plasm | Copy number type observed | Germplasm designation |
|---|---|---|
| | | PI603730C, PI603729, PI603727, PI603725, PI603724D, PI603724C, PI603723, PI603722, PI603721, PI603719C, PI603719B, PI603718B, PI603718A, PI603717, PI603716, PI603715, PI603714, PI603711B, PI603711A, PI603707, PI603704A, PI603690, PI603683, PI603673G, PI603673F, PI603673D, PI603673A, PI603669, PI603668B, PI603668A, PI603667B, PI603664, PI603662B, PI603660, PI603658, PI603654, PI603653, PI603643, PI603642, PI603640, PI603636, PI603633, PI603631, PI603629B, PI603629A, PI603628, PI603623, PI603622, PI603612, PI603611A, PI603599A, PI603598B, PI603598A, PI603594, PI603551A, PI603548B, PI603548A, PI603528, PI603523, PI603519, PI603513B, PI603513A, PI603487B, PI603483, PI603460, PI602993, PI599508, PI597464, PI597380, PI594903, PI594889, PI594879, PI594878, PI594877, PI594876, PI594874, PI594871, PI594856, PI594852C, PI594852B, PI594852A, PI594844, PI594836, PI594835B, PI594835A, PI594834A, PI594833, PI594832B, PI594832A, PI594828B, PI594828A, PI594823, PI594821B, PI594819, PI594810B, PI594807A, PI594794B, PI594789B, PI594788, PI594786B, PI594779, PI594777, PI594776, PI594775, PI594770A, PI594769, PI594768, PI594767B, PI594767A, PI594759D, PI594758C, PI594754, PI594752, PI594751D, PI594751C, PI594750, PI594748B, PI594748A, PI594747A, PI594746, PI594744, PI594742, PI594741B, PI594741A, PI594732, PI594730B, PI594730A, PI594728A, PI594727, PI594726, PI594717A, PI594712, PI594711B, PI594711A, PI594710, PI594708A, PI594706, PI594705, PI594704, PI594703, PI594698, PI594694, PI594691, PI594690B, PI594689, PI594686, PI594685A, PI594684, PI594682A, PI594677, PI594675, PI594674A, PI594670D, PI594670B, PI594650B, PI594644B, PI594644A, PI594641, PI594639, PI594636, PI594632, PI594616, PI594603B, PI594601, PI594596, PI594593, PI594584, PI594582, PI594581, PI594580, PI594579, PI594576, PI594570B, PI594570A, PI594564, PI594555B, PI594550, PI594549C, PI594549B, PI594531, PI594529, PI594526, PI594518, PI594505B, PI594501A, PI594500A, PI594486B, PI594480A, PI594476, PI594473, PI594471E, PI594467, PI594463A, PI594461A, PI594460, PI594458A, PI594457B, PI594456B, PI594454B, PI594451, PI594444B, PI594444A, PI594442B, PI594439A, PI594438, PI594437, PI594430C, PI594430B, PI594430A, PI592954, PI592949, PI592935, PI592904, PI588052C, PI588052B, PI588050B, PI588039, PI588033C, PI588033B, PI588033A, PI588026C, PI588024B, PI588024A, PI588010B, PI588007A, PI588005C, PI587999C, PI587999A, PI587998F, PI587998D, PI587998C, PI587998A, PI587991, PI587989A, PI587988A, PI587987B, PI587986B, PI587986A, PI587985A, PI587984B, PI587983B, PI587983A, PI587982B, PI587982A, PI587980A, PI587979A, PI587976C, PI587971, PI587968C, PI587962, PI587958, PI587956, PI587951B, PI587946B, PI587939, PI587934, PI587931, PI587929, PI587927, PI587922B, PI587915A, PI587914B, PI587914A, PI587911C, PI587911B, PI587911A, PI587887C, PI587887B, PI587887A, PI587870, PI587862D, PI587834, PI587833, PI587831, PI587830B, PI587830A, PI587829, PI587821B, PI587821A, PI587813, PI587812B, PI587807, PI587806A, PI587801, PI587794, PI587792, PI587791, PI587790A, PI587788C, PI587788A, PI587782, PI587779, PI587776, PI587767B, PI587747, PI587744, PI587731, PI587722, PI587716C, PI587716A, PI587709A, PI587708, PI587701, PI587700C, PI587700B, PI587700A, PI587689, PI587687B, PI587679, PI587668C, PI587658C, PI587654, PI587642B, PI587637, PI587633C, PI587633B, PI587633A, PI587632A, PI587631B, PI587628, PI587624, PI587622A, PI587620D, PI587620C, PI587614, PI587612F, PI587612D, PI587612C, PI587612B, PI587612A, PI587608B, PI587607B, PI587606A, PI587605, PI587603A, PI587600C, PI587600B, PI587597A, PI587596C, PI587596B, PI587594, PI587592B, PI587592A, PI587588A, PI587587B, PI587585C, PI587585B, PI587583B, PI587577G, PI587577F, PI587577E, PI587577B, PI587560A, PI587559B, PI587558C, PI587558B, PI587558A, PI587550B, PI578498A, PI578485B, PI578485A, PI578482C, PI578482B, PI578482A, PI578481, PI578474, PI578471B, PI578455A, PI578448, PI578444B, PI578444A, PI578441, PI578365, PI578363, PI578359, PI574478B, PI567775B, PI567775A, PI567771E, PI567771D, PI567771B, PI567768, PI567755C, PI567755B, PI567753C, PI567753B, PI567753A, PI567752, PI567749A, PI567743, PI567741, PI567740, PI567739B, PI567739A, PI567738B, PI567738A, PI567729, PI567720A, PI567712, PI567706A, PI567700, PI567697, PI567695, PI567691, PI567690, PI567688A, PI567686, PI567682A, PI567680, PI567672, PI567670, PI567667C, PI567661A, PI567657, PI567655, PI567645B, PI567645A, PI567643, PI567634, PI567625, PI567624, PI567623, PI567619, PI567618B, PI567613, PI567612, PI567608, PI567603B, PI567603A, PI567599, PI567586B, PI567583C, PI567582B, PI567567, PI567562A, PI567559, PI567532, PI567526, PI567513, PI567499, PI567493, PI567492, PI567489B, PI567482B, PI567482A, PI567432C, PI567395, PI567394B, PI567265, PI567236, PI567189B, PI567186, PI567185, PI567182, PI567181A, PI567180, PI567144B, PI567134, PI567117A, PI567115A, PI567113, PI567111, PI567097A, PI567096, PI567087C, PI567049B, PI567049A, PI567036, PI567031B, PI567010B, PI567005C, PI567002C, PI567002B, PI567001B, PI567001A, PI567000B, PI567000A, PI566986, PI566959, PI562547, PI561380, PI561374, PI561359, PI561357, PI548495, PI548491, PI548490, PI548489, PI548478, PI548472, PI548469, PI548462, PI548461, PI548459, PI548454, PI548446, PI548444, PI548437, PI538402B, PI532461, PI532460B, PI518729, PI518727, PI518723, PI507024, PI506639, PI504510, PI495019, PI490769, PI490768, PI486331, PI486330, PI476943, PI476942, PI476939, PI476931, PI476926, PI476922, PI476910, PI476898, PI476894, PI476888, PI476887, PI476880, PI476879, PI468966, PI468965, PI468912, PI468911, PI468910, PI468909, PI468908, PI468904, PI458201, PI445827B, PI442003A, PI437749, PI437709, PI437667, PI437594B, PI437594A, PI437591, PI437563, PI437562, PI434981, PI430626, PI430600C, PI430600B, PI427276, PI417502, PI417501, PI417500, PI417498, PI417382, PI417318, PI417316, PI417313, PI417127, PI417115, PI417093, PI417014B, PI407764, PI407763, PI407759, PI407755, PI407753, PI407752, PI407751, PI407736, PI407735, PI407734, PI407732, PI407730, PI407658C, PI407658B, PI407658A, PI407318A, PI407198, PI404186, PI404185, PI404179A, PI404164, PI393543, PI393542, PI381661, PI381660, PI377578, PI377575, PI376844, PI371607, PI341246, PI341244B, PI331795, PI330633, PI326578, PI325779, PI322695, PI322693, PI281906A, PI281890D, PI281887B, PI263044, PI262180, PI261272A, PI253651C, PI253651A, PI221716, PI221714, PI205906, PI204338, PI203400, PI203399, PI200524, PI200487, PI200484, PI200448, PI171439, PI171434, PI165676, PI159925, PI158765, PI157488, PI123577B, PI085897, PI079861, PI063945, PI060970, FC031919, FC031676, FC031665, FC031649, FC031592 |
| Cluster17 | 1 | PI507584 |
| Cluster18 | 3 | PI549030B, PI549030A, PI507643 |
| Cluster19 | 7 | PI562562, PI464889C, PI464889B, PI464889A, PI424109A, PI424055, PI407204 |
| Cluster20 | 1538 | PI648388, PI639625, PI639613, PI639612A, PI639611, PI639610, PI639609, PI639608, PI639602, PI639600B, PI639598, PI639597B, PI639593, PI639591, PI639590B, PI639590, PI639589, PI639588A, PI639585, PI639581, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI639573, PI639541B, PI639541A, PI639529B, PI639529A, PI639527, PI632749, PI632747, PI612733, PI612705, PI612616, PI612612B, PI605819B, PI603917, PI603916, PI603915C, PI603915B, PI603912, PI603911B, PI603909B, PI603907, PI603759B, PI603600, PI603599B, PI603541B, PI603488, PI603464, PI603462, PI603461, PI603457B, PI603448, PI603419C, PI603419B, PI603419A, PI603416, PI603413, PI603412A, PI603410, PI603397, PI603386, PI603370, PI603368, PI603312, PI603301B, PI603292, PI603166, PI603164, PI603160, PI603159, PI597451B, PI597428, PI594516, PI594503, PI594471C, PI594463B, PI594400, PI594394, PI594267, PI594249, PI594225A, PI594014B, PI594013, PI594006, PI594005B, PI594005A, PI593993A, PI592951, PI592909, PI588027C, PI588019B, PI588006B, PI588006A, PI588005B, PI588005A, PI588004, PI588003, PI587763, PI587644, PI587607A, PI587606E, PI587606D, PI587606C, PI587606B, PI578477A, PI578433, PI578431, PI578428A, PI578395, PI578355, PI578354, PI578353B, PI578353A, PI578352, PI578351, PI567583B, PI567570, PI567563B, PI567553, PI567517, PI567516B, PI567281B, PI567281A, PI567280, PI567195, PI567194, PI567166, PI567163, PI567157A, PI562541, PI562540, PI562539, PI562538, PI562535, PI561346, PI561318B, PI561318A, PI561311A, PI561302B, PI561299A, PI561298, PI561295, PI561231, PI553043, PI553038, PI549028, PI549021A, PI548669, PI548548, PI548514, PI548471, PI548456, PI548351, PI548312, PI548308, PI548276, PI548169, PI538391, PI532434, PI522192B, PI520732, PI518833, PI518280, PI518279, PI509111, PI509097, PI509090, PI509082, PI509080, PI509079, PI509076, PI508297, PI508296D, PI507718B, PI507638, PI507636, PI507631, PI507627, PI507590B, PI507589, PI507555, PI507528, PI507469, PI507457, PI507427, PI507421, PI507418, PI507410, PI507402, PI507389, PI507385, PI507336, PI507286A, PI507272, PI507263, PI507253, PI507244, PI507228, PI507214, PI507211, PI507179, PI507160, PI507158, PI507121, PI507114, PI507098, PI507095B, PI507028, PI506979, PI506962, PI506946, PI506917, PI506893, PI506835, PI506811, PI506810, PI506796, PI506747, PI506733A, PI506687, PI506608, PI506597, PI506590D, PI506590A, PI506550A, PI506545, PI506541, PI506489, PI495020, PI491578, PI487428, PI482602, PI482601, PI482600, PI482599, PI479738, PI479727, PI479713, PI479711, PI473572, PI470227B, PI470227A, PI468408B, PI468385, PI467347, PI467310, PI464941, PI464940, PI464923, PI464909, PI464884, PI464881, PI464876, PI461508, PI458522, PI458512, PI458296, PI458294, PI458293, PI458283, PI458279, PI458278B, PI458273, PI458271, PI458268, PI458266, PI458264, PI458263, PI458260, PI458250, PI458244B, PI458239, PI458238, PI458234, PI458230B, PI458227, PI458226, PI458224, PI458223, PI458221, PI458214, PI458206, PI458200, PI458195, PI458188, PI458183, PI458181, PI458179, PI458175D, PI458172B, PI458172A, PI458171A, PI458169B, PI458169A, PI458165, PI458161, PI458158, PI458156, PI458155, PI458154, PI458151, PI458150C, PI458149, PI458143, PI458137, PI458135, PI458134, PI458132, PI458131, PI458127, PI458125, PI458123A, PI458119, PI458118, PI458113, PI458112A, PI458110, PI458109, PI458108, PI458100, PI458099, PI458097, PI458096, PI458092, PI458090B, PI458089, PI458087, PI458084, PI458081, PI458080, PI458076, PI458072B, PI458071, PI458070C, PI458070B, PI458070A, PI458069, PI458066, PI458064, PI458062A, PI458060B, PI458060A, PI458058, PI458055, PI458053B, PI458053A, PI458052, PI458051B, PI458051A, PI458049, PI458048, PI458045B, PI458045A, PI458044, PI458043, PI458041, PI458036, PI458025, PI458023, PI458019, PI452432, PI449460B, PI449460A, PI449459, PI445821, PI438453, PI438437, PI438405, PI438399, PI438392, PI438390, PI438377, PI438359, PI438355, PI438348A, PI438345, PI438318, PI438308B, PI438304B, PI438304A, PI438302B, PI438298, PI438297, PI438296, PI438292, PI438289, PI438285, PI438274, PI438265, PI438199, PI438198, PI438163, PI438156, PI438099, PI438027A, PI438023, PI437964A, PI437906, PI437885, PI437852, PI437842, PI437816, PI437815, PI437813, PI437767, PI437761, PI437750, PI437748, PI437746, PI437712, PI437694, PI437615A, PI437596, PI437586C, PI437574, PI437573B, PI437561, PI437523, PI437509, PI437476, PI437474B, PI437474A, PI437407, PI437385B, PI437375A, PI437332, PI437326, PI437320, PI437311A, PI437308, PI437183, PI437142, PI437138, PI437104, PI430624, PI430623, PI430599, PI424616, PI424615, PI424614, PI424608B, PI424606, PI424605B, PI424605A, PI424597, PI424592, PI424591, PI424583, PI424579, PI424571, PI424570, PI424567, PI424565, PI424559, PI424552, PI424547, PI424546B, PI424537, PI424535A, PI424532, PI424529, PI424525, PI424523A, PI424518, PI424516, PI424513, PI424510, PI424509, PI424498, PI424497, PI424490, PI424486, PI424482, PI424481B, PI424479, PI424472A, PI424470, PI424466, PI424465, PI424460, PI424455, PI424446, PI424445, PI424440, PI424436, PI424430, PI424429, PI424428, PI424427, PI424421, PI424420, PI424419, PI424416, PI424414, PI424412, PI424406A, PI424404, PI424403, PI424402B, PI424402A, PI424400, PI424399, PI424387, PI424384, PI424376, PI424374, PI424371, PI424370B, PI424370A, PI424370, PI424368A, PI424366, PI424358, PI424353, PI424351, PI424349C, PI424349B, PI424348A, PI424343, PI424342A, PI424336, PI424334, PI424325, PI424324B, PI424321, PI424315, PI424314, PI424313, PI424311, PI424300A, PI424299A, PI424294C, PI424294B, PI424291, PI424288, PI424287, PI424285A, PI424282, PI424281B, PI424278B, PI424275, PI424273B, PI424273A, PI424271, PI424270C, PI424270B, PI424269C, PI424268, PI424267, PI424261, PI424256, PI424255B, PI424253, PI424250B, PI424247B, PI424247A, PI424246, PI424245, PI424244, PI424227A, PI424224, PI424223, PI424222C, PI424221A, PI424219A, PI424213, PI424207, PI424189, PI424186, PI424182A, PI424180, PI424178B, PI424176, PI424174, PI424172C, PI424171A, PI424169B, PI424159A, PI424152, PI424150, PI424144, PI424143, PI424142, PI424136, PI424135, PI424122, PI424121, PI424083B, PI424073, PI424046B, PI424043B, PI424011, PI423975, PI423965, PI423922, PI423918, PI423910, PI423895, PI423863B, PI423861, PI423858, PI423854, PI423853, PI423849, PI423846, PI423844, PI423842, PI423841, PI423840, PI423838, PI423836, PI423834, PI423833A, PI423828, PI423827A, PI423826B, PI423826A, PI423820, PI423819, PI423814B, PI423809, PI423796A, PI423795, PI423791, PI423788, PI423787, PI423785, PI423784, PI423780, PI423777, PI423776, PI423774, PI423773, PI423770, PI423764, PI423763, PI423759, PI423758, PI423756B, PI423754, PI423752B, PI423748C, PI423740, PI423739, PI423737, PI423734, PI423730B, PI423730A, PI423726, PI423721, PI423715, PI417560, PI417518, PI417514, PI417508, PI417496, PI417440, PI417431, PI417410, PI417409, PI417407, PI417406, PI417405, PI417402, PI417392, PI417379, PI417351, PI417348, PI417347, PI417337, PI417331, PI417309B, PI417309A, PI417266, PI417229, PI417199, PI417181, PI417160, PI417157, PI417090, PI417039, PI417019, PI416997, PI416995, PI416960, PI416942, PI416885, PI416841, PI416809, PI416807, PI416795, PI416756, PI416755, PI408327A, PI408318, PI408317, PI408314, PI408311_2, PI408308B, PI408307B, PI408307A, PI408305, PI408299, PI408298A, PI408295A, PI408293_2, PI408293_1, PI408291, PI408289, PI408288, PI408285C, PI408271, PI408270C, PI408264, PI408263, PI408262D, PI408262B, PI408260B, PI408259A, PI408258, PI408256, PI408250, PI408248A, PI408247, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI408246_2, PI408245, PI408243, PI408238_2, PI408228A, PI408227, PI408226A, PI408225B, PI408221C, PI408219, PI408218, PI408217C, PI408216B, PI408216A, PI408215B, PI408212B, PI408212A, PI408209C, PI408209B, PI408206_1, PI408203B, PI408203A, PI408201B, PI408198, PI408186A, PI408185, PI408184B, PI408180_1, PI408178, PI408176, PI408173, PI408172, PI408169D, PI408169C, PI408169B, PI408169A, PI408167B, PI408166C, PI408158, PI408156, PI408148, PI408146, PI408145, PI408136, PI408135A, PI408133, PI408132, PI408131B, PI408131A, PI408127, PI408125B, PI408124A, PI408122, PI408116, PI408111, PI408095C, PI408095A, PI408094_2, PI408090, PI408089, PI408083A, PI408082, PI408081, PI408080, PI408079B, PI408079A, PI408078, PI408072, PI408068B, PI408067B, PI408066B, PI408065, PI408062, PI408057, PI408055B, PI408055A, PI408050B, PI408050A, PI408033, PI408019A, PI408017, PI408016B, PI408016A, PI408007, PI408004_1, PI408000, PI407998C, PI407997, PI407994, PI407992, PI407989, PI407987, PI407985, PI407984, PI407981C, PI407981A, PI407978, PI407975B, PI407972C, PI407972B, PI407967, PI407966C, PI407962_2, PI407961_2, PI407961_1, PI407960A, PI407959B, PI407959A, PI407951, PI407950_1, PI407944, PI407942, PI407941A, PI407939A, PI407936, PI407931, PI407929, PI407928, PI407927B, PI407924, PI407922, PI407914B, PI407914A, PI407912, PI407908, PI407907A, PI407895, PI407892C, PI407890_1, PI407888, PI407881, PI407880, PI407877A, PI407876, PI407867A, PI407863, PI407860, PI407859_2, PI407854, PI407848, PI407847, PI407846, PI407845A, PI407844, PI407843, PI407841, PI407839_1, PI407835, PI407834, PI407826, PI407825, PI407822, PI407821B, PI407820, PI407819, PI407818B, PI407818A, PI407816, PI407815, PI407814_2, PI407814_1, PI407813, PI407811, PI407808_2, PI407808_1, PI407807, PI407805D, PI407804, PI407803, PI407802, PI407801, PI407800, PI407798, PI407797, PI407794, PI407793, PI407791, PI407790_2, PI407790_1, PI407789, PI407788B, PI407786B, PI407786A, PI407784, PI407781A, PI407779, PI407777, PI407776, PI407775, PI407773B, PI407773A, PI407772A, PI407709, PI407386C, PI407254, PI407244, PI407237, PI407192, PI407183, PI407166, PI407137, PI407114, PI407089, PI407088, PI407085, PI407083, PI407067, PI407052, PI407049, PI407048, PI407046, PI407045, PI407039, PI407038, PI407037, PI407036, PI407035, PI407034, PI407033, PI407027, PI406709, PI406708, PI406684, PI404191, PI399125, PI399124, PI399123, PI399120, PI399118, PI399117, PI399116, PI399115, PI399113, PI399110, PI399107, PI399105, PI399103, PI399096, PI399086, PI399085, PI399084, PI399083, PI399081, PI399069, PI399067, PI399060, PI399059, PI399054, PI399050, PI399042, PI399040, PI399039, PI399038, PI399032, PI399031, PI399029, PI399028, PI399027, PI399024, PI399021, PI399019, PI399017, PI399016, PI399014, PI399013, PI399012, PI399006, PI399005, PI399004, PI399003, PI399002, PI399000, PI398994, PI398990, PI398985, PI398984, PI398976, PI398970, PI398968, PI398962, PI398961, PI398959, PI398953, PI398951, PI398946, PI398944, PI398943, PI398930, PI398918, PI398917, PI398914, PI398913, PI398912, PI398911, PI398905, PI398901, PI398900, PI398897, PI398894, PI398884, PI398880, PI398869, PI398866, PI398861, PI398857, PI398851, PI398842, PI398839, PI398838, PI398837, PI398833, PI398825, PI398815, PI398805, PI398804, PI398792, PI398791, PI398790, PI398788, PI398787, PI398786, PI398784, PI398778, PI398777, PI398776, PI398774, PI398773, PI398771, PI398763, PI398762, PI398761, PI398752, PI398748, PI398747, PI398745, PI398743, PI398739, PI398733, PI398730, PI398729, PI398724, PI398722, PI398721, PI398713, PI398711, PI398703, PI398700, PI398699, PI398697, PI398694, PI398693, PI398689, PI398679, PI398676, PI398674, PI398667, PI398665, PI398659, PI398655, PI398653, PI398652, PI398651, PI398650, PI398649, PI398632, PI398630, PI398629, PI398628, PI398627, PI398617, PI398616, PI398615, PI398584, PI398583, PI398582, PI398581, PI398580, PI398579, PI398577, PI398573, PI398572, PI398567, PI398566, PI398565, PI398563, PI398561, PI398559, PI398554, PI398553, PI398552, PI398551, PI398548, PI398542, PI398541, PI398539, PI398538, PI398536, PI398530, PI398528, PI398526, PI398525, PI398520, PI398519, PI398518, PI398515, PI398513, PI398510, PI398508, PI398507, PI398502, PI398496, PI398493, PI398491, PI398490, PI398486, PI398483, PI398477, PI398476, PI398468, PI398467, PI398466, PI398465, PI398464, PI398459, PI398458, PI398454, PI398453, PI398451, PI398450, PI398449, PI398445, PI398443, PI398441, PI398439, PI398434, PI398433, PI398432, PI398430, PI398423, PI398422, PI398421, PI398410, PI398408, PI398407, PI398405, PI398403, PI398402, PI398401, PI398396, PI398387, PI398373, PI398344, PI398339, PI398332, PI398328, PI398327, PI398326, PI398324, PI398323, PI398313, PI398312, PI398311, PI398308, PI398307, PI398305, PI398297, PI398296, PI398285, PI398279, PI398275, PI398272, PI398269, PI398268, PI398265, PI398261, PI398260, PI398257, PI398255, PI398252, PI398244, PI398243, PI398240, PI398237, PI398236, PI398234, PI398232, PI398229, PI398220, PI398219, PI398212, PI398207, PI398198, PI398193, PI398192, PI398189, PI398186, PI393551, PI393541A, PI391585, PI385943, PI381684, PI381678, PI381677, PI381676, PI381675, PI381673, PI381672, PI381670, PI381667, PI381666, PI381665, PI381663, PI381662, PI381656, PI378702, PI378701B, PI378701A, PI378692, PI378688, PI378673, PI366123, PI366036, PI361103, PI361071B, PI361060, PI360845, PI360842, PI347570, PI347552A, PI340053B, PI340048, PI340044, PI340043, PI340035, PI340032, PI340030, PI340028, PI340026, PI340024, PI340021B, PI340019, PI340004, PI339999, PI339997, PI339978, PI339866, PI297550, PI297541, PI297524, PI297520, PI291331, PI291329, PI291328, PI291326, PI291319B, PI291310A, PI291274A, PI291273, PI291272, PI290158, PI290155, PI290151, PI290148, PI290138, PI290137, PI290136, PI290120, PI273483F, PI273483D, PI248515, PI248410, PI246365, PI245331, PI243549, PI243546, PI243535, PI243531, PI243526, PI238925, PI232995, PI232902, PI229347, PI229320, PI227327, PI227325, PI227160, PI221715, PI209333, PI208789, PI203404, PI200534, PI196167, PI189965, PI189960, PI189956, PI189955, PI189952, PI189944, PI189877, PI189876, PI187155, PI181568, PI181564, PI180532, PI180530, PI180521, PI180519, PI171436, PI170899, PI170893, PI170891, PI166147, PI159593A, PI157487B, PI157482, PI157477, PI157472, PI157454, PI157448, PI157447, PI157443, PI157439, PI157431, PI157430, PI157428, PI157410, PI157402, PI154195, PI154194, PI154193, PI154192, PI154189, PI153682, PI153286, PI153284, PI153283, PI153282, PI153281, PI153279, PI153278, PI153277, PI153275, PI153274, PI153273, PI153272, PI153270, PI153261, PI153259, PI153204, PI148260, PI132205, PI132204, PI123439, PI105579, PI097225, PI097161, PI097081, PI097066, PI096786, PI096550, PI096354, PI096169B, PI096093, PI095853, PI095801, PI092734, PI092707, PI092649, PI092630, PI092619, PI092617, PI092611, PI092608, PI092607, PI092605, PI092603, PI092601_1, PI092601, PI092600, PI092594, PI092592, PI092590, PI092572, PI092569, PI092567, PI092557, PI092469, PI091733, PI091725_4, PI091725, PI091684, PI091178, PI091174, PI091164, PI091149, PI091127, PI091100, PI091073, PI090768, PI090305, PI090243, PI090241, PI090233, PI090208, PI089143, |

TABLE 7-continued 15,996 soybean germplasm accessions clustered by maximum parsimony phylogenetic analysis of the sequence region near the Rhg1 allele, indicating germplasm accessions predicted to carry Rhg1.

| | No of germ-plasm | Copy number type observed | Germplasm designation |
|---|---|---|---|
| | | | PI089074, PI089061_3, PI089061, PI089060, PI089058, PI089013, PI089012_1, PI089005_4, PI089002, PI088815, PI088814, PI088782, PI088780, PI088491, PI088486, PI088479, PI088466_1, PI088447, PI088359, PI088354, PI088352, PI088298, PI088297, PI088282, PI087600_1, PI087542, PI087540, PI087465_1, PI087457, PI087029, PI087013, PI087002, PI086978, PI086878, PI086740, PI086144, PI086113, PI086109B, PI086089, PI086084, PI086062, PI085658, PI085630, PI085559, PI085506, PI085490, PI085469, PI085420_1, PI085010, PI084949, PI084939, PI084874, PI084742, PI084724, PI084674, PI084671, PI084669N, PI084666_1, PI084664, PI084594, PI083923, PI083915, PI083893, PI083874, PI083853, PI082581, PI082555, PI082527, PI082509, PI082312, PI082295, PI082263_2, PI082259, PI082184S, PI081780S, PI081774, PI081044_1, PI081037, PI081034_2, PI080473, PI080468, PI080461, PI079862, PI079586, PI071570, PI071506, PI070520, PI070478, PI070469, PI070466_4, PI070027, PI070009, PI068756, PI068736, PI064747, PI055089, PI054862, PI054600, PI054583, PI036906, Noir, FC033243_2, FC033243_1, FC033243, FC032175, FC031933, FC031918, FC031709 |
| Cluster21 | 5 | | PI507649, PI507603, PI407170, PI407169, PI407168 |
| Cluster22 | 3 | | PI507614A, PI504289, PI407029 |
| Cluster23 | 3 | | PI605884A, PI415701B, PI407749 |
| Cluster24 | 19 | | PI605787D, PI605783, PI605779E, PI603785, PI597462B, PI597459D, PI597459C, PI594841A, PI594723, PI588048, PI587579B, PI578473D, PI549047, PI424108, PI417380, PI323561, PI171427, PI086078, FC019979_2 |
| Cluster25 | 1 | | PI423748A |
| Cluster26 | 5 | | PI549045B, PI504288, PI464936B, PI407306, PI407304 |
| Cluster27 | 209 | | PI628822, PI597450A, PI597449, PI597448D, PI597448B, PI597448A, PI594215, PI578346A, PI578342A, PI567059, PI562566, PI562555, PI562551, PI562542, PI549037, PI549035B, PI549034, PI549032, PI548435, PI548416, PI532453B, PI532449, PI522235B, PI522233, PI522229, PI522220B, PI522215, PI522216, PI522215, PI522214B, PI522181, PI522180, PI507830A, PI507812A, PI507803, PI507800A, PI507794, PI507777, PI507734, PI507664, PI507658, PI507655, PI507654, PI507653, PI507637, PI507625, PI507587, PI507581, PI507515, PI507344, PI507282, PI507221, PI507200, PI507197B, PI507091, PI507054, PI507047, PI506762B, PI506762A, PI506710, PI506709, PI506609, PI506588, PI506587, PI506562, PI504287B, PI479744, PI464928, PI464892, PI464866B, PI464866A, PI458539B, PI458535, PI458301, PI458253, PI458209, PI424477, PI424451, PI424119, PI424115A, PI424114B, PI424114A, PI424106B, PI424097, PI424088, PI424076B, PI424071, PI424070A, PI424069, PI424060, PI424056, PI424054B, PI424054A, PI424053, PI424051A, PI424049, PI424048, PI424046A, PI424044, PI424043A, PI424042, PI424041, PI424040, PI424039B, PI424039A, PI424038B, PI424033, PI424032, PI424021B, PI424021A, PI424020B, PI424020A, PI424019, PI424018, PI424014, PI424012, PI424006B, PI424006A, PI423944, PI423938, PI423936, PI417487, PI417472D, PI417472C, PI417452, PI417447, PI417384, PI417274, PI417198, PI417189, PI417151, PI417082, PI417062, PI417054, PI417050, PI416965, PI416956, PI416896, PI416879, PI416863, PI407937_2, PI407322, PI407313, PI407299, PI407278, PI407269, PI407243, PI407242, PI407231, PI407229, PI407227, PI407213, PI407212, PI407211, PI407205, PI407193, PI407188, PI407184, PI407176, PI407164, PI407158, PI407157, PI407156, PI407145, PI407144, PI407142, PI407140, PI407139, PI407135, PI407134, PI407129, PI407080, PI407078, PI407070, PI407068, PI391587, PI378696B, PI378696A, PI378689, PI366120, PI366119, PI349647, PI339871A, PI339735A, PI339731, PI230972, PI227218, PI205092, PI200545, PI200542, PI200522, PI200518, PI200517, PI200508, PI200499, PI200478, PI200473, PI097155, PI094159, PI090481, PI087630, PI086134_3, PI086112, PI085625, PI085492, PI084992, PI083881A, PI082263_1, FC019979_4 |
| Cluster28 | 1 | | PI088813 |
| Cluster29 | 3 | | PI597452B, PI587854B, PI553050 |
| Cluster30 | 4 | | PI407318B, PI407044, PI407042, PI378685, |
| Cluster31 | 2 | | PI588032B, PI588020 |
| Cluster32 | 8 | | PI549017, PI483464B, PI483464A, PI483462B, PI479753B, PI468919, PI468400A, PI464938 |
| Cluster33 | 1 | | PI578346B |
| Cluster34 | 4 | | PI587630C, PI587630B, PI587630A, PI587570B |
| Cluster35 | 1 | | PI398270 |
| Cluster36 | 3 | | PI518282, PI507642, PI424107B |
| Cluster37 | 2 | | PI603502C, PI567269D |
| Cluster38 | 10 | | PI522211C, PI522182B, PI522182A, PI464929B, PI464871B, PI464871A, PI458540D, PI458540C, PI458540A, PI407216 |
| Cluster39 | 2 | | PI588021B, PI171437 |
| Cluster40 | 61 | | PI644059, PI644058, PI644057, PI644056, PI644054, PI628892, PI628886, PI628869, PI614156, PI603698J, PI603387, PI603172, PI603171, PI603162, PI603155, PI594690A, PI594005E, PI594005C, PI578369, PI572238, PI548186, PI548158, PI508267, PI479723, PI437891, PI424575, PI424562, PI424499A, PI424386A, PI424348C, PI424259, PI424178A, PI423848, PI417401, PI408272C, PI408196B, PI408196A, PI408165, PI408134B, PI408074C, PI408074B, PI408008, PI407973B, PI407973A, PI399106, PI399026, PI399025, PI399020, PI399015, PI398986, PI398489, PI398338, PI398190, PI340045, PI092641, PI088448, PI083942, PI082325, PI070541, PI070242_2, FC030967 |
| Cluster41 | 5 | | PI522205B, PI507641, PI407257, PI378699B, PI378691 |
| Cluster42 | 1814 | | PI647086, PI644053, PI644052, PI644051, PI644050, PI644049, PI644048, PI642768, PI639578, PI639574, PI639570, PI639565, PI639564, PI639563, PI639562, PI639561, PI639528C, PI639528B, PI636462, PI636460, PI633735, PI632944A, PI632940, PI632937, PI632667, PI632664, PI632663B, PI632662, PI632659, PI632652, PI632647, PI632641A, PI632636A, PI629014, PI629008, PI628958, PI628953, PI628952, PI628949, PI628947, PI628942, PI628918, PI628917, PI628916, PI628915, PI628908, PI628906, PI628901, PI628899, PI628898, PI628894, PI628893, PI628890, PI628889, PI628888, PI628887, PI628884, PI628883, PI628882, PI628876, PI628875, PI628873, PI628870, PI628868, PI628866, PI628864, PI628863, PI628860, PI628859, PI628856, PI628855, PI628853, PI628851, PI628848A, PI628846, PI628845, PI628843, PI628842, PI628838, PI628836, PI628835, PI628834, PI628832, PI628830, PI628829, PI628825, PI628824, PI628816, PI628809, PI628808, PI628805, PI628803, PI628802, PI628801, PI628800, PI619615, PI618809, PI615514, PI615499, PI615493, PI615458, PI615452, PI615451B, PI614155, PI613055, PI612735, PI612732, PI612622A, PI606411, PI606395, |

TABLE 7-continued 15,996 soybean germplasm accessions clustered by maximum parsimony phylogenetic analysis of the
sequence region near the Rhg1 allele, indicating germplasm accessions predicted to carry Rhg1.

| No of germ-plasm | Copy number type observed | Germplasm designation |
|---|---|---|
| | | PI606375, PI606371, PI605906, PI605898, PI605897B, PI605888, PI605847, PI605846D, PI605846A, PI605804B, PI605804A, PI605793, PI605792D, PI605791A, PI605790, PI605787C, PI605787B, PI605787A, PI605781A, PI605755, PI605754, PI603908, PI603768, PI603764A, PI603757C, PI603757B, PI603756, PI603755E, PI603755D, PI603754, PI603753B, PI603753A, PI603752, PI603750B, PI603750A, PI603749, PI603661B, PI603602, PI603597, PI603596, PI603503, PI603502B, PI603502A, PI603501, PI603495B, PI603495A, PI603487C, PI603487A, PI603400, PI603347, PI603290, PI602994, PI602493, PI602059, PI599811, PI597487, PI597484, PI597483, PI597478B, PI597478A, PI597477, PI597476, PI597471D, PI597469, PI597467, PI597389, PI594902, PI594869, PI594857, PI594837A, PI594765, PI594747B, PI594733, PI594716B, PI594568B, PI594568A, PI594567B, PI594567A, PI594542, PI594541, PI594540, PI594530, PI594505A, PI594455A, PI594397B, PI594397A, PI594308, PI594295, PI594288, PI594276, PI594268B, PI594268A, PI594255, PI594252B, PI594252A, PI594250, PI594235, PI594219, PI594212, PI594193, PI594188, PI594164, PI594019, PI594011, PI593948, PI593648, PI592972, PI592950, PI592940, PI592933, PI592932, PI592913, PI592910, PI592756, PI588026B, PI588019C, PI588010A, PI587997B, PI587990, PI587884, PI587883A, PI587847, PI587815A, PI587808A, PI587784, PI587757A, PI587718, PI587709B, PI587707, PI587705A, PI587698B, PI587688, PI587687A, PI587663, PI587652, PI587651, PI587650, PI587649, PI587648, PI587647B, PI587647A, PI587646, PI587645, PI587643B, PI587643A, PI587639, PI587620B, PI587616, PI587608C, PI587604C, PI587604B, PI587604A, PI587601D, PI587601C, PI587601B, PI587601A, PI587600A, PI587598B, PI587597C, PI587596A, PI587595C, PI587591, PI587585A, PI587583D, PI587583C, PI587577I, PI587577H, PI587577C, PI587577A, PI587572B, PI587563C, PI587557C, PI587557B, PI587550A, PI584470, PI578499C, PI578480, PI578479, PI578478A, PI578476, PI578473C, PI578471C, PI578462, PI578456, PI578454, PI578446B, PI578442, PI578334, PI578333, PI578332A, PI578328C, PI578328B, PI578328A, PI578246, PI572243, PI572241, PI570668, PI568260, PI567742B, PI567713E, PI567713D, PI567352C, PI567273B, PI567273A, PI567267B, PI567267A, PI567266D, PI567266C, PI567266B, PI567266A, PI567264D, PI567264C, PI567263, PI567262E, PI567262D, PI567262A, PI567261D, PI567253, PI567239, PI567188, PI567178, PI567155C, PI567152, PI567150B, PI567150A, PI567147C, PI567147B, PI567145C, PI567145A, PI567140B, PI567137B, PI567135B, PI567132B, PI567131A, PI567130B, PI567124, PI567123A, PI567122D, PI567122C, PI567120, PI567119, PI567118B, PI567115C, PI567114, PI567112, PI567110B, PI567109, PI567106A, PI567105, PI567100A, PI567099A, PI567093A, PI567083B, PI567081, PI567077A, PI567076, PI567068B, PI567068A, PI567066, PI567056B, PI567051, PI567048B, PI567048A, PI567043B, PI567041D, PI567041C, PI567041B, PI567032B, PI567023B, PI567019, PI567015, PI567012, PI567010A, PI567009B, PI567009A, PI567008, PI567007B, PI567006B, PI566995B, PI566994, PI566993B, PI566991, PI566988A, PI566987B, PI566987A, PI566985C, PI566985A, PI566980B, PI566980A, PI566972, PI566969, PI566968C, PI566968A, PI566964A, PI566963, PI566960, PI566957, PI561575, PI561571, PI561396, PI561393, PI561392, PI561391, PI561379B, PI561379A, PI561358A, PI561315, PI561286, PI559371, PI553049, PI553046, PI553045, PI553039, PI549071, PI549063, PI549053, PI548985, PI548984, PI548980, PI548979, PI548978, PI548697, PI548696, PI548675, PI548666, PI548664, PI548663, PI548661, PI548659, PI548657, PI548625, PI548624, PI548599, PI548579, PI548554, PI548494, PI548493, PI548492, PI548488, PI548485, PI548479, PI548476, PI548474, PI548442, PI548411, PI548397, PI548391, PI548382, PI548358, PI548347, PI548343, PI548342, PI548334, PI548315, PI548301, PI548296, PI548277, PI548266, PI548240, PI548237, PI548195, PI548173, PI543832, PI539867, PI539863, PI539860, PI538403, PI536637, PI536547A, PI536009, PI531520, PI518825, PI518759, PI518728, PI518297, PI518287, PI518284, PI509104, PI508298, PI508296A, PI508266, PI507718A, PI507692B, PI507692A, PI507575, PI507573, PI507568, PI507566, PI507562, PI507560, PI507557, PI507555, PI507552, PI507539, PI507538, PI507537, PI507536, PI507532, PI507531, PI507526, PI507521, PI507520, PI507519, PI507518, PI507512, PI507510, PI507507, PI507487, PI507485, PI507477, PI507467, PI507463, PI507459, PI507446, PI507441B, PI507441A, PI507436, PI507434, PI507431, PI507430, PI507428, PI507424, PI507415, PI507414, PI507412, PI507409, PI507405, PI507401, PI507398, PI507393, PI507388, PI507384, PI507375, PI507371, PI507370, PI507358, PI507357, PI507351, PI507345, PI507341, PI507339, PI507337, PI507331, PI507327, PI507326, PI507324, PI507308, PI507307, PI507303, PI507302, PI507300, PI507292, PI507287, PI507285, PI507280, PI507279, PI507275, PI507265, PI507262, PI507261, PI507259, PI507254, PI507249, PI507246, PI507241, PI507235, PI507232, PI507231, PI507220, PI507219, PI507215, PI507208, PI507205, PI507202, PI507195, PI507194, PI507193, PI507189B, PI507189A, PI507187, PI507184B, PI507184A, PI507169, PI507156, PI507142, PI507138, PI507136, PI507134, PI507133, PI507127, PI507126, PI507125, PI507119, PI507104, PI507099, PI507096, PI507094, PI507093, PI507089B, PI507087, PI507085, PI507080, PI507077, PI507068, PI507067, PI507061, PI507060, PI507058, PI507056, PI507053, PI507046, PI507038, PI507036, PI507032, PI507019, PI507017, PI507016, PI507015, PI507014, PI507011, PI506998, PI506986, PI506985, PI506975, PI506939, PI506938, PI506921, PI506919, PI506915, PI506914, PI506910, PI506905, PI506891, PI506889, PI506888, PI506880, PI506879, PI506873, PI506872, PI506851, PI506848, PI506847, PI506846, PI506845, PI506844, PI506832, PI506824, PI506817, PI506813, PI506808, PI506788, PI506776, PI506771, PI506768, PI506766, PI506761, PI506755, PI506740, PI506738, PI506732, PI506730, PI506729, PI506727, PI506714, PI506707, PI506699, PI506698, PI506694, PI506688, PI506681, PI506670, PI506667, PI506666, PI506661, PI506653, PI506647, PI506643, PI506604, PI506603, PI506600, PI506595B, PI506585A, PI506580, PI506575B, PI506575A, PI506574, PI506563, PI506557, PI506555, PI506552, PI506534, PI506520, PI506516, PI506515, PI506514, PI506509, PI506508, PI506506, PI506505, PI506501, PI506499, PI506495, PI506494, PI506493, PI506491, PI506490, PI506477, PI505649A, PI504499, PI504495, PI504494, PI504488, PI504487, PI504485, PI504482, PI503334, PI500648, PI499957, PI494851, PI490766, PI486355, PI486354B, PI486354A, PI483082B, PI483082A, PI479729, PI476919, PI476905B, PI476905A, PI476903, PI476892, PI471943B, PI471943A, PI471938, PI468969, PI468968, PI464932, PI462312, PI459072, PI458307B, PI458307A, PI458304, PI458278A, PI458259, PI458245, PI458244A, PI458237, PI458233, PI458229, PI458207, PI458205, PI458197, PI458189B, PI458189A, PI458186, PI458178, PI458175C, PI458175A, PI458160, PI458153, PI458147, PI458140, PI458123B, PI458117, PI458101, PI458061B, PI458061A, PI458042, PI458040, PI458022, PI445817, PI445810B, PI445810A, PI445797, PI445794B, PI441381, PI441380, PI441360A, PI441359, PI441355, PI438480, PI438431, PI438430, PI438428, PI438414, PI438403, PI438365, PI438357B, PI438357A, PI438347, PI438344, PI438308A, PI438295, PI438293, PI438287, PI438277, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI438273, PI438262, PI437867B, PI437726, PI437721B, PI437721A, PI437697, PI437685D, PI437685C, PI437685B, PI437651B, PI437649B, PI437586B, PI437586A, PI437522, PI437485, PI437475, PI437339B, PI437339A, PI437304, PI437188, PI437184, PI437182, PI437179, PI437178, PI437177, PI437146, PI437145B, PI437141, PI437136, PI437106, PI437085, PI436565, PI434977B, PI434976, PI434973B, PI434973A, PI430901, PI430736, PI430596, PI430595, PI429330, PI429328, PI429327, PI427141, PI427138, PI424607, PI424603, PI424569B, PI424569A, PI424568, PI424563, PI424561, PI424550, PI424540, PI424533, PI424526, PI424507, PI424502, PI424501, PI424499D, PI424499C, PI424499B, PI424491B, PI424488A, PI424478, PI424475, PI424474_1, PI424473, PI424444A, PI424435, PI424425, PI424423, PI424422, PI424405C, PI424397, PI424389, PI424388, PI424382, PI424381, PI424359, PI424355, PI424337_2, PI424337_1, PI424327, PI424326, PI424319, PI424297, PI424293, PI424265, PI424264, PI424263, PI424249E, PI424249C, PI424249A, PI424242, PI424234A, PI424155B, PI424148, PI424134, PI423987A, PI423973, PI423969, PI423968, PI423964, PI423963, PI423961B, PI423960A, PI423958, PI423957, PI423955, PI423954, PI423953, PI423949, PI423948B, PI423948A, PI423947, PI423945, PI423942, PI423941, PI423940, PI423939, PI423933, PI423932, PI423931, PI423930A, PI423929, PI423920, PI423917, PI423916, PI423908, PI423905, PI423891, PI423890A, PI423889, PI423879, PI423877, PI423867, PI423860, PI423829, PI423818, PI423817, PI423798B, PI423798A, PI423796B, PI423716, PI417580, PI417568, PI417567, PI417562, PI417542, PI417541, PI417537A, PI417536B, PI417536A, PI417529, PI417511, PI417505, PI417503, PI417493, PI417492, PI417489, PI417486, PI417484, PI417480, PI417479, PI417477, PI417471, PI417470, PI417466, PI417464, PI417458, PI417454, PI417451, PI417450, PI417449, PI417446, PI417443, PI417442, PI417435, PI417421, PI417420, PI417411, PI417404, PI417403, PI417391, PI417389A, PI417388, PI417387, PI417372, PI417371, PI417370, PI417369, PI417368, PI417367, PI417366, PI417365A, PI417356, PI417355B, PI417355A, PI417354, PI417342, PI417339, PI417338, PI417336, PI417327, PI417326, PI417325, PI417323, PI417321, PI417319, PI417317, PI417315, PI417314, PI417312, PI417311, PI417308, PI417306, PI417305, PI417302, PI417289, PI417287, PI417284, PI417283, PI417281, PI417279, PI417271, PI417268, PI417267, PI417265, PI417262, PI417261, PI417260A, PI417256, PI417253, PI417251, PI417241, PI417237, PI417231, PI417225, PI417224, PI417218, PI417215, PI417213, PI417211, PI417209, PI417208, PI417201, PI417200, PI417196B, PI417196A, PI417195, PI417192, PI417190, PI417186, PI417185, PI417183, PI417174, PI417171, PI417170, PI417165, PI417164, PI417162, PI417161, PI417159, PI417154, PI417150, PI417149, PI417148, PI417146, PI417145, PI417144, PI417143, PI417136, PI417130, PI417124, PI417122, PI417117, PI417114, PI417105, PI417101, PI417096, PI417075, PI417071, PI417067, PI417066, PI417060, PI417056, PI417053, PI417052, PI417048, PI417046, PI417042, PI417040B, PI417038, PI417036, PI417035, PI417033B, PI417033A, PI417032, PI417031, PI417028, PI417024, PI417017, PI417016, PI417015, PI417013, PI417012, PI417010, PI417004, PI417001, PI417000, PI416998, PI416996, PI416993, PI416992, PI416991, PI416985, PI416981, PI416980, PI416974, PI416973, PI416968, PI416967, PI416964, PI416963, PI416961, PI416957, PI416952, PI416946, PI416945, PI416944, PI416943, PI416937, PI416931, PI416925, PI416924, PI416922, PI416921, PI416920, PI416917, PI416916, PI416915, PI416914, PI416911, PI416910, PI416909, PI416906, PI416901, PI416898, PI416895, PI416889, PI416888, PI416887, PI416880B, PI416880A, PI416878, PI416875, PI416874A, PI416873C, PI416873A, PI416869, PI416860, PI416856, PI416855, PI416846, PI416845, PI416842, PI416830, PI416819A, PI416812, PI416811, PI416808, PI416806, PI416800, PI416791, PI416790, PI416787, PI416782, PI416781, PI416780, PI416777, PI416773, PI416769C, PI416769B, PI416764, PI416757, PI416749, PI416748, PI416747, PI408342, PI408340, PI408321, PI408315B, PI408312B, PI408312A, PI408303, PI408287, PI408279, PI408278, PI408270A, PI408266, PI408255A, PI408253, PI408241, PI408240, PI408239, PI408223, PI408213, PI408211A, PI408210, PI408206_2, PI408205, PI408200B, PI408199, PI408130, PI408123, PI408097, PI408086, PI408076A, PI408075, PI408074A, PI408052C, PI408052B, PI408052A, PI408048A, PI408028, PI408026, PI408025, PI408023, PI408005, PI408003_2, PI407974A, PI407952B, PI407952A, PI407946_1, PI407933, PI407926B, PI407926A, PI407925, PI407903B, PI407903A, PI407889, PI407877B, PI407875B, PI407875A, PI407870, PI407865, PI407862, PI407861C, PI407861B, PI407861A, PI407851, PI407850, PI407849, PI407845B, PI407832A, PI407821A, PI407812, PI407778B, PI407778A, PI407766, PI407744, PI407286, PI406707, PI404188B, PI404159, PI399080, PI399076, PI399074, PI399063, PI399051, PI399043, PI399036, PI399018, PI399008, PI399001, PI398996, PI398992, PI398989, PI398988, PI398980, PI398957, PI398956, PI398955, PI398954, PI398939, PI398934, PI398933, PI398927, PI398923, PI398919, PI398910, PI398908, PI398903, PI398902, PI398898, PI398887, PI398885, PI398859, PI398845, PI398841, PI398832, PI398831, PI398826, PI398822, PI398821, PI398814, PI398813, PI398806, PI398764, PI398751, PI398749, PI398728, PI398727, PI398726, PI398725, PI398712, PI398710, PI398709, PI398687, PI398686, PI398685, PI398684, PI398654, PI398641, PI398640, PI398639, PI398638, PI398637, PI398636, PI398601, PI398600, PI398599, PI398505, PI398504, PI398503, PI398440, PI398337, PI398262, PI398253, PI393540, PI385942, PI381685, PI381668, PI381664, PI379561, PI379559D, PI379559C, PI379559B, PI379559A, PI378679, PI376070, PI376069, PI374174, PI374171, PI374167, PI374166, PI374156, PI361116, PI361115, PI361111, PI361102, PI361073, PI360851, PI360848, PI360847, PI360846, PI360841, PI360839, PI360838, PI360836, PI358316C, PI342005, PI341264, PI341263, PI341261, PI341260B, PI341260A, PI341258, PI341250, PI341242, PI341241B, PI340900B, PI340899, PI340898B, PI340898A, PI340053A, PI340049, PI340047, PI340041, PI340033, PI340020, PI340018, PI340013, PI340011, PI340007, PI340003, PI339993, PI339991, PI339868F, PI339868D, PI339868C, PI339868A, PI339864A, PI339863B, PI331794, PI331793, PI324189, PI324187B, PI324068, PI323580, PI323567, PI323564, PI322690, PI319533, PI319531, PI319530, PI319529, PI319526, PI309655E, PI309655D, PI309655C, PI309655B, PI307899B, PI307899A, PI307897, PI307894, PI307892, PI307891B, PI307891A, PI307889C, PI307886, PI307883, PI307882F, PI307882E, PI307882C, PI307882B, PI307882A, PI307880E, PI307880C, PI307879, PI307878B, PI307878A, PI307877, PI307876B, PI307876A, PI307875, PI307874, PI307873B, PI307873A, PI307872C, PI307872B, PI307872A, PI307868, PI307860, PI307857, PI307856, PI307855, PI307851A, PI307850B, PI307847, PI307846, PI307844, PI307842B, PI307840, PI307839, PI307838E, PI307838D, PI307838B, PI306702B, PI297545, PI290156, PI285096, PI285095, PI285094, PI285092, PI285090, PI285089, PI284816B, PI284816A, PI284814, PI281913B, PI281913A, PI281912, PI281911C, PI281911B, PI281911A, PI281910, PI281909, PI281907, PI281906B, PI281905, PI281902, PI281899C, PI281899B, PI281898A, PI281897A, PI281896G, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI281896F, PI281896E, PI281896C, PI281896A, PI281893, PI281892A, PI281891B, PI281891A, PI281890B, PI281890A, PI281887A, PI281883C, PI281883A, PI274582, PI274507, PI274456, PI274455, PI274423, PI274420, PI274212, PI274206, PI273483E, PI273483A, PI264555, PI262181, PI261469, PI261466, PI261272D, PI261272B, PI257434, PI257429, PI248514, PI247679, PI246369, PI246366, PI243551, PI243544, PI243527, PI240670, PI240669, PI240667B, PI240667A, PI240666, PI239236, PI239235, PI238931, PI238929, PI235347, PI235344, PI235340, PI235339, PI235335, PI232996, PI230979, PI230978, PI230976, PI230973, PI230971, PI229362, PI229361, PI229354, PI229353, PI229352, PI229349, PI229345, PI229342, PI229341, PI229334, PI229331, PI229330, PI229328, PI229327, PI229326, PI229325, PI229322, PI229319, PI229314, PI228056, PI227686, PI227685, PI227684, PI227224, PI227222, PI227214, PI226591, PI226589, PI226588, PI224275, PI224273, PI224271, PI224268, PI222548, PI222547, PI221717, PI219785, PI219783, PI215755, PI215691, PI215690, PI210353, PI210352, PI210351B, PI210350, PI209839B, PI209335, PI208784, PI208782, PI208435, PI208203, PI205912, PI205911, PI205903, PI205902, PI205901B, PI205899, PI205089, PI205085, PI203406, PI203405, PI203403, PI203398, PI201431, PI201428, PI200832, PI200551, PI200547, PI200546, PI200543, PI200541, PI200539, PI200535, PI200531, PI200528, PI200525, PI200510, PI200507, PI200504, PI200502, PI200500, PI200498, PI200492, PI200491, PI200488, PI200486, PI200482, PI200480, PI200479, PI200476, PI200474, PI200469, PI200468, PI200465, PI200464, PI200462, PI200460, PI200458, PI200452, PI200451, PI200450, PI200449, PI200445, PI198067, PI197182, PI196525, PI196164, PI194773, PI189958, PI189940, PI189932, PI189923, PI189899, PI189874, PI189871, PI189867, PI187153, PI183485, PI181699, PI181571, PI181570, PI181566, PI181558, PI181557, PI181555, PI181551, PI181550, PI181546, PI181545, PI181544, PI181543, PI180508, PI174860, PI173994, PI171450, PI170890, PI170889, PI170887, PI170886, PI165671, PI164885, PI159322, PI159321, PI159097, PI159095, PI159094, PI157487A, PI157475, PI157444, PI157440, PI157409, PI154191, PI153303, PI153288, PI153264, PI153230, PI153225, PI153223, PI153222, PI153221, PI153219, PI153218, PI153217, PI153216, PI153212, PI153211, PI153210, PI153208, PI153203, PI152573, PI151249, PI145079, PI132217, PI132214, PI132203, PI103415, PI096783, PI096333, PI096169, PI096162, PI095780, PI094159_3, PI092706, PI092688_2, PI092623, PI092602, PI092595, PI091725_2, PI091646, PI091162, PI091113, PI090354, PI088803, PI088789, PI087076, PI087026, PI086903_4, PI086876, PI086510, PI086491, PI086490_4, PI086490_3, PI086138R, PI086091, PI086078_1, PI086045S, PI086023, PI086006, PI085666S, PI085420, PI085356, PI085342, PI085014, PI085012, PI085009_2, PI085009_1, PI084979, PI084750, PI084669, PI084646, PI083945_1, PI082588, PI082312N, PI082302, PI082291, PI082232, PI080841, PI080471, PI080466_2, PI080466_1, PI080466, PI079870_1, PI070188, PI068522, PI060272, PI054855, FC031745, FC031732, FC031731, FC031689, FC030691, FC030689, FC030685, FC030267, FC021340, FC019976 |
| Cluster43 | 15 | PI597460B, PI597460A, PI578345, PI578340B, PI578340A, PI522212A, PI522209A, PI522198B, PI424130, PI424128B, PI424128A, PI424127B, PI424126, PI424125, PI407285 |
| Cluster44 | 2 | PI424017B, PI424017A |
| Cluster45 | 38 | PI632939, PI615489, PI606443, PI606441, PI606417, PI606415, PI606374, PI603780, PI603746, PI603719A, PI594687, PI594685B, PI594682B, PI594676, PI594638B, PI594635A, PI594501B, PI594471A, PI594464, PI594454A, PI594448A, PI594441, PI594415B, PI588026A, PI588015C, PI588015B, PI588013, PI588007B, PI587963, PI587900A, PI587855, PI587684B, PI587682A, PI587634B, PI587634A, PI587633D, PI476899, PI434974 |
| Cluster46 | 2 | PI597472, PI597450B |
| Cluster47 | 1 | PI407289 |
| Cluster48 | 1 | PI407178 |
| Cluster49 | 1 | PI424118 |
| Cluster50 | 1 | PI562554 |
| Cluster51 | 144 | PI642055, PI639566D, PI634913, PI634871, PI614832, PI603564C, PI603564B, PI603564A, PI603559, PI603543C, PI603543B, PI603543A, PI603472C, PI603339A, PI603307, PI593961, PI572245, PI567470, PI567213B, PI548673, PI548620, PI548601, PI548578, PI548577, PI548516, PI548406, PI548339, PI548241, PI548234, PI548232, PI548206, PI548203, PI547797, PI518291C, PI518291B, PI518291A, PI507694, PI507678, PI438260, PI438256A, PI438230B, PI438139, PI438135, PI438124B, PI438124A, PI438111B, PI438108, PI438106, PI438090, PI438089, PI438080, PI438077, PI438069B, PI438051B, PI438051A, PI438046, PI438044, PI437986, PI437966, PI437957A, PI437901, PI437650A, PI437646B, PI437642, PI437626, PI437625, PI437620, PI437619, PI437616, PI437598B, PI437502, PI437375B, PI437169B, PI437083, PI424557, PI416902, PI416853, PI404173B, PI355070S, PI355069S, PI355069, PI347543, PI347542, PI347541, PI291310C, PI248396, PI200592, PI167240, PI157470, PI096193, PI092719, PI092690, PI092640, PI092639, PI092604, PI091178_1, PI091141, PI091082, PI090567_1, PI089130, PI088806, PI088461, PI088393, PI088351, PI088350, PI088349, PI088291, PI086504, PI086502, PI086456, PI086449_2, PI086112_1, PI085456, PI085340, PI084679, PI084657, PI084656, PI084644, PI081761, PI080834_1, PI079846, PI079835, PI079746, PI079602, PI073780, PI071461, PI070519, PI070476, PI070201, PI070197, PI068748_1, PI068725, PI068622, PI068535, PI068474_2, PI068011, PI054608_3, FC004007B, FC003654N, FC002109, FC002108 |
| Cluster52 | 12 | PI562550, PI561355, PI522183B, PI522183A, PI479767, PI464925B, PI464925A, PI464891B, PI464869B, PI464869A, PI458536, PI424102B |
| Cluster53 | 10 | PI562559, PI458138, PI424111, PI424103A, PI424102A, PI424101, PI407273, PI398853, PI398251, PI398250 |
| Cluster54 | 1 | PI562558 |
| Cluster55 | 2 | PI175189, PI166032 |
| Cluster56 | 11 | PI603592, PI587869, PI567473B, PI437918, PI437661A, PI437570, PI437558, PI081772, PI079727, PI079691_4, PI079691 |
| Cluster57 | 4 | PI597454A, PI597453, PI587694, PI567299B |
| Cluster58 | 2 | PI507808, PI507791 |
| Cluster59 | 7 | PI578344B, PI532452B, PI507784, PI507761, PI479745, PI464891A, PI407250 |
| Cluster60 | 5 | PI483466, PI407210, PI407209, PI407054, PI407053 |
| Cluster61 | 3 | PI567424A, PI424104, PI408019B |
| Cluster62 | 1 | PI507657 |

TABLE 7-continued 15,996 soybean germplasm accessions clustered by maximum parsimony phylogenetic analysis of the sequence region near the Rhg1 allele, indicating germplasm accessions predicted to carry Rhg1.

| | No of germ-plasm | Copy number type observed | Germplasm designation |
|---|---|---|---|
| Cluster63 | 3 | | PI603568, PI424236, PI424227B |
| Cluster64 | 7 | | PI407086, PI407081, PI407066, PI407065, PI407064, PI407063, PI407059 |
| Cluster65 | 1 | | PI378684A |
| Cluster66 | 45 | | PI639607, PI639603, PI639601B, PI639601A, PI639597A, PI597459A, PI578343, PI522231A, PI522217, PI522200B, PI507607, PI507606, PI507594A, PI483460B, PI479747, PI464934, PI464927C, PI424091B, PI424091A, PI424090, PI424087, PI424084, PI424074, PI424072B, PI424072A, PI424070B, PI424068, PI424067, PI424066, PI424064, PI424061A, PI424052, PI424045, PI424037, PI424036, PI424035, PI407272, PI407262, PI407215, PI407201, PI407130, PI378687B, PI339735B, PI339732, PI326581 |
| Cluster67 | 2 | | PI407259, PI407091 |
| Cluster68 | 1639 | | PI632935B, PI632650, PI615504, PI613559F, PI613559E, PI613559D, PI613559C, PI613559B, PI612613, PI606436, PI603915E, PI603913C, PI603913B, PI603911C, PI603909C, PI603909A, PI603775A, PI603761, PI603743A, PI603742D, PI603742A, PI603737C, PI603737B, PI603672B, PI603672A, PI603666, PI603613, PI603567B, PI603562B, PI603562A, PI603538F, PI603538D, PI603484, PI603481, PI603480, PI603477B, PI603475, PI603473, PI603471, PI603468, PI603467, PI603465D, PI603465C, PI603465B, PI603465A, PI603459, PI603452, PI603423B, PI603407, PI603382B, PI603331, PI603200, PI603198, PI603167, PI603158, PI602992, PI597485, PI597474, PI594908, PI594858A, PI594849, PI594848, PI594830, PI594806, PI594805B, PI594793, PI594760A, PI594619, PI594618C, PI594558, PI594495, PI594455B, PI594450, PI594448, PI594428, PI594427C, PI594427B, PI594298, PI594238, PI594172B, PI594172A, PI594153, PI594149, PI594148, PI594023B, PI594015, PI594008, PI593995B, PI593994, PI593993B, PI593990, PI593989, PI593988, PI593987, PI593986, PI593985, PI593984, PI593966, PI592955, PI587893, PI587772, PI587728, PI587715, PI587705B, PI587698A, PI587686B, PI587686A, PI587661B, PI587661A, PI587653, PI587640, PI587636, PI587632B, PI587618D, PI587618B, PI587613, PI587608A, PI587602, PI587575A, PI587567A, PI587566A, PI578497A, PI578470, PI578401D, PI578364, PI578358, PI578323B, PI578313B, PI578312, PI572297, PI567781, PI567761, PI567734, PI567732, PI567721, PI567684B, PI567681, PI567679A, PI567676A, PI567675, PI567654, PI567650D, PI567607B, PI567501, PI567477, PI567472, PI567465, PI567464, PI567462, PI567461, PI567460, PI567442, PI567435B, PI567427, PI567406B, PI567394C, PI567394A, PI567392, PI567350A, PI567333A, PI567320, PI567286, PI567285, PI567282B, PI567274, PI567245, PI567237, PI567234C, PI567179, PI567176, PI567155A, PI567151, PI567149, PI567061, PI567058D, PI567058C, PI567058B, PI567033A, PI561701, PI561399, PI561394, PI561378, PI561339, PI561294, PI561291, PI549065, PI549027B, PI548483, PI548457, PI548419, PI548413, PI548412, PI548390, PI548346, PI548327, PI548323, PI548282, PI548160, PI538381, PI536547C, PI532443, PI518831, PI509113, PI509107, PI509105, PI509103, PI509102, PI509099, PI509096, PI509093, PI509086, PI509081, PI509078, PI507579, PI507578, PI507572, PI507564, PI507563, PI507559, PI507558, PI507554, PI507551, PI507549, PI507527, PI507523, PI507514, PI507511, PI507509B, PI507509A, PI507508, PI507506, PI507499, PI507498, PI507495, PI507494, PI507489, PI507488, PI507484, PI507482, PI507481, PI507480, PI507453, PI507450, PI507448, PI507438, PI507433, PI507406B, PI507406A, PI507396, PI507379, PI507372, PI507363, PI507359, PI507346, PI507342, PI507333, PI507332, PI507330, PI507323, PI507322, PI507318, PI507317, PI507314, PI507313, PI507310, PI507306, PI507299, PI507298, PI507293B, PI507288, PI507284, PI507271, PI507270, PI507268, PI507267, PI507266, PI507260, PI507258, PI507257, PI507252, PI507247, PI507243, PI507242, PI507238, PI507237, PI507236, PI507234, PI507233, PI507230, PI507225, PI507224, PI507223, PI507218, PI507217, PI507212, PI507209, PI507206, PI507203, PI507198, PI507196, PI507192, PI507183, PI507182, PI507181, PI507177, PI507170, PI507159, PI507157, PI507151, PI507150, PI507146, PI507145, PI507144, PI507143, PI507140, PI507131, PI507128, PI507120, PI507118, PI507117B, PI507117A, PI507116, PI507115, PI507113, PI507112, PI507111, PI507110, PI507109, PI507107, PI507105, PI507103, PI507102, PI507082B, PI507082A, PI507081, PI507074, PI507071A, PI507070, PI507064, PI507057, PI507055, PI507052, PI507050, PI507048, PI507045, PI507044, PI507042, PI507041, PI507039, PI507034, PI507033, PI507030, PI507026, PI507022, PI507018, PI507010, PI507009, PI507007, PI507006, PI507005, PI507003, PI507001, PI507000, PI506997, PI506996, PI506991, PI506990, PI506988, PI506978, PI506976, PI506974, PI506973, PI506972, PI506966, PI506965, PI506964, PI506959, PI506956, PI506955, PI506953, PI506952, PI506949, PI506948, PI506947, PI506943, PI506941, PI506937, PI506934, PI506931, PI506928, PI506926, PI506918, PI506890, PI506886, PI506884, PI506878, PI506875, PI506871, PI506860, PI506859, PI506858, PI506853, PI506852, PI506833, PI506831, PI506828, PI506807, PI506806, PI506804, PI506801B, PI506801A, PI506800A, PI506799, PI506795, PI506792, PI506791, PI506790, PI506789, PI506786, PI506784, PI506783, PI506781, PI506779, PI506778, PI506777, PI506773, PI506770, PI506765, PI506756, PI506754, PI506750, PI506748, PI506746, PI506743, PI506742, PI506741, PI506736, PI506735B, PI506735A, PI506716, PI506713, PI506711B, PI506711A, PI506708, PI506695, PI506682, PI506674, PI506657, PI506650, PI506648, PI506646, PI506645, PI506644, PI506640, PI506629, PI506627, PI506626, PI506625, PI506624, PI506622, PI506620, PI506619, PI506617, PI506616, PI506614, PI506613, PI506611, PI506610, PI506606, PI506605, PI506602, PI506599, PI506591, PI506585B, PI506584, PI506582, PI506579, PI506578, PI506564, PI506561, PI506556, PI506554, PI506553, PI506546, PI506544, PI506543, PI506542, PI506540, PI506538, PI506537, PI506531, PI506530, PI506529, PI506527, PI506526, PI506523, PI506522, PI506519, PI506518, PI506496, PI506492, PI506488, PI506485, PI506484, PI506481, PI506480, PI506479, PI506472, PI506471, PI497967, PI486353, PI483084, PI479732, PI476901, PI475829A, PI467318B, PI467318A, PI467315, PI466749B, PI466749A, PI464921, PI464893, PI464879, PI458517, PI458505, PI458302, PI458289, PI458286, PI458270, PI458256, PI458241, PI458235, PI458230A, PI458228, PI458225, PI458222, PI458219, PI458218, PI458217, PI458210, PI458208, PI458204, PI458202B, PI458202A, PI458196, PI458194, PI458191, PI458190, PI458187, PI458182, PI458177, PI458174, PI458170, PI458163, PI458159, PI458152, PI458148, PI458145, PI458144, PI458142, PI458139, PI458128, PI458126, PI458124, PI458121, PI458120, PI458115, PI458114, PI458104, PI458098, PI458091, PI458088, PI458083, PI458078, PI458074B, PI458074A, PI458072A, PI458068, PI458067B, PI458067A, PI458065B, PI458065A, PI458063, PI458057, PI458054, PI458039, PI458038, PI458035, PI458031, PI458029, PI458028, PI458027, PI458024B, PI458024A, PI442017, PI442013, PI442011, PI442009B, PI442007B, PI442007A, PI438425, PI438424, PI438323, PI438302A, PI438300, PI438278, PI437959, PI437765, PI437734, PI437724, PI437716B, PI437687, PI437683, PI437678B, PI437678A, PI437630A, PI437629, PI427241, PI424604, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI424602, PI424601, PI424600, PI424599, PI424593, PI424590B, PI424590A, PI424588, PI424587, PI424586, PI424584, PI424576, PI424573, PI424572, PI424566, PI424564, PI424556, PI424554, PI424548, PI424546A, PI424544, PI424543, PI424539, PI424538, PI424534, PI424531, PI424530, PI424528, PI424524, PI424522, PI424521B, PI424521A, PI424520, PI424517B, PI424517A, PI424515, PI424512, PI424511, PI424505, PI424504A, PI424500, PI424493B, PI424493A, PI424491A, PI424489B, PI424489A, PI424488B, PI424487B, PI424487A, PI424485, PI424483, PI424481A, PI424469, PI424464, PI424463, PI424462C, PI424462B, PI424462A, PI424459, PI424450, PI424444C, PI424444B, PI424443, PI424442, PI424438, PI424437, PI424434, PI424432, PI424431, PI424426, PI424424, PI424415, PI424410, PI424407, PI424401, PI424398, PI424396, PI424386B, PI424385, PI424383, PI424375, PI424372, PI424369, PI424368B, PI424365, PI424364B, PI424364A, PI424363, PI424362, PI424357B, PI424357A, PI424354, PI424347B, PI424347A, PI424341, PI424340A, PI424333, PI424330, PI424328, PI424323, PI424322, PI424316, PI424312, PI424309B, PI424307, PI424306, PI424303, PI424301, PI424300B, PI424299C, PI424299B, PI424296C, PI424296B, PI424296A, PI424290, PI424289, PI424285D, PI424284B, PI424284A, PI424283, PI424280, PI424269A, PI424266, PI424262, PI424260, PI424257A, PI424255A, PI424251A, PI424249D, PI424249B, PI424243, PI424241, PI424240, PI424239, PI424238, PI424237B, PI424237A, PI424235, PI424234C, PI424233, PI424231, PI424230, PI424229A, PI424228, PI424225, PI424221B, PI424220B, PI424220A, PI424219B, PI424217B, PI424217A, PI424215, PI424214B, PI424192B, PI424188B, PI424185, PI424184, PI424181, PI424179B, PI424179A, PI424177, PI424175, PI424173, PI424168B, PI424168A, PI424164B, PI424162, PI424161, PI424160, PI424158, PI424157B, PI424157A, PI424156D, PI424156C, PI424156B, PI424156A, PI424154B, PI424154A, PI424153, PI424147, PI424146, PI424145, PI424141B, PI424139, PI423987B, PI423986, PI423985, PI423984, PI423982, PI423981, PI423977, PI423974, PI423971D, PI423971B, PI423971A, PI423970, PI423966, PI423962, PI423930B, PI423928, PI423925, PI423923, PI423904, PI423902, PI423901_2, PI423901_1, PI423898, PI423893, PI423874, PI423868, PI423855, PI423847, PI423845B, PI423845A, PI423833B, PI423830A, PI423824, PI423823, PI423808A, PI423807, PI423806, PI423805, PI423804, PI423803, PI423802, PI423799C, PI423799A, PI423797, PI423794, PI423793, PI423790, PI423786, PI423783, PI423782, PI423779, PI423771, PI423769B, PI423768, PI423765, PI423761, PI423753B, PI423751, PI423749, PI423747B, PI423743C, PI423743A, PI423736A, PI423728B, PI423728A, PI423725, PI419043, PI417569, PI417495, PI417490, PI417485, PI417481, PI417475, PI417474, PI417473, PI417467, PI417462, PI417444, PI417423, PI417422, PI417414B, PI417414A, PI417400, PI417399, PI417397, PI417393, PI417373, PI417364, PI417352, PI417344, PI417343, PI417341, PI417333, PI417332, PI417322, PI417307, PI417303, PI417297, PI417293, PI417288, PI417286, PI417276, PI417263, PI417259, PI417255, PI417252, PI417249, PI417246, PI417239, PI417238, PI417233, PI417232, PI417230, PI417223, PI417221, PI417220, PI417207, PI417204, PI417202, PI417197, PI417194, PI417188, PI417179B, PI417179A, PI417178, PI417177, PI417175, PI417169, PI417167, PI417158, PI417147, PI417137, PI417133, PI417129B, PI417128, PI417113, PI417110, PI417109, PI417102B, PI417099, PI417097, PI417095, PI417089B, PI417079, PI417074, PI417073, PI417070, PI417069, PI417064, PI417051, PI417049, PI417037, PI417027, PI417026, PI417021, PI417020, PI417014A, PI417011, PI417003, PI417002, PI416984, PI416982, PI416977, PI416975, PI416971, PI416970, PI416969, PI416962, PI416955, PI416954, PI416949, PI416948, PI416947, PI416938, PI416933, PI416932, PI416928, PI416927, PI416919, PI416905, PI416904B, PI416904A, PI416899, PI416893, PI416892, PI416883, PI416882, PI416881, PI416876, PI416851, PI416850, PI416849, PI416847, PI416843, PI416838, PI416837, PI416821, PI416820, PI416818, PI416817, PI416815, PI416810, PI416804, PI416798, PI416794, PI416785, PI416784, PI416778, PI416769A, PI416766, PI416765, PI416759, PI416758, PI416752, PI416750, PI408336, PI408331, PI408329, PI408326, PI408325, PI408324, PI408319C, PI408319B, PI408319A, PI408310A, PI408309, PI408308A, PI408307C, PI408306, PI408301, PI408298B, PI408292, PI408285B, PI408284, PI408283, PI408282, PI408281B, PI408277, PI408276, PI408273, PI408270B, PI408267, PI408265C, PI408265B, PI408265A, PI408262C, PI408262A, PI408260C, PI408254, PI408248B, PI408244, PI408234B, PI408234A, PI408233A, PI408232, PI408234I, PI408230, PI408229A, PI408224B, PI408224A, PI408222B, PI408222A, PI408221B, PI408221A, PI408215A, PI408214, PI408209A, PI408197B, PI408197A, PI408194, PI408188, PI408181C, PI408181A, PI408164, PI408163, PI408161, PI408159, PI408154, PI408153, PI408144, PI408140A, PI408139, PI408138D, PI408138A, PI408126B, PI408126A, PI408119, PI408118, PI408114, PI408109B, PI408108, PI408105B, PI408103, PI408102, PI408100A, PI408098, PI408095B, PI408094_1, PI408092C, PI408092B, PI408092A, PI408091, PI408087, PI408076B, PI408073, PI408070B, PI408066A, PI408060, PI408049, PI408040_1, PI408039, PI408038, PI408036, PI408034, PI408032A, PI408027, PI408021, PI408020C, PI408020B, PI408018, PI408011, PI408010_2, PI408006, PI408004_2, PI408003_1, PI407995, PI407993, PI407990, PI407988B, PI407988A, PI407983, PI407982, PI407980, PI407979, PI407976B, PI407976A, PI407969, PI407966B, PI407966A, PI407950_2, PI407948, PI407947, PI407946_2, PI407945, PI407939B, PI407932B, PI407932A, PI407927, PI407921, PI407913A, PI407904, PI407901, PI407898A, PI407897, PI407891, PI407883, PI407873, PI407872C, PI407869B, PI407869A, PI407868A, PI407867B, PI407858, PI407856, PI407855, PI407778C, PI407746, PI407711B, PI407659B, PI406710, PI404196B, PI404196A, PI404182, PI404180, PI404163, PI399126, PI399119, PI399112, PI399093, PI399092, PI399091, PI399087, PI399073, PI399066, PI399055, PI399053, PI399052, PI399049, PI399048, PI399046, PI399037, PI399034, PI399030, PI399010, PI399009, PI398995, PI398982, PI398972, PI398971, PI398969, PI398960, PI398948, PI398938, PI398937, PI398936, PI398935, PI398931, PI398929, PI398925, PI398924, PI398921, PI398920, PI398916, PI398915, PI398907, PI398906, PI398899, PI398891, PI398888, PI398883, PI398879, PI398872, PI398871, PI398858, PI398856, PI398855, PI398850, PI398848, PI398843, PI398840, PI398834, PI398817, PI398816, PI398807, PI398800, PI398799, PI398798, PI398797, PI398796, PI398795, PI398794, PI398783, PI398780, PI398779, PI398772, PI398770, PI398766, PI398757, PI398756, PI398746, PI398741, PI398740, PI398735, PI398734, PI398732, PI398719, PI398718, PI398717, PI398716, PI398715, PI398702, PI398701, PI398698, PI398695, PI398681, PI398672, PI398670, PI398666, PI398664, PI398663, PI398662, PI398660, PI398648, PI398647, PI398646, PI398644, PI398634, PI398626, PI398625, PI398624, PI398622, PI398588, PI398586, PI398585, PI398578, PI398575, PI398574, PI398571, PI398568, PI398562, PI398560, PI398558, PI398532, PI398531, PI398522, PI398521, PI398517, PI398511, PI398509, PI398506, PI398501, PI398497, PI398494, PI398492, PI398485, PI398475, PI398472, PI398470, PI398463, PI398457, PI398448, |

TABLE 7-continued 15,996 soybean germplasm accessions clustered by maximum parsimony phylogenetic analysis of the sequence region near the Rhg1 allele, indicating germplasm accessions predicted to carry Rhg1.

| | No of germ-plasm | Copy number type observed | Germplasm designation |
|---|---|---|---|
| | | | PI398447, PI398437, PI398436, PI398420, PI398418, PI398416, PI398415, PI398413, PI398409, PI398406, PI398404, PI398400, PI398393, PI398384, PI398383, PI398379, PI398363, PI398362, PI398360, PI398359, PI398358, PI398356, PI398352, PI398351, PI398350, PI398348, PI398347, PI398341, PI398340, PI398336, PI398335, PI398334, PI398333, PI398331, PI398320, PI398325, PI398321, PI398320, PI398319, PI398318, PI398314, PI398310, PI398303, PI398302, PI398300, PI398294, PI398293, PI398292, PI398289, PI398281, PI398278, PI398277, PI398276, PI398274, PI398273, PI398271, PI398266, PI398263, PI398256, PI398249, PI398246, PI398245, PI398241, PI398233, PI398226, PI398222, PI398221, PI398215, PI398208, PI398206, PI398205, PI398204, PI398197, PI398196, PI398195, PI398188, PI398185, PI393535, PI391594, PI391588, PI384469B, PI384469A, PI384467, PI379623, PI379621, PI379562B, PI379562A, PI379556, PI378693A, PI378690, PI376845, PI368039, PI361053, PI346309, PI341256C, PI341256B, PI341256A, PI340038, PI340027, PI340023, PI340015, PI340012, PI340009, PI339994, PI339988, PI339986, PI339983, PI339979, PI339865A, PI339864B, PI323573, PI323568, PI323562, PI323560, PI323558, PI323557, PI323554, PI323552, PI303653, PI290143, PI283328, PI274421, PI274211, PI274207, PI273484, PI269518C, PI266807D, PI261472, PI253662, PI253658C, PI253653B, PI253650A, PI248513, PI243532, PI243530, PI243529, PI243523, PI243522, PI243521, PI243515, PI243514, PI238932, PI229360, PI229357, PI229344, PI229343, PI229316, PI229315, PI228065, PI227566, PI227563, PI227560, PI227558, PI227555, PI227321, PI227221, PI227159, PI227158, PI222397, PI219784, PI219782, PI219780, PI205087, PI205083, PI200596, PI200553, PI200550, PI200544, PI200527, PI200526, PI200523, PI200516, PI200515, PI200509, PI200506, PI200494, PI200493, PI200477, PI200466, PI200463, PI200457, PI200456, PI200446, PI196166, PI196161, PI196156, PI196150, PI196148, PI189898, PI189897, PI187154, PI187150, PI181569, PI181565, PI181562, PI181560, PI181559, PI181556, PI181553, PI181547, PI181541, PI181540, PI180445, PI179825, PI173995, PI171652, PI171454, PI165672, PI159923B, PI157491, PI157490, PI157474, PI157471, PI157469, PI157460, PI157459, PI157458, PI157456, PI157452, PI157451, PI157450, PI157446, PI157445, PI157442, PI157438, PI157429, PI157424, PI157417, PI157414, PI157408, PI157398, PI157395, PI153313, PI153306, PI153304, PI153241, PI153229, PI097222, PI097100, PI096978, PI096321, PI095740, PI094159B, PI092691, PI092689, PI092641B, PI092636, PI091732_2, PI091729, PI091159_4, PI090760, PI090563, PI090479_1, PI090407, PI089007, PI089006, PI088965, PI088823, PI088818, PI087606, PI087465_2, PI086982, PI086904_1, PI086543, PI086482, PI086463, PI086145, PI086134_2, PI086128, PI086123, PI086111, PI086098, PI086029, PI086024, PI086004, PI085590, PI085550, PI085519, PI085441, PI085424, PI085355, PI085272, PI085021, PI084985, PI084965, PI084946_2, PI084908_2, PI084908_1, PI084807, PI084734, PI084660, PI084632S, PI084632, PI084631, PI084509, PI083946, PI083944, PI083891, PI083889, PI083881, PI082558, PI082554, PI082534, PI082308, PI082307, PI082246, PI082235, PI081785, PI081780, PI081041_1, PI080831, PI080828_2, PI080828_1, PI080498, PI080459, PI079583, PI071677, PI071667, PI070243, PI054604, FC003981 |
| Cluster69 | 1 | | PI407056 |
| Cluster70 | 2 | | PI594804, PI594802B |
| Cluster71 | 17 | | PI562534, PI562532, PI562531, PI507652, PI507632, PI507615, PI424038A, PI424027A, PI424026, PI407271, PI407194, PI407182, PI407095, PI407093, PI407092, PI209577, PI209340 |
| Cluster72 | 15 | | PI522201, PI507640, PI507634, PI479752, PI447003A, PI424029, PI424015, PI407253, PI407240, PI407155, PI407152, PI407151, PI407150, PI407149, PI407132 |
| Cluster73 | 8 | | PI507660, PI507645, PI479753A, PI438282B, PI424107A, PI424025B, PI407171, PI378698 |
| Cluster74 | 1 | | PI507661 |
| Cluster75 | 1 | | PI567379A |
| Cluster76 | 20 | | PI603578, PI603499, PI567411, PI567410C, PI567410B, PI567385, PI567381B, PI424608A, PI424595, PI424585, PI407842, PI407838, PI407831, PI407824, PI407738, PI399058, PI398942, PI398512, PI201423, PI171443 |
| Cluster77 | 6 | | PI593992, PI507622, PI507608, PI507595, PI464935, PI378699A |
| Cluster78 | 31 | | PI639618, PI639605, PI597462A, PI532453A, PI522235C, PI522223, PI507843, PI507836, PI507818B, PI507798, PI507797, PI507792, PI507789, PI507785, PI507778, PI507776, PI507775, PI507772, PI507771, PI507770, PI507769, PI507768, PI507760, PI507736, PI507730, PI507728, PI507725B, PI424002, PI423995, PI342618B, PI326582B |
| Cluster79 | 2 | | PI594839B, PI594796 |
| Cluster80 | 3 | | PI567676B, PI567648C, PI567647B |
| Cluster81 | 160 | 4, 6, 7, 9, 10 | PI639740, PI636474, PI635053, PI633609, PI632352, PI620883, PI618808, PI618613, PI615582, PI614088, PI612761B, PI612157, PI608033, PI607380, PI606748, PI603742C, PI603587C, PI603587B, PI603587A, PI603575, PI603574, PI603572, PI603567A, PI603558, PI603557, PI603556, PI603551B, PI603502D, PI603493, PI603446, PI603438E, PI603438C, PI603438A, PI603436B, PI603374, PI603372, PI602496, PI599333, PI598358, PI598222, PI597649, PI597456, PI597386, PI597385, PI595765, PI595363, PI595099, PI593653, PI593257, PI593238, PI592389, PI584506, PI584441, PI583364, PI578399, PI578332C, PI578247, PI578057, PI578002, PI577798, PI576857, PI574541, PI574532, PI573188, PI567512B, PI567491B, PI567479, PI567475, PI567463, PI567449, PI567443, PI567437, PI567434, PI567432A, PI567429E, PI567429D, PI567429C, PI567429B, PI567429A, PI567233, PI567232A, PI567175D, PI564999, PI564849, PI564524, PI561328, PI561313, PI561218, PI560207, PI560206, PI556932, PI556859, PI556781, PI556738, PI553040, PI548981, PI548693, PI548316, PI542043, PI540556, PI540554, PI533602, PI518675, PI518674, PI518668, PI518663, PI512039, PI507458, PI506417, PI495017C, PI483071A, PI479749, PI468400B, PI468399B, PI468399A, PI468398C, PI468398A, PI468397B, PI468397A, PI467332, PI467312, PI464912, PI461509, PI458520, PI458257, PI438503A, PI437770, PI437655, PI437580, PI437488, PI436611, PI424439, PI417100, PI417091, PI416768, PI416762, PI404170, PI399068, PI253665C, PI232993, PI209332, PI157416, PI096188, PI092733, PI092720, PI092468, PI091102, PI090577, PI089783, PI089008, PI088788, PI087631_1, PI087628, PI086069, PI086031, PI084673, PI079726, PI079609, PI054591 |
| Cluster82 | 1725 | | PI647960, PI642732, PI639558, PI639282, PI636463, PI633732, PI633730, PI633622, PI632942B, PI632942A, PI632936, PI632933, PI628950, PI628936, PI628935, PI628929, PI628919, PI628849, PI628833, PI628823, PI628812, PI628807, PI628806, PI628804, PI628797, PI619083, PI615510C, PI615510B, PI615509B, PI615509A, PI615500, PI615496, PI615495, PI615491, PI615485, PI615483, PI615477, PI615476, PI615474, PI615470, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI615464, PI615462, PI613056, PI612761A, PI612760, PI612759D, PI612759C, PI612759B, PI612759A, PI612758B, PI612757, PI612756, PI612752, PI612730, PI612727, PI612726, PI612715, PI612713B, PI612713A, PI612612A, PI607835, PI606440C, PI606438B, PI606433, PI606418B, PI606398, PI606391, PI606386, PI606384, PI605896C, PI605887A, PI605886C, PI605886B, PI605886A, PI605885B, PI605884F, PI605884E, PI605884C, PI605882A, PI605879, PI605877B, PI605876G, PI605876F, PI605876C, PI605874C, PI605874B, PI605872, PI605867, PI605863A, PI605860, PI605859B, PI605859A, PI605858, PI605857A, PI605856, PI605854A, PI605853C, PI605853B, PI605853A, PI605850B, PI605850A, PI605846F, PI605846E, PI605846C, PI605846B, PI605845D, PI605845B, PI605844F, PI605844E, PI605844D, PI605842B, PI605841A, PI605840G, PI605840F, PI605840D, PI605839B, PI605834C, PI605834A, PI605832B, PI605831C, PI605831A, PI605830B, PI605830A, PI605828C, PI605828A, PI605827C, PI605827A, PI605826D, PI605826C, PI605826A, PI605825B, PI605825A, PI605824B, PI605821C, PI605821B, PI605821A, PI605819A, PI605818A, PI605817A, PI605810C, PI605810B, PI605810A, PI605808, PI605806B, PI605806A, PI605805A, PI605799A, PI605792B, PI605789B, PI605788, PI605786C, PI605785, PI605782B, PI605782, PI605780C, PI605780B, PI605780A, PI605779B, PI605771, PI605758C, PI605758B, PI603913D, PI603913A, PI603775B, PI603770, PI603769, PI603767, PI603765, PI603751A, PI603743B, PI603740B, PI603736, PI603735B, PI603734, PI603731B, PI603724B, PI603724A, PI603712, PI603705B, PI603705A, PI603703A, PI603696, PI603694A, PI603693B, PI603692, PI603687B, PI603687A, PI603686, PI603684, PI603682, PI603681A, PI603680, PI603679, PI603678B, PI603678A, PI603677B, PI603676, PI603673E, PI603671, PI603641, PI603639, PI603627, PI603626, PI603625, PI603621, PI603619, PI603617, PI603616, PI603611B, PI603610A, PI603609, PI603608, PI603606, PI603603, PI603588, PI603586, PI603583, PI603579, PI603570B, PI603569A, PI603560, PI603553, PI603552, PI603550, PI603545A, PI603539D, PI603539C, PI603539B, PI603539A, PI603538E, PI603532, PI603533B, PI603531A, PI603521, PI603517B, PI603517A, PI603511B, PI603511A, PI603510, PI603509, PI603508, PI603504, PI603498B, PI603498A, PI603494, PI603491, PI603490, PI603486, PI603482, PI603479, PI603478, PI603477A, PI603474, PI603466B, PI603466A, PI603463, PI603458C, PI603458B, PI603458A, PI603457C, PI603457A, PI603456, PI603455A, PI603451A, PI603450, PI603449, PI603438D, PI603437A, PI603431, PI603430B, PI603427C, PI603427B, PI603426B, PI603424A, PI603422D, PI603422C, PI603422B, PI603422A, PI603421A, PI603420, PI603418D, PI603415, PI603401, PI603394, PI603381C, PI603381B, PI603381A, PI603378B, PI603361, PI603352, PI603350, PI603349, PI603346B, PI603346A, PI603344, PI603343B, PI603343A, PI603324B, PI603321, PI603317, PI603302, PI603298, PI603293B, PI603184, PI602991, PI602501, PI602490, PI602451, PI602448, PI602447, PI597480B, PI597480A, PI597473, PI597461C, PI597461B, PI597458C, PI597454B, PI597435, PI597417, PI596414, PI594901, PI594900B, PI594900A, PI594899B, PI594899A, PI594888, PI594863B, PI594855, PI594851, PI594846, PI594845, PI594843, PI594826B, PI594826A, PI594820C, PI594820B, PI594820A, PI594810A, PI594786A, PI594785, PI594784B, PI594784A, PI594782, PI594781, PI594772B, PI594771, PI594764, PI594757, PI594753C, PI594753A, PI594738A, PI594737, PI594736, PI594724, PI594722, PI594720, PI594718A, PI594702, PI594699, PI594693B, PI594680, PI594679, PI594678, PI594673, PI594672, PI594668, PI594666A, PI594665, PI594664, PI594661, PI594660C, PI594660B, PI594659C, PI594656, PI594652B, PI594652A, PI594651, PI594650A, PI594649, PI594648B, PI594648A, PI594647B, PI594647A, PI594646, PI594645, PI594640, PI594638A, PI594631A, PI594630, PI594627A, PI594608A, PI594607, PI594606, PI594597, PI594594, PI594591B, PI594586B, PI594586A, PI594585, PI594574, PI594571, PI594563, PI594562B, PI594562A, PI594561, PI594560C, PI594560B, PI594560A, PI594559, PI594557B, PI594554, PI594552B, PI594549A, PI594547, PI594545, PI594544, PI594532, PI594527, PI594519, PI594517, PI594514, PI594504, PI594496, PI594492B, PI594492A, PI594486A, PI594484, PI594483, PI594482, PI594475B, PI594475A, PI594469B, PI594468, PI594462, PI594461B, PI594439B, PI594434, PI594433A, PI594432, PI594426B, PI594425, PI594423, PI594422, PI594421, PI594420, PI594419, PI594418B, PI594418A, PI594417, PI594416, PI594415A, PI594414B, PI594414A, PI594392, PI594254, PI593982, PI593975, PI593968, PI593964, PI593942, PI593939, PI592979, PI592943, PI592942, PI592926, PI592919, PI592907C, PI592901, PI588053B, PI588051, PI588045, PI588043, PI588042, PI588041, PI588037, PI588036, PI588035, PI588034, PI588032C, PI588032A, PI588031, PI588030, PI588029, PI588023A, PI588019A, PI588018, PI588017A, PI588016, PI588014D, PI588009, PI588008D, PI588008C, PI588008B, PI588008A, PI588002, PI588001, PI588000, PI587998H, PI587995, PI587992G, PI587992B, PI587970B, PI587970A, PI587966C, PI587964, PI587961, PI587953, PI587951A, PI587947, PI587945, PI587942, PI587940, PI587937, PI587935B, PI587935A, PI587933, PI587932, PI587930, PI587928, PI587916C, PI587916A, PI587910, PI587909, PI587905, PI587904, PI587903B, PI587903A, PI587902B, PI587902A, PI587900B, PI587897, PI587894, PI587889, PI587888, PI587879, PI587877B, PI587877A, PI587876, PI587875, PI587874, PI587873, PI587871, PI587868, PI587867, PI587866, PI587864B, PI587864A, PI587863B, PI587863A, PI587862A, PI587861, PI587858, PI587856B, PI587856A, PI587854A, PI587851B, PI587851A, PI587849, PI587846B, PI587846A, PI587844B, PI587844A, PI587841B, PI587841A, PI587839B, PI587839A, PI587837, PI587836, PI587835, PI587832, PI587827, PI587826, PI587825A, PI587824, PI587823, PI587822B, PI587822A, PI587820B, PI587820A, PI587818, PI587816, PI587814D, PI587814C, PI587812A, PI587811A, PI587809A, PI587808B, PI587803, PI587802, PI587800, PI587799, PI587798, PI587793, PI587788B, PI587787, PI587783, PI587781, PI587778, PI587777, PI587775, PI587774, PI587771, PI587770, PI587765, PI587764, PI587762, PI587761, PI587759, PI587757B, PI587756, PI587755, PI587754, PI587753B, PI587753A, PI587746, PI587743, PI587742A, PI587741, PI587739B, PI587739A, PI587737, PI587736B, PI587734, PI587733, PI587732, PI587730C, PI587730B, PI587730A, PI587729, PI587726B, PI587726A, PI587725C, PI587725B, PI587725A, PI587723B, PI587721C, PI587721B, PI587721A, PI587720, PI587717, PI587716B, PI587714B, PI587714A, PI587711, PI587710, PI587706, PI587700D, PI587699, PI587698C, PI587696, PI587691, PI587687E, PI587675, PI587674B, PI587674A, PI587672, PI587670A, PI587669, PI587668A, PI587667, PI587666, PI587665, PI587664B, PI587662B, PI587660B, PI587660A, PI587658A, PI587657, PI587656, PI587655, PI587641C, PI587641B, PI587641A, PI587638, PI587627C, PI587627B, PI587626, PI587625B, PI587620A, PI587619, PI587618C, PI587618A, PI587617, PI587615, PI587611, PI587610, PI587609B, PI587603D, PI587603C, PI587603B, PI587599, PI587597B, PI587590, PI587589, PI587584, PI587582, PI587580A, PI587574B, PI587573A, PI587569, PI587568B, PI587566B, PI587565B, PI587564C, PI587564B, PI587563A, PI587557A, PI587556B, PI587556A, |

TABLE 7-continued 15,996 soybean germplasm accessions clustered by maximum parsimony phylogenetic analysis of the
sequence region near the Rhg1 allele, indicating germplasm accessions predicted to carry Rhg1.

| No of germ-plasm | Copy number type observed | Germplasm designation |
|---|---|---|
| | | PI587555B, PI587553A, PI587552, PI587550C, PI583366, PI583295, PI578506, PI578498B, PI578494B, PI578487, PI578466, PI578465, PI578464B, PI578464A, PI578463, PI578460, PI578455B, PI578452, PI578446A, PI578438, PI578436, PI578427, PI578421, PI578420, PI578419B, PI578418, PI578409A, PI578401C, PI578401B, PI578401A, PI578398, PI578397, PI578379, PI578370, PI578368, PI578332B, PI578331, PI578330, PI578324H, PI578324G, PI578324F, PI578324E, PI578324D, PI578324C, PI578324B, PI578324A, PI578323A, PI578321, PI578320, PI578319E, PI578319C, PI578318A, PI578317, PI578316C, PI578315A, PI578311A, PI578309, PI578308B, PI578308A, PI578307C, PI578307B, PI578306B, PI578306A, PI578305B, PI574480A, PI574479B, PI574479A, PI574478C, PI574478A, PI574476B, PI574476A, PI573286, PI572237, PI567789, PI567788, PI567780B, PI567780A, PI567779A, PI567778, PI567777, PI567774B, PI567774A, PI567772, PI567771C, PI567771A, PI567770C, PI567770B, PI567770A, PI567769, PI567767C, PI567767A, PI567766, PI567765B, PI567764, PI567763, PI567762C, PI567762A, PI567760, PI567759, PI567757, PI567754, PI567751B, PI567750, PI567747, PI567746, PI567745, PI567744C, PI567744B, PI567744A, PI567737, PI567735, PI567730, PI567728, PI567727B, PI567727A, PI567726, PI567723, PI567722, PI567714, PI567711B, PI567702A, PI567694, PI567693, PI567692, PI567689, PI567687, PI567683B, PI567683A, PI567679B, PI567660B, PI567660A, PI567659, PI567658, PI567651, PI567650C, PI567648B, PI567648A, PI567646B, PI567646A, PI567642B, PI567642A, PI567641, PI567640, PI567639, PI567638, PI567637, PI567635, PI567633, PI567632B, PI567629B, PI567629A, PI567628A, PI567627A, PI567621A, PI567620B, PI567620A, PI567614D, PI567614C, PI567604B, PI567604A, PI567602D, PI567602C, PI567602A, PI567601, PI567596, PI567593A, PI567588B, PI567587A, PI567584, PI567583A, PI567582A, PI567581, PI567580B, PI567580A, PI567579, PI567577, PI567575, PI567574B, PI567573B, PI567568B, PI567566, PI567565, PI567564, PI567561, PI567558, PI567556, PI567555, PI567552, PI567551, PI567550, PI567549B, PI567549A, PI567544, PI567543C, PI567543B, PI567542, PI567541B, PI567541A, PI567540B, PI567539, PI567538B, PI567538A, PI567536, PI567535B, PI567533, PI567530, PI567529, PI567528B, PI567528A, PI567525, PI567523, PI567520B, PI567520A, PI567519, PI567518, PI567516A, PI567515, PI567514B, PI567509, PI567508B, PI567508A, PI567507E, PI567507D, PI567507C, PI567507A, PI567505, PI567504, PI567503, PI567502, PI567500, PI567498, PI567497, PI567496, PI567490, PI567489A, PI567488C, PI567488B, PI567488A, PI567486B, PI567485, PI567482C, PI567444, PI567431, PI567430, PI567425A, PI567404F, PI567404E, PI567404D, PI567404C, PI567404B, PI567403B, PI567401, PI567396D, PI567396C, PI567396A, PI567393, PI567389B, PI567389A, PI567384, PI567381A, PI567379C, PI567372A, PI567371B, PI567367, PI567366A, PI567362B, PI567361, PI567354, PI567353, PI567352B, PI567351B, PI567348, PI567346, PI567341, PI567340, PI567332, PI567331, PI567327, PI567324, PI567323C, PI567321B, PI567319A, PI567314, PI567312, PI567311A, PI567310B, PI567308, PI567307, PI567303B, PI567303A, PI567300A, PI567295, PI567292, PI567289B, PI567287, PI567270C, PI567269B, PI567269A, PI567268, PI567259, PI567257C, PI567257B, PI567251, PI567250B, PI567246, PI567244, PI567242, PI567211B, PI567183, PI567144A, PI567139B, PI567136A, PI567132A, PI567131C, PI567131B, PI567130A, PI567127A, PI567126, PI567123B, PI567122A, PI567108D, PI567108C, PI567100B, PI567099B, PI567098B, PI567098A, PI567095A, PI567092B, PI567092A, PI567091, PI567087B, PI567087A, PI567085B, PI567085A, PI567084, PI567083D, PI567083A, PI567082B, PI567080, PI567079, PI567078, PI567077B, PI567075B, PI567074B, PI567073B, PI567072B, PI567070B, PI567070A, PI567067B, PI567064B, PI567063, PI567062, PI567054B, PI567053, PI567052, PI567050, PI567031A, PI567023A, PI567004, PI566975, PI566971B, PI566971A, PI566970C, PI566966B, PI566964B, PI566962, PI566961, PI566958, PI561702, PI561572, PI561377, PI561358B, PI561356, PI561341B, PI561334, PI561325, PI561309A, PI561305, PI561304A, PI561296B, PI561241, PI561240, PI561237, PI561235, PI561234, PI561233B, PI561233A, PI561232, PI561227, PI559369, PI556805, PI555399, PI555397, PI553042, PI549029, PI549021B, PI548662, PI548660, PI548658, PI548656, PI548613, PI548604, PI548602, PI548564, PI548480, PI548473, PI548448, PI548447, PI548443, PI548400, PI548360, PI548260, PI548258, PI542402, PI538389, PI538385B, PI538377, PI538375, PI532463A, PI532455A, PI532451, PI532448, PI532439, PI518757, PI518726, PI518721, PI518712, PI518285, PI515961, PI511866, PI507696B, PI507696A, PI507684, PI507483, PI507340, PI507325, PI507155, PI507082C, PI507072, PI507066, PI507065, PI507020, PI506942, PI506933, PI506930, PI506920, PI506656, PI506649, PI506634, PI506571, PI506525, PI506524, PI506482, PI506478, PI505649B, PI504507, PI503339A, PI499955, PI497968, PI497962, PI497958, PI495017A, PI495016, PI486335, PI486332, PI486328, PI483459, PI483253, PI483251, PI483071B, PI481690, PI481686, PI481679, PI479758, PI479741, PI479720, PI479718A, PI479716, PI479715, PI476934, PI476930, PI476927, PI476923, PI476920, PI476917, PI476915, PI476909, PI476904, PI476897, PI476896, PI476895, PI476885, PI476883, PI476878, PI475830, PI475822B, PI475785, PI475784, PI475783A, PI471942, PI471941, PI471940, PI471939, PI471937, PI471936, PI471934, PI471933, PI471932, PI471930, PI471929A, PI471925, PI471903, PI471900, PI470222, PI470221, PI468971, PI468964, PI468408C, PI468396B, PI468396A, PI468378, PI468131, PI467343, PI467338, PI467334B, PI467330, PI467325, PI467321, PI467320, PI467314, PI464931, PI464920B, PI464920A, PI464917, PI464915B, PI464914B, PI464914A, PI464913, PI464900, PI464880, PI464875A, PI464865, PI461419, PI458826B, PI458826A, PI458531, PI458529, PI458523, PI458519B, PI458515, PI458511, PI458508B, PI458507, PI458506, PI458274, PI458047, PI458046, PI452433, PI449456A, PI445848A, PI445846B, PI445846A, PI445842, PI445683, PI441378, PI441360B, PI441358, PI441353, PI438442A, PI438439, PI438438, PI438435B, PI438429, PI438426, PI438341, PI438312, PI438303, PI438284, PI438259B, PI438242, PI438192, PI438153, PI438152, PI438133A, PI438065, PI437970, PI437944, PI437909B, PI437909A, PI437877C, PI437874, PI437860B, PI437851A, PI437791, PI437790, PI437789, PI437783, PI437751, PI437745, PI437743, PI437737, PI437730, PI437728, PI437722, PI437719, PI437710, PI437708, PI437695C, PI437684, PI437672, PI437671, PI437663, PI437661B, PI437658, PI437652, PI437640B, PI437634, PI437631, PI437614B, PI437612, PI437576, PI437565, PI437550B, PI437550A, PI437457, PI437444, PI437428B, PI437423, PI437410, PI437405, PI437404, PI437367, PI437355, PI437351, PI437350, PI437346, PI437345, PI437336B, PI437327, PI437143, PI437130, PI437116, PI437110B, PI437110A, PI437109B, PI437094, PI437088B, PI437078A, PI436682, PI436568, PI436566, PI434979, PI430625, PI428692, PI428691, PI427242, PI427106, PI423971C, PI417398, PI417383, PI417345B, PI417345A, PI417340, PI417278, PI417275, PI417269, PI417243, PI417180, PI417172, PI417140, PI417138, PI417092, PI417058, PI417022, PI416983, PI416936, PI416900, PI416894D, PI416868B, PI416868A, PI416854, PI416797, PI416751, PI407810, PI407796, PI407769, PI407767, PI407765, PI407762, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI407761, PI407742, PI407737, PI407733, PI407731, PI407727, PI407721, PI407710, PI407706B, PI407657, PI407656, PI405691, PI404199, PI404197, PI404195, PI404194, PI404193, PI404192C, PI404190, PI404189, PI404187, PI404183, PI404181, PI404179B, PI404176, PI404175, PI404174, PI404173A, PI404172, PI404169B, PI404168, PI404162, PI404152, PI398997, PI398446, PI393999, PI393550, PI393549, PI393548, PI393547, PI393546, PI393545, PI393544, PI391577, PI384473, PI383277, PI381681, PI381680, PI378677C, PI378677B, PI378677A, PI378671, PI377577, PI377573, PI374186, PI374184, PI374183, PI374182, PI374179, PI374176, PI374175, PI374173, PI374172, PI374169, PI374168, PI374165, PI374164, PI374163, PI374162, PI374159, PI374158, PI374157, PI374154, PI372415A, PI361112B, PI360843, PI347539A, PI346306, PI346305, PI346302, PI346298, PI341255, PI341254, PI340904B, PI326580, PI326579, PI323578, PI323574, PI323572, PI323569, PI323565, PI323553, PI323551, PI323550, PI323276, PI323275, PI319534B, PI319532, PI319527, PI310441, PI307881, PI307865, PI307836, PI306712, PI306704B, PI297544, PI297533, PI297523, PI297510, PI297509, PI297504, PI291324, PI291309C, PI291278, PI291277, PI291276, PI290126B, PI290126A, PI283332, PI279081, PI269518B, PI269518A, PI266807A, PI261474, PI261271, PI259539, PI255734, PI253665A, PI253664, PI253663, PI253660B, PI253660A, PI253659, PI253657, PI253654, PI253652A, PI253651D, PI253651B, PI248509B, PI248398, PI245008, PI240665, PI239484, PI238933, PI232992, PI232991, PI232990, PI232989, PI232988, PI232987, PI227333, PI227328, PI227322, PI227320, PI221713, PI219732, PI219653, PI215811, PI215688, PI212605, PI212604, PI210349, PI210348, PI210178, PI209836, PI208788, PI208433, PI208432, PI208431, PI208429, PI205914, PI205910, PI205908, PI205907, PI205384, PI204333, PI204332, PI201422, PI200520, PI200495, PI200454, PI198078, PI192871, PI189951, PI189930, PI189866, PI189402, PI183930, PI183929, PI183900, PI181698, PI180051, PI175198, PI175192, PI175191, PI175190, PI175188, PI175184, PI175181, PI175180, PI175178, PI175177, PI174867, PI174866, PI174865, PI174862, PI174861, PI174859, PI174858, PI174857, PI174855, PI174854, PI174853, PI174852, PI171446, PI171445, PI171444, PI171440, PI171438, PI171431, PI171429, PI166141, PI166140, PI166105, PI166048, PI165947, PI165943, PI165929, PI165926, PI165896, PI165675, PI165674, PI165583, PI165578, PI165563, PI165524, PI159926, PI159922, PI159319, PI157413, PI153292, PI153289, PI153280, PI148226, PI135589, PI135589, PI133226, PI123590, PI123440, PI103091, PI103080, PI103079, PI093563, PI092661, PI092629, PI092627, PI092465, PI091341, PI091167, PI091156, PI091153, PI091152, PI091129, PI091126, PI091121_2, PI091100_1, PI091091, PI090495N, PI090486, PI090392, PI090369, PI090180, PI089784, PI089167, PI089073, PI089053, PI088886, PI088798, PI088490_2, PI088455, PI088308, PI088294_1, PI087614, PI087167, PI086046, PI086002, PI084964, PI084954, PI084921, PI084914, PI083945_3, PI082532, PI082326, PI082263_3, PI082184, PI081773, PI081771, PI081770, PI081767, PI081766, PI081763, PI081037_4, PI080488_1, PI079694, PI079648, PI079616, PI079593, PI071465, PI071444, PI070229, PI070080, PI069993, PI069507_1, PI068500, PI065388, PI062204, PI062199, PI060269_2, PI060269, PI056563, PI054615_2, PI054607, FC031416 |
| Cluster83 | 3 | PI615518, PI548482, PI165673 |
| Cluster84 | 4 | PI615450, PI594427A, PI424077, PI424057 |
| Cluster85 | 5 | PI603530C, PI603530A, PI597451A, PI587790B, PI567610A |
| Cluster86 | 90 | PI639620, PI639617A, PI639616, PI639615, PI639606, PI639604, PI639599, PI639594, PI639592, PI639583, PI639582B, PI639582A, PI578338A, PI578336, PI567175A, PI567174A, PI538411B, PI522234, PI522211B, PI522207B, PI522207A, PI522179, PI507845, PI507844B, PI507839, PI507838B, PI507837, PI507833, PI507822, PI507817, PI507816, PI507815, PI507813, PI507811, PI507793, PI507790, PI507787, PI507763, PI507759, PI507758, PI507754, PI507753, PI507750, PI507747, PI507745, PI507743, PI507742, PI507740, PI507739A, PI507737, PI507735, PI507733, PI507732, PI507731, PI507726, PI507725A, PI507724, PI507722, PI507721, PI507720, PI507719, PI507648, PI507592, PI464927B, PI464927A, PI464926, PI464890A, PI464867, PI458537B, PI458537A, PI424113, PI424000, PI423999B, PI423999A, PI423998, PI423997, PI423996, PI423992, PI407321, PI407249, PI407110, PI407109, PI407108, PI407107, PI407030, PI407019, PI407018, PI342621C, PI342621B, PI342621A |
| Cluster87 | 886 | 1 | PI653109, PI652935, PI647962, PI639634, PI639631, PI639630B, PI639630A, PI639571B, PI639566C, PI639566A, PI639555B, PI639555A, PI639539B, PI636464, PI636461, PI636444, PI634903, PI634873, PI634365, PI633731, PI633610, PI632963, PI632949, PI632948, PI632947, PI632946, PI631123, PI629005, PI628965, PI628954, PI628932, PI628927, PI628925, PI628923, PI628920, PI628912, PI628907, PI628885, PI628881, PI628880, PI628879, PI628877, PI628871, PI628862, PI628858, PI628852, PI628840, PI628837, PI628831, PI628821, PI628817, PI628815, PI628799, PI615556, PI615510A, PI614674, PI613561, PI612751, PI612745, PI612740, PI612739, PI612738, PI612728, PI612721A, PI612718, PI612714B, PI612709B, PI612708D, PI612708C, PI612708B, PI612708A, PI612707A, PI612706A, PI612608, PI608726, PI607385, PI605909C, PI605819C, PI603915A, PI603911A, PI603786, PI603670, PI603663, PI603662A, PI603656, PI603655, PI603646, PI603614A, PI603570D, PI603536, PI603534A, PI603496A, PI603485, PI603470, PI603451B, PI603439, PI603437C, PI603435A, PI603432C, PI603426D, PI603426C, PI603418C, PI603418B, PI603418A, PI603417, PI603414, PI603409, PI603405A, PI603403, PI603396, PI603392, PI603390B, PI603388, PI603385, PI603375, PI603369, PI603363B, PI603362, PI603359, PI603355, PI603353, PI603351, PI603348C, PI603348B, PI603348A, PI603345, PI603335A, PI603325, PI603318, PI603314, PI603311, PI603310, PI603309, PI603303, PI603301A, PI603291, PI603202, PI603196, PI603190, PI603169, PI603157, PI603156, PI602502B, PI602502A, PI602491, PI597664, PI597663, PI597443, PI597442, PI597431, PI597430A, PI597427B, PI597427A, PI597421, PI597419, PI597413, PI597412, PI597411B, PI597411A, PI597409, PI597408, PI597407B, PI597407A, PI597381, PI595926, PI594898, PI594897, PI594895, PI594850, PI594600, PI594456A, PI594418E, PI594142, PI594000, PI593969, PI593967, PI593958, PI593955, PI593256, PI592981, PI592978, PI592975, PI592973, PI592971, PI592969, PI592964, PI592960, PI592928, PI592925, PI592924, PI592923, PI592922, PI592920, PI592917, PI592915, PI592900, PI587795, PI587745, PI587693, PI578505, PI578503, PI578496, PI578429, PI578428B, PI578424, PI578423, PI578419A, PI578413, PI578410, PI578409B, PI578407, PI578406, PI578405, PI578403, PI578402, PI578396, PI578394, PI578393, PI578392B, PI578391, PI578390, PI578384, PI578381, PI578367, PI578329C, PI578329B, PI576440, PI567597B, PI567560, PI567554A, PI567524, PI567512A, PI567506, PI567487, PI567484, PI567480B, PI567480A, PI567272B, PI567272A, PI567252, PI567240, PI567231, PI567223, PI567175C, PI567173, PI567170A, PI567159B, PI567159A, PI567156A, PI564261, PI561407, PI561405, |

TABLE 7-continued 15,996 soybean germplasm accessions clustered by maximum parsimony phylogenetic analysis of the sequence region near the Rhg1 allele, indicating germplasm accessions predicted to carry Rhg1.

| No of germ-plasm | Copy number type observed | Germplasm designation |
|---|---|---|
| | | PI561387, PI561370, PI561354, PI561344, PI561338A, PI561335, PI561327D, PI561327C, PI561327A, PI561326, PI561317, PI561316, PI561307, PI561304B, PI561303, PI561302C, PI561292B, PI561292A, PI561285B, PI561228, PI560911, PI560910, PI560909, PI550740, PI549078, PI549077, PI549076B, PI549076A, PI549075, PI549073, PI549070, PI549069, PI549061, PI549060, PI549054, PI549027A, PI549023B, PI549023A, PI548983, PI548695, PI548691, PI548685, PI548654, PI548627, PI548619, PI548529, PI548528, PI548527, PI548525, PI548521, PI548519, PI548512, PI548511, PI548510, PI548450, PI548424, PI548401, PI548385, PI548377, PI548364, PI548357, PI548344, PI548330, PI548309, PI548297, PI548292, PI548283, PI548271, PI548267, PI548257, PI548250, PI548248, PI548247, PI548188, PI547821, PI546487, PI542042, PI539866, PI538408, PI538406, PI538400, PI538397, PI538393, PI536636, PI533655, PI533601, PI532834, PI532833, PI532471, PI532463B, PI532462B, PI532462A, PI522189, PI522188B, PI518751, PI518711, PI518706A, PI518704, PI518664, PI511869, PI508268, PI507697, PI507691, PI507687A, PI507685B, PI507543, PI507296, PI507295, PI507294A, PI507201, PI506945, PI504506, PI503338, PI491548, PI483252, PI479762, PI479737, PI479730, PI479724B, PI479721, PI479719, PI479718B, PI475831, PI475829B, PI475827, PI471931, PI470224, PI470223, PI468377, PI468376, PI467346, PI467345, PI467342, PI467336, PI467333, PI467329, PI467328, PI467326, PI467323B, PI467323A, PI467322A, PI467319, PI467317, PI467311E, PI467311D, PI467311C, PI467311B, PI467311A, PI464924, PI464905, PI464902, PI464901, PI464899, PI464898, PI464897, PI464895, PI464894, PI464888B, PI464888A, PI464883, PI464878, PI458828, PI458824, PI458541, PI458510, PI458509, PI458107, PI449458B, PI449458A, PI438442B, PI438413, PI438267, PI438266B, PI438266A, PI438263, PI438261, PI438251, PI438228, PI438227, PI438194, PI438191, PI438190, PI438189, PI438187, PI438186, PI438185, PI438179, PI438178, PI438177, PI438176, PI438175, PI438173, PI438172, PI438168, PI438167, PI438166A, PI438165, PI438164A, PI438151, PI438150, PI438146, PI438143, PI438130, PI438129, PI438123B, PI438123A, PI438118, PI438103, PI438095, PI438085, PI438084, PI438067, PI438064, PI438050A, PI438018, PI437978, PI437974A, PI437969, PI437955B, PI437904, PI437895C, PI437895A, PI437889, PI437870, PI437867A, PI437864B, PI437864A, PI437858, PI437856B, PI437856A, PI437854, PI437847B, PI437847A, PI437845D, PI437845C, PI437845B, PI437845A, PI437821, PI437811, PI437807, PI437806, PI437784, PI437763, PI437752C, PI437752B, PI437738B, PI437738A, PI437729, PI437723, PI437720, PI437715, PI437714, PI437700, PI437698, PI437692, PI437675, PI437673, PI437666, PI437648A, PI437639, PI437636B, PI437636A, PI437630B, PI437609A, PI437602, PI437593B, PI437592, PI437589, PI437585, PI437584, PI437581, PI437567, PI437554, PI437552, PI437545, PI437525, PI437472, PI437435, PI437427C, PI437427B, PI437399, PI437385A, PI437344D, PI437344C, PI437344A, PI437340C, PI437315, PI437156B, PI437133, PI437131, PI437128, PI437105D, PI436683, PI436681, PI436620, PI436618, PI436617, PI436613, PI430460B, PI430460A, PI427107B, PI427107A, PI427105B, PI427105A, PI427099, PI427088I, PI427088H, PI427088G, PI427088E, PI427088D, PI427088B, PI427088A, PI424612, PI424474_2, PI423900, PI417520, PI417077, PI417059, PI417040A, PI417030, PI415072, PI408339, PI408338, PI408107, PI408088, PI407729, PI407723, PI407722, PI407719, PI407107, PI407718, PI407717, PI407716, PI407714, PI407711A, PI407707, PI407706A, PI407705, PI407704, PI407701, PI407386A, PI405690, PI404192B, PI404160B, PI404160A, PI404156, PI404154, PI399045, PI399044, PI399035, PI398963, PI398928, PI393563, PI391584, PI391583, PI391581B, PI391578, PI383278, PI383276, PI378676B, PI378669A, PI378664B, PI372416B, PI372404C, PI371612, PI370057B, PI361112A, PI361109, PI361081, PI361075, PI361074, PI361055, PI358319, PI358315C, PI358315A, PI347552B, PI319535A, PI303650, PI297538, PI297536, PI297515, PI297514, PI297513, PI297511, PI297505, PI291327, PI291322, PI291306B, PI291305, PI291303A, PI291301, PI291295, PI290134, PI283334, PI283326, PI266807B, PI266806B, PI266085A, PI253665B, PI253661C, PI253661A, PI253658B, PI253658A, PI253653D, PI253653A, PI253652C, PI253652B, PI248509A, PI240079, PI227334, PI227329, PI227324, PI189931, PI189929, PI157468, PI157437, PI153255, PI103414, PI097139, PI096089, PI093055S, PI092707S, PI092707_2, PI092705, PI092704, PI092702, PI092688, PI092687, PI092683, PI092662, PI092660, PI092651, PI092633, PI092618, PI092598, PI092596, PI092593, PI092589, PI092563, PI091559, PI091163, PI091150, PI091132_3, PI091120, PI091116, PI091114, PI091107, PI091104, PI091100_4, PI090576_1, PI090567, PI090566_1, PI090560, PI090495, PI089471, PI089171, PI089154_1, PI089154, PI089152, PI089067, PI089064, PI089012, PI089010, PI089009, PI088499, PI088484, PI088459, PI088452, PI088444, PI088358, PI088356, PI088355, PI088310, PI088309, PI088304, PI088303, PI088301, PI088296, PI088294, PI088293A, PI087615, PI087588, PI087065, PI086903_3, PI086454, PI086449, PI086301, PI085666, PI085508, PI084910, PI084683A, PI084680, PI084668, PI081971, PI081034_1, PI081030_1, PI081029N, PI081029_1, PI080845_2, PI080837, PI080476, PI080469, PI079885, PI079874, PI079848, PI079832, PI079747, PI079745, PI079732_4, PI079732_3, PI079712, PI079703, PI079613, PI073772, PI072341, PI072232, PI072227, PI071850_1, PI071850, PI071845, PI071161, PI070561, PI070559, PI070528, PI070470, PI070463, PI070457, PI070456, PI070453, PI070253, PI070242_4, PI070241, PI070213, PI070199, PI070091, PI070089, PI070084, PI070036, PI070021, PI070019, PI069996, PI069995, PI069992, PI069991, PI069533, PI069503, PI069501, PI068795, PI068788, PI068770, PI068761, PI068748, PI068741, PI068729, PI068713, PI068708, PI068706, PI068704, PI068701, PI068692_2, PI068685, PI068680_2, PI068680, PI068676, PI068671, PI068670_2, PI068663, PI068658, PI068655, PI068642, PI068639, PI068629, PI068627, PI068600, PI068599, PI068598, PI068585, PI068564, PI068543, PI068530, PI068528, PI068526, PI068521, PI068508, PI068503, PI068488, PI068484_4, PI068483, PI068481, PI068480, PI068479, PI068475, PI068474, PI068470, PI068466, PI068465, PI068461_1, PI068461, PI068457, PI068448, PI068443, PI068439, PI068427, PI065346, PI065341, PI065338, PI062203, PI061940, PI060279, PI060273, PI057334, PI055887, PI054818, PI054620, PI054619, PI054618, PI054614, PI054610_4, PI054610_1, PI054610, PI054606_2, PI030600, FC032176, FC031707, FC031702, FC031685, FC031683, FC031678, FC031579, FC031572_3, FC004007A, FC001547 |
| Cluster88 | 147 | PI594890, PI594886, PI594867, PI594860, PI594854, PI594842, PI594809A, PI594803A, PI594617, PI594610, PI594605B, PI594605A, PI594572B, PI594572A, PI587917, PI587915D, PI587704, PI587692B, PI567256, PI562549, PI509110B, PI507548, PI507291, PI507124, PI506838B, PI506686, PI506685, PI506483, PI458203B, PI458203A, PI458173, PI458168, PI458166, PI458150B, PI458150A, PI458136, PI458133, PI458116, PI458090A, PI458059, PI458021, PI442003B, PI424589, PI424558B, PI424558A, PI424536, PI424527, PI424519, PI424492, PI424471, PI424449, PI424417, PI424395, PI424257B, PI424250A, PI424211, PI424170, PI424166, PI423839, PI423800, PI423781A, PI423778, PI423755, PI423750, PI417353, PI417334, PI417304, PI417248, PI417244, |

TABLE 7-continued 15,996 soybean germplasm accessions clustered by maximum parsimony phylogenetic analysis of the sequence region near the Rhg1 allele, indicating germplasm accessions predicted to carry Rhg1.

| | No of germ-plasm | Copy number type observed | Germplasm designation |
|---|---|---|---|
| | | | PI417212, PI417057, PI417023, PI416994, PI416986, PI416822, PI416814, PI416767, PI408332C, PI408332B, PI408332A, PI408296B, PI408296A, PI408290, PI408261, PI408249, PI408189, PI408181D, PI408175, PI408174, PI408115, PI408071, PI408070A, PI408069, PI408058, PI407991, PI407964, PI407958, PI407905, PI407902B, PI407902A, PI407872A, PI407871, PI407866, PI407864, PI404178, PI399088, PI398977, PI398966, PI398895, PI398893, PI398868, PI398867, PI398865, PI398847, PI398818, PI398781, PI398769, PI398736, PI398576, PI398557, PI398556, PI398498, PI398484, PI398456, PI398455, PI398438, PI398381, PI398380, PI398378, PI398377, PI398366, PI398365, PI398355, PI398239, PI398211, PI398209, PI398200, PI398191, PI398182, PI340001, PI243520, PI200552, PI157493, PI087074, PI086736, PI083868, PI082544 |
| Cluster89 | 284 | | PI655521, PI634889, PI634870, PI628948, PI619617, PI619616, PI603777, PI603635, PI603624, PI603620, PI603618, PI603614B, PI603604, PI601983, PI601982, PI594575, PI594486C, PI594477, PI594401C, PI594401B, PI594401A, PI594302, PI594217C, PI594217B, PI594208, PI594177, PI594156, PI594017, PI594012, PI593972, PI592953, PI592952, PI592914, PI592906, PI587919, PI587916D, PI587892C, PI587892B, PI587880B, PI587880A, PI587814E, PI587814B, PI587814A, PI587797, PI587767A, PI587760, PI587752, PI587740, PI587738, PI587735, PI587727, PI587719C, PI587719B, PI587719A, PI587713, PI587712B, PI587712A, PI587662A, PI578484, PI567671B, PI561390, PI548694, PI548618, PI548588, PI548567, PI548553, PI548552, PI548550, PI548536, PI548426, PI548425, PI548423, PI548356, PI548324, PI548303, PI548302, PI548170, PI535807, PI518756, PI507623, PI507613, PI507609, PI507585, PI507582, PI507580, PI507544, PI507444, PI507437, PI507394, PI507377, PI507343, PI507309, PI507301, PI507286C, PI507269, PI507264, PI507186, PI507132B, PI507130, PI507100, PI507088, PI507075, PI507049, PI507043, PI507035, PI507025, PI506983, PI506911, PI506897, PI506885, PI506876, PI506809, PI506696, PI506680, PI506633, PI506559, PI506475, PI504286, PI494181, PI438485, PI438286, PI438070, PI437478, PI437171, PI436777, PI436567, PI436563, PI430620, PI427140, PI427137, PI424172A, PI424127A, PI424117, PI424112, PI424100B, PI424099B, PI423935, PI423921, PI423914B, PI423911, PI423909, PI423907, PI423892, PI423878, PI423876, PI423875, PI417472B, PI417472A, PI417417, PI417408, PI417362, PI417361, PI417359, PI417346, PI417298, PI417290, PI417285, PI417282, PI417277, PI417260B, PI417257, PI417214, PI417184C, PI417141, PI417107, PI417106, PI417088, PI417065, PI417061, PI417045, PI417044, PI417043, PI416903, PI416894C, PI416894A, PI416891, PI416865, PI416848, PI416833, PI416827, PI416825B, PI416825A, PI416816, PI416803, PI416774, PI416763, PI416753, PI407261, PI407208, PI407126, PI407125, PI407082, PI398830, PI366124, PI360837, PI355068, PI355067S, PI342434, PI342003, PI317337, PI274454, PI274453, PI261473, PI243525, PI238930, PI238928, PI238926, PI238109, PI238108, PI230977, PI230975, PI229358, PI229350, PI229321, PI227219, PI227212, PI226590, PI224269, PI221973, PI221972, PI208785, PI208783, PI205086, PI203246, PI200533, PI200485, PI200471, PI200470, PI200461, PI196162, PI196158, PI196152, PI189907, PI181567, PI181561, PI181537, PI181536, PI171451, PI163308, PI103419B, PI097627, PI096983, PI090258, PI090221, PI089156, PI089154S, PI089154_2, PI089134, PI089133, PI088825, PI087631_3, PI087623, PI087622, PI086469, PI086457, PI086146, PI086081, PI086075, PI086071, PI086032, PI085437, PI084987A, PI084987, PI084976, PI084973, PI084957, PI084944, PI084896, PI084668_1, PI084646_2, PI083925, PI082296, PI081765, PI081037_5, PI081037_2, PI080845_1, PI080844_3, PI080494, PI079825_1, PI064698, PI062202_2, PI059849, PI058955, FC019979_5 |

The invention claimed is:

1. A method of determining copy number of a variable copy number version of a replicated target nucleic acid sequence in a sample from a plant, comprising:
contacting a sample comprising single-stranded genomic nucleic acids with:
(1) a pair of oligonucleotide primers that anneal upstream and downstream, respectively, of a sequence within the both the defined copy number version and the variable copy number versions of replicated target nucleic acid sequence;
(2) a first non-extendable oligonucleotide probe, with a first 5' fluorescent reporter label and an internal or 3' quencher dye, which first probe anneals specifically to the defined copy number version of the replicated target sequence between the pair of oligonucleotide primers; and
(3) a second non-extendable oligonucleotide probe, with a second 5' fluorescent reporter label and an internal or 3' quencher dye, which second probe anneals specifically to the variable copy number version of the replicated target sequence between the pair of oligonucleotide primers to produce a mixture, wherein the defined copy number version and the variable copy number versions of the target nucleic acid are in the same genome and wherein the defined copy number version of the replicated target nucleic acid sequence is a homeolog of the variable copy number version;
maintaining the mixture with a template-dependent nucleic acid polymerase having a 5' to 3' nuclease activity under conditions sufficient to permit the 5' to 3' nuclease activity of the polymerase to cleave the annealed probes and release labeled fragments;
measuring the release of nucleic acid fragments containing fluorescent report label; and
determining the relative amount of released first and second fluorescent reporter fragments, thereby determining copy number of the variable copy number version of the replicated target nucleic acid sequence.

2. The method of claim 1, wherein the first and second non-extendable probes bind to a sequence that differs by only one single nucleotide variation (SNV) between the variable copy number version and the defined copy number version of the replicated target sequence.

3. The method of claim 1, wherein the target sequence is selected from the group consisting of:
soybean rhg1;
soybean Rag1;
soybean Rag2;
maize MATE1;
barley Bot1;
wheat Photoperiod-B1 (Pbd-B1);
wheat Vernalization-A1 (Vrn-A1);
rice Grain Length on Chromosome 7 (GL7); and
a plant gene that impacts a crop trait through copy number.

4. A method of selecting a soybean plant or soybean germplasm with one or more of increased resistance to soybean cyst nematode (SCN), optimized yield, or emergence compared to a control soybean plant, the method comprising:

quantifying the number of Rhg1 copies in the genome of the soybean plant or the soybean germplasm using the method of claim 1;

selecting the soybean plant or germplasm from a population of plants, some of which having an increased or decreased number of Rhg1 copies relative to an ancestor;

crossing the selected soybean plant or a soybean plant derived from the selected germplasm; and selecting one or more progeny of the crossing having an altered number of Rhg1 copies.

5. The method of claim 4, wherein the copy number of the Rhg1 locus is maintained at a predetermined number of copies.

6. The method of claim 4, wherein the method further comprises:

quantifying the number and type of different Rhg1 copies in the genome of the soybean plant or the soybean germplasm using the method of claim 1;

selecting soybean plant or germplasm having an altered diversity of Rhg1 sequence repeats.

7. The method of claim 6, wherein the soybean plant or germplasm is selected so that it includes at least one Rhg1 P-type repeat and at least one Rhg1 F-type repeat.

8. A method of determining copy number of a variable copy number version of a replicated target nucleic acid sequence in a sample, comprising:

contacting a sample comprising single-stranded genomic nucleic acids with:

(1) a pair of oligonucleotide primers that anneal upstream and downstream, respectively, of a sequence within the both the defined copy number version and the variable copy number versions of replicated target nucleic acid sequence;

(2) a first non-extendable oligonucleotide probe, with a first 5' fluorescent reporter label and an internal or 3' quencher dye, which first probe anneals specifically to the defined copy number version of the replicated target sequence between the pair of oligonucleotide primers; and (3) a second non-extendable oligonucleotide probe, with a second 5' fluorescent reporter label and an internal or 3' quencher dye, which second probe anneals specifically to the variable copy number version of the replicated target sequence between the pair of oligonucleotide primers to produce a mixture, wherein the defined copy number version and the variable copy number versions of the target nucleic acid are in the same genome and wherein the defined copy number version of the replicated target nucleic acid sequence is a homeolog of the variable copy number version;

maintaining the mixture with a template-dependent nucleic acid polymerase having a 5' to 3' nuclease activity under conditions sufficient to permit the 5' to 3' nuclease activity of the polymerase to cleave the annealed probes and release labeled fragments;

measuring the release of nucleic acid fragments containing fluorescent report label;

determining the relative amount of released first and second fluorescent reporter fragments, thereby determining copy number of the variable copy number version of the replicated target nucleic acid sequence; and determining copy number of at least one additional variable copy number version of the replicated target nucleic acid comprising contacting the sample with a different non-extendable probe that binds to a different SNV at a different locus, thereby determining the copy number of at least a second variable copy number version of the replicated target nucleic acid.

* * * * *

UNITED STATES PATENT AND TRADEMARK OFFICE
CERTIFICATE OF CORRECTION

PATENT NO. : 10,337,072 B2  
APPLICATION NO. : 14/991733  
DATED : July 2, 2019  
INVENTOR(S) : Hudson et al.

Page 1 of 1

It is certified that error appears in the above-identified patent and that said Letters Patent is hereby corrected as shown below:

In the Claims

Column 127, Line 45, Claim 1, "sequence within the both the defined copy number" should read --sequence within both the defined copy number--.

Column 129, Line 32, Claim 8, "sequence within the both the defined copy number" should read --sequence within both the defined copy number--.

Signed and Sealed this  
Seventh Day of December, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 26

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 1
agcctgctcc tcacaaattc ttgc                                          24

<210> SEQ ID NO 2
<211> LENGTH: 24
<212> TYPE: DNA
<213> ORGANISM: Artificial sequence
<220> FEATURE:
<223> OTHER INFORMATION: Synthetic oliogonucleotide

<400> SEQUENCE: 2
tcctcttgat ctcgtaggaa aaga                                          24

<210> SEQ ID NO 3

```
<211> LENGTH: 20
<212> TYPE: DNA
<213> ORGANISM: Artificial sequence
<220> FEATURE:
<223> OTHER INFORMATION: Synthetic oliogonucleotide

<400> SEQUENCE: 3
tggagtgggc tgaatctctt                                               20

<210> SEQ ID NO 4
<211> LENGTH: 20
<212> TYPE: DNA
<213> ORGANISM: Artificial sequence
<220> FEATURE:
<223> OTHER INFORMATION: Synthetic oliogonucleotide

<400> SEQUENCE: 4
atggaagcaa gagcagcatt                                               20

<210> SEQ ID NO 5
<211> LENGTH: 25
<212> TYPE: DNA
<213> ORGANISM: Artificial sequence
<220> FEATURE:
<223> OTHER INFORMATION: Synthetic oliogonucleotide

<400> SEQUENCE: 5
gcagctgttg gaatcattct ttgtt                                         25

<210> SEQ ID NO 6
<211> LENGTH: 29
<212> TYPE: DNA
<213> ORGANISM: Artificial sequence
<220> FEATURE:
<223> OTHER INFORMATION: Synthetic oliogonucleotide

<400> SEQUENCE: 6
aggatccaaa tgagaaagag gttcaattt                                     29

<210> SEQ ID NO 7
<211> LENGTH: 16
<212> TYPE: DNA
<213> ORGANISM: Artificial sequence
<220> FEATURE:
<223> OTHER INFORMATION: Synthetic oliogonucleotide

<400> SEQUENCE: 7
ggtttattgt atggtg                                                   16

<210> SEQ ID NO 8
<211> LENGTH: 16
<212> TYPE: DNA
<213> ORGANISM: Artificial sequence
<220> FEATURE:
<223> OTHER INFORMATION: Synthetic oliogonucleotide

<400> SEQUENCE: 8
ggtttactgt atggtg                                                   16

<210> SEQ ID NO 9
<211> LENGTH: 27
<212> TYPE: DNA
<213> ORGANISM: Artificial sequence
<220> FEATURE:
<223> OTHER INFORMATION: Synthetic oliogonucleotide

<400> SEQUENCE: 9
```
ctgaagtatg gagttaaagg acacctt                                    27

<210> SEQ ID NO 10
<211> LENGTH: 28
<212> TYPE: DNA
<213> ORGANISM: Artificial sequence
<220> FEATURE:
<223> OTHER INFORMATION: Synthetic oliogonucleotide

<400> SEQUENCE: 10
cgttctaatg cattggttat agcaacaa                                   28

<210> SEQ ID NO 11
<211> LENGTH: 16
<212> TYPE: DNA
<213> ORGANISM: Artificial sequence
<220> FEATURE:
<223> OTHER INFORMATION: Synthetic oliogonucleotide

<400> SEQUENCE: 11
cagagttggc agatgc                                                16

<210> SEQ ID NO 12
<211> LENGTH: 16
<212> TYPE: DNA
<213> ORGANISM: Artificial sequence
<220> FEATURE:
<223> OTHER INFORMATION: Synthetic oliogonucleotide

<400> SEQUENCE: 12
cagagtttgc agatgc                                                16

<210> SEQ ID NO 13
<211> LENGTH: 23
<212> TYPE: DNA
<213> ORGANISM: Artificial sequence
<220> FEATURE:
<223> OTHER INFORMATION: Synthetic oliogonucleotide

<400> SEQUENCE: 13
caccttctta atgctggcat ctg                                        23

<210> SEQ ID NO 14
<211> LENGTH: 25
<212> TYPE: DNA
<213> ORGANISM: Artificial sequence
<220> FEATURE:
<223> OTHER INFORMATION: Synthetic oliogonucleotide

<400> SEQUENCE: 14
ctgatatcgt tctaatgcat tggtt                                      25

<210> SEQ ID NO 15
<211> LENGTH: 18
<212> TYPE: DNA
<213> ORGANISM: Artificial sequence
<220> FEATURE:
<223> OTHER INFORMATION: Synthetic oliogonucleotide

<400> SEQUENCE: 15
tagcaacaac gtcctctt                                              18

<210> SEQ ID NO 16
<211> LENGTH: 18
<212> TYPE: DNA

<213> ORGANISM: Artificial sequence
<220> FEATURE:
<223> OTHER INFORMATION: Synthetic oliogonucleotide

<400> SEQUENCE: 16
tagcaacaac ctcctctt                                                 18

<210> SEQ ID NO 17
<211> LENGTH: 26
<212> TYPE: DNA
<213> ORGANISM: Artificial sequence
<220> FEATURE:
<223> OTHER INFORMATION: Synthetic oliogonucleotide

<400> SEQUENCE: 17
ggttcgttta gaagggatga aaatgc                                        26

<210> SEQ ID NO 18
<211> LENGTH: 27
<212> TYPE: DNA
<213> ORGANISM: Artificial sequence
<220> FEATURE:
<223> OTHER INFORMATION: Synthetic oliogonucleotide

<400> SEQUENCE: 18
ttcacaatgt tcaggtgtg ttgaaag                                        27

<210> SEQ ID NO 19
<211> LENGTH: 15
<212> TYPE: DNA
<213> ORGANISM: Artificial sequence
<220> FEATURE:
<223> OTHER INFORMATION: Synthetic oliogonucleotide

<400> SEQUENCE: 19
agcaccgtca tctaa                                                    15

<210> SEQ ID NO 20
<211> LENGTH: 16
<212> TYPE: DNA
<213> ORGANISM: Artificial sequence
<220> FEATURE:
<223> OTHER INFORMATION: Synthetic oliogonucleotide

<400> SEQUENCE: 20
cagcaccgtt atctaa                                                   16

<210> SEQ ID NO 21
<211> LENGTH: 25
<212> TYPE: DNA
<213> ORGANISM: Glycine max

<400> SEQUENCE: 21
ttttctcttg aactgataat caaat                                         25

<210> SEQ ID NO 22
<211> LENGTH: 25
<212> TYPE: DNA
<213> ORGANISM: Glycine max

<400> SEQUENCE: 22
ttctaaaatg gacttgtaat tggtg                                         25

<210> SEQ ID NO 23
<211> LENGTH: 31

```
<212> TYPE: DNA
<213> ORGANISM: Glycine max

<400> SEQUENCE: 23
aattttttga atggtgataa cggccaataa t                                31

<210> SEQ ID NO 24
<211> LENGTH: 5
<212> TYPE: PRT
<213> ORGANISM: Glycine max

<400> SEQUENCE: 24

Gln His Glu Ala Ile
1               5

<210> SEQ ID NO 25
<211> LENGTH: 5
<212> TYPE: PRT
<213> ORGANISM: Glycine max

<400> SEQUENCE: 25

Glu Tyr Glu Val Ile
1               5

<210> SEQ ID NO 26
<211> LENGTH: 4
<212> TYPE: PRT
<213> ORGANISM: Glycine max

<400> SEQUENCE: 26

Glu Asp Asp Leu
1
```